United States Patent
Deng et al.

(10) Patent No.: US 11,078,213 B2
(45) Date of Patent: Aug. 3, 2021

(54) THIENOPYRIMIDINE COMPOUND, PREPARATION METHOD THEREOF, PHARMACEUTICAL COMPOSITION AND APPLICATION THEREOF

(71) Applicant: HONGYUN BIOTECH CO., LTD., Nanjing (CN)

(72) Inventors: Xianming Deng, Xiamen (CN); Baoding Zhang, Xiamen (CN); Shuang Liu, Xiamen (CN); Chao Dong, Xiamen (CN); Xihuan Sun, Xiamen (CN); Xiaoxing Huang, Xiamen (CN); Zhou Deng, Xiamen (CN); Yunzhan Li, Xiamen (CN); Yue Lu, Xiamen (CN); Li Li, Xiamen (CN); Zhiyu Hu, Xiamen (CN)

(73) Assignee: HONGYUN BIOTECH CO., LTD., Jiangsu (CN)

( * ) Notice: Subject to any disclaimer, the term of this patent is extended or adjusted under 35 U.S.C. 154(b) by 0 days.

(21) Appl. No.: 16/324,040

(22) PCT Filed: Sep. 28, 2017

(86) PCT No.: PCT/CN2017/103983
§ 371 (c)(1),
(2) Date: Feb. 7, 2019

(87) PCT Pub. No.: WO2018/028721
PCT Pub. Date: Feb. 15, 2018

(65) Prior Publication Data
US 2019/0211030 A1    Jul. 11, 2019
US 2020/0207779 A2    Jul. 2, 2020

(30) Foreign Application Priority Data
Aug. 9, 2016 (CN) .......................... 201610646949.8

(51) Int. Cl.
| C07D 495/04 | (2006.01) |
| A61P 35/04 | (2006.01) |
| A61P 35/02 | (2006.01) |
| A61P 35/00 | (2006.01) |
| A61K 31/5377 | (2006.01) |
| A61K 31/519 | (2006.01) |

(52) U.S. Cl.
CPC .......... *C07D 495/04* (2013.01); *A61K 31/519* (2013.01); *A61K 31/5377* (2013.01); *A61P 35/00* (2018.01); *A61P 35/02* (2018.01); *A61P 35/04* (2018.01)

(58) Field of Classification Search
CPC .................................................. C07D 495/04
USPC ....................................................... 544/278
See application file for complete search history.

(56) References Cited

U.S. PATENT DOCUMENTS 10,342,798 B2 * 7/2019 Gray ................... A61K 31/437

FOREIGN PATENT DOCUMENTS

| CN | 102105150 A | 6/2011 | |
| CN | 102947316 A | 2/2013 | |
| CN | 103242341 A | 8/2013 | |
| CN | 103242341 * | 4/2014 | .......... C07D 495/04 |
| CN | 104311573 A | 1/2015 | |
| CN | 106083742 A | 11/2016 | |
| CN | 107698603 A | 2/2018 | |
| GB | 1057612 | 2/1967 | |
| JP | 2008013527 * | 8/2004 | .......... C07D 495/04 |
| JP | 2008013527 A | 1/2008 | |
| JP | 2013529630 A | 7/2013 | |
| KR | 20140118575 A | 10/2014 | |
| WO | 03/055890 A1 | 7/2003 | |
| WO | WO 2003055890 * | 7/2003 | .......... C07D 495/04 |
| WO | 2006105056 A2 | 10/2006 | |
| WO | 2007/070872 A1 | 6/2007 | |
| WO | 2009062258 A1 | 5/2009 | |
| WO | 2011162515 A2 | 12/2011 | |
| WO | 2014/014314 A1 | 1/2014 | |
| WO | 2016/210291 A1 | 12/2016 | |

OTHER PUBLICATIONS

Venkatesh, J. Pharm. Sci. 89, 145-154 (2000) (p. 146, left column).*

(Continued)

*Primary Examiner* — Nizal S Chandrakumar
(74) *Attorney, Agent, or Firm* — Heslin Rothenberg Farley & Mesiti P.C.

(57) ABSTRACT

The present invention relates to thienopyrimidine compound, preparation method thereof, pharmaceutical composition and use thereof, and in particular to a type of compounds having ALK and/or c-Met selective inhibitory activity, a method for the preparation thereof, a pharmaceutical composition comprising the same, and use of these compounds in the manufacture of a medicament for preventing or treating a disease associated with anaplastic lymphoma kinase in vivo, and in the manufacture of a medicament for preventing or treating a disease associated with angiogenesis or cancer metastasis, in particular in the manufacture of a medicament for preventing or treating tumor growth and metastasis.

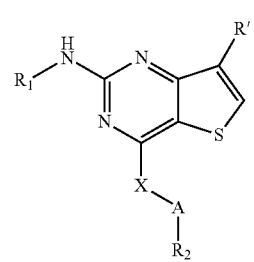

13 Claims, 1 Drawing Sheet

(56) References Cited

OTHER PUBLICATIONS

J. G. Cannon, Chapter Nineteen in Burger's Medicinal Chemistry and Drug Discovery, Fifth Edition, vol. I: Principles and Practice, Wiley-Interscience 1995, pp. 783-802, 784.*
Wolff, Burger's medicinal Chemistry and Drug Discovery, vol. 1, Principles and Practice, John Wiley & sons, New York, 1997.*
West, Solid State Chemistry and Its Applications, john Wiley & Sons, 1984.*
Temburnikar, Kartik W. et al., Antiproliferative Activities of Halogenated Thieno[3,2-$d$]Pyrimidines, Bioorganic & Medicinal Chemistry, vol. 22, Mar. 3, 2014, pp. 2113-2122.
Metz, James T. et al., "Navigating the Kinome," Nature Chemical Biology, vol. 7, Apr. 2011, pp. 200-202.
International Search Report (and English translation) and Written Opinion of the International Searching Authority for PCT/CN2017/103983 dated Jan. 3, 2018.
Gibson, P.R., et al., "Optimization of 2-Anilino 4-Amino Substituted Quinazolines into Potent Antimalarial Agents with Oral in Vivo Activity", Journal of Medicinal Chemistry, vol. 60, pp. 1171-1188 (2017).
RN: 1347894-34-1 STN: Registry (2017) and RN: 1348708-37-1 STN: Registry (2011).

* cited by examiner

THIENOPYRIMIDINE COMPOUND, PREPARATION METHOD THEREOF, PHARMACEUTICAL COMPOSITION AND APPLICATION THEREOF

CROSS REFERENCE TO RELATED APPLICATIONS

This application is a national stage filing under section 371 of International Application No. PCT/CN2017/103983, filed on Sep. 28, 2017, and published on Feb. 15, 2018 as WO 2018/028721, which claims priority to Chinese Application No. 201610646949.8, filed on Aug. 9, 2016. The entire contents of WO 2018/028721 are hereby incorporated herein by reference.

TECHNICAL FIELD

The invention relates to the field of medicinal chemistry, and in particular to a type of compounds having ALK and/or c-Met selective inhibitory activity, a method for the preparation thereof, a pharmaceutical composition comprising the same, and use of these compounds in the manufacture of a medicament for preventing or treating a disease associated with anaplastic lymphoma kinase in vivo, and in the manufacture of a medicament for preventing or treating a disease associated with angiogenesis or cancer metastasis, in particular in the manufacture of a medicament for preventing or treating tumor growth and metastasis.

BACKGROUND ART

Anaplastic lymphoma kinase (ALK) is a receptor tyrosine kinase that belongs to insulin receptor superfamily. Its protein structure includes, in the order from N-terminus to C-terminus, an extracellular receptor domain, a transmembrane domain, and an intracellular tyrosine kinase domain. Normal ALK protein is mainly expressed in central nervous system and peripheral nervous system. The expression level of ALK gene in human body shows a decreasing trend 189 with the degree of brain development, and is in particular low in mature brain tissue. The expression of ALK has not been found in other systems, in particular in hematopoietic system, and its expression and distribution have been shown to be local.

Under normal circumstances, human ALK gene can encode a 1602 amino acid, 200 kDa type I transmembrane protein ALK, but the gene is usually dormant. In the case of fusion with other genes, ALK gene can be a very potent oncogene. The genes that have been found to be fused to ALK gene include nuclear phosphoprotein gene (NPM, anaplastic large cell lymphoma ALCL), echinoderm microtubule associated protein like 4 gene (EML4, non-small cell lung cancer NSCLC), tropomyosin 3 gene (TPM3, Inflammatory myofibroblastic tumor IMT), etc. (Nat. Rev. Cancer, 2008, 8, 11-23.; Nat. Rev. Cancer, 2013, 13, 685-700; Expert Opin. Ther. Pat., 2014. 24(4): p. 417-42).

In non-small cell lung cancer, it is mainly in fusion with EML4 gene, and the fusion gene (EML4-ALK) has an incidence of 4% to 7% in NSCLC. With the deepening of molecular biology research on non-small cell lung cancer (NSCLC), personalized biomarker-based treatment has progressed from the laboratory to the clinic, and great clinical progress has been made in the treatment of patients with advanced non-small cell lung cancer. This means that, in addition to the traditional histopathological classification of NSCLC, molecular phenotypic classification can be performed based on different expression levels of different molecular markers of a particular patient. NSCLC patients are tested for relevant molecular markers prior to treatment. In the clinic, doctors can carry out targeted treatment according to the phenotypic characteristics of their tumor molecules, thereby improving the therapeutic effect. Under such a background, research and development of new drugs targeting driver genes or their encoded proteins closely related to tumorigenesis and development has become a hot spot in anti-tumor drug research.

Currently, U.S. Food and Drug Administration (FDA) has approved the small molecule inhibitor Crizotinib developed by Pfizer Co. (J. Thorac. Oncol., 2010. 5(12): p. 2044-6.), Ceritinib developed by Novartis Co. (J. Med. Chem., 2013. 56(14): p. 5675-90.), Alectinib developed by Chugai PharmaceutICal (Cancer Lett., 2014. 351(2): p. 215-21.). However, clinical studies have shown that some patients have developed resistance to Crizotinib, and the bioavailability of Crizotinib needs to be improved. Ceritinib can target some patients who are resistant or intolerant to Crizotinib. Therefore, compounds to substitute them are highly desirable in clinical practice for improving efficacy and coping with drug resistance.

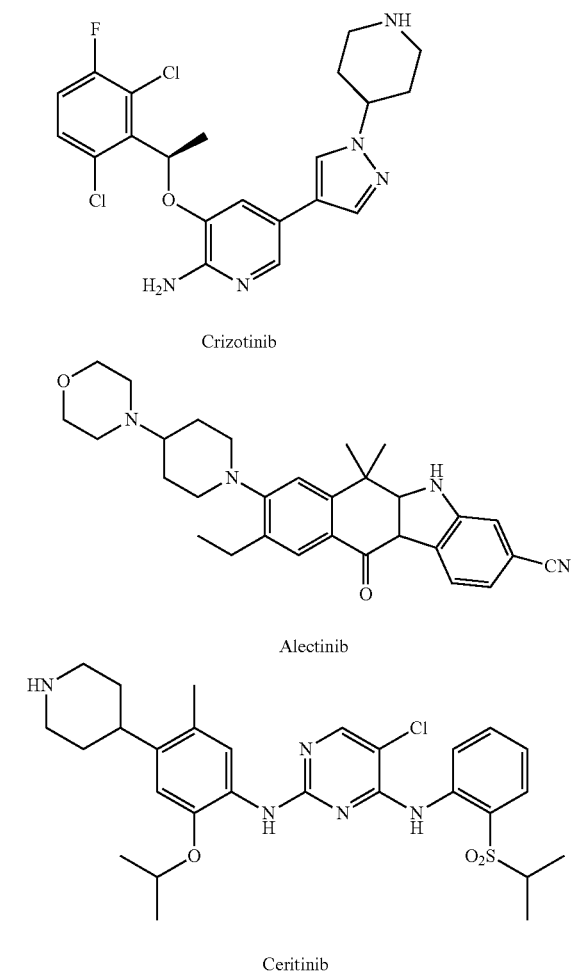

Crizotinib

Alectinib

Ceritinib

SUMMARY OF INVENTION

In order to find new ALK inhibitors, after extensive and in-depth research, the inventors of the present invention have designed and synthesized a series of polysubstituted thienopyrimidine (thiophene [3,2-d] pyrimidine) derivatives having novel structures, high safety and high activity for various tyrosine kinases (EGFR, PDGFR, c-Met, etc.), in particular ALK, and have studied antitumor activity of this novel type of derivatives.

The compound has the general formula:

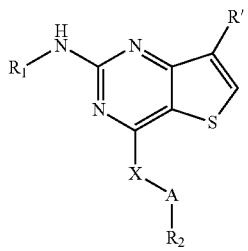

The definitions of substituents and symbols are described in detail below.

One object of the present invention is to provide a compound having ALK and/or c-Met selective inhibitory activity, and a pharmaceutically acceptable salt or pharmaceutically acceptable solvate thereof.

Another object of the present invention is to provide a method for the preparation of the above compound.

Another object of the present invention is to provide a pharmaceutical composition comprising the above compound.

Another object of the present invention is to provide use of the above compound in the manufacture of a medicament for preventing or treating a disease associated with anaplastic lymphoma kinase accompanied by abnormal cell proliferation, morphological changes, hyperkinesia and the like in vivo, and in the manufacture of a medicament for preventing or treating a disease associated with angiogenesis or cancer metastasis, in particular in the manufacture of a medicament for preventing or treating tumor growth and metastasis.

SPECIFIC MODES FOR CARRYING OUT THE INVENTION

Figure 1:
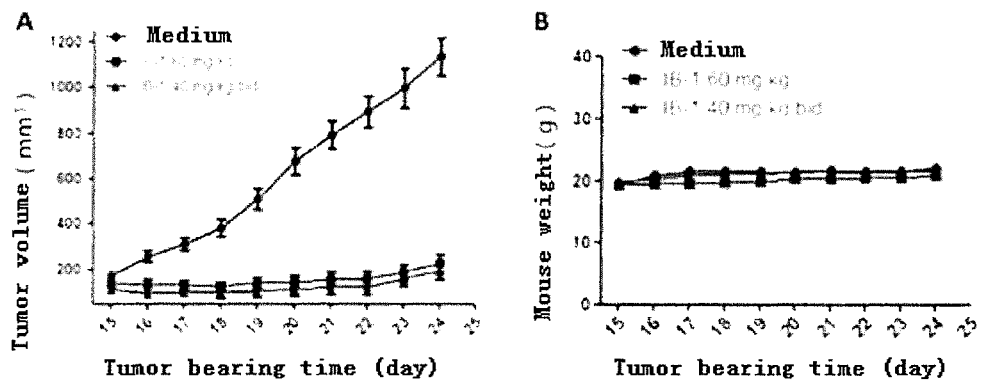
FIG. 1 shows that compound IB-1 significantly inhibits tumor growth in the nude mouse xenograft model of EML4-ALK(G1202R)-Ba/F3. A) Compound IB-1 was orally administered at doses of 60 mg/kg (once/day) and 40 mg/kg (twice/day, bid), respectively, for 10 consecutive days, both of which significantly inhibited tumor growth; B) during administration, the mice in the drug group showed no significant changes in body weight, indicating that the mice were well tolerable to the drug, and IB-1 had no obvious side effects.

The present invention is achieved by the following technical solutions.

In a first aspect, the present invention provides a compound of Formula I, a stereoisomer thereof, a prodrug thereof, a pharmaceutically acceptable salt thereof or a pharmaceutically acceptable solvate thereof,

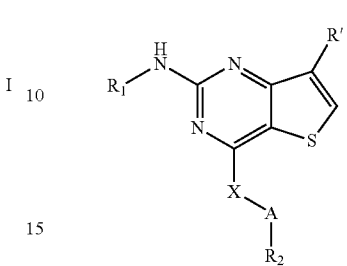

wherein: R' is H, Cl or Br;
$R_1$ is selected from:
1) C1-C6 alkyl, 2-N,N-dimethylaminoethyl, 2-hydroxyethyl, 2-N,N-diethylaminoethyl, 2-N,N-diisopropylaminoethyl, 2-morpholinylethyl, 2-(4-methylpiperazinyl)ethyl, 3-N,N-dimethylaminopropyl, 3-N,N-diethylaminopropyl, 3-N,N-diisopropylaminopropyl, 3-morpholinylpropyl, 3-(4-methylpiperazinyl)propyl, C3-C6 cycloalkyl, 4-N,N-dimethylaminocyclohexyl, 4-N,N-diethylaminocyclohexyl, N-methyl-4-piperidinyl, N-ethyl-4-piperidinyl, N-isopropyl-4-piperidinyl, 1,3-dimethyl-5-pyrazolyl, 1-methyl-4-pyrazolyl, 3-methyl-5-isoxazolinyl, 1-(N-methyl-4-piperidinyl)-4-pyrazolyl, 1-(N-t-butoxycarbonyl-4-piperidinyl)-4-pyrazolyl;

2)

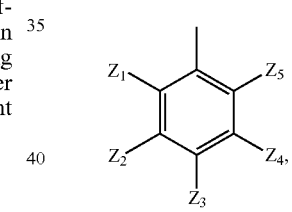

wherein $Z_1$, $Z_2$, $Z_3$, $Z_4$, $Z_5$ each are independently selected from:
(1) H, F, Cl, Br, I, nitro, cyano,
(2) C1-C6 alkyl, C1-C6 alkoxy, C1-C6 oxygen-containing alkyl, C1-C6 fluorine-containing alkyl, C1-C6 fluorine-containing alkoxy, N-methyl-4-piperidinyl,
(3) N,N-dimethylamino, N,N-diethylamino, N,N-diisopropylamino, 2-N,N-dimethylaminoethylamino, 2-morpholinylethylamino, 2-(4-methylpiperazinyl)ethylamino, 3-N,N-dimethylaminopropylamino, 3-N,N-diethylaminopropylamino, 3-N,N-diisopropylaminopropylamino, 3-morpholinylpropylamino, 3-(4-methylpiperazinyl)propylamino, N-methylpiperidinyl-4-amino, N-ethylpiperidinyl-4-amino, N-isopropylpiperidinyl-4-amino,
(4) 2-N,N-dimethylaminoethoxy, 2-N,N-diethylaminoethoxy, 2-N,N-diisopropylaminoethoxy, 2-(4-methylpiperazinyl)ethoxy, 2-(4-acetylpiperazinyl)ethoxy, 2-morpholinylethoxy, 2-thiomorpholinylethoxy, 2-piperidinylethoxy, 3-N,N-dimethylaminopropoxy, 3-N,N-diethylaminopropoxy, 3-N,N-diisopropylaminopropoxy, 3-(4-methylpiperazinyl)propoxy, 3-(4-acetylpiperazinyl)propoxy, 3-morpholinylpropoxy, 3-thiomorpholinylpropoxy, 3-piperidinylpropoxy, pyridin-2-ylmethoxy, pyridin-3-ylmethoxy, pyridin-4-ylmethoxy, phenylmethoxy, monohalo-substituted phenylmethoxy, gem-dihalo-substituted phenylmethoxy, hetero-dihalo-substituted phenylmethoxy, (5) piperidinyl, 4-N,N-dimethylaminopiperidinyl, 4-N,N-diethylaminopiperidinyl, 4-N,N-diisopropylaminopiperidinyl, 4-hydroxypiperidinyl, morpholinyl, 3,5-dimethylmorpholinyl, thiomorpholinyl, tetrahydropyrrolyl, 3-N,N-dimethylaminotetrahydropyrrolyl, 3-N,N-diethylaminotetrahydropyrrolyl, 4-methylpiperazinyl, 4-ethylpiperazinyl, 4-isopropylpiperazinyl, 4-acetylpiperazinyl, 4-t-butoxycarbonylpiperazinyl, 4-methylsulfonylpiperazinyl, 4-(2-hydroxyethyl)piperazinyl, 4-(2-cyanoethyl)piperazinyl, 4-(3-hydroxypropyl)piperazinyl, 4-(2-N,N-dimethylaminoethyl)piperazinyl, 4-(2-N,N-diethylaminoethyl)piperazinyl, 4-(3-N,N-dimethylaminopropyl)piperazinyl, 4-(3-N,N-diethylaminopropyl)piperazinyl, 2-oxo-piperazin-4-yl, imidazolyl, 4-methylimidazolyl, (6) 4-(4-methylpiperazinyl)piperidinyl, 4-(4-ethylpiperazinyl)piperidinyl, 4-(4-isopropylpiperazinyl)piperidinyl, 4-(4-acetylpiperazinyl)piperidinyl, 4-(4-t-butoxycarbonylpiperazinyl)piperidinyl, 4-(4-methylsulfonylpiperazinyl)piperidinyl, 4-(4-(2-hydroxyethyl)piperazinyl)piperidinyl, 4-(4-(2-cyanoethyl)piperazinyl)piperidinyl, 4-(4-(3-hydroxypropyl)piperazinyl)piperidinyl, 4-(4-(2-N,N-dimethylaminoethyl)piperazinyl)piperidinyl, 4-(4-(2-N,N-diethylaminoethyl)piperazinyl)piperidinyl, 4-(4-(3-N,N-dimethylaminopropyl)piperazinyl)piperidinyl, 4-(4-(3-N,N-diethylaminopropyl)piperazinyl)piperidinyl, 4-(tetrahydropyrrolyl)piperidinyl, 4-(3-N,N-dimethylaminotetrahydropyrrolyl)piperidinyl, 4-(N-methyl-4-piperidinyl)piperazinyl, 4-(N-ethyl-4-piperidinyl)piperazinyl, (7) hydroxysulfonyl, aminosulfonyl, methylaminosulfonyl, ethylaminosulfonyl, propylaminosulfonyl, isopropylaminosulfonyl, cyclopropylaminosulfonyl, cyclobutylaminosulfonyl, cyclopentylaminosulfonyl, piperidin-1-ylsulfonyl, 4-hydroxypiperidin-1-ylsulfonyl, 4-N,N-dimethylaminopiperidin-1-ylsulfonyl, 4-N,N-diethylaminopiperidin-1-ylsulfonyl, tetrahydropyrrolyl-1-sulfonyl, 3-N,N-dimethylaminotetrahydropyrrolyl-1-sulfonyl, 3-N,N-diethylaminotetrahydropyrrolyl-1-sulfonyl, 4-methylpiperazin-1-ylsulfonyl, 4-ethylpiperazin-1-ylsulfonyl, 4-acetylpiperazin-1-ylsulfonyl, 4-t-butoxycarbonylpiperazin-1-ylsulfonyl, 4-(2-hydroxyethyl)piperazin-1-ylsulfonyl, 4-(2-cyanoethyl)piperazin-1-ylsulfonyl, 4-(2-N,N-dimethylaminoethyl)piperazin-1-ylsulfonyl, 4-(2-N,N-diethylethyl)piperazin-1-ylsulfonyl, 4-(3-hydroxypropyl)piperazin-1-ylsulfonyl, 4-(3-N,N-dimethylaminopropyl)piperazin-1-ylsulfonyl, 4-(3-N,N-diethylaminopropyl)piperazin-1-ylsulfonyl, morpholin-1-ylsulfonyl, 3,5-dimethylmorpholin-1-ylsulfonyl, 4-(tetrahydropyrroyl)piperidin-1-ylsulfonyl, 4-(4-methyl-piperazin-1-yl)piperidin-1-ylsulfonyl, 4-(4-ethylpiperazin-1-yl)piperidin-1-ylsulfonyl, 4-(4-acetyl-1-piperazinyl)piperidin-1-ylsulfonyl, 4-(N-methyl-4-piperidinyl)piperazin-1-ylsulfonyl, (8) hydroxycarbonyl, aminocarbonyl, methylaminocarbonyl, ethylaminocarbonyl, propylaminocarbonyl, isopropylaminocarbonyl, cyclopropylaminocarbonyl, cyclobutylaminocarbonyl, cyclopentylaminocarbonyl, piperidinyl-1-carbonyl, 4-hydroxypiperidinyl-1-carbonyl, 4-N,N-dimethylaminopiperidinyl-1-carbonyl, 4-N,N-diethylaminopiperidinyl-1-carbonyl, 4-(tetrahydropyrrolyl)piperidinyl-1-carbonyl, tetrahydropyrrolyl-1-carbonyl, 3-N,N-dimethylaminotetrahydropyrrolyl-1-carbonyl, 3-N,N-diethylaminotetrahydropyrrolyl-1-carbonyl, 4-methylpiperazin-1-ylcarbonyl, 4-ethylpiperazinyl-1-carbonyl, 4-acetylpiperazinyl-1-carbonyl, 4-t-butoxycarbonylpiperazinyl-1-carbonyl, 4-(2-hydroxyethyl)piperazinyl-1-carbonyl, 4-(2-cyanoethyl)piperazinyl-1-carbonyl, 4-(2-N,N-dimethylaminoethyl)piperazin-1-ylcarbonyl, 4-(2-N,N-diethylaminoethyl)piperazin-1-ylcarbonyl, 4-(3-hydroxypropyl)piperazin-1-ylcarbonyl, 4-(3-N,N-dimethylaminopropyl)piperazin-1-ylcarbonyl, 4-(3-N,N-diethylaminopropyl)piperazin-1-ylcarbonyl, morpholinyl-1-carbonyl, 3,5-dimethylmorpholinyl-1-carbonyl, 4-(4-methyl-piperazin-1-yl)piperidin-1-ylcarbonyl, 4-(4-ethyl-1-piperazinyl)piperidinyl-1-carbonyl, 4-(4-acetyl-piperazin-1-yl)piperidinyl-1-carbonyl, 4-(N-methyl-4-piperidinyl)piperazin-1-ylcarbonyl, (9) methoxycarbonyl, ethoxycarbonyl, propoxycarbonyl, isopropoxycarbonyl, n-butoxycarbonyl, isobutoxycarbonyl, tert-butoxycarbonyl,

(10) aminoformamido, methylaminoformamido, ethylaminoformamido, propylaminoformamido, isopropylaminoformamido, cyclopropylaminoformamido, cyclobutylaminoformamido, cyclopentylaminoformamido, piperidinyl-1-formamido, 4-hydroxypiperidinyl-1-formamido, 4-N,N-dimethylaminopiperidinyl-1-formamido, 4-N,N-diethylaminopiperidinyl-1-formamido, tetrahydropyrrolyl-1-formamido, 3-N,N-dimethylaminotetrahydropyrrolyl-1-formamido, 3-N,N-diethylaminotetrahydropyrrolyl-1-formamido, 4-methylpiperazin-1-ylformamido, 4-ethylpiperazin-1-ylformamido, 4-acetylpiperazin-1-ylformamido, 4-t-butoxycarbonylpiperazin-1-ylformamido, 4-(2-hydroxyethyl)piperazin-1-ylformamido, 4-(2-cyanoethyl)piperazin-1-ylformamido, 4-(2-N,N-dimethylaminoethyl)piperazin-1-ylformamido, 4-(2-N,N-diethylaminoethyl)piperazin-1-ylformamido, 4-(3-hydroxypropyl)piperazin-1-ylformamido, 4-(3-N,N-dimethylaminopropyl)piperazin-1-ylformamido, 4-(3-N,N-diethylaminopropyl)piperazin-1-ylformamido, morpholin-1-ylformamido, 3,5-dimethylmorpholin-1-ylformamido, 4-(tetrahydropyrrolyl)piperidin-1-ylformamido, 4-(4-methyl-piperazin-1-yl)piperidin-1-ylformamido, 4-(4-ethylpiperazin-1-yl)piperidin-1-ylformamido, 4-(4-acetyl-piperazin-1-yl)piperidin-1-ylformamido, 4-(N-methyl-4-piperidinyl)piperazin-1-ylformamido; or

(11) aminoacetamido, 2-dimethylaminoacetamido, N-t-butoxycarbonylacetamido, N-acetylaminoacetamido, acrylamido, cyclopropionamido, chloroacetamido, piperidinylacetamido, 4-hydroxypiperidinylacetamido, 4-N,N-dimethylaminopiperidinylacetamido, 4-N,N-diethylaminopiperidinylacetamido, tetrahydropyrrolylacetamido, 3-N,N-dimethylaminotetrahydropyrrolylacetamido, 3-N,N-diethylaminotetrahydropyrrolylacetamido, 4-methylpiperazinylacetamido, 4-ethylpiperazinylacetamido, 4-acetylpiperazinylacetamido, 4-t-butoxycarbonylpiperazinylacetamido, 4-(2-hydroxyethyl)piperazinylacetamido, 4-(2-cyanoethyl)piperazinylacetamido, 4-(2-N,N-dimethylaminoethyl)piperazinylacetamido, 4-(2-N,N-diethylaminoethyl)piperazinylacetamido, 4-(3-hydroxypropyl)piperazinylacetamido, 4-(3-N,N-dimethylaminopropyl)piperazinylacetamido, 4-(3-N,N-diethylaminopropyl)piperazinylacetamido, morpholinylacetamido, 3,5-dimethylmorpholinylacetamido, 4-(4-methyl-piperazin-1-yl)piperidinylacetamido, 4-(4-ethyl-1-piperazinyl)piperidinylacetamido, 4-(4-acetyl-1-piperazinyl)piperidinylacetamido, N—(N-methyl-4-piperidinyl)piperidinylacetamido, 4-(tetrahydropyrrol-1-yl)piperidinylacetamido; 2-methylaminoacetamido, 2-(1-methylethyl)aminoacetamido; N-benzyloxycarbonyl-2methylaminoacetamido;

(12) $Z_2$ and $Z_3$ or $Z_3$ and $Z_4$ form an oxygen-containing substituted or unsubstituted 5- or 6-membered ring; the substituent may be selected from the same substituents as described above for $Z_1$,

(13) $Z_2$ and $Z_3$ or $Z_3$ and $Z_4$ form a nitrogen-containing substituted or unsubstituted 5- or 6-membered ring; the substituent may be selected from the same substituents as described above for $Z_1$,

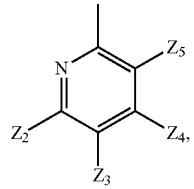

3)

wherein $Z_2$, $Z_3$, $Z_4$, $Z_5$ are the same as defined in 2) above;

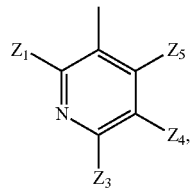

4)

wherein $Z_1$, $Z_3$, $Z_4$, $Z_5$ are the same as defined in 2) above;

A is a direct bond or methylene;

X is NH, S or O;

$R_2$ is selected from:

1) C1-C6 alkyl, C2-C6 alkenyl, C2-C6 alkynyl, C3-C6 cycloalkyl;

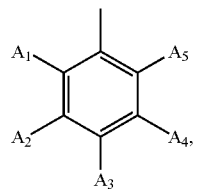

2)

wherein $A_1$, $A_2$, $A_3$, $A_4$, $A_5$ each are independently selected from:

(1) H, F, Cl, Br, I, cyano, trifluoromethyl, trifluoromethoxy, nitro, (2) methylthio, ethylthio, isopropylthio, methylsulfinyl, ethylsulfinyl, isopropylsulfinyl, methylsulfonyl, ethylsulfonyl, isopropylsulfonyl, tert-butyl sulfonyl, dimethylaminosulfonyl, methylsulfonamido, methoxycarbonyl, ethoxycarbonyl, propoxycarbonyl, isopropoxycarbonyl, n-butoxycarbonyl, isobutoxycarbonyl, tert-butoxycarbonyl, methylaminocarbonyl, dimethylaminocarbonyl, ethylaminocarbonyl, propylaminocarbonyl, isopropylaminocarbonyl, cyclopropylaminocarbonyl, cyclobutylaminocarbonyl, cyclopentylaminocarbonyl, dimethylphosphinyl, diethylphosphinyl, diisopropylphosphinyl,

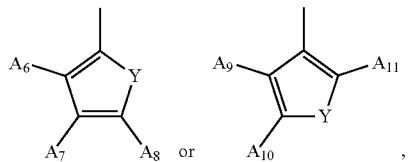

3)

wherein, Y is NH, S or O atom, $A_6$, $A_7$, $A_8$, $A_9$, $A_{10}$, $A_{11}$ each are independently selected from:

(1) H, F, C, Br, I, cyano, trifluoromethyl, trifluoromethoxy, nitro, (2) methoxycarbonyl, ethoxycarbonyl, propoxycarbonyl, isopropoxycarbonyl, n-butoxycarbonyl, isobutoxycarbonyl, tert-butoxycarbonyl, methylaminocarbonyl, ethylaminocarbonyl, propylaminocarbonyl, isopropylaminocarbonyl, cyclopropylaminocarbonyl, cyclobutylaminocarbonyl, cyclopentylaminocarbonyl;

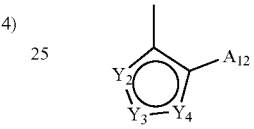

4)

wherein $A_{12}$ is selected from:

(1) H, F, Cl, Br, I, cyano, trifluoromethyl, trifluoromethoxy, nitro, (2) methoxycarbonyl, ethoxycarbonyl, propoxycarbonyl, isopropoxycarbonyl, n-butoxycarbonyl, isobutoxycarbonyl, tert-butoxycarbonyl, methylaminocarbonyl, ethylaminocarbonyl, propylaminocarbonyl, isopropylaminocarbonyl, cyclopropylaminocarbonyl, cyclobutylaminocarbonyl, cyclopentylaminocarbonyl, methylsulfinyl, ethylsulfinyl, isopropylsulfinyl, methylsulfonyl, ethylsulfonyl, isopropylsulfonyl;

$Y_2$, $Y_3$, $Y_4$ are selected from one combination of the following:

$Y_2$ is N, $Y_3$ is N-$A_{13}$, $Y_4$ is CH or N;
$Y_2$ is N, $Y_3$ is C-$A_{13}$, $Y_4$ is N, O or S;
$Y_2$ is O or S, $Y_3$ is N-$A_{13}$, $Y_4$ is CH;
$Y_2$ is O or S, $Y_3$ is C-$A_{13}$, $Y_4$ is N; and
$Y_2$ is C, $Y_3$ is N-$A_{13}$, $Y_4$ is O or S;
$Y_2$ is C, $Y_3$ is N-$A_{13}$, $Y_4$ is N;

wherein $A_{13}$ is H, C1-C6 alkyl, C2-C6 alkenyl, C2-C6 alkynyl, C3-C6 cycloalkyl;

5) piperidinyl, 4-N,N-dimethylaminopiperidinyl, 4-N,N-diethylaminopiperidinyl, 4-N,N-diisopropylaminopiperidinyl, 4-hydroxypiperidinyl, morpholinyl, 3,5-dimethylmorpholinyl, thiomorpholinyl, tetrahydropyrrolyl, 3-N,N-dimethylaminotetrahydropyrrolyl, 3-N,N-diethylaminotetrahydropyrrolyl, 4-methylpiperazinyl, 4-ethylpiperazinyl, 4-isopropylpiperazinyl, 4-acetylpiperazinyl, 4-t-butoxycarbonylpiperazinyl, 4-methylsulfonylpiperazinyl, 4-(2-hydroxyethyl)piperazinyl, 4-(2-cyanoethyl)piperazinyl, 4-(3-hydroxypropyl)piperazinyl, 4-(2-N,N-dimethylaminoethyl)piperazinyl, 4-(2-N,N-diethylaminoethyl)piperazinyl, 4-(3-N,N-dimethylaminopropyl)piperazinyl, 4-(3-N,N-diethylaminopropyl)piperazinyl.

In some embodiments, R' is H.

In some embodiments, wherein, $R_1$ is selected from:

1) C1-C6 alkyl, 2-N,N-dimethylaminoethyl, 2-hydroxyethyl, 2-N,N-diethylaminoethyl, 2-N,N-diisopropylaminoethyl, 2-morpholinylethyl, 2-(4-methylpiperazinyl)ethyl, C3-C6 cycloalkyl, 4-N,N-dimethylaminocyclohexyl, 4-N,N-diethylaminocyclohexyl, N-methyl-4-piperidinyl, N-ethyl-4-piperidinyl, N-isopropyl-4-piperidinyl, 1,3-dimethyl-5-pyrazolyl, 1-(N-methyl-4-piperidinyl)-4-pyrazolyl;

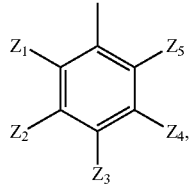
(2)

wherein $Z_1$, $Z_2$, $Z_3$, $Z_4$, $Z_5$ each are independently selected from:

(1) H, F, Cl, Br, nitro, (2) C1-C6 alkyl, C1-C6 alkoxy, C1-C6 oxygen-containing alkyl, C1-C6 fluorine-containing alkyl, C1-C6 fluorine-containing alkoxy, N-methyl-4-piperidinyl, (3) N,N-dimethylamino, N,N-diethylamino, N,N-diisopropylamino, 2-N,N-dimethylaminoethylamino, 2-morpholinylethylamino, 3-morpholinylpropylamino, 3-(4-methylpiperazinyl)propylamino, N-methylpiperidinyl-4-amino, N-ethylpiperidinyl-4-amino, (4) 2-N,N-dimethylaminoethoxy, 2-N,N-diethylaminoethoxy, 2-N,N-diisopropylaminoethoxy, 2-(4-methylpiperazinyl)ethoxy, 2-(4-acetylpiperazinyl)ethoxy, 2-morpholinylethoxy, 2-thiomorpholinylethoxy, 2-piperidinylethoxy, 3-N,N-diisopropylaminopropoxy, 3-(4-acetylpiperazinyl)propoxy, 3-morpholinylpropoxy, 3-thiomorpholinylpropoxy, 3-piperidinylpropoxy, pyridin-2-ylmethoxy, phenylmethoxy, monohalo-substituted phenylmethoxy, gem-dihalo-substituted phenylmethoxy, (5) piperidinyl, 4-N,N-dimethylaminopiperidinyl, 4-N,N-diethylaminopiperidinyl, 4-N,N-diisopropylaminopiperidinyl, 4-hydroxypiperidinyl, morpholinyl, 3,5-dimethylmorpholinyl, thiomorpholinyl, tetrahydropyrrolyl, 3-N,N-dimethylaminotetrahydropyrrolyl, 3-N,N-diethylaminotetrahydropyrrolyl, 4-methylpiperazinyl, 4-ethylpiperazinyl, 4-isopropylpiperazinyl, 4-acetylpiperazinyl, 4-(2-hydroxyethyl)piperazinyl, 4-(3-N,N-diethylaminopropyl)piperazinyl, 2-oxo-piperazin-4-yl, imidazolyl, 4-methylimidazolyl, (6) 4-(4-methylpiperazinyl)piperidinyl, 4-(4-ethylpiperazinyl)piperidinyl, 4-(4-isopropylpiperazinyl)piperidinyl, 4-(4-acetylpiperazinyl)piperidinyl, 4-(4-t-butoxycarbonylpiperazinyl)piperidinyl, 4-(4-methylsulfonylpiperazinyl)piperidinyl, 4-(4-(2-hydroxyethyl)piperazinyl)piperidinyl, 4-(4-(3-hydroxypropyl)piperazinyl)piperidinyl, 4-(4-(2-N,N-dimethylaminoethyl)piperazinyl)piperidinyl, 4-(4-(2-N,N-diethylaminoethyl)piperazinyl)piperidinyl, 4-(4-(3-N,N-dimethylaminopropyl)piperazinyl)piperidinyl, 4-(3-N,N-dimethylaminotetrahydropyrrolyl)piperidinyl, 4-(N-methyl-4-piperidinyl)piperazinyl, 4-(N-ethyl-4-piperidinyl)piperazinyl, (7) hydroxysulfonyl, aminosulfonyl, methylaminosulfonyl, ethylaminosulfonyl, propylaminosulfonyl, isopropylaminosulfonyl, cyclopropylaminosulfonyl, cyclobutylaminosulfonyl, cyclopentylaminosulfonyl, piperidin-1-ylsulfonyl, 4-hydroxypiperidin-1-ylsulfonyl, 3-N,N-dimethyltetrahydropyrrol-1-ylsulfonyl, 3-N,N-diethylaminotetrahydropyrro-1-ylsulfonyl, 4-methylpiperazin-1-ylsulfonyl, 4-ethylpiperazin-1-ylsulfonyl, 4-acetylpiperazin-1-ylsulfonyl, 4-t-butoxycarbonylpiperazinyl-1-sulfonyl, N-(2-hydroxyethyl)piperazinyl-1-sulfonyl, 4-(2-cyanoethyl)piperazin-1-ylsulfonyl, 4-(3-hydroxypropyl)piperazin-1-ylsulfonyl, 4-(3-N,N-dimethylaminopropyl)piperazin-1-ylsulfonyl, 4-(3-N,N-diethylaminopropyl)piperazin-1-ylsulfonyl, 4-(4-acetylpiperazin-1-yl)piperidin-1-ylsulfonyl, 4-(N-methyl-4-piperidinyl)piperazin-1-ylsulfonyl, (8) hydroxycarbonyl, aminocarbonyl, methylaminocarbonyl, ethylaminocarbonyl, propylaminocarbonyl, isopropylaminocarbonyl, cyclopropylaminocarbonyl, cyclobutylaminocarbonyl, cyclopentylaminocarbonyl, piperidinyl-1-carbonyl, 4-hydroxypiperidinyl-1-carbonyl, 4-N,N-dimethylaminopiperidinyl-1-carbonyl, 4-N,N-diethylaminopiperidinyl-1-carbonyl, tetrahydropyrrolyl-1-carbonyl, 3-N,N-dimethylaminotetrahydropyrrolyl-1-carbonyl, 4-(2-N,N-dimethylaminoethyl)piperazin-1-ylcarbonyl, 4-(2-N,N-diethylaminoethyl)piperazin-1-ylcarbonyl, 4-(3-N,N-diethylaminopropyl)piperazin-1-ylcarbonyl, morpholin-1-ylcarbonyl, 3,5-dimethylmorpholin-1-ylcarbonyl, 4-(4-methyl-piperazin-1-yl)piperidin-1-ylcarbonyl, 4-(4-acetyl-1-piperazinyl)piperidin-1-ylcarbonyl, 4-(N-methyl-4-piperidinyl)piperazin-1-ylcarbonyl, (9) methoxycarbonyl, ethoxycarbonyl, propoxycarbonyl, isopropoxycarbonyl, tert-butoxycarbonyl,

(10) aminoformamido, methylaminoformamido, ethylaminoformamido, propylaminoformamido, isopropylaminoformamido, cyclopropylaminoformamido, piperidinyl-1-formamido, 4-hydroxypiperidinyl-1-formamido, 4-N,N-dimethylaminopiperidinyl-1-formamido, 4-N,N-diethylaminopiperidinyl-1-formamido, 4-acetylpiperazin-1-ylformamido, 4-(2-hydroxyethyl)piperazin-1-ylformamido, 4-(2-cyanoethyl)piperazin-1-ylformamido, 4-(2-N,N-dimethylaminoethyl)piperazin-1-ylformamido, 4-(3-N,N-dimethylaminopropyl)piperazin-1-ylformamido, 4-(3-N,N-diethylaminopropyl)piperazin-1-ylformamido, morpholin-1-ylformamido, 4-(4-acetylpiperazin-1-yl)piperidin-1-ylformamido, 4-(N-methyl-4-piperidinyl)piperazin-1-ylformamido; or

(11) aminoacetamido, N-t-butoxycarbonylacetamido, N-acetylaminoacetamido, acrylamido, cyclopropionamido, chloroacetamido, piperidinylacetamido, 4-hydroxypiperidinylacetamido, 4-N,N-dimethylaminopiperidinylacetamido, 4-N,N-diethylaminopiperidinylacetamido, 3-N,N-dimethylaminotetrahydropyrrolylacetamido, N-ethylpiperazinylacetamido, 4-acetylpiperazinylacetamido, 4-t-butoxycarbonylpiperazinylacetamido, 4-(2-cyanoethyl)piperazinylacetamido, N-(2-N,N-dimethylaminoethyl)piperazinylacetamido, 4-(2-N,N-diethylaminoethyl)piperazinylacetamido, 4-(3-N,N-dimethylaminopropyl)piperazinylacetamido, 4-(3-N,N-diethylaminopropyl)piperazinylacetamido, 4-(4-methyl-piperazin-1-yl)piperidinylacetamido, 4-(4-ethyl-1-piperazinyl)piperidinylacetamido, 4-(4-acetyl-1-piperazinyl)piperidinylacetamido, N-benzyloxycarbonyl-2methylaminoacetamido;

(12) $Z_2$ and $Z_3$ or $Z_3$ and $Z_4$ form an oxygen-containing substituted or unsubstituted 5- or 6-membered ring; the substituent may be selected from the same substituents as described above for $Z_1$,

(13) $Z_2$ and $Z_3$ or $Z_3$ and $Z_4$ form a nitrogen-containing substituted or unsubstituted 5- or 6-membered ring; the substituent may be selected from the same substituents as described above for $Z_1$,

3)

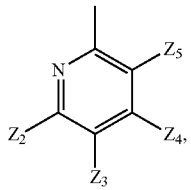

wherein $Z_2$, $Z_3$, $Z_4$, $Z_5$ are the same as defined in 2) above;

4)

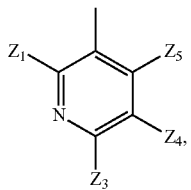

wherein $Z_1$, $Z_3$, $Z_4$, $Z_5$ are the same as defined in 2) above.

In some embodiments, $R_1$ is selected from:

1)

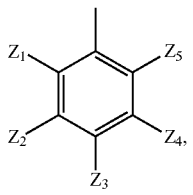

wherein $Z_1$, $Z_2$, $Z_3$, $Z_4$, $Z_5$ each are independently selected from:

(1) H, F, Cl, Br, nitro, (2) C1-C6 alkyl, C1-C6 alkoxy, C1-C6 fluorine-containing alkyl, C1-C6 fluorine-containing alkoxy, (3) N,N-dimethylamino, N,N-diethylamino, N,N-diisopropylamino, 2-N,N-dimethylaminoethylamino, 2-morpholinylethylamino, 3-morpholinylpropylamino, 3-(4-methylpiperazinyl)propylamino, N-methylpiperidinyl-4-amino, N-ethylpiperidinyl-4-amino, (4) 2-N,N-dimethylaminoethoxy, 2-N,N-diethylaminoethoxy, 2-N,N-diisopropylaminoethoxy, 2-(4-methylpiperazinyl)ethoxy, 2-(4-acetylpiperazinyl)ethoxy, 2-morpholinylethoxy, 2-thiomorpholinylethoxy, 2-piperidinylethoxy, 3-N,N-diisopropylaminopropoxy, 3-(4-acetylpiperazinyl)propoxy, 3-morpholinylpropoxy, 3-thiomorpholinylpropoxy, 3-piperidinylpropoxy, pyridin-2-ylmethoxy, phenylmethoxy, monohalo-substituted phenylmethoxy, (5) piperidinyl, 4-N,N-dimethylaminopiperidinyl, 4-N,N-diethylaminopiperidinyl, 4-N,N-diisopropylaminopiperidinyl, 4-hydroxypiperidinyl, morpholinyl, 3,5-dimethylmorpholinyl, thiomorpholinyl, tetrahydropyrrolyl, 3-N,N-dimethylaminotetrahydropyrrolyl, 3-N,N-diethylaminotetrahydropyrrolyl, 4-methylpiperazinyl, 4-ethylpiperazinyl, 4-isopropypiperazinyl, 4-acetylpiperazinyl, 4-(2-hydroxyethyl)piperazinyl, 4-(3-N,N-diethylaminopropyl)piperazinyl, 2-oxo-piperazin-4-yl, imidazolyl, 4-methylimidazolyl, (6) 4-(4-methylpiperazinyl)piperidinyl, 4-(4-ethylpiperazinyl)piperidinyl, 4-(4-isopropylpiperazinyl)piperidinyl, 4-(4-acetylpiperazinyl)piperidinyl, 4-(4-t-butoxycarbonylpiperazinyl)piperidinyl, 4-(4-methylsulfonylpiperazinyl)piperidinyl, 4-(4-(2-hydroxyethyl)piperazinyl)piperidinyl, 4-(4-(3-hydroxypropyl)piperazinyl)piperidinyl, 4-(4-(2-N,N-dimethylaminoethyl)piperazinyl)piperidinyl, 4-(4-(3-N,N-dimethylaminopropyl)piperazinyl)piperidinyl, 4-(3-N,N-dimethylaminotetrahydropyrrolyl)piperidinyl, 4-(N-methyl-4-piperidinyl)piperazinyl, 4-(N-ethyl-4-piperidinyl)piperazinyl, (7) hydroxysulfonyl, aminosulfonyl, methylaminosulfonyl, ethylaminosulfonyl, propylaminosulfonyl, isopropylaminosulfonyl, cyclopropylaminosulfonyl, cyclobutylaminosulfonyl, cyclopentylaminosulfonyl, piperidin-1-ylsulfonyl, 4-hydroxypiperidin-1-ylsulfonyl, 3-N,N-dimethylaminotetrahydropyrrolyl-1-sulfonyl, 3-N,N-diethylaminotetrahydropyrrolyl-1-sulfonyl, 4-methylpiperazin-1-ylsulfonyl, 4-ethylpiperazinyl-1-sulfonyl, 4-acetylpiperazinyl-1-sulfonyl, 4-t-butoxycarbonylpiperazinyl-1-sulfonyl, 4-(2-hydroxyethyl)piperazinyl-1-sulfonyl, 4-(2-cyanoethyl)piperazinyl-1-sulfonyl, 4-(3-N,N-dimethylaminopropyl)piperazinyl-1-sulfonyl, 4-(N-methyl-4-piperidinyl)piperazinyl-1-sulfonyl, (8) hydroxycarbonyl, aminocarbonyl, methylaminocarbonyl, ethylaminocarbonyl, propylaminocarbonyl, isopropylaminocarbonyl, cyclopropylaminocarbonyl, cyclobutylaminocarbonyl, cyclopentylaminocarbonyl, piperidinyl-1-carbonyl, 4-hydroxypiperidinyl-1-carbonyl, 4-N,N-dimethylaminopiperidinyl-1-carbonyl, 4-N,N-diethylaminopiperidinyl-1-carbonyl, tetrahydropyrrolyl-1-carbonyl, 3-N,N-dimethylaminotetrahydropyrrolyl-1-carbonyl, 4-(2-N,N-dimethylaminoethyl)piperazinyl-1-carbonyl, 4-(2-N,N-diethylaminoethyl)piperazinyl-1-carbonyl, 4-(3-N,N-diethylaminopropyl)piperazinyl-1-carbonyl, morpholinyl-1-carbonyl, 3,5-dimethylmorpholinyl-1-carbonyl, 4-(N-methyl-4-piperidinyl)piperazinyl-1-carbonyl, (9) methoxycarbonyl, ethoxycarbonyl, propoxycarbonyl, isopropoxycarbonyl, tert-butoxycarbonyl,

(10) aminoformamido, methylaminoformamido, ethylaminoformamido, propylaminoformamido, isopropylaminoformamido, cyclopropylaminoformamido, piperidinyl-1-formamido, 4-hydroxypiperidinyl-1-formamido, 4-N,N-dimethylaminopiperidinyl-1-formamido, 4-N,N-diethylaminopiperidinyl-1-formamido, 4-acetylpiperazinyl-1-formamido, 4-(2-hydroxyethyl)piperazinyl-1-formamido, 4-(2-cyanoethyl)piperazinyl-1-formamido, 4-(2-N,N-dimethylaminoethyl)piperazinyl-1-formamido, 4-(3-N,N-dimethylaminopropyl)piperazinyl-1-formamido, 4-(3-N,N-diethylaminopropyl)piperazinyl-1-formamido, morpholinyl-1-formamido, 4-(4-acetyl-1-piperazinyl)piperidinyl-1-formamido, 4-(N-methyl-4-piperidinyl)piperazinyl-1-formamido; or

(11) aminoacetamido, N-t-butoxycarbonylacetamido, N-acetylaminoacetamido, acrylamido, cyclopropionamido, chloroacetamido, piperidinylacetamido, 4-hydroxypiperidinylacetamido, 4-N,N-dimethylaminopiperidinylacetamido, 4-N,N-diethylaminopiperidinylacetamido, 3-N,N-dimethylaminotetrahydropyrrolylacetamido, 4-ethylpiperazinylacetamido, 4-acetylpiperazinylacetamido, 4-t-butoxycarbonylpiperazinylacetamido, 4-(2-cyanoethyl)piperazinylacetamido, 4-(2-N,N-dimethylaminoethyl)piperazinylacetamido, 4-(2-N,N-diethylaminoethyl)piperazinylacetamido, 4-(3-N,N-dimethylaminopropyl)piperazinylacetamido, 4-(3-N,N-diethylaminopropyl)piperazinylacetamido, 4-(4-methyl-piperazin-1-yl)piperidinylacetamido, 4-(4-ethyl-1-piperazinyl)

piperidinylacetamido, 4-(4-acetyl-1-piperazinyl)piperidinylacetamido, N-benzyloxycarbonyl-2methylaminoacetamido;

(12) $Z_2$ and $Z_3$ or $Z_3$ and $Z_4$ form an oxygen-containing substituted or unsubstituted 5- or 6-membered ring; the substituent may be selected from the same substituents as described above for $Z_1$,

(13) $Z_2$ and $Z_3$ or $Z_3$ and $Z_4$ form a nitrogen-containing substituted or unsubstituted 5- or 6-membered ring; the substituent may be selected from the same substituents as described above for $Z_1$,

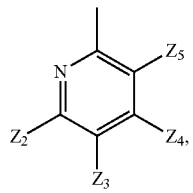
2)

wherein $Z_2$, $Z_3$, $Z_4$, $Z_5$ are the same as defined in 2) above;

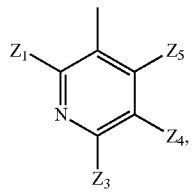
3)

wherein $Z_1$, $Z_3$, $Z_4$, $Z_5$ are the same as defined in 2) above.

In some embodiments, A is a direct bond.

In some embodiments, A is methylene.

In some embodiments, $R_2$ is selected from:

1) C1-C6 alkyl, C2-C6 alkenyl, C2-C6 alkynyl, C3-C6 cycloalkyl;

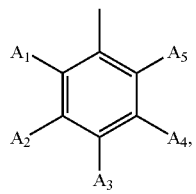
2)

wherein $A_1$, $A_2$, $A_3$, $A_4$, $A_5$ each are independently selected from:

(1) H, F, Cl, Br, I, nitro, (2) methylthio, ethylthio, isopropylthio, ethylsulfinyl, isopropylsulfinyl, methylsulfonyl, ethylsulfonyl, isopropylsulfonyl, tert-butyl sulfonyl, dimethylaminosulfonyl, methylsulfonamido, methoxycarbonyl, isopropoxycarbonyl, n-butoxycarbonyl, isobutoxycarbonyl, cyclobutylaminocarbonyl, methylaminocarbonyl, dimethylaminocarbonyl, isopropylaminocarbonyl, dimethylphosphinyl, diethylphosphinyl, diisopropylphosphinyl,

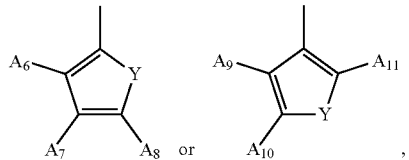
3)

wherein, Y is NH, S or O atom, $A_6$, $A_7$, $A_8$, $A_9$, $A_{10}$, $A_{11}$ each are independently selected from:

(1) H, F, Cl, Br, I, cyano, trifluoromethyl, trifluoromethoxy, nitro, (2) methoxycarbonyl, ethoxycarbonyl, propoxycarbonyl, isopropoxycarbonyl, n-butoxycarbonyl, isobutoxycarbonyl, tert-butoxycarbonyl, methylaminocarbonyl, ethylaminocarbonyl, propylaminocarbonyl, isopropylaminocarbonyl, cyclopentylaminocarbonyl;

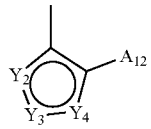
4)

wherein $A_{12}$ is selected from:

(1) H, F, Cl, Br, I, cyano, trifluoromethyl, trifluoromethoxy, nitro, (2) methoxycarbonyl, ethoxycarbonyl, propoxycarbonyl, isopropoxycarbonyl, isobutoxycarbonyl, tert-butoxycarbonyl, methylaminocarbonyl, ethylaminocarbonyl, propylaminocarbonyl, isopropylaminocarbonyl, cyclobutylaminocarbonyl, methylsulfinyl, methylsulfonyl, ethylsulfonyl, isopropylsulfonyl;

$Y_2$, $Y_3$, $Y_4$ are selected from one combination of the following:

$Y_2$ is N, $Y_3$ is N-$A_{13}$, $Y_4$ is CH or N;
$Y_2$ is O or S, $Y_3$ is C-$A_{13}$, $Y_4$ is N; and
$Y_2$ is C, $Y_3$ is N-$A_{13}$, $Y_4$ is O or S;
$Y_2$ is C, $Y_3$ is N-$A_{13}$, $Y_4$ is N;

wherein $A_{13}$ is H, C1-C6 alkyl, C2-C6 alkenyl, C2-C6 alkynyl, C3-C6 cycloalkyl; 5) piperidinyl, 4-N,N-dimethylaminopiperidinyl, 4-N,N-diethylaminopiperidinyl, 4-N,N-diisopropylaminopiperidinyl, 4-hydroxypiperidinyl, morpholinyl, 3,5-dimethylmorpholinyl, 3-N,N-dimethylaminotetrahydropyrrolyl, 3-N,N-diethylaminotetrahydropyrrolyl, 4-methylpiperazinyl, 4-ethylpiperazinyl, 4-isopropylpiperazinyl, 4-acetylpiperazinyl, 4-(2-N,N-diethylaminoethyl)piperazinyl, 4-(3-N,N-dimethylaminopropyl)piperazinyl, 4-(3-N,N-diethylaminopropyl)piperazinyl.

In some embodiments, $R_2$ is selected from:

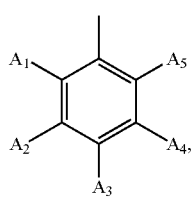
1)

wherein $A_1$, $A_2$, $A_3$, $A_4$, $A_5$ each are independently selected from:

(1) H, F, Cl, (2) methylthio, ethylthio, isopropylthio, ethylsulfinyl, isopropylsulfinyl, methylsulfonyl, ethylsulfonyl, isopropylsulfonyl, tert-butyl sulfonyl, dimethylaminosulfonyl, methylsulfonamido, methoxycarbonyl, isopropoxycarbonyl, n-butoxycarbonyl, isobutoxycarbonyl, cyclobutylaminocarbonyl, methylaminocarbonyl, dimethylaminocarbonyl, isopropylaminocarbonyl, dimethylphosphinyl, diethylphosphinyl, diisopropylphosphinyl,

2)

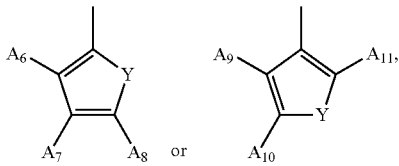

wherein, Y is NH, S or O atom, $A_6, A_7, A_8, A_9, A_{10}, A_{11}$ each are independently selected from:

(1) H, F, Cl, Br, I, cyano, trifluoromethyl, trifluoromethoxy, nitro, (2) methoxycarbonyl, ethoxycarbonyl, propoxycarbonyl, isopropoxycarbonyl, n-butoxycarbonyl, isobutoxycarbonyl, tert-butoxycarbonyl, methylaminocarbonyl, ethylaminocarbonyl, propylaminocarbonyl, isopropylaminocarbonyl, cyclopentylaminocarbonyl;

3)

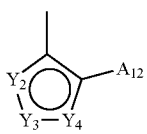

wherein $A_{12}$ is selected from:

(1) H, F, Cl, Br, I, cyano, trifluoromethyl, trifluoromethoxy, nitro, (2) methoxycarbonyl, ethoxycarbonyl, propoxycarbonyl, isopropoxycarbonyl, isobutoxycarbonyl, tert-butoxycarbonyl, methylaminocarbonyl, ethylaminocarbonyl, propylaminocarbonyl, isopropylaminocarbonyl, cyclobutylaminocarbonyl, methylsulfinyl, methylsulfonyl, ethylsulfonyl, isopropylsulfonyl;

$Y_2, Y_3, Y_4$ are selected from one combination of the following:

$Y_2$ is N, $Y_3$ is N-$A_{13}$, $Y_4$ is CH or N;

$Y_2$ is O or S, $Y_3$ is C-$A_{13}$, $Y_4$ is N; and $Y_2$ is C, $Y_3$ is N-$A_{13}$, $Y_4$ is O or S;

$Y_2$ is C, $Y_3$ is N-$A_{13}$, $Y_4$ is N;

wherein $A_{13}$ is H, C1-C6 alkyl, C2-C6 alkenyl, C2-C6 alkynyl, C3-C6 cycloalkyl.

In some embodiments, the pharmaceutically acceptable salt is an inorganic acid salt or an organic acid salt, wherein the inorganic acid salt is hydrochloride, hydrobromide, hydroiodide, nitrate, bicarbonate and carbonate, sulfate or phosphate, the organic acid salt is formate, acetate, propionate, benzoate, maleate, fumarate, succinate, tartrate, citrate, ascorbate, α-ketoglutarate, trifluoroacetate, α-glycerophosphate, alkyl sulfonate or aryl sulfonate; preferably, the alkyl sulfonate is methyl sulfonate or ethyl sulfonate; the aryl sulfonate is benzenesulfonate or p-toluenesulfonate.

In a second aspect, the present invention provides a compound of Formula V, a stereoisomer thereof, a prodrug thereof, a pharmaceutically acceptable salt thereof or a pharmaceutically acceptable solvate thereof:

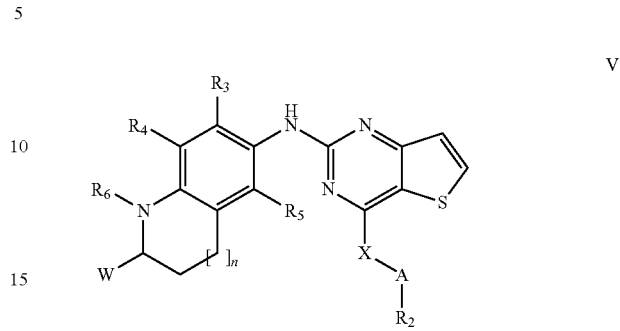

V wherein: W is oxo, thio, or H;

n=0, or 1;

$R_3, R_4, R_5$ each are independently selected from:

(1) H, F, Cl, Br, I, nitro, cyano, (2) C1-C6 alkyl, C1-C6 alkoxy, C1-C6 oxygen-containing alkyl, C1-C6 fluorine-containing alkyl, C1-C6 fluorine-containing alkoxy;

$R_6$ is selected from:

(1) H, C1-C6 alkyl, acetyl, propionyl, n-butyryl, isobutyryl, (2) aminoacetyl, 2-N,N-dimethylacetyl, 2-N,N-diethylacetyl, 2-N,N-diisopropylacetyl, piperidinylacetyl, 4-hydroxypiperidinylacetyl, 4-N,N-dimethylaminopiperidinylacetyl, 4-N,N-diethylaminopiperidinylacetyl, tetrahydropyrrolylacetyl, 3-N,N-dimethylaminotetrahydropyrrolylacetyl, 3-N,N-diethylaminotetrahydropyrrolylacetyl, 4-methylpiperazinylacetyl, 4-ethylpiperazinylacetyl, 4-acetylpiperazinylacetyl, 4-t-butoxycarbonylpiperazinylacetyl, 4-(2-hydroxyethyl)piperazinylacetyl, 4-(2-cyanoethyl)piperazinylacetyl, 4-(2-N,N-dimethylaminoethyl)piperazinylacetyl, 4-(2-N,N-diethylaminoethyl)piperazinylacetyl, 4-(3-hydroxypropyl)piperazinylacetyl, 4-(3-N,N-dimethylaminopropyl)piperazinylacetyl, 4-(3-N,N-diethylaminopropyl)piperazinylacetyl, morpholinylacetyl, 3,5-dimethylmorpholinylacetyl, 4-(4-methyl-piperazin-1-yl)piperidinylacetyl, 4-(4-ethyl-1-piperazinyl)piperidinylacetyl, 4-(4-acetyl-1-piperazinyl)piperidinylacetyl, 4-(N-methyl-4-piperidinyl)piperazinylacetyl;

A, X, $R_2$ are the same as defined in the above technical solution.

In some embodiments, W is oxo.

In some embodiments, n=1.

In some embodiments, n=0.

In some embodiments, $R_3, R_4, R_5$ each are independently selected from:

(1) H, F, Cl, Br, I;

(2) C1-C6 alkyl, C1-C6 alkoxy.

In some embodiments, $R_6$ is selected from:

(1) H, C1-C6 alkyl, acetyl, propionyl, (2) aminoacetyl, 2-N,N-dimethylacetyl, 2-N,N-diethylacetyl, 2-N,N-diisopropylacetyl, piperidinylacetyl, 4-hydroxypiperidinylacetyl, 4-N,N-dimethylaminopiperidinylacetyl, 4-N,N-diethylaminopiperidinylacetyl, tetrahydropyrrolylacetyl, 4-acetylpiperazinylacetyl, 4-t-butoxycarbonylpiperazinylacetyl, 4-(2-hydroxyethyl)piperazinylacetyl, 4-(2-cyanoethyl)piperazinylacetyl, 4-(2-N,N-dimethylaminoethyl)piperazinylacetyl, 4-(2-N,N- diethylaminoethyl)piperazinylacetyl, morpholinylacetyl, 3,5-dimethylmorpholinylacetyl, 4-(4-methyl-piperazin-1-yl)piperidinylacetyl, 4-(4-ethyl-1-piperazinyl)piperidinylacetyl.

In some embodiments, the pharmaceutically acceptable salt is an inorganic acid salt or an organic acid salt, wherein the inorganic acid salt is hydrochloride, hydrobromide, hydroiodide, nitrate, bicarbonate and carbonate, sulfate or phosphate, the organic acid salt is formate, acetate, propionate, benzoate, maleate, fumarate, succinate, tartrate, citrate, ascorbate, α-ketoglutarate, trifluoroacetate, ax-glycerophosphate, alkyl sulfonate or aryl sulfonate; preferably, the alkyl sulfonate is methyl sulfonate or ethyl sulfonate; the aryl sulfonate is benzenesulfonate or p-toluenesulfonate.

In a third aspect, the present invention provides a compound of Formula IA, a stereoisomer thereof, a prodrug thereof, a pharmaceutically acceptable salt thereof or a pharmaceutically acceptable solvate thereof,

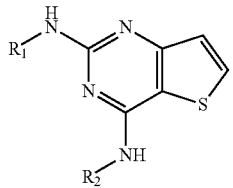

IA wherein, $R_1$ is selected from:

1) C1-C6 alkyl, 2-N,N-dimethylaminoethyl, 2-hydroxyethyl, 2-N,N-diethylaminoethyl, 2-N,N-diisopropylaminoethyl, 2-morpholinylethyl, 2-(4-methylpiperazinyl)ethyl, 3-N,N-dimethylaminopropyl, 3-N,N-diethylaminopropyl, 3-N,N-diisopropylaminopropyl, 3-morpholinylpropyl, 3-(4-methylpiperazinyl)propyl, C3-C6 cycloalkyl, 4-N,N-dimethylaminocyclohexyl, 4-N,N-diethylaminocyclohexyl, N-methyl-4-piperidinyl, N-ethyl-4-piperidinyl, N-isopropyl-4-piperidinyl, 1,3-dimethyl-5-pyrazolyl, 1-methyl-4-pyrazolyl, 3-methyl-5-isoxazolinyl, 1-(N-methyl-4-piperidinyl)-4-pyrazolyl, 1-(N-t-butoxycarbonyl-4-piperidinyl)-4-pyrazolyl;

2)

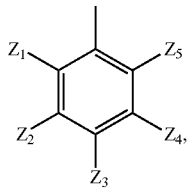

wherein $Z_1$, $Z_2$, $Z_3$, $Z_4$, $Z_5$ each are independently selected from:

(1) H, F, Cl, Br, I, nitro, cyano, (2) C1-C6 alkyl, C1-C6 alkoxy, C1-C6 oxygen-containing alkyl, C1-C6 fluorine-containing alkyl, C1-C6 fluorine-containing alkoxy, (3) piperidinyl, N-methyl-4-piperidinyl, 4-N,N-dimethylaminopiperidinyl, 4-N,N-diethylaminopiperidinyl, 4-N,N-diisopropylaminopiperidinyl, 4-hydroxypiperidinyl, 4-(4-methylpiperazinyl)piperidinyl, 4-(4-ethylpiperazinyl)piperidinyl, 4-(4-isopropylpiperazinyl)piperidinyl, 4-(4-acetylpiperazinyl)piperidinyl, 4-(4-t-butoxycarbonylpiperazinyl)piperidinyl, 4-(4-methylsulfonylpiperazinyl)piperidinyl, 4-(4-(2-hydroxyethyl)piperazinyl)piperidinyl, 4-(4-(2-cyanoethyl)piperazinyl)piperidinyl, 4-(4-(3-hydroxypropyl)piperazinyl)piperidinyl, 4-(4-(2-N,N-dimethylaminoethyl)piperazinyl)piperidinyl, 4-(4-(2-N,N-diethylaminoethyl)piperazinyl)piperidinyl, 4-(4-(3-N,N-dimethylaminopropyl)piperazinyl)piperidinyl, 4-(4-(3-N,N-diethylaminopropyl)piperazinyl)piperidinyl, 4-(tetrahydropyrrolyl)piperidinyl, 4-(3-N,N-dimethylaminotetrahydropyrrolyl)piperidinyl, (4) 4-methylpiperazinyl, 4-ethylpiperazinyl, 4-isopropylpiperazinyl, 4-acetylpiperazinyl, 4-t-butoxycarbonylpiperazinyl, 4-methylsulfonylpiperazinyl, 4-(2-hydroxyethyl)piperazinyl, 4-(2-cyanoethyl)piperazinyl, 4-(3-hydroxypropyl)piperazinyl, 4-(2-N,N-dimethylaminoethyl)piperazinyl, 4-(2-N,N-diethylaminoethyl)piperazinyl, 4-(3-N,N-dimethylaminopropyl)piperazinyl, 4-(3-N,N-diethylaminopropyl)piperazinyl, 4-(N-methyl-4-piperidinyl)piperazinyl, 4-(N-ethyl-4-piperidinyl)piperazinyl, (5) N,N-dimethylamino, N,N-diethylamino, N,N-diisopropylamino, 2-N,N-dimethylaminoethylamino, 2-morpholinylethylamino, 2-(4-methylpiperazinyl)ethylamino, 3-N,N-dimethylaminopropylamino, 3-N,N-diethylaminopropylamino, 3-N,N-diisopropylaminopropylamino, 3-morpholinylpropylamino, 3-(4-methylpiperazinyl)propylamino, N-methylpiperidinyl-4-amino, N-ethylpiperidinyl-4-amino, N-isopropylpiperidinyl-4-amino, (6) 2-N,N-dimethylaminoethoxy, 2-N,N-diethylaminoethoxy, 2-N,N-diisopropylaminoethoxy, 2-(4-methylpiperazinyl)ethoxy, 2-(4-acetylpiperazinyl)ethoxy, 2-morpholinylethoxy, 2-thiomorpholinylethoxy, 2-piperidinylethoxy, 3-N,N-dimethylaminopropoxy, 3-N,N-diethylaminopropoxy, 3-N,N-diisopropylaminopropoxy, 3-(4-methylpiperazinyl)propoxy, 3-(4-acetylpiperazinyl)propoxy, 3-morpholinylpropoxy, 3-thiomorpholinylpropoxy, 3-piperidinylpropoxy, pyridin-2-ylmethoxy, pyridin-3-ylmethoxy, pyridin-4-ylmethoxy, phenylmethoxy, monohalo-substituted phenylmethoxy, gem-dihalo-substituted phenylmethoxy, hetero-dihalo-substituted phenylmethoxy, (7) hydroxysulfonyl, aminosulfonyl, methylaminosulfonyl, ethylaminosulfonyl, propylaminosulfonyl, isopropylaminosulfonyl, cyclopropylaminosulfonyl, cyclobutylaminosulfonyl, cyclopentylaminosulfonyl, piperidin-1-ylsulfonyl, 4-hydroxypiperidin-1-ylsulfonyl, 4-N,N-dimethylaminopiperidin-1-ylsulfonyl, 4-N,N-diethylaminopiperidin-1-ylsulfonyl, tetrahydropyrrolyl-1-sulfonyl, 3-N,N-dimethylaminotetrahydropyrrolyl-1-sulfonyl, 3-N,N-diethylaminotetrahydropyrrolyl-1-sulfonyl, 4-methylpiperazin-1-ylsulfonyl, 4-ethylpiperazinyl-1-sulfonyl, 4-acetylpiperazinyl-1-sulfonyl, 4-t-butoxycarbonylpiperazinyl-1-sulfonyl, 4-(2-hydroxyethyl)piperazinyl-1-sulfonyl, 4-(2-cyanoethyl)piperazinyl-1-sulfonyl, 4-(2-N,N-dimethylaminoethyl)piperazinyl-1-sulfonyl, 4-(2-N,N-diethylethyl)piperazinyl-1-sulfonyl, 4-(3-hydroxypropyl)piperazinyl-1-sulfonyl, 4-(3-N,N-dimethylaminopropyl)piperazinyl-1-sulfonyl, 4-(3-N,N-diethylaminopropyl)piperazinyl-1-sulfonyl, morpholinyl-1-sulfonyl, 3,5-dimethylmorpholinyl-1-sulfonyl, 4-(4-methyl-piperazin-1-yl)piperidin-1-ylsulfonyl, 4-(4-ethyl-1-piperazinyl)piperidin-1-ylsulfonyl, 4-(4-acetyl-1-piperazinyl)piperidin-1-ylsulfonyl, 4-(N-methyl-4-piperidinyl)piperazinyl-1-sulfonyl, (8) hydroxycarbonyl, aminocarbonyl, methylaminocarbonyl, ethylaminocarbonyl, propylaminocarbonyl, isopropylaminocarbonyl, cyclopropylaminocarbonyl, cyclobutylaminocarbonyl, cyclopentylaminocarbonyl, piperidinyl-1-carbonyl, 4-hydroxypiperidinyl-1-carbonyl, 4-N,N-dimethylaminopiperidinyl-1-carbonyl, 4-N,N- diethylaminopiperidinyl-1-carbonyl, tetrahydropyrrolyl-1-carbonyl, 3-N,N-dimethylaminotetrahydropyrrolyl-1-carbonyl, 3-N,N-diethylaminotetrahydropyrrolyl-1-carbonyl, 4-methylpiperazin-1-ylcarbonyl, 4-ethylpiperazinyl-1-carbonyl, 4-acetylpiperazinyl-1-carbonyl, 4-t-butoxycarbonylpiperazinyl-1-carbonyl, 4-(2-hydroxyethyl)piperazinyl-1-carbonyl, 4-(2-cyanoethyl)piperazinyl-1-carbonyl, 4-(2-N,N-dimethylaminoethyl)piperazinyl-1-carbonyl, 4-(2-N,N-diethylaminoethyl)piperazinyl-1-carbonyl, 4-(3-hydroxypropyl)piperazinyl-1-carbonyl, 4-(3-N,N-dimethylaminopropyl)piperazinyl-1-carbonyl, 4-(3-N,N-diethylaminopropyl)piperazinyl-1-carbonyl, morpholinyl-1-carbonyl, 3,5-dimethylmorpholinyl-1-carbonyl, 4-(4-methyl-piperazin-1-yl)piperidin-1-ylcarbonyl, 4-(4-ethyl-1-piperazinyl)piperidinyl-1-carbonyl, 4-(4-acetyl-1-piperazinyl)piperidinyl-1-carbonyl, 4-(N-methyl-4-piperidinyl)piperazinyl-1-carbonyl, methoxycarbonyl, ethoxycarbonyl, propoxycarbonyl, isopropoxycarbonyl, n-butoxycarbonyl, isobutoxycarbonyl, tert-butoxycarbonyl, (9) aminoformamido, methylaminoformamido, ethylaminoformamido, propylaminoformamido, isopropylaminoformamido, cyclopropylaminoformamido, cyclobutylaminoformamido, cyclopentylaminoformamido, piperidinyl-1-formamido, 4-hydroxypiperidinyl-1-formamido, 4-N,N-dimethylaminopiperidinyl-1-formamido, 4-N,N-diethylaminopiperidinyl-1-formamido, tetrahydropyrrolyl-1-formamido, 3-N,N-dimethylaminotetrahydropyrrolyl-1-formamido, 3-N,N-diethylaminotetrahydropyrrolyl-1-formamido, 4-methylpiperazinyl-1-formamido, 4-ethylpiperazinyl-1-formamido, 4-acetylpiperazinyl-1-formamido, 4-t-butoxycarbonylpiperazinyl-1-formamido, 4-(2-hydroxyethyl)piperazinyl-1-formamido, 4-(2-cyanoethyl)piperazinyl-1-formamido, 4-(2-N,N-dimethylaminoethyl)piperazinyl-1-formamido, 4-(2-N,N-diethylaminoethyl)piperazinyl-1-formamido, 4-(3-hydroxypropyl)piperazinyl-1-formamido, 4-(3-N,N-dimethylaminopropyl)piperazinyl-1-formamido, 4-(3-N,N-diethylaminopropyl)piperazinyl-1-formamido, morpholinyl-1-formamido, 3,5-dimethylmorpholinyl-1-formamido, 4-(4-methyl-piperazin-1-yl)piperidinyl-1-formamido, 4-(4-ethyl-1-piperazinyl)piperidinyl-1-formamido, 4-(4-acetyl-1-piperazinyl)piperidinyl-1-formamido, 4-(N-methyl-4-piperidinyl)piperazinyl-1-formamido; or

(10) $Z_2$ and $Z_3$ or $Z_3$ and $Z_4$ form a nitrogen- or oxygen-containing substituted or unsubstituted 5- or 6-membered ring, the substituent may be selected from the same substituents as described above for $Z_1$;

$R_2$ is selected from:

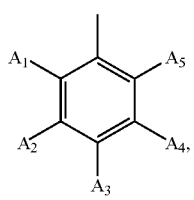

wherein $A_1$, $A_2$, $A_3$, $A_4$, $A_5$ each are independently selected from:

(1) H, F, C, Br, I, cyano, trifluoromethyl, trifluoromethoxy, nitro, (2) methylthio, ethylthio, isopropylthio, methylsulfinyl, ethylsulfinyl, isopropylsulfinyl, methylsulfonyl, ethylsulfonyl, isopropylsulfonyl, methylsulfonamido, methoxycarbonyl, ethoxycarbonyl, propoxycarbonyl, isopropoxycarbonyl, n-butoxycarbonyl, isobutoxycarbonyl, tert-butoxycarbonyl, methylaminocarbonyl, ethylaminocarbonyl, propylaminocarbonyl, isopropylaminocarbonyl, cyclopropylaminocarbonyl, cyclobutylaminocarbonyl, cyclopentylaminocarbonyl, dimethylphosphinyl, diethylphosphinyl, diisopropylphosphinyl.

In some embodiments, $R_1$ is selected from:

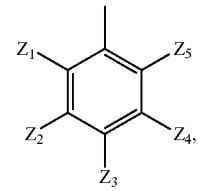

wherein $Z_1$, $Z_2$, $Z_3$, $Z_4$, $Z_5$ each are independently selected from:

(1) H,
(2) C1-C6 alkyl,
(3) C1-C6 alkoxy,
(4) piperidinyl, N-methyl-4-piperidinyl, 4-N,N-dimethylaminopiperidinyl, 4-N,N-diethylaminopiperidinyl, 4-N,N-diisopropylaminopiperidinyl, 4-hydroxypiperidinyl,
(5) 4-(4-methylpiperazinyl)piperidinyl, 4-(4-ethylpiperazinyl)piperidinyl, 4-(4-isopropylpiperazinyl)piperidinyl, 4-(4-acetylpiperazinyl)piperidinyl, 4-(4-t-butoxycarbonylpiperazinyl)piperidinyl, 4-(4-methylsulfonylpiperazinyl)piperidinyl, 4-(4-(2-hydroxyethyl)piperazinyl)piperidinyl, 4-(4-(2-cyanoethyl)piperazinyl)piperidinyl, 4-(4-(3-hydroxypropyl)piperazinyl)piperidinyl, 4-(4-(2-N,N-dimethylaminoethyl)piperazinyl)piperidinyl, 4-(4-(2-N,N-diethylaminoethyl)piperazinyl)piperidinyl, 4-(4-(3-N,N-dimethylaminopropyl)piperazinyl)piperidinyl, 4-(4-(3-N,N-diethylaminopropyl)piperazinyl)piperidinyl, 4-(tetrahydropyrrolyl)piperidinyl, 4-(3-N,N-dimethylaminotetrahydropyrrolyl)piperidinyl,
(6) 4-methylpiperazinyl, 4-ethylpiperazinyl, 4-isopropylpiperazinyl, 4-acetylpiperazinyl, 4-t-butoxycarbonylpiperazinyl, 4-methylsulfonylpiperazinyl, 4-(2-hydroxyethyl)piperazinyl, 4-(2-cyanoethyl)piperazinyl, 4-(3-hydroxypropyl)piperazinyl, 4-(2-N,N-dimethylaminoethyl)piperazinyl, 4-(2-N,N-diethylaminoethyl)piperazinyl, 4-(3-N,N-dimethylaminopropyl)piperazinyl, 4-(3-N,N-diethylaminopropyl)piperazinyl, 4-(N-methyl-4-piperidinyl)piperazinyl, 4-(N-ethyl-4-piperidinyl)piperazinyl, or
(7) $Z_2$ and $Z_3$ or $Z_3$ and $Z_4$ form a nitrogen- or oxygen-containing substituted or unsubstituted 5- or 6-membered ring, the substituent may be selected from the same substituents as described above for $Z_1$.

In some embodiments, $R_1$ is selected from:

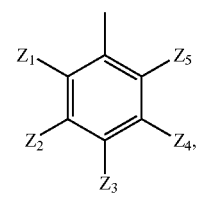

wherein $Z_1$, $Z_2$, $Z_3$, $Z_4$, $Z_5$ each are independently selected from:

(1) H,
(2) methyl,
(3) methoxy, (4) N-methyl-4-piperidinyl,
(5) 4-methylpiperazinyl,
(6) 4-(4-methylpiperazinyl)piperidinyl,
(7) 4-(tetrahydropyrrol-1-yl)piperidinyl, or
(8) $Z_2$ and $Z_3$ or $Z_3$ and $Z_4$ form

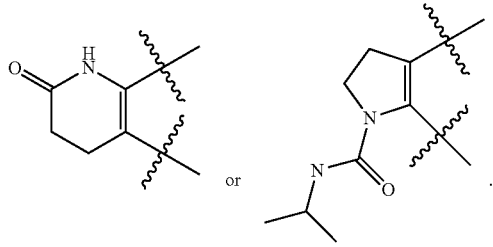 [SMILES: *C1=C(*)NC(=O)CC1 ; *C1=C(*)N(C(=O)NC(C)C)CC1]

In some embodiments, $R_1$ is selected from:

1)

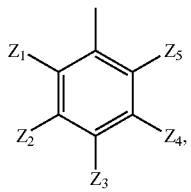

wherein one of $Z_1$ and $Z_5$ is H, the other is methoxy;
one of $Z_2$ and $Z_4$ is H, the other is methyl;
$Z_3$ is selected from: N-methyl-4-piperidinyl, 4-methylpiperazinyl, 4-(4-methylpiperazinyl)piperidinyl, 4-(tetrahydropyrrol-1-yl)piperidinyl, or
$Z_2$ and $Z_3$ or $Z_3$ and $Z_4$ form

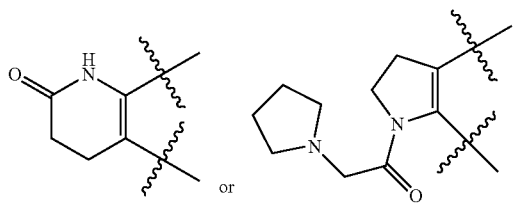

In some embodiments, $R_2$ is selected from:

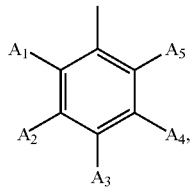

wherein $A_1$, $A_2$, $A_3$, $A_4$, $A_5$ each are independently selected from: (1) H, (2) methylsulfonyl.
In some embodiments, $R_2$ is selected from:

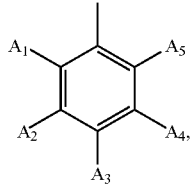

wherein one of $A_1$ and $A_5$ is H, the other is methylsulfonyl; $A_2$, $A_3$, $A_4$ are all H.
In a fourth aspect, the present invention provides a compound of Formula IB, a stereoisomer thereof, a prodrug thereof, a pharmaceutically acceptable salt thereof or a pharmaceutically acceptable solvate thereof,

IB

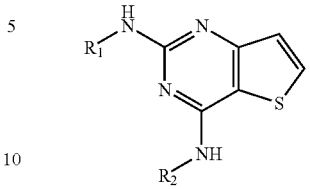

wherein, $R_1$ is selected from:
1) C1-C6 alkyl, 2-N,N-dimethylaminoethyl, 2-hydroxyethyl, 2-N,N-diethylaminoethyl, 2-N,N-diisopropylaminoethyl, 2-morpholinylethyl, 2-(4-methylpiperazinyl)ethyl, 3-N,N-dimethylaminopropyl, 3-N,N-diethylaminopropyl, 3-N,N-diisopropylaminopropyl, 3-morpholinylpropyl, 3-(4-methylpiperazinyl)propyl, C3-C6 cycloalkyl, 4-N,N-dimethylaminocyclohexyl, 4-N,N-diethylaminocyclohexyl, N-methyl-4-piperidinyl, N-ethyl-4-piperidinyl, N-isopropyl-4-piperidinyl, 1,3-dimethyl-5-pyrazolyl, 1-methyl-4-pyrazolyl, 3-methyl-5-isoxazolinyl, 1-(N-methyl-4-piperidinyl)-4-pyrazolyl, 1-(N-t-butoxycarbonyl-4-piperidinyl)-4-pyrazolyl;

2)

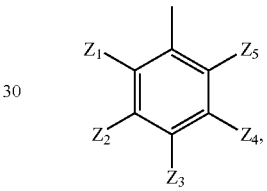

wherein $Z_1$, $Z_2$, $Z_3$, $Z_4$, $Z_5$ each are independently selected from:
(1) H, F, Cl, Br, I, nitro, cyano,
(2) C1-C6 alkyl, C1-C6 alkoxy, C1-C6 oxygen-containing alkyl, C1-C6 fluorine-containing alkyl, C1-C6 fluorine-containing alkoxy,
(3) piperidinyl, N-methyl-4-piperidinyl, 4-N,N-dimethylaminopiperidinyl, 4-N,N-diethylaminopiperidinyl, 4-N,N-diisopropylaminopiperidinyl, 4-hydroxypiperidinyl, 4-(4-methylpiperazinyl)piperidinyl, 4-(4-ethylpiperazinyl)piperidinyl, 4-(4-isopropylpiperazinyl)piperidinyl, 4-(4-acetylpiperazinyl)piperidinyl, 4-(4-t-butoxycarbonylpiperazinyl)piperidinyl, 4-(4-methylsulfonylpiperazinyl)piperidinyl, 4-(4-(2-hydroxyethyl)piperazinyl)piperidinyl, 4-(4-(2-cyanoethyl)piperazinyl)piperidinyl, 4-(4-(3-hydroxypropyl)piperazinyl)piperidinyl, 4-(4-(2-N,N-dimethylaminoethyl)piperazinyl)piperidinyl, 4-(4-(2-N,N-diethylaminoethyl)piperazinyl)piperidinyl, 4-(4-(3-N,N-dimethylaminopropyl)piperazinyl)piperidinyl, 4-(4-(3-N,N-diethylaminopropyl)piperazinyl)piperidinyl, 4-(tetrahydropyrrolyl)piperidinyl, 4-(3-N,N-dimethylaminotetrahydropyrrolyl)piperidinyl,
(4) 4-methylpiperazinyl, 4-ethylpiperazinyl, 4-isopropylpiperazinyl, 4-acetylpiperazinyl, 4-t-butoxycarbonylpiperazinyl, 4-methylsulfonylpiperazinyl, 4-(2-hydroxyethyl)piperazinyl, 4-(2-cyanoethyl)piperazinyl, 4-(3-hydroxypropyl)piperazinyl, 4-(2-N,N-dimethylaminoethyl)piperazinyl, 4-(2-N,N-diethylaminoethyl)piperazinyl, 4-(3-N,N-dimethylaminopropyl)piperazinyl, 4-(3-N,N-diethylaminopropyl)piperazinyl, 4-(N-methyl-4-piperidinyl)piperazinyl, 4-(N-ethyl-4-piperidinyl)piperazinyl, 2-oxo-piperazin-4-yl,
(5) morpholinyl, 3,5-dimethylmorpholinyl, thiomorpholinyl, (6) hydroxysulfonyl, aminosulfonyl, methylaminosulfonyl, ethylaminosulfonyl, propylaminosulfonyl, isopropylaminosulfonyl, cyclopropylaminosulfonyl, cyclopentylaminosulfonyl, piperidin-1-ylsulfonyl, 4-hydroxypiperidin-1-ylsulfonyl, 4-N,N-dimethylaminopiperidin-1-ylsulfonyl, 4-N,N-diethylaminopiperidin-1-ylsulfonyl, tetrahydropyrrolyl-1-sulfonyl, 3-N,N-diethylaminotetrahydropyrrolyl-1-sulfonyl, 4-methylpiperazin-1-ylsulfonyl, 4-ethylpiperazinyl-1-sulfonyl, 4-acetylpiperazinyl-1-sulfonyl, 4-(2-hydroxyethyl)piperazinyl-1-sulfonyl, 4-(2-cyanoethyl)piperazinyl-1-sulfonyl, 4-(2-N,N-dimethylaminoethyl)piperazinyl-1-sulfonyl, 4-(2-N,N-diethylethyl)piperazinyl-1-sulfonyl, 4-(3-hydroxypropyl)piperazinyl-1-sulfonyl, 4-(3-N,N-diethylaminopropyl)piperazinyl-1-sulfonyl, morpholinyl-1-sulfonyl, 3,5-dimethylmorpholinyl-1-sulfonyl, 4-(4-methyl-piperazin-1-yl)piperidin-1-ylsulfonyl, 4-(4-ethyl-1-piperazinyl)piperidin-1-ylsulfonyl, 4-(N-methyl-4-piperidinyl)piperazinyl-1-sulfonyl, (7) 4-(4-methyl-piperazin-1-yl)piperidin-1-ylcarbonyl, 4-methylpiperazin-1-ylcarbonyl, 4-ethylpiperazinyl-1-carbonyl, cyclobutylaminocarbonyl, cyclopentylaminocarbonyl, piperidinyl-1-carbonyl, 4-hydroxypiperidinyl-1-carbonyl, 4-N,N-dimethylaminopiperidinyl-1-carbonyl, 4-N,N-diethylaminopiperidinyl-1-carbonyl, tetrahydropyrrolyl-1-carbonyl, 3-N,N-dimethylaminotetrahydropyrrolyl-1-carbonyl, 3-N,N-dimethylaminotetrahydropyrrolyl-1-carbonyl, 3-N,N-diethylaminotetrahydropyrrolyl-1-carbonyl, 4-(2-hydroxyethyl)piperazinyl-1-carbonyl, 3-N,N-diethylaminotetrahydropyrrolyl-1-carbonyl, 4-(3-hydroxypropyl)piperazinyl-1-carbonyl, 4-(3-N,N-dimethylaminopropyl)piperazinyl-1-carbonyl, 4-(3-N,N-diethylaminopropyl)piperazinyl-1-carbonyl, morpholinyl-1-carbonyl, hydroxycarbonyl, aminocarbonyl, methylaminocarbonyl, ethylaminocarbonyl, propylaminocarbonyl, isopropylaminocarbonyl, cyclopropylaminocarbonyl, 3,5-dimethylmorpholinyl-1-carbonyl, methoxycarbonyl, ethoxycarbonyl, propoxycarbonyl, isopropoxycarbonyl, n-butoxycarbonyl, isobutoxycarbonyl, tert-butoxycarbonyl, (8) pyridin-2-ylmethoxy, pyridin-3-ylmethoxy, pyridin-4-ylmethoxy, phenylmethoxy, monohalo-substituted phenylmethoxy, or (9) $Z_2$ and $Z_3$ or $Z_3$ and $Z_4$ form a nitrogen- or oxygen-containing substituted or unsubstituted 5- or 6-membered ring, the substituent may be selected from the same substituents as described above for $Z_1$;

3)

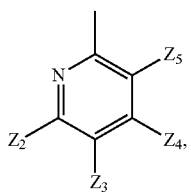

wherein $Z_2$, $Z_3$, $Z_4$, $Z_5$ are the same as defined in 2) above;

4)

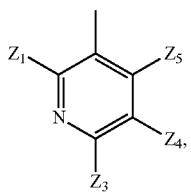

wherein $Z_1$, $Z_3$, $Z_4$, $Z_5$ are the same as defined in 2) above;

$R_2$ is selected from:

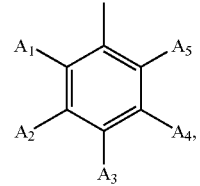

wherein $A_1$, $A_2$, $A_3$, $A_4$, $A_5$ each are independently selected from:

(1) H, F, Cl, Br, I, cyano, trifluoromethyl, trifluoromethoxy, nitro, (2) methylthio, ethylthio, isopropylthio, methylsulfinyl, ethylsulfinyl, isopropylsulfinyl, methylsulfonyl, ethylsulfonyl, isopropylsulfonyl, methylsulfonamido, methoxycarbonyl, ethoxycarbonyl, propoxycarbonyl, isopropoxycarbonyl, n-butoxycarbonyl, isobutoxycarbonyl, tert-butoxycarbonyl, methylaminocarbonyl, ethylaminocarbonyl, propylaminocarbonyl, isopropylaminocarbonyl, cyclopropylaminocarbonyl, cyclobutylaminocarbonyl, cyclopentylaminocarbonyl, dimethylphosphinyl, diethylphosphinyl, diisopropylphosphinyl.

In some embodiments, $R_1$ is selected from:

1)

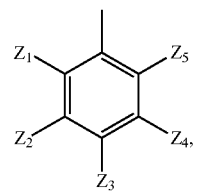

wherein $Z_1$, $Z_2$, $Z_3$, $Z_4$, $Z_5$ each are independently selected from:

(1) H,
(2) C1-C6 alkyl,
(3) C1-C6 alkoxy,
(4) N-methyl-4-piperidinyl, 4-hydroxypiperidinyl, 4-(4-methylpiperazinyl)piperidinyl, 4-(tetrahydropyrrolyl)piperidinyl, piperidinyl, 4-N,N-dimethylaminopiperidinyl, 4-N,N-diethylaminopiperidinyl, 4-N,N-diisopropylaminopiperidinyl,
(5) 4-methylpiperazinyl, 4-ethylpiperazinyl, 4-isopropylpiperazinyl, 4-acetylpiperazinyl, 4-t-butoxycarbonylpiperazinyl, 4-methylsulfonylpiperazinyl, 4-(2-hydroxyethyl)piperazinyl, 4-(2-cyanoethyl)piperazinyl, 4-(3-hydroxypropyl)piperazinyl, 4-(2-N,N-dimethylaminoethyl)piperazinyl, 4-(2-N,N-diethylaminoethyl)piperazinyl, 4-(3-N,N-dimethylaminopropyl)piperazinyl, 4-(3-N,N-diethylaminopropyl)piperazinyl, 2-oxo-piperazin-4-yl
(6) morpholinyl, 3,5-dimethylmorpholinyl,
(7) 4-hydroxypiperidin-1-ylsulfonyl, 4-methylpiperazin-1-ylsulfonyl, hydroxysulfonyl, aminosulfonyl, methylaminosulfonyl, propylaminosulfonyl, isopropylaminosulfonyl, cyclopropylaminosulfonyl, cyclobutylaminosulfonyl, piperidin-1-ylsulfonyl, 4-hydroxypiperidin-1-ylsulfonyl, 4-N,N-dimethylaminopiperidin-1-ylsulfonyl, 4-N,N-diethylaminopiperidin-1-ylsulfonyl, tetrahydropyrrolyl-1-sulfonyl, 3-N,N-dimethylaminotetrahydropyrrolyl-1-sulfonyl, 3-N,N-diethylaminotetrahydropyrrolyl-1-sulfonyl, 4-ethylpiperazinyl-1-sulfonyl, (8) 4-(4-methyl-piperazin-1-yl)piperidin-1-ylcarbonyl, 4-methylpiperazin-1-ylcarbonyl, cyclobutylaminocarbonyl, cyclopentylaminocarbonyl, piperidinyl-1-carbonyl, 4-hydroxypiperidinyl-1-carbonyl, 4-N,N-dimethylaminopiperidinyl-1-carbonyl, 4-N,N-diethylaminopiperidinyl-1-carbonyl, tetrahydropyrrolyl-1-carbonyl, 3-N,N-dimethylaminotetrahydropyrrolyl-1-carbonyl, 3-N,N-diethylaminotetrahydropyrrolyl-1-carbonyl, 4-(3-hydroxypropyl)piperazinyl-1-carbonyl, 4-(3-N,N-dimethylaminopropyl)piperazinyl-1-carbonyl, 4-(3-N,N-diethylaminopropyl)piperazinyl-1-carbonyl, morpholinyl-1-carbonyl, (9) pyridin-2-ylmethoxy, pyridin-2-ylmethoxy, pyridin-3-ylmethoxy, pyridin-4-ylmethoxy, phenylmethoxy, mono-halo-substituted phenylmethoxy, or

(10) $Z_2$ and $Z_3$ or $Z_3$ and $Z_4$ form a nitrogen- or oxygen-containing substituted or unsubstituted 5- or 6-membered ring, the substituent may be selected from the same substituents as described above for $Z_1$;

2)

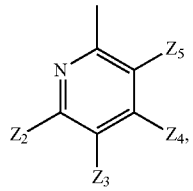

wherein $Z_2$, $Z_3$, $Z_4$, $Z_5$ are the same as defined in 2) above;

3)

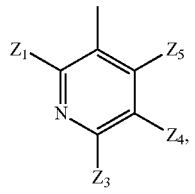

wherein $Z_1$, $Z_3$, $Z_4$, $Z_5$ are the same as defined in 2) above.
In some embodiments, $R_1$ is selected from:

1)

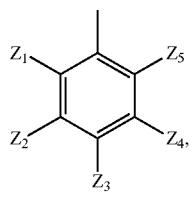

wherein $Z_1$, $Z_2$, $Z_3$, $Z_4$, $Z_5$ each are independently selected from:
(1) H,
(2) methyl,
(3) methoxy, ethoxy, isopropoxy,
(4) N-methyl-4-piperidinyl, 4-hydroxypiperidinyl, 4-(4-methylpiperazinyl)piperidinyl, 4-(tetrahydropyrrol-1-yl)piperidinyl, 4-dimethylamino-piperidinyl,
(5) 4-methylpiperazinyl, 4-t-butoxycarbonylpiperazinyl,
(6) morpholinyl, (7) 4-hydroxypiperidin-1-ylsulfonyl, 4-methylpiperazin-1-ylsulfonyl, (8) 4-(4-methyl-piperazin-1-yl)piperidin-1-ylcarbonyl, 4-methylpiperazin-1-ylcarbonyl, (9) pyridin-2-ylmethoxy,

(10) 2-dimethylaminoacetamido,

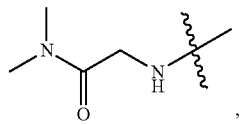 [SMILES: *NCC(=O)N(C)C]

(12) $Z_2$ and $Z_3$ or $Z_3$ and $Z_4$ form

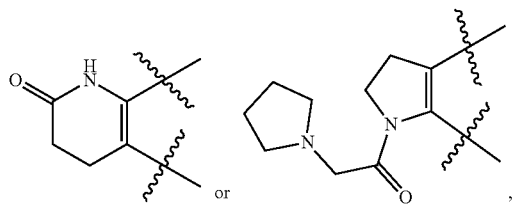 [SMILES: *C1=C(*)NC(=O)CC1 ; *C1=C(*)N(C(=O)CN2CCCC2)CC1]

2)

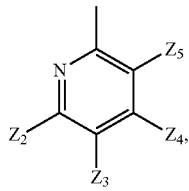

wherein $Z_2$, $Z_3$, $Z_4$, $Z_5$ each are independently selected from: morpholinyl, 4-methylpiperazinyl, 4-hydroxypiperidinyl;

3)

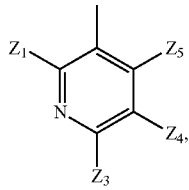

wherein $Z_1$, $Z_3$, $Z_4$, $Z_5$ each are independently selected from: morpholinyl, 4-hydroxypiperidinyl.
In-some-embodiments, $R_1$ is selected from:

1)

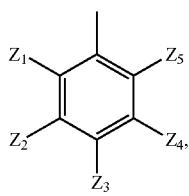

wherein one of $Z_1$ and $Z_5$ is H, the other is selected from: methoxy, ethoxy, isopropoxy;

one of $Z_2$ and $Z_4$ is H, the other is methyl, 2-dimethylaminoacetamido,

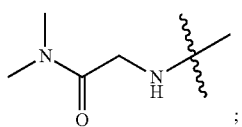 [SMILES: *NCC(=O)N(C)C]

$Z_3$ is selected from: N-methyl-4-piperidinyl, 4-hydroxypiperidinyl, 4-(4-methylpiperazinyl)piperidinyl, 4-(tetrahydropyrrol-1-yl)piperidinyl, 4-methylpiperazinyl, 4-t-butoxycarbonylpiperazinyl, morpholinyl, 4-hydroxypiperidin-1-ylsulfonyl, 4-methylpiperazin-1-ylsulfonyl, 4-(4-methylpiperazin-1-yl)piperidin-1-ylcarbonyl, 4-methylpiperazin-1-ylcarbonyl, pyridin-2-ylmethoxy, 4-dimethylaminopiperidinyl, —F; or $Z_2$ and $Z_3$ or $Z_3$ and $Z_4$ form

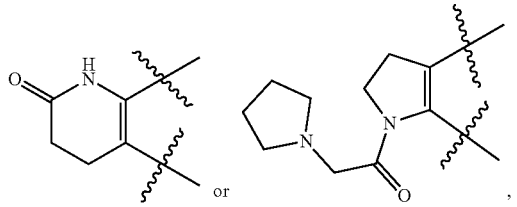 [SMILES: *C1=C(*)NC(=O)CC1 ; *C1=C(*)N(C(=O)CN2CCCC2)CC1]

2)

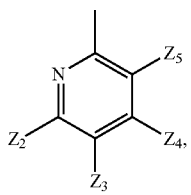

wherein $Z_3$ is selected from: morpholinyl, 4-methylpiperazinyl, 4-hydroxypiperidinyl; $Z_1$, $Z_2$ and $Z_4$ are all H;

3)

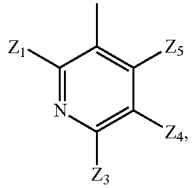

wherein $Z_3$ is selected from: morpholinyl, 4-hydroxypiperidinyl; $Z_1$, $Z_2$ and $Z_4$ are all H.

In some embodiments, $R_2$ is selected from:

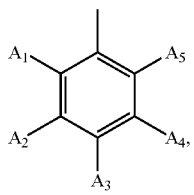

wherein $A_1$, $A_2$, $A_3$, $A_4$, $A_5$ each are independently selected from: (1) H, (2) isopropylsulfonyl.

In some embodiments, $R_2$ is selected from:

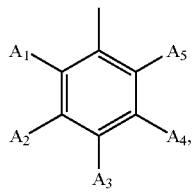

wherein one of $A_1$ and $A_5$ is H, the other is isopropylsulfonyl; $A_2$, $A_3$, $A_4$ are all H.

In a fifth aspect, the present invention provides a compound of Formula IO, a stereoisomer thereof, a prodrug thereof, a pharmaceutically acceptable salt thereof or a pharmaceutically acceptable solvate thereof,

IO

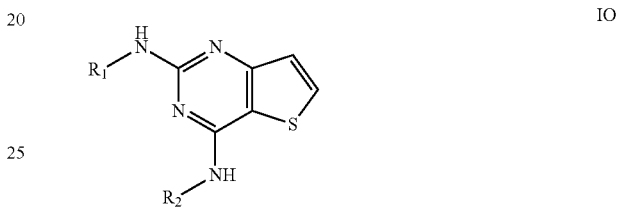

wherein, $R_1$ is selected from:
1) C1-C6 alkyl, 2-N,N-dimethylaminoethyl, 2-hydroxyethyl, 2-N,N-diethylaminoethyl, 2-N,N-diisopropylaminoethyl, 2-morpholinylethyl, 2-(4-methylpiperazinyl)ethyl, 3-N,N-dimethylaminopropyl, 3-N,N-diethylaminopropyl, 3-N,N-diisopropylaminopropyl, 3-morpholinylpropyl, 3-(4-methylpiperazinyl)propyl, C3-C6 cycloalkyl, 4-N,N-dimethylaminocyclohexyl, 4-N,N-diethylaminocyclohexyl, N-methyl-4-piperidinyl, N-ethyl-4-piperidinyl, N-isopropyl-4-piperidinyl, 1,3-dimethyl-5-pyrazolyl, 1-methyl-4-pyrazolyl, 3-methyl-5-isoxazolinyl, 1-(N-methyl-4-piperidinyl)-4-pyrazolyl, 1-(N-t-butoxycarbonyl-4-piperidinyl)-4-pyrazolyl;

2)

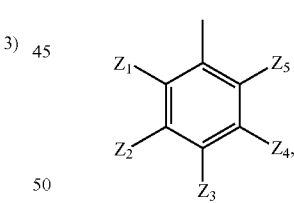

wherein $Z_1$, $Z_2$, $Z_3$, $Z_4$, $Z_5$ each are independently selected from:
(1) H, F, Cl, Br, I, nitro, cyano,
(2) C1-C6 alkyl, C1-C6 alkoxy, C1-C6 oxygen-containing alkyl, C1-C6 fluorine-containing alkyl, C1-C6 fluorine-containing alkoxy,
(3) piperidinyl, N-methyl-4-piperidinyl, 4-dimethylaminopiperidinyl, 4-N,N-diethylaminopiperidinyl, 4-N,N-diisopropylaminopiperidinyl, 4-hydroxypiperidinyl, 4-(4-methylpiperazinyl)piperidinyl, 4-(4-ethylpiperazinyl)piperidinyl, 4-(4-isopropylpiperazinyl)piperidinyl, 4-(4-acetylpiperazinyl)piperidinyl, 4-(4-t-butoxycarbonylpiperazinyl)piperidinyl, 4-(4-methylsulfonylpiperazinyl)piperidinyl, 4-(4-(2-hydroxyethyl)piperazinyl)piperidinyl, 4-(4-(2-cyanoethyl)piperazinyl)piperidinyl, 4-(4-(3-hydroxypropyl)piperazinyl)piperidinyl, 4-(4-(2-N,N-dimethylaminoethyl)piperazinyl)

piperidinyl, 4-(4-(2-N,N-diethylaminoethyl)piperazinyl)piperidinyl, 4-(4-(3-N,N-dimethylaminopropyl)piperazinyl)piperidinyl, 4-(4-(3-N,N-diethylaminopropyl)piperazinyl)piperidinyl, 4-(tetrahydropyrrolyl)piperidinyl, 4-(3-N,N-dimethylaminotetrahydropyrrolyl)piperidinyl, (4) 4-methylpiperazinyl, 4-ethylpiperazinyl, 4-isopropylpiperazinyl, 4-acetylpiperazinyl, 4-t-butoxycarbonylpiperazinyl, 4-methylsulfonylpiperazinyl, 4-(2-hydroxyethyl)piperazinyl, 4-(2-cyanoethyl)piperazinyl, 4-(3-hydroxypropyl)piperazinyl, 4-(2-N,N-dimethylaminoethyl)piperazinyl, 4-(2-N,N-diethylaminoethyl)piperazinyl, 4-(3-N,N-dimethylaminopropyl)piperazinyl, 4-(3-N,N-diethylaminopropyl)piperazinyl, 4-(N-methyl-4-piperidinyl)piperazinyl, 4-(N-ethyl-4-piperidinyl)piperazinyl, (5) N,N-dimethylamino, N,N-diethylamino, N,N-diisopropylamino, 2-N,N-dimethylaminoethylamino, 2-morpholinylethylamino, 2-(4-methylpiperazinyl)ethylamino, 3-N,N-dimethylaminopropylamino, 3-N,N-diethylaminopropylamino, 3-N,N-diisopropylaminopropylamino, 3-morpholinylpropylamino, 3-(4-methylpiperazinyl)propylamino, N-methylpiperidinyl-4-amino, N-ethylpiperidinyl-4-amino, N-isopropylpiperidinyl-4-amino, (6) 2-N,N-dimethylaminoethoxy, 2-N,N-diethylaminoethoxy, 2-N,N-diisopropylaminoethoxy, 2-(4-methylpiperazinyl)ethoxy, 2-(4-acetylpiperazinyl)ethoxy, 2-morpholinylethoxy, 2-thiomorpholinylethoxy, 2-piperidinylethoxy, 3-N,N-dimethylaminopropoxy, 3-N,N-diethylaminopropoxy, 3-N,N-diisopropylaminopropoxy, 3-(4-methylpiperazinyl)propoxy, 3-(4-acetylpiperazinyl)propoxy, 3-morpholinylpropoxy, 3-thiomorpholinylpropoxy, 3-piperidinylpropoxy, pyridin-2-ylmethoxy, pyridin-3-ylmethoxy, pyridin-4-ylmethoxy, phenylmethoxy, monohalo-substituted phenylmethoxy, gem-dihalo-substituted phenylmethoxy, hetero-dihalo-substituted phenylmethoxy, (7) hydroxysulfonyl, aminosulfonyl, methylaminosulfonyl, ethylaminosulfonyl, propylaminosulfonyl, isopropylaminosulfonyl, cyclopropylaminosulfonyl, cyclobutylaminosulfonyl, cyclopentylaminosulfonyl, piperidin-1-ylsulfonyl, 4-hydroxypiperidin-1-ylsulfonyl, 4-N,N-dimethylaminopiperidin-1-ylsulfonyl, 4-N,N-diethylaminopiperidin-1-ylsulfonyl, tetrahydropyrrolyl-1-sulfonyl, 3-N,N-dimethylaminotetrahydropyrrolyl-1-sulfonyl, 3-N,N-diethylaminotetrahydropyrrolyl-1-sulfonyl, 4-methylpiperazin-1-ylsulfonyl, 4-ethylpiperazinyl-1-sulfonyl, 4-acetylpiperazinyl-1-sulfonyl, 4-t-butoxycarbonylpiperazinyl-1-sulfonyl, 4-(2-hydroxyethyl)piperazinyl-1-sulfonyl, 4-(2-cyanoethyl)piperazinyl-1-sulfonyl, 4-(2-N,N-dimethylaminoethyl)piperazinyl-1-sulfonyl, 4-(2-N,N-diethylethyl)piperazinyl-1-sulfonyl, 4-(3-hydroxypropyl)piperazinyl-1-sulfonyl, 4-(3-N,N-dimethylaminopropyl)piperazinyl-1-sulfonyl, 4-(3-N,N-diethylaminopropyl)piperazinyl-1-sulfonyl, morpholinyl-1-sulfonyl, 3,5-dimethylmorpholinyl-1-sulfonyl, 4-(4-methyl-piperazin-1-yl)piperidin-1-ylsulfonyl, 4-(4-ethyl-1-piperazinyl)piperidin-1-ylsulfonyl, 4-(4-acetyl-1-piperazinyl)piperidin-1-ylsulfonyl, 4-(N-methyl-4-piperidinyl)piperazinyl-1-sulfonyl, (8) hydroxycarbonyl, aminocarbonyl, methylaminocarbonyl, ethylaminocarbonyl, propylaminocarbonyl, isopropylaminocarbonyl, cyclopropylaminocarbonyl, cyclobutylaminocarbonyl, cyclopentylaminocarbonyl, piperidinyl-1-carbonyl, 4-hydroxypiperidinyl-1-carbonyl, 4-N,N-dimethylaminopiperidinyl-1-carbonyl, 4-N,N-diethylaminopiperidinyl-1-carbonyl, tetrahydropyrrolyl-1-carbonyl, 3-N,N-dimethylaminotetrahydropyrrolyl-1-carbonyl, 3-N,N-diethylaminotetrahydropyrrolyl-1-carbonyl, 4-methylpiperazin-1-ylcarbonyl, 4-ethylpiperazinyl-1-carbonyl, 4-acetylpiperazinyl-1-carbonyl, 4-t-butoxycarbonylpiperazinyl-1-carbonyl, 4-(2-hydroxyethyl)piperazinyl-1-carbonyl, 4-(2-cyanoethyl)piperazinyl-1-carbonyl, 4-(2-N,N-dimethylaminoethyl)piperazinyl-1-carbonyl, 4-(2-N,N-diethylaminoethyl)piperazinyl-1-carbonyl, 4-(3-hydroxypropyl)piperazinyl-1-carbonyl, 4-(3-N,N-dimethylaminopropyl)piperazinyl-1-carbonyl, 4-(3-N,N-diethylaminopropyl)piperazinyl-1-carbonyl, morpholinyl-1-carbonyl, 3,5-dimethylmorpholinyl-1-carbonyl, 4-(4-methyl-piperazin-1-yl)piperidin-1-ylcarbonyl, 4-(4-ethyl-1-piperazinyl)piperidinyl-1-carbonyl, 4-(4-acetyl-1-piperazinyl)piperidinyl-1-carbonyl, 4-(N-methyl-4-piperidinyl)piperazinyl-1-carbonyl, methoxycarbonyl, ethoxycarbonyl, propoxycarbonyl, isopropoxycarbonyl, n-butoxycarbonyl, isobutoxycarbonyl, tert-butoxycarbonyl, (9) aminoformamido, methylaminoformamido, ethylaminoformamido, propylaminoformamido, isopropylaminoformamido, cyclopropylaminoformamido, cyclobutylaminoformamido, cyclopentylaminoformamido, piperidinyl-1-formamido, 4-hydroxypiperidinyl-1-formamido, 4-N,N-dimethylaminopiperidinyl-1-formamido, 4-N,N-diethylaminopiperidinyl-1-formamido, tetrahydropyrrolyl-1-formamido, 3-N,N-dimethylaminotetrahydropyrrolyl-1-formamido, 3-N,N-diethylaminotetrahydropyrrolyl-1-formamido, 4-methylpiperazinyl-1-formamido, 4-ethylpiperazinyl-1-formamido, 4-acetylpiperazinyl-1-formamido, 4-t-butoxycarbonylpiperazinyl-1-formamido, 4-(2-hydroxyethyl)piperazinyl-1-formamido, 4-(2-cyanoethyl)piperazinyl-1-formamido, 4-(2-N,N-dimethylaminoethyl)piperazinyl-1-formamido, 4-(2-N,N-diethylaminoethyl)piperazinyl-1-formamido, 4-(3-hydroxypropyl)piperazinyl-1-formamido, 4-(3-N,N-dimethylaminopropyl)piperazinyl-1-formamido, 4-(3-N,N-diethylaminopropyl)piperazinyl-1-formamido, morpholinyl-1-formamido, 3,5-dimethylmorpholinyl-1-formamido, 4-(4-methyl-piperazin-1-yl)piperidinyl-1-formamido, 4-(4-ethyl-1-piperazinyl)piperidinyl-1-formamido, 4-(4-acetyl-1-piperazinyl)piperidinyl-1-formamido, 4-(N-methyl-4-piperidinyl)piperazinyl-1-formamido; or

(10) $Z_2$ and $Z_3$ or $Z_3$ and $Z_4$ form a nitrogen- or oxygen-containing substituted or unsubstituted 5- or 6-membered ring, the substituent may be selected from the same substituents as described above for $Z_1$;

$R_2$ is selected from

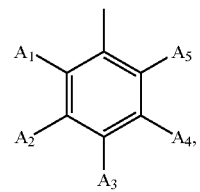

wherein $A_1$, $A_2$, $A_3$, $A_4$, $A_5$ each are independently selected from:

(1) H, F, Cl, Br, I, cyano, trifluoromethyl, trifluoromethoxy, nitro, (2) methylthio, ethylthio, isopropylthio, methylsulfinyl, ethylsulfinyl, isopropylsulfinyl, methylsulfonyl, ethylsulfonyl, isopropylsulfonyl, tert-butyl sulfonyl, methylsulfonamido, methoxycarbonyl, ethoxycarbonyl, propoxycarbonyl, isopropoxycarbonyl, n-butoxycarbonyl, isobutoxycarbonyl, tert-butoxycarbonyl, methylaminocarbonyl, ethylaminocarbonyl, propylaminocarbonyl, isopropylaminocarbonyl, cyclopropylaminocarbonyl, cyclobutylaminocarbonyl, cyclopentylaminocarbonyl, dimethylphosphinyl, diethylphosphinyl, diisopropylphosphinyl.

In some embodiments, $R_1$ is selected from

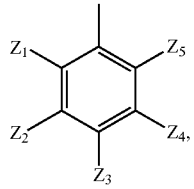

wherein $Z_1$, $Z_2$, $Z_3$, $Z_4$, $Z_5$ each are independently selected from:

(1) H, (2) C1-C6 alkoxy, (3) piperidinyl, N-methyl-4-piperidinyl, 4-dimethylaminopiperidinyl, 4-N,N-diethylaminopiperidinyl, 4-N,N-diisopropylaminopiperidinyl, 4-hydroxypiperidinyl, 4-(4-methylpiperazinyl)piperidinyl, 4-(4-ethylpiperazinyl)piperidinyl, 4-(4-isopropylpiperazinyl)piperidinyl, 4-(4-acetylpiperazinyl)piperidinyl, 4-(4-t-butoxycarbonylpiperazinyl)piperidinyl, 4-(4-methylsulfonylpiperazinyl)piperidinyl, 4-(4-(2-hydroxyethyl)piperazinyl)piperidinyl, 4-(4-(2-cyanoethyl)piperazinyl)piperidinyl, 4-(4-(3-hydroxypropyl)piperazinyl)piperidinyl, 4-(4-(2-N,N-dimethylaminoethyl)piperazinyl)piperidinyl, 4-(4-(2-N,N-diethylaminoethyl)piperazinyl)piperidinyl, 4-(4-(3-N,N-dimethylaminopropyl)piperazinyl)piperidinyl, 4-(4-(3-N,N-diethylaminopropyl)piperazinyl)piperidinyl, 4-(tetrahydropyrrolyl)piperidinyl, 4-(3-N,N-dimethylaminotetrahydropyrrolyl)piperidinyl, (4) 4-methylpiperazinyl, 4-ethylpiperazinyl, 4-isopropylpiperazinyl, 4-acetylpiperazinyl, 4-t-butoxycarbonylpiperazinyl, 4-methylsulfonylpiperazinyl, 4-(2-hydroxyethyl)piperazinyl, 4-(2-cyanoethyl)piperazinyl, 4-(3-hydroxypropyl)piperazinyl, 4-(2-N,N-dimethylaminoethyl)piperazinyl, 4-(2-N,N-diethylaminoethyl)piperazinyl, 4-(3-N,N-dimethylaminopropyl)piperazinyl, 4-(3-N,N-diethylaminopropyl)piperazinyl, 4-(N-methyl-4-piperidinyl)piperazinyl, 4-(N-ethyl-4-piperidinyl)piperazinyl or (5) $Z_2$ and $Z_3$ or $Z_3$ and $Z_4$ form a nitrogen- or oxygen-containing substituted or unsubstituted 5-membered ring, the substituent may be selected from the same substituents as described above for $Z_1$.

In some embodiments, $R_1$ is selected from:

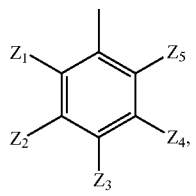

wherein $Z_1$, $Z_2$, $Z_3$, $Z_4$, $Z_5$ each are independently selected from:

(1) H, (2) C1-C6 alkoxy (3) 4-(4-methylpiperazin-1-yl)piperidinyl, 4-methylpiperazinyl, 4-dimethylamino-piperidinyl, (4) $Z_2$ and $Z_3$ may form a nitrogen-containing substituted or unsubstituted 5-membered ring N

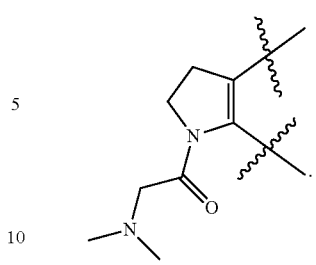

In some embodiments, $R_1$ is selected from:

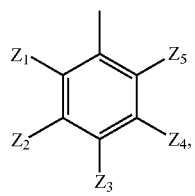

wherein, $Z_1$ is methoxy, and $Z_3$ is selected from: 4-dimethylaminopiperidinyl, 4-methylpiperazinyl, 4-(4-methylpiperazinyl)piperidinyl, the rest being H; or $Z_3$ and $Z_4$ form

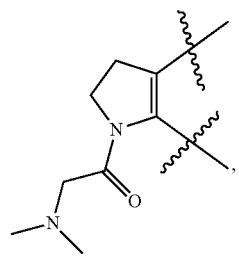 [SMILES: *C1=C(*)N(C(=O)CN(C)C)CC1]

and $Z_1$ is methoxy, the rest being H.

In some embodiments, $R_2$ is selected from

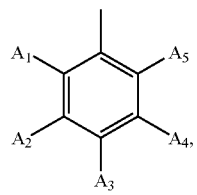

wherein $A_1$, $A_2$, $A_3$, $A_4$, $A_5$ each are independently selected from:

(1) H; (2) tert-butyl sulfonyl.

In some embodiments, $R_2$ is selected from:

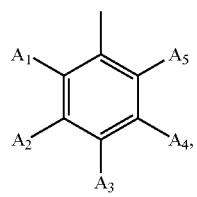

wherein one of $A_1$ and $A_5$ is H, the other is tert-butyl sulfonyl; $A_2$, $A_3$, $A_4$ are all H.

In a sixth aspect, the present invention provides a compound of Formula IC, a stereoisomer thereof, a prodrug thereof, a pharmaceutically acceptable salt thereof or a pharmaceutically acceptable solvate thereof,

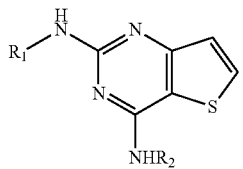

IC wherein, $R_1$ is selected from:
1) C1-C6 alkyl, 2-N,N-dimethylaminoethyl, 2-hydroxyethyl, 2-N,N-diethylaminoethyl, 2-N,N-diisopropylaminoethyl, 2-morpholinylethyl, 2-(4-methylpiperazinyl)ethyl, 3-N,N-dimethylaminopropyl, 3-N,N-diethylaminopropyl, 3-N,N-diisopropylaminopropyl, 3-morpholinylpropyl, 3-(4-methylpiperazinyl)propyl, C3-C6 cycloalkyl, 4-N,N-dimethylaminocyclohexyl, 4-N,N-diethylaminocyclohexyl, N-methyl-4-piperidinyl, N-ethyl-4-piperidinyl, N-isopropyl-4-piperidinyl, 1,3-dimethyl-5-pyrazolyl, 1-methyl-4-pyrazolyl, 3-methyl-5-isoxazolinyl, 1-(N-methyl-4-piperidinyl)-4-pyrazolyl, 1-(N-t-butoxycarbonyl-4-piperidinyl)-4-pyrazolyl;

2)

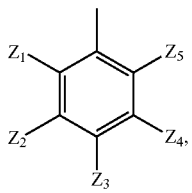

wherein $Z_1$, $Z_2$, $Z_3$, $Z_4$, $Z_5$ each are independently selected from:
(1) H, F, Cl, Br, I, nitro, cyano,
(2) C1-C6 alkyl, C1-C6 alkoxy, C1-C6 oxygen-containing alkyl, C1-C6 fluorine-containing alkyl, C1-C6 fluorine-containing alkoxy
(3) piperidinyl, N-methyl-4-piperidinyl, 4-N,N-dimethylaminopiperidinyl, 4-N,N-diethylaminopiperidinyl, 4-N,N-diisopropylaminopiperidinyl, 4-hydroxypiperidinyl, 4-(4-methylpiperazinyl)piperidinyl, 4-(4-ethylpiperazinyl)piperidinyl, 4-(4-isopropylpiperazinyl)piperidinyl, 4-(4-acetylpiperazinyl)piperidinyl, 4-(4-t-butoxycarbonylpiperazinyl)piperidinyl, 4-(4-methylsulfonylpiperazinyl)piperidinyl, 4-(4-(2-hydroxyethyl)piperazinyl)piperidinyl, 4-(4-(2-cyanoethyl)piperazinyl)piperidinyl, 4-(4-(3-hydroxypropyl)piperazinyl)piperidinyl, 4-(4-(2-N,N-dimethylaminoethyl)piperazinyl)piperidinyl, 4-(4-(2-N,N-diethylaminoethyl)piperazinyl)piperidinyl, 4-(4-(3-N,N-dimethylaminopropyl)piperazinyl)piperidinyl, 4-(4-(3-N,N-diethylaminopropyl)piperazinyl)piperidinyl, 4-(tetrahydropyrrolyl)piperidinyl, 4-(3-N,N-dimethylaminotetrahydropyrrolyl)piperidinyl,
(4) 4-methylpiperazinyl, 4-ethylpiperazinyl, 4-isopropylpiperazinyl, 4-acetylpiperazinyl, 4-t-butoxycarbonylpiperazinyl, 4-methylsulfonylpiperazinyl, 4-(2-hydroxyethyl)piperazinyl, 4-(2-cyanoethyl)piperazinyl, 4-(3-hydroxypropyl)piperazinyl, 4-(2-N,N-dimethylaminoethyl)piperazinyl, 4-(2-N,N-diethylaminoethyl)piperazinyl, 4-(3-N,N-dimethylaminopropyl)piperazinyl, 4-(3-N,N-diethylaminopropyl)piperazinyl, 4-(N-methyl-4-piperidinyl)piperazinyl, 4-(N-ethyl-4-piperidinyl)piperazinyl, or
(5) N,N-dimethylamino, N,N-diethylamino, N,N-diisopropylamino, 2-N,N-dimethylaminoethylamino, 2-morpholinylethylamino, 2-(4-methylpiperazinyl)ethylamino, 3-N,N-dimethylaminopropylamino, 3-N,N-diethylaminopropylamino, 3-N,N-diisopropylaminopropylamino, 3-morpholinylpropylamino, 3-(4-methylpiperazinyl)propylamino, N-methylpiperidinyl-4-amino, N-ethylpiperidinyl-4-amino, N-isopropylpiperidinyl-4-amino,
(6) 2-N,N-dimethylaminoethoxy, 2-N,N-diethylaminoethoxy, 2-N,N-diisopropylaminoethoxy, 2-(4-methylpiperazinyl)ethoxy, 2-(4-acetylpiperazinyl)ethoxy, 2-morpholinylethoxy, 2-thiomorpholinylethoxy, 2-piperidinylethoxy, 3-N,N-dimethylaminopropoxy, 3-N,N-diethylaminopropoxy, 3-N,N-diisopropylaminopropoxy, 3-(4-methylpiperazinyl)propoxy, 3-(4-acetylpiperazinyl)propoxy, 3-morpholinylpropoxy, 3-thiomorpholinylpropoxy, 3-piperidinylpropoxy, pyridin-2-ylmethoxy, pyridin-3-ylmethoxy, pyridin-4-ylmethoxy, phenylmethoxy, monohalo-substituted phenylmethoxy, gem-dihalo-substituted phenylmethoxy, hetero-dihalo-substituted phenylmethoxy,
(7) hydroxysulfonyl, aminosulfonyl, methylaminosulfonyl, ethylaminosulfonyl, propylaminosulfonyl, isopropylaminosulfonyl, cyclopropylaminosulfonyl, cyclobutylaminosulfonyl, cyclopentylaminosulfonyl, piperidin-1-ylsulfonyl, 4-hydroxypiperidin-1-ylsulfonyl, 4-N,N-dimethylaminopiperidin-1-ylsulfonyl, 4-N,N-diethylaminopiperidin-1-ylsulfonyl, tetrahydropyrrolyl-1-sulfonyl, 3-N,N-dimethylaminotetrahydropyrrolyl-1-sulfonyl, 3-N,N-diethylaminotetrahydropyrrolyl-1-sulfonyl, 4-methylpiperazin-1-ylsulfonyl, 4-ethylpiperazinyl-1-sulfonyl, 4-acetylpiperazinyl-1-sulfonyl, 4-t-butoxycarbonylpiperazinyl-1-sulfonyl, 4-(2-hydroxyethyl)piperazinyl-1-sulfonyl, 4-(2-cyanoethyl)piperazinyl-1-sulfonyl, 4-(2-N,N-dimethylaminoethyl)piperazinyl-1-sulfonyl, 4-(2-N,N-diethylethyl)piperazinyl-1-sulfonyl, 4-(3-hydroxypropyl)piperazinyl-1-sulfonyl, 4-(3-N,N-dimethylaminopropyl)piperazinyl-1-sulfonyl, 4-(3-N,N-diethylaminopropyl)piperazinyl-1-sulfonyl, morpholinyl-1-sulfonyl, 3,5-dimethylmorpholinyl-1-sulfonyl, 4-(4-methyl-piperazin-1-yl)piperidin-1-ylsulfonyl, 4-(4-ethyl-1-piperazinyl)piperidin-1-ylsulfonyl, 4-(4-acetyl-1-piperazinyl)piperidin-1-ylsulfonyl, 4-(N-methyl-4-piperidinyl)piperazinyl-1-sulfonyl,
(8) hydroxycarbonyl, aminocarbonyl, methylaminocarbonyl, ethylaminocarbonyl, propylaminocarbonyl, isopropylaminocarbonyl, cyclopropylaminocarbonyl, cyclobutylaminocarbonyl, cyclopentylaminocarbonyl, piperidinyl-1-carbonyl, 4-hydroxypiperidinyl-1-carbonyl, 4-N,N-dimethylaminopiperidinyl-1-carbonyl, 4-N,N-diethylaminopiperidinyl-1-carbonyl, tetrahydropyrrolyl-1-carbonyl, 3-N,N-dimethylaminotetrahydropyrrolyl-1-carbonyl, 3-N,N-diethylaminotetrahydropyrrolyl-1-carbonyl, 4-methylpiperazin-1-ylcarbonyl, 4-ethylpiperazinyl-1-carbonyl, 4-acetylpiperazinyl-1-carbonyl, 4-t-butoxycarbonylpiperazinyl-1-carbonyl, 4-(2-hydroxyethyl)piperazinyl-1-carbonyl, 4-(2-cyanoethyl)piperazinyl-1-carbonyl, 4-(2-N,N-dimethylaminoethyl)piperazinyl-1-carbonyl, 4-(2-N,N-diethylaminoethyl)piperazinyl-1-carbonyl, 4-(3-hydroxypropyl)piperazinyl-1-carbonyl, 4-(3-N,N-dimethylaminopropyl)piperazinyl-1-carbonyl, 4-(3-N,N-diethylaminopropyl)piperazinyl-1-carbonyl, morpholinyl-1-carbonyl, 3,5-dimethylmorpholinyl-1-carbonyl, 4-(4-methyl-piperazin-1-yl)piperidin-1-ylcarbonyl, 4-(4-ethyl-1-piperazinyl)

piperidinyl-1-carbonyl, 4-(4-acetyl-1-piperazinyl)piperidinyl-1-carbonyl, 4-(N-methyl-4-piperidinyl)piperazinyl-1-carbonyl, methoxycarbonyl, ethoxycarbonyl, propoxycarbonyl, isopropoxycarbonyl, n-butoxycarbonyl, isobutoxycarbonyl, tert-butoxycarbonyl, (9) aminoformamido, methylaminoformamido, ethylaminoformamido, propylaminoformamido, isopropylaminoformamido, cyclopropylaminoformamido, cyclobutylaminoformamido, cyclopentylaminoformamido, piperidinyl-1-formamido, 4-hydroxypiperidinyl-1-formamido, 4-N,N-dimethylaminopiperidinyl-1-formamido, 4-N,N-diethylaminopiperidinyl-1-formamido, tetrahydropyrrolyl-1-formamido, 3-N,N-dimethylaminotetrahydropyrrolyl-1-formamido, 3-N,N-diethylaminotetrahydropyrrolyl-1-formamido, 4-methylpiperazinyl-1-formamido, 4-ethylpiperazinyl-1-formamido, 4-acetylpiperazinyl-1-formamido, 4-t-butoxycarbonylpiperazinyl-1-formamido, 4-(2-hydroxyethyl)piperazinyl-1-formamido, 4-(2-cyanoethyl)piperazinyl-1-formamido, 4-(2-N,N-dimethylaminoethyl)piperazinyl-1-formamido, 4-(2-N,N-diethylaminoethyl)piperazinyl-1-formamido, 4-(3-hydroxypropyl)piperazinyl-1-formamido, 4-(3-N,N-dimethylaminopropyl)piperazinyl-1-formamido, 4-(3-N,N-diethylaminopropyl)piperazinyl-1-formamido, morpholinyl-1-formamido, 3,5-dimethylmorpholinyl-1-formamido, 4-(4-methyl-piperazin-1-yl)piperidinyl-1-formamido, 4-(4-ethyl-1-piperazinyl)piperidinyl-1-formamido, 4-(4-acetyl-1-piperazinyl)piperidinyl-1-formamido, 4-(N-methyl-4-piperidinyl)piperazinyl-1-formamido

(10) $Z_2$ and $Z_3$ or $Z_3$ and $Z_4$ form a nitrogen- or oxygen-containing substituted or unsubstituted 5-membered ring, the substituent may be selected from the same substituents as described above for $Z_1$;

$R_2$ is selected from: 1)

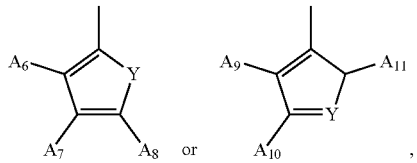

wherein, Y is NH, S or O atom, $A_6$, $A_7$, $A_8$, $A_9$, $A_{10}$, $A_{11}$ each are independently selected from:

(1) H, F, C, Br, I, cyano, trifluoromethyl, trifluoromethoxy, nitro, (2) methoxycarbonyl, ethoxycarbonyl, propoxycarbonyl, isopropoxycarbonyl, n-butoxycarbonyl, isobutoxycarbonyl, tert-butoxycarbonyl, methylaminocarbonyl, ethylaminocarbonyl, propylaminocarbonyl, isopropylaminocarbonyl, cyclopropylaminocarbonyl, cyclobutylaminocarbonyl, cyclopentylaminocarbonyl;

2)

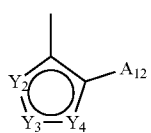

wherein $A_{12}$ is selected from:

(1) H, F, Cl, Br, I, cyano, trifluoromethyl, trifluoromethoxy, nitro, (2) methoxycarbonyl, ethoxycarbonyl, propoxycarbonyl, isopropoxycarbonyl, n-butoxycarbonyl, isobutoxycarbonyl, tert-butoxycarbonyl, methylaminocarbonyl, ethylaminocarbonyl, propylaminocarbonyl, isopropylaminocarbonyl, cyclopropylaminocarbonyl, cyclobutylaminocarbonyl, cyclopentylaminocarbonyl, methylsulfinyl, ethylsulfinyl, isopropylsulfinyl, methylsulfonyl, ethylsulfonyl, isopropylsulfonyl;

$Y_2$, $Y_3$, $Y_4$ are selected from one combination of the following:

$Y_2$ is C, $Y_3$ is N-$A_{13}$, $Y_4$ is N, or
$Y_2$ is N, $Y_3$ is N-$A_{13}$, $Y_4$ is CH or N;
wherein $A_{13}$ is H, C1-C6 alkyl.

In some embodiments, $R_1$ is selected from:

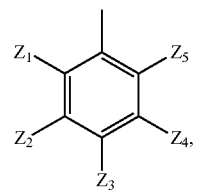

wherein $Z_1$, $Z_2$, $Z_3$, $Z_4$, $Z_5$ each are independently selected from:

(1) H, (2) C1-C6 alkoxy, (3) 4-hydroxypiperidinyl, piperidinyl, N-methyl-4-piperidinyl, 4-N,N-dimethylaminopiperidinyl, 4-N,N-diethylaminopiperidinyl, 4-N,N-diisopropylaminopiperidinyl, (4) 4-methylpiperazinyl, 4-ethylpiperazinyl, 4-isopropylpiperazinyl, 4-acetylpiperazinyl, 4-t-butoxycarbonylpiperazinyl, 4-methylsulfonylpiperazinyl, 4-(2-hydroxyethyl)piperazinyl, 4-(2-cyanoethyl)piperazinyl, 4-(3-hydroxypropyl)piperazinyl, 4-(2-N,N-dimethylaminoethyl)piperazinyl, 4-(2-N,N-diethylaminoethyl)piperazinyl, 4-(3-N,N-dimethylaminopropyl)piperazinyl, 4-(3-N,N-diethylaminopropyl)piperazinyl, 4-(N-methyl-4-piperidinyl)piperazinyl, 4-(N-ethyl-4-piperidinyl)piperazinyl, (5) 4-(4-methylpiperazinyl)piperidinyl, 4-(4-ethylpiperazinyl)piperidinyl, 4-(4-isopropylpiperazinyl)piperidinyl, 4-(4-acetylpiperazinyl)piperidinyl, 4-(4-t-butoxycarbonylpiperazinyl)piperidinyl, 4-(4-methylsulfonylpiperazinyl)piperidinyl, 4-(4-(2-hydroxyethyl)piperazinyl)piperidinyl, 4-(4-(2-cyanoethyl)piperazinyl)piperidinyl, 4-(4-(3-hydroxypropyl)piperazinyl)piperidinyl, 4-(4-(2-N,N-dimethylaminoethyl)piperazinyl)piperidinyl, 4-(4-(2-N,N-diethylaminoethyl)piperazinyl)piperidinyl, 4-(4-(3-N,N-dimethylaminopropyl)piperazinyl)piperidinyl, 4-(4-(3-N,N-diethylaminopropyl)piperazinyl)piperidinyl, 4-(tetrahydropyrrolyl)piperidinyl, 4-(3-N,N-dimethylaminotetrahydropyrrolyl)piperidinyl, or (6) $Z_2$ and $Z_3$ or $Z_3$ and $Z_4$ form a nitrogen- or oxygen-containing substituted or unsubstituted 5-membered ring, the substituent may be selected from the same substituents as described above for $Z_1$.

In some embodiments, $R_1$ is selected from:

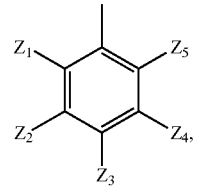

wherein $Z_1$, $Z_2$, $Z_3$, $Z_4$, $Z_5$ each are independently selected from:
(1) H,
(2) methoxy,
(3) 4-hydroxypiperidinyl,
(4) 4-methylpiperazinyl,
(5) 4-(4-methylpiperazinyl)piperidinyl, or
(6) $Z_2$ and $Z_3$ or $Z_3$ and $Z_4$ form

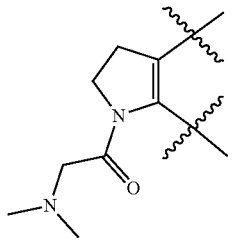

In some embodiments, $R_1$ is selected from:

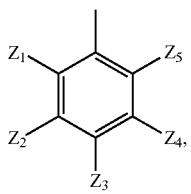

wherein one of Z and $Z_5$ is H, e other is methoxy, $Z_4$ is H;
$Z_3$ is selected from: 4-hydroxypiperidinyl, 4-methylpiperazinyl, 4-(4-methylpiperazinyl)piperidinyl, or
$Z_2$ and $Z_3$ form

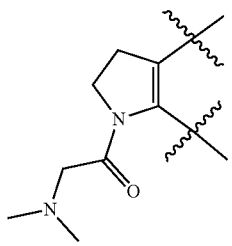

In some embodiments, $R_2$ is selected from:

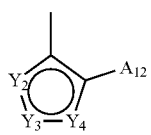

wherein $A_{12}$ is selected from:
(1) H, methyl, F, Cl, Br, I, cyano, trifluoromethyl, trifluoromethoxy, nitro,
(2) methoxycarbonyl, ethoxycarbonyl, propoxycarbonyl, isopropoxycarbonyl, n-butoxycarbonyl, isobutoxycarbonyl, tert-butoxycarbonyl, methylaminocarbonyl, ethylaminocarbonyl, propylaminocarbonyl, isopropylaminocarbonyl, cyclopropylaminocarbonyl, cyclobutylaminocarbonyl, cyclopentylaminocarbonyl, methylsulfinyl, ethylsulfinyl, isopropylsulfinyl, methylsulfonyl, ethylsulfonyl, isopropylsulfonyl;

$Y_2$, $Y_3$, $Y_4$ are selected from one combination of the following:
$Y_2$ is C, $Y_3$ is N-$A_{13}$, $Y_4$ is N, or
$Y_2$ is N, $Y_3$ is N-$A_{13}$, $Y_4$ is CH or N;
wherein $A_{13}$ is H, C1-C6 alkyl.

In some embodiments, $R_2$ is selected from:

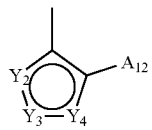

wherein $A_{12}$ is selected from:
(1) H, methyl,
(2) isopropylsulfonyl;
$Y_2$, $Y_3$, $Y_4$ are selected from one combination of the following:
$Y_2$ is C, $Y_3$ is N-$A_{13}$, $Y_4$ is N,
wherein $A_{13}$ is H, C1-C6 alkyl.

In some embodiments, $R_2$ is selected from:

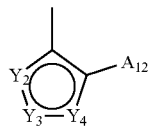

wherein $A_{12}$ is selected from isopropylsulfonyl;
$Y_2$, $Y_3$, $Y_4$ are selected from one combination of the following: $Y_2$ is C, $Y_3$ is N-$A_{13}$, $Y_4$ is N, wherein $A_{13}$ is methyl.

In a seventh aspect, the present invention provides a compound of Formula ID, a stereoisomer thereof, a prodrug thereof, a pharmaceutically acceptable salt thereof or a pharmaceutically acceptable solvate thereof,

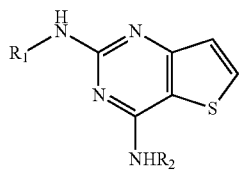

ID wherein, $R_1$ is selected from:
1) C1-C6 alkyl, 2-N,N-dimethylaminoethyl, 2-hydroxyethyl, 2-N,N-diethylaminoethyl, 2-N,N-diisopropylaminoethyl, 2-morpholinylethyl, 2-(4-methylpiperazinyl)ethyl, 3-N,N-dimethylaminopropyl, 3-N,N-diethylaminopropyl, 3-N,N-diisopropylaminopropyl, 3-morpholinylpropyl, 3-(4-methylpiperazinyl)propyl, C3-C6 cycloalkyl, 4-N,N-dimethylaminocyclohexyl, 4-N,N-diethylaminocyclohexyl, N-methyl-4-piperidinyl, N-ethyl-4-piperidinyl, N-isopropyl-4-piperidinyl, 1,3-dimethyl-5-pyrazolyl, 1-methyl-4-pyrazolyl, 3-methyl-5-isoxazolinyl, 1-(N-methyl-4-piperidinyl)-4-pyrazolyl, 1-(N-t-butoxycarbonyl-4-piperidinyl)-4-pyrazolyl;

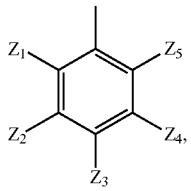

wherein $Z_1$, $Z_2$, $Z_3$, $Z_4$, $Z_5$ each are independently selected from:

(1) H, F, Cl, Br, I, nitro, cyano, (2) C1-C6 alkyl, C1-C6 alkoxy, C1-C6 oxygen-containing alkyl, C1-C6 fluorine-containing alkyl, C1-C6 fluorine-containing alkoxy, (3) piperidinyl, N-methyl-4-piperidinyl, 4-N,N-dimethylaminopiperidinyl, 4-N,N-diethylaminopiperidinyl, 4-N,N-diisopropylaminopiperidinyl, 4-hydroxypiperidinyl, 4-(4-methylpiperazinyl)piperidinyl, 4-(4-ethylpiperazinyl) piperidinyl, 4-(4-isopropylpiperazinyl)piperidinyl, 4-(4-acetylpiperazinyl)piperidinyl, 4-(4-t-butoxycarbonylpiperazinyl)piperidinyl, 4-(4-methylsulfonylpiperazinyl)piperidinyl, 4-(4-(2-hydroxyethyl)piperazinyl)piperidinyl, 4-(4-(2-cyanoethyl)piperazinyl)piperidinyl, 4-(4-(3-hydroxypropyl)piperazinyl) piperidinyl, 4-(4-(2-N,N-dimethylaminoethyl)piperazinyl) piperidinyl, 4-(4-(2-N,N-diethylaminoethyl)piperazinyl) piperidinyl, 4-(4-(3-N,N-dimethylaminopropyl)piperazinyl) piperidinyl, 4-(4-(3-N,N-diethylaminopropyl)piperazinyl) piperidinyl, 4-(tetrahydropyrrolyl)piperidinyl, 4-(3-N,N-dimethylaminotetrahydropyrrolyl)piperidinyl, (4) 4-methylpiperazinyl, 4-ethylpiperazinyl, 4-isopropylpiperazinyl, 4-acetylpiperazinyl, 4-t-butoxycarbonylpiperazinyl, 4-methylsulfonylpiperazinyl, 4-(2-hydroxyethyl)piperazinyl, 4-(2-cyanoethyl)piperazinyl, 4-(3-hydroxypropyl) piperazinyl, 4-(2-N,N-dimethylaminoethyl)piperazinyl, 4-(2-N,N-diethylaminoethyl)piperazinyl, 4-(3-N,N-dimethylaminopropyl)piperazinyl, 4-(3-N,N-diethylaminopropyl) piperazinyl, 4-(N-methyl-4-piperidinyl)piperazinyl, 4-(N-ethyl-4-piperidinyl)piperazinyl, (5) N,N-dimethylamino, N,N-diethylamino, N,N-diisopropylamino, 2-N,N-dimethylaminoethylamino, 2-morpholinylethylamino, 2-(4-methylpiperazinyl)ethylamino, 3-N,N-dimethylaminopropylamino, 3-N,N-diethylaminopropylamino, 3-N,N-diisopropylaminopropylamino, 3-morpholinylpropylamino, 3-(4-methylpiperazinyl)propylamino, N-methylpiperidinyl-4-amino, N-ethylpiperidinyl-4-amino, N-isopropylpiperidinyl-4-amino, (6) 2-N,N-dimethylaminoethoxy, 2-N,N-diethylaminoethoxy, 2-N,N-diisopropylaminoethoxy, 2-(4-methylpiperazinyl)ethoxy, 2-(4-acetylpiperazinyl)ethoxy, 2-morpholinylethoxy, 2-thiomorpholinylethoxy, 2-piperidinylethoxy, 3-N,N-dimethylaminopropoxy, 3-N,N-diethylaminopropoxy, 3-N,N-diisopropylaminopropoxy, 3-(4-methylpiperazinyl)propoxy, 3-(4-acetylpiperazinyl)propoxy, 3-morpholinylpropoxy, 3-thiomorpholinylpropoxy, 3-piperidinylpropoxy, pyridin-2-ylmethoxy, pyridin-3-ylmethoxy, pyridin-4-ylmethoxy, phenylmethoxy, monohalo-substituted phenylmethoxy, gem-dihalo-substituted phenylmethoxy, hetero-dihalo-substituted phenylmethoxy, (7) hydroxysulfonyl, aminosulfonyl, methylaminosulfonyl, ethylaminosulfonyl, propylaminosulfonyl, isopropylaminosulfonyl, cyclopropylaminosulfonyl, cyclobutylaminosulfonyl, cyclopentylaminosulfonyl, piperidinyl-1-ylsulfonyl, 4-hydroxypiperidin-1-ylsulfonyl, 4-N,N-dimethylaminopiperidin-1-ylsulfonyl, 4-N,N-diethylaminopiperidin-1-ylsulfonyl, tetrahydropyrrolyl-1-sulfonyl, 3-N,N-dimethylaminotetrahydropyrrolyl-1-sulfonyl, 3-N,N-diethylaminotetrahydropyrrolyl-1-sulfonyl, 4-methylpiperazin-1-ylsulfonyl, 4-ethylpiperazinyl-1-sulfonyl, 4-acetylpiperazinyl-1-sulfonyl, 4-t-butoxycarbonylpiperazinyl-1-sulfonyl, 4-(2-hydroxyethyl)piperazinyl-1-sulfonyl, 4-(2-cyanoethyl)piperazinyl-1-sulfonyl, 4-(2-N,N-dimethylaminoethyl)piperazinyl-1-sulfonyl, 4-(2-N,N-diethylethyl)piperazinyl-1-sulfonyl, 4-(3-hydroxypropyl) piperazinyl-1-sulfonyl, 4-(3-N,N-dimethylaminopropyl) piperazinyl-1-sulfonyl, 4-(3-N,N-diethylaminopropyl) piperazinyl-1-sulfonyl, morpholinyl-1-sulfonyl, 3,5-dimethylmorpholinyl-1-sulfonyl, 4-(4-methyl-piperazin-1-yl)piperidin-1-ylsulfonyl, 4-(4-ethyl-1-piperazinyl) piperidin-1-ylsulfonyl, 4-(4-acetyl-1-piperazinyl)piperidin-1-ylsulfonyl, 4-(N-methyl-4-piperidinyl)piperazinyl-1-sulfonyl, (8) hydroxycarbonyl, aminocarbonyl, methylaminocarbonyl, ethylaminocarbonyl, propylaminocarbonyl, isopropylaminocarbonyl, cyclopropylaminocarbonyl, cyclobutylaminocarbonyl, cyclopentylaminocarbonyl, piperidinyl-1-carbonyl, 4-hydroxypiperidinyl-1-carbonyl, 4-N,N-dimethylaminopiperidinyl-1-carbonyl, 4-N,N-diethylaminopiperidinyl-1-carbonyl, tetrahydropyrrolyl-1-carbonyl, 3-N,N-dimethylaminotetrahydropyrrolyl-1-carbonyl, 3-N,N-diethylaminotetrahydropyrrolyl-1-carbonyl, 4-methylpiperazin-1-ylcarbonyl, 4-ethylpiperazinyl-1-carbonyl, 4-acetylpiperazinyl-1-carbonyl, 4-t-butoxycarbonylpiperazinyl-1-carbonyl, 4-(2-hydroxyethyl)piperazinyl-1-carbonyl, 4-(2-cyanoethyl)piperazinyl-1-carbonyl, 4-(2-N,N-dimethylaminoethyl) piperazinyl-1-carbonyl, 4-(2-N,N-diethylaminoethyl) piperazinyl-1-carbonyl, 4-(3-hydroxypropyl)piperazinyl-1-carbonyl, 4-(3-N,N-dimethylaminopropyl)piperazinyl-1-carbonyl, 4-(3-N,N-diethylaminopropyl)piperazinyl-1-carbonyl, morpholinyl-1-carbonyl, 3,5-dimethylmorpholinyl-1-carbonyl, 4-(4-methyl-piperazin-1-yl)piperidin-1-ylcarbonyl, 4-(4-ethyl-1-piperazinyl) piperidinyl-1-carbonyl, 4-(4-acetyl-1-piperazinyl) piperidinyl-1-carbonyl, 4-(N-methyl-4-piperidinyl) piperazinyl-1-carbonyl, methoxycarbonyl, ethoxycarbonyl, propoxycarbonyl, isopropoxycarbonyl, n-butoxycarbonyl, isobutoxycarbonyl, tert-butoxycarbonyl, (9) aminoformamido, methylaminoformamido, ethylaminoformamido, propylaminoformamido, isopropylaminoformamido, cyclopropylaminoformamido, cyclobutylaminoformamido, cyclopentylaminoformamido, piperidinyl-1-formamido, 4-hydroxypiperidinyl-1-formamido, 4-N,N-dimethylaminopiperidinyl-1-formamido, 4-N,N-diethylaminopiperidinyl-1-formamido, tetrahydropyrrolyl-1-formamido, 3-N,N-dimethylaminotetrahydropyrrolyl-1-formamido, 3-N,N-diethylaminotetrahydropyrrolyl-1-formamido, 4-methylpiperazinyl-1-formamido, 4-ethylpiperazinyl-1-formamido, 4-acetylpiperazinyl-1-formamido, 4-t-butoxycarbonylpiperazinyl-1-formamido, 4-(2-hydroxyethyl)piperazinyl-1-formamido, 4-(2-cyanoethyl) piperazinyl-1-formamido, 4-(2-N,N-dimethylaminoethyl) piperazinyl-1-formamido, 4-(2-N,N-diethylaminoethyl) piperazinyl-1-formamido, 4-(3-hydroxypropyl)piperazinyl-1-formamido, 4-(3-N,N-dimethylaminopropyl)piperazinyl-1-formamido, 4-(3-N,N-diethylaminopropyl)piperazinyl-1-formamido, morpholinyl-1-formamido, 3,5-dimethylmorpholinyl-1-formamido, 4-(4-methyl-piperazin-1-yl)piperidinyl-1-formamido, 4-(4-ethyl-1-piperazinyl) piperidinyl-1-formamido, 4-(4-acetyl-1-piperazinyl) piperidinyl-1-formamido, 4-(N-methyl-4-piperidinyl) piperazinyl-1-formamido; or

(10) $Z_2$ and $Z_3$ or $Z_3$ and $Z_4$ form a nitrogen- or oxygen-containing substituted or unsubstituted 5- or 6-membered ring, the substituent may be selected from the same substituents as described above for $Z_1$;

$R_2$ is selected from

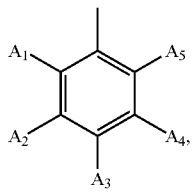

wherein $A_1$, $A_2$, $A_3$, $A_4$, $A_5$ each are independently selected from:

(1) H, F, Cl, Br, I, cyano, trifluoromethyl, trifluoromethoxy, nitro, (2) methylthio, ethylthio, isopropylthio, methylsulfinyl, ethylsulfinyl, isopropylsulfinyl, methylsulfonyl, ethylsulfonyl, isopropylsulfonyl, methylsulfonamido, methoxycarbonyl, ethoxycarbonyl, propoxycarbonyl, isopropoxycarbonyl, n-butoxycarbonyl, isobutoxycarbonyl, tert-butoxycarbonyl, methylaminocarbonyl, ethylaminocarbonyl, propylaminocarbonyl, isopropylaminocarbonyl, cyclopropylaminocarbonyl, cyclobutylaminocarbonyl, cyclopentylaminocarbonyl, dimethylphosphinyl, diethylphosphinyl, diisopropylphosphinyl.

In some embodiments, $R_1$ is selected from

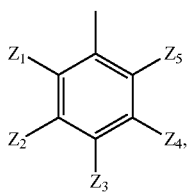

wherein $Z_1$, $Z_2$, $Z_3$, $Z_4$, $Z_5$ each are independently selected from:

(1) H,
(2) C1-C6 alkyl,
(3) C1-C6 alkoxy,
(4) piperidinyl, N-methyl-4-piperidinyl, 4-N,N-dimethylaminopiperidinyl, 4-N,N-diethylaminopiperidinyl, 4-N,N-diisopropylaminopiperidinyl, 4-hydroxypiperidinyl,
(5) 4-(4-methylpiperazinyl)piperidinyl, 4-(4-ethylpiperazinyl)piperidinyl, 4-(4-isopropylpiperazinyl)piperidinyl, 4-(4-acetylpiperazinyl)piperidinyl, 4-(4-t-butoxycarbonylpiperazinyl)piperidinyl, 4-(4-methylsulfonylpiperazinyl)piperidinyl, 4-(4-(2-hydroxyethyl)piperazinyl)piperidinyl, 4-(4-(2-cyanoethyl)piperazinyl)piperidinyl, 4-(4-(3-hydroxypropyl)piperazinyl)piperidinyl, 4-(4-(2-N,N-dimethylaminoethyl)piperazinyl)piperidinyl, 4-(4-(2-N,N-diethylaminoethyl)piperazinyl)piperidinyl, 4-(4-(3-N,N-dimethylaminopropyl)piperazinyl)piperidinyl, 4-(4-(3-N,N-diethylaminopropyl)piperazinyl)piperidinyl, 4-(tetrahydropyrrolyl)piperidinyl, 4-(3-N,N-dimethylaminotetrahydropyrrolyl)piperidinyl,
(6) 4-methylpiperazinyl, 4-ethylpiperazinyl, 4-isopropylpiperazinyl, 4-acetylpiperazinyl, 4-t-butoxycarbonylpiperazinyl, 4-methylsulfonylpiperazinyl, 4-(2-hydroxyethyl)piperazinyl, 4-(2-cyanoethyl)piperazinyl, 4-(3-hydroxypropyl) piperazinyl, 4-(2-N,N-dimethylaminoethyl)piperazinyl, 4-(2-N,N-diethylaminoethyl)piperazinyl, 4-(3-N,N-dimethylaminopropyl)piperazinyl, 4-(3-N,N-diethylaminopropyl)piperazinyl, 4-(N-methyl-4-piperidinyl)piperazinyl, 4-(N-ethyl-4-piperidinyl)piperazinyl or (7) $Z_2$ and $Z_3$ or $Z_3$ and $Z_4$ form a nitrogen- or oxygen-containing substituted or unsubstituted 5-membered ring, the substituent may be selected from the same substituents as described above for $Z_1$.

In some embodiments, $R_1$ is selected from:

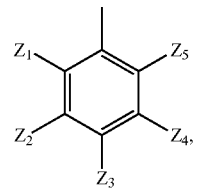

wherein $Z_1$, $Z_2$, $Z_3$, $Z_4$, Z each are independently selected from:

(1) H,
(2) methyl,
(3) methoxy, isopropoxy,
(4) N-methyl-4-piperidinyl, 4-(4-methylpiperazinyl)piperidinyl, 4-(tetrahydropyrrol-1-yl)piperidinyl,
(5) 4-methylpiperazinyl, or
(6) $Z_2$ and $Z_3$ or $Z_3$ and $Z_4$ form

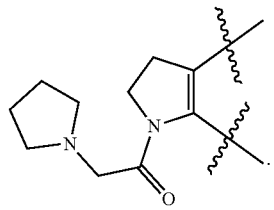 [SMILES: *C1=C(*)N(C(=O)CN2CCCC2)CC1]

In some embodiments, $R_1$ is selected from:

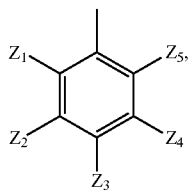

wherein one of $Z_2$ and $Z_4$ is H, the other is methyl, one of $Z_1$ and $Z_5$ is H, the other is selected from: methoxy, isopropoxy, $Z_3$ is selected from: N-methyl-4-piperidinyl, 4-methylpiperazinyl, 4-(4-methylpiperazinyl)piperidinyl, 4-tetrahydropyrrol-1-yl)piperidinyl, or $Z_2$ and $Z_3$ or $Z_3$ and $Z_4$ form

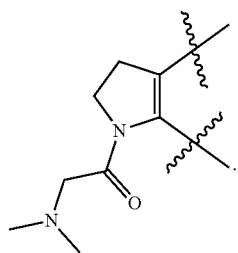 [SMILES: *C1=C(*)N(C(=O)CN(C)C)CC1]

In some embodiments, R$_2$ is selected from

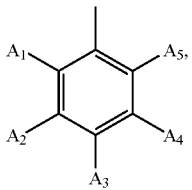

wherein A$_1$, A$_2$, A$_3$, A$_4$, A$_5$ each are independently selected from:
(1) H; (2) methoxycarbonyl.

In some embodiments, R$_2$ is selected from:

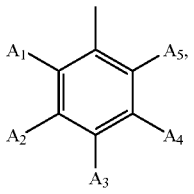

wherein one of A$_2$ and A$_4$ is H, the other is methoxycarbonyl; A$_1$, A$_3$, A$_5$ are all H.

In a eighth aspect, the present invention provides a compound of Formula IE, a stereoisomer thereof, a prodrug thereof, a pharmaceutically acceptable salt thereof or a pharmaceutically acceptable solvate thereof,

IE

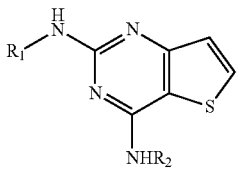

wherein, R$_1$ is selected from:
1) C1-C6 alkyl, 2-N,N-dimethylaminoethyl, 2-hydroxyethyl, 2-N,N-diethylaminoethyl, 2-N,N-diisopropylaminoethyl, 2-morpholinylethyl, 2-(4-methylpiperazinyl)ethyl, 3-N,N-dimethylaminopropyl, 3-N,N-diethylaminopropyl, 3-N,N-diisopropylaminopropyl, 3-morpholinylpropyl, 3-(4-methylpiperazinyl)propyl, C3-C6 cycloalkyl, 4-N,N-dimethylaminocyclohexyl, 4-N,N-diethylaminocyclohexyl, N-methyl-4-piperidinyl, N-ethyl-4-piperidinyl, N-isopropyl-4-piperidinyl, 1,3-dimethyl-5-pyrazolyl, 1-methyl-4-pyrazolyl, 3-methyl-5-isoxazolinyl, 1-(N-methyl-4-piperidinyl)-4-pyrazolyl, 1-(N-t-butoxycarbonyl-4-piperidinyl)-4-pyrazolyl;

2)

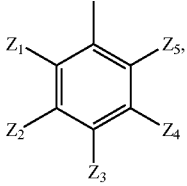

wherein Z$_1$, Z$_2$, Z$_3$, Z$_4$, Z$_5$ each are independently selected from:
(1) H, F, Cl, Br, I, nitro, cyano,
(2) C1-C6 alkyl, C1-C6 alkoxy, C1-C6 oxygen-containing alkyl, C1-C6 fluorine-containing alkyl, C1-C6 fluorine-containing alkoxy (3) piperidinyl, N-methyl-4-piperidinyl, 4-N,N-dimethylaminopiperidinyl, 4-N,N-diethylaminopiperidinyl, 4-N,N-diisopropylaminopiperidinyl, 4-hydroxypiperidinyl, 4-(4-methylpiperazinyl)piperidinyl, 4-(4-ethylpiperazinyl)piperidinyl, 4-(4-isopropylpiperazinyl)piperidinyl, 4-(4-acetylpiperazinyl)piperidinyl, 4-(4-t-butoxycarbonylpiperazinyl)piperidinyl, 4-(4-methylsulfonylpiperazinyl)piperidinyl, 4-(4-(2-hydroxyethyl)piperazinyl)piperidinyl, 4-(4-(2-cyanoethyl)piperazinyl)piperidinyl, 4-(4-(3-hydroxypropyl)piperazinyl)piperidinyl, 4-(4-(2-N,N-dimethylaminoethyl)piperazinyl)piperidinyl, 4-(4-(2-N,N-diethylaminoethyl)piperazinyl)piperidinyl, 4-(4-(3-N,N-dimethylaminopropyl)piperazinyl)piperidinyl, 4-(4-(3-N,N-diethylaminopropyl)piperazinyl)piperidinyl, 4-(tetrahydropyrrolyl)piperidinyl, 4-(3-N,N-dimethylaminotetrahydropyrrolyl)piperidinyl, (4) 4-methylpiperazinyl, 4-ethylpiperazinyl, 4-isopropylpiperazinyl, 4-acetylpiperazinyl, 4-t-butoxycarbonylpiperazinyl, 4-methylsulfonylpiperazinyl, 4-(2-hydroxyethyl)piperazinyl, 4-(2-cyanoethyl)piperazinyl, 4-(3-hydroxypropyl)piperazinyl, 4-(2-N,N-dimethylaminoethyl)piperazinyl, 4-(2-N,N-diethylaminoethyl)piperazinyl, 4-(3-N,N-dimethylaminopropyl)piperazinyl, 4-(3-N,N-diethylaminopropyl)piperazinyl, 4-(N-methyl-4-piperidinyl)piperazinyl, 4-(N-ethyl-4-piperidinyl)piperazinyl, (5) N,N-dimethylamino, N,N-diethylamino, N,N-diisopropylamino, 2-N,N-dimethylaminoethylamino, 2-morpholinylethylamino, 2-(4-methylpiperazinyl)ethylamino, 3-N,N-dimethylaminopropylamino, 3-N,N-diethylaminopropylamino, 3-N,N-diisopropylaminopropylamino, 3-morpholinylpropylamino, 3-(4-methylpiperazinyl)propylamino, N-methylpiperidinyl-4-amino, N-ethylpiperidinyl-4-amino, N-isopropylpiperidinyl-4-amino, (6) 2-N,N-dimethylaminoethoxy, 2-N,N-diethylaminoethoxy, 2-N,N-diisopropylaminoethoxy, 2-(4-methylpiperazinyl)ethoxy, 2-(4-acetylpiperazinyl)ethoxy, 2-morpholinylethoxy, 2-thiomorpholinylethoxy, 2-piperidinylethoxy, 3-N,N-dimethylaminopropoxy, 3-N,N-diethylaminopropoxy, 3-N,N-diisopropylaminopropoxy, 3-(4-methylpiperazinyl)propoxy, 3-(4-acetylpiperazinyl)propoxy, 3-morpholinylpropoxy, 3-thiomorpholinylpropoxy, 3-piperidinylpropoxy, pyridin-2-ylmethoxy, pyridin-3-ylmethoxy, pyridin-4-ylmethoxy, phenylmethoxy, monohalo-substituted phenylmethoxy, gem-dihalo-substituted phenylmethoxy, hetero-dihalo-substituted phenylmethoxy, (7) hydroxysulfonyl, aminosulfonyl, methylaminosulfonyl, ethylaminosulfonyl, propylaminosulfonyl, isopropylaminosulfonyl, cyclopropylaminosulfonyl, cyclobutylaminosulfonyl, cyclopentylaminosulfonyl, piperidin-1-ylsulfonyl, 4-hydroxypiperidin-1-ylsulfonyl, 4-N,N-dimethylaminopiperidin-1-ylsulfonyl, 4-N,N-diethylaminopiperidin-1-ylsulfonyl, tetrahydropyrrolyl-1-sulfonyl, 3-N,N-dimethylaminotetrahydropyrrolyl-1-sulfonyl, 3-N,N-diethylaminotetrahydropyrrolyl-1-sulfonyl, 4-methylpiperazin-1-ylsulfonyl, 4-ethylpiperazinyl-1-sulfonyl, 4-acetylpiperazinyl-1-sulfonyl, 4-t-butoxycarbonylpiperazinyl-1-sulfonyl, 4-(2-hydroxyethyl)piperazinyl-1-sulfonyl, 4-(2-cyanoethyl)piperazinyl-1-sulfonyl, 4-(2-N,N-dimethylaminoethyl)piperazinyl-1-sulfonyl, 4-(2-N,N-diethylethyl)piperazinyl-1-sulfonyl, 4-(3-hydroxypropyl)piperazinyl-1-sulfonyl, 4-(3-N,N-dimethylaminopropyl)piperazinyl-1-sulfonyl, 4-(3-N,N-diethylaminopropyl)piperazinyl-1-sulfonyl, morpholinyl-1-sulfonyl, 3,5-dimethylmorpholinyl-1-sulfonyl, 4-(4-methyl-piperazin-1-yl)piperidin-1-ylsulfonyl, 4-(4-ethyl-1-piperazinyl)

piperidin-1-ylsulfonyl, 4-(4-acetyl-1-piperazinyl)piperidin-1-ylsulfonyl, 4-(N-methyl-4-piperidinyl)piperazinyl-1-sulfonyl, (8) hydroxycarbonyl, aminocarbonyl, methylaminocarbonyl, ethylaminocarbonyl, propylaminocarbonyl, isopropylaminocarbonyl, cyclopropylaminocarbonyl, cyclobutylaminocarbonyl, cyclopentylaminocarbonyl, piperidinyl-1-carbonyl, 4-hydroxypiperidinyl-1-carbonyl, 4-N,N-dimethylaminopiperidinyl-1-carbonyl, 4-N,N-diethylaminopiperidinyl-1-carbonyl, tetrahydropyrrolyl-1-carbonyl, 3-N,N-dimethylaminotetrahydropyrrolyl-1-carbonyl, 3-N,N-diethylaminotetrahydropyrrolyl-1-carbonyl, 4-methylpiperazin-1-ylcarbonyl, 4-ethylpiperazinyl-1-carbonyl, 4-acetylpiperazinyl-1-carbonyl, 4-t-butoxycarbonylpiperazinyl-1-carbonyl, 4-(2-hydroxyethyl)piperazinyl-1-carbonyl, 4-(2-cyanoethyl)piperazinyl-1-carbonyl, 4-(2-N,N-dimethylaminoethyl)piperazinyl-1-carbonyl, 4-(2-N,N-diethylaminoethyl)piperazinyl-1-carbonyl, 4-(3-hydroxypropyl)piperazinyl-1-carbonyl, 4-(3-N,N-dimethylaminopropyl)piperazinyl-1-carbonyl, 4-(3-N,N-diethylaminopropyl)piperazinyl-1-carbonyl, morpholinyl-1-carbonyl, 3,5-dimethylmorpholinyl-1-carbonyl, 4-(4-methyl-piperazin-1-yl)piperidin-1-ylcarbonyl, 4-(4-ethyl-1-piperazinyl)piperidinyl-1-carbonyl, 4-(4-acetyl-1-piperazinyl)piperidinyl-1-carbonyl, 4-(N-methyl-4-piperidinyl)piperazinyl-1-carbonyl, methoxycarbonyl, ethoxycarbonyl, propoxycarbonyl, isopropoxycarbonyl, n-butoxycarbonyl, isobutoxycarbonyl, tert-butoxycarbonyl, (9) aminoformamido, methylaminoformamido, ethylaminoformamido, propylaminoformamido, isopropylaminoformamido, cyclopropylaminoformamido, cyclobutylaminoformamido, cyclopentylaminoformamido, piperidinyl-1-formamido, 4-hydroxypiperidinyl-1-formamido, 4-N,N-dimethylaminopiperidinyl-1-formamido, 4-N,N-diethylaminopiperidinyl-1-formamido, tetrahydropyrrolidinyl-1-formamido, 3-N,N-dimethylaminotetrahydropyrrolyl-1-formamido, 3-N,N-diethylaminotetrahydropyrrolyl-1-formamido, 4-methylpiperazinyl-1-formamido, 4-ethylpiperazinyl-1-formamido, 4-acetylpiperazinyl-1-formamido, 4-t-butoxycarbonylpiperazinyl-1-formamido, 4-(2-hydroxyethyl)piperazinyl-1-formamido, 4-(2-cyanoethyl)piperazinyl-1-formamido, 4-(2-N,N-dimethylaminoethyl)piperazinyl-1-formamido, 4-(2-N,N-diethylaminoethyl)piperazinyl-1-formamido, 4-(3-hydroxypropyl)piperazinyl-1-formamido, 4-(3-N,N-dimethylaminopropyl)piperazinyl-1-formamido, 4-(3-N,N-diethylaminopropyl)piperazinyl-1-formamido, morpholinyl-1-formamido, 3,5-dimethylmorpholinyl-1-formamido, 4-(4-methyl-piperazin-1-yl)piperidinyl-1-formamido, 4-(4-ethyl-1-piperazinyl)piperidinyl-1-formamido, 4-(4-acetyl-1-piperazinyl)piperidinyl-1-formamido, 4-(N-methyl-4-piperidinyl)piperazin-1-formamido;

$R_2$ is selected from

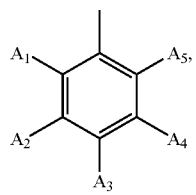

wherein $A_1$, $A_2$, $A_3$, $A_4$, $A_5$ each are independently selected from:
(1) H, F, Cl, Br, I, cyano, trifluoromethyl, trifluoromethoxy, nitro,
(2) methylthio, ethylthio, methylsulfinyl, ethylsulfinyl, methylsulfonyl, ethylsulfonyl, methylsulfonamido, methoxycarbonyl, ethoxycarbonyl, propoxycarbonyl, isopropoxycarbonyl, n-butoxycarbonyl, methylaminocarbonyl, ethylaminocarbonyl, propylaminocarbonyl, cyclopropylaminocarbonyl, cyclobutylaminocarbonyl, cyclopentylaminocarbonyl, dimethylphosphinyl.

In some embodiments, $R_1$ is selected from:

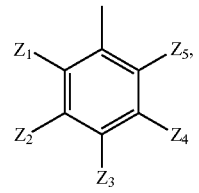

wherein $Z_1$, $Z_2$, $Z_3$, $Z_4$, $Z_5$ each are independently selected from:
(1) H,
(2) C1-C6 alkyl,
(3) C1-C6 alkoxy,
(4) piperidinyl, N-methyl-4-piperidinyl, 4-N,N-dimethylaminopiperidinyl, 4-N,N-diethylaminopiperidinyl, 4-N,N-diisopropylaminopiperidinyl, 4-hydroxypiperidinyl,
(5) 4-(4-methylpiperazinyl)piperidinyl, 4-(4-ethylpiperazinyl)piperidinyl, 4-(4-isopropylpiperazinyl)piperidinyl, 4-(4-acetylpiperazinyl)piperidinyl, 4-(4-t-butoxycarbonylpiperazinyl)piperidinyl, 4-(4-methylsulfonylpiperazinyl)piperidinyl, 4-(4-(2-hydroxyethyl)piperazinyl)piperidinyl, 4-(4-(2-cyanoethyl)piperazinyl)piperidinyl, 4-(4-(3-hydroxypropyl)piperazinyl)piperidinyl, 4-(4-(2-N,N-dimethylaminoethyl)piperazinyl)piperidinyl, 4-(4-(2-N,N-diethylaminoethyl)piperazinyl)piperidinyl, 4-(4-(3-N,N-dimethylaminopropyl)piperazinyl)piperidinyl, 4-(4-(3-N,N-diethylaminopropyl)piperazinyl)piperidinyl, 4-(tetrahydropyrrolyl)piperidinyl, 4-(3-N,N-dimethylaminotetrahydropyrrolyl)piperidinyl,
(6) 4-methylpiperazinyl, 4-ethylpiperazinyl, 4-isopropylpiperazinyl, 4-acetylpiperazinyl, 4-t-butoxycarbonylpiperazinyl, 4-methylsulfonylpiperazinyl, 4-(2-hydroxyethyl)piperazinyl, 4-(2-cyanoethyl)piperazinyl, 4-(3-hydroxypropyl)piperazinyl, 4-(2-N,N-dimethylaminoethyl)piperazinyl, 4-(2-N,N-diethylaminoethyl)piperazinyl, 4-(3-N,N-dimethylaminopropyl)piperazinyl, 4-(3-N,N-diethylaminopropyl)piperazinyl, 4-(N-methyl-4-piperidinyl)piperazinyl, 4-(N-ethyl-4-piperidinyl)piperazinyl.

In some embodiments, $R_1$ is selected from

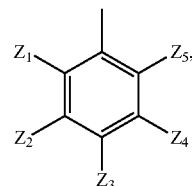

wherein $Z_1$, $Z_2$, $Z_3$, $Z_4$, $Z_5$ each are independently selected from:
(1) H,
(2) methyl, methoxy, ethoxy, isopropoxy,
(3) N-methyl-4-piperidinyl, 4-hydroxypiperidinyl, 4-(4-methylpiperazinyl)piperidinyl, 4-(tetrahydropyrrol-1-yl)piperidinyl,
(4) 4-methylpiperazinyl.

In some embodiments, $R_1$ is selected from:

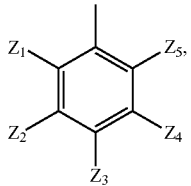

wherein one of $Z_1$ and $Z_5$ is H, the other is selected from: methoxy, ethoxy, isopropoxy;
one of $Z_2$ and $Z_4$ is H, the other is methyl;
$Z_3$ is selected from: N-methyl-4-piperidinyl, 4-hydroxypiperidinyl, 4-methylpiperazinyl, 4-(4-methylpiperazinyl)piperidinyl, 4-(tetrahydropyrrol-1-yl)piperidinyl.

In some embodiments, $R_2$ is selected from

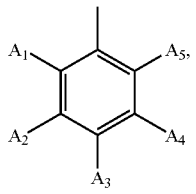

wherein $A_1$, $A_2$, $A_3$, $A_4$, $A_5$ each are independently selected from:
(1) H, (2) methoxycarbonyl.

In some embodiments, $R_2$ is selected from

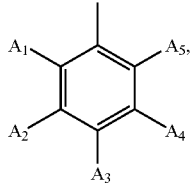

wherein one of $A_1$ and $A_5$ is H, the other is methoxycarbonyl; $A_2$, $A_3$, $A_4$ are all H.

In a ninth aspect, the present invention provides a compound of Formula IF, a stereoisomer thereof, a prodrug thereof, a pharmaceutically acceptable salt thereof or a pharmaceutically acceptable solvate thereof,

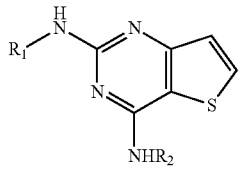

IF wherein, $R_1$ is selected from:
1) C1-C6 alkyl, 2-N,N-dimethylaminoethyl, 2-hydroxyethyl, 2-N,N-diethylaminoethyl, 2-N,N-diisopropylaminoethyl, 2-morpholinylethyl, 2-(4-methylpiperazinyl)ethyl, 3-N,N-dimethylaminopropyl, 3-N,N-diethylaminopropyl, 3-N,N-diisopropylaminopropyl, 3-morpholinylpropyl, 3-(4-methylpiperazinyl)propyl, C3-C6 cycloalkyl, 4-N,N-dimethylaminocyclohexyl, 4-N,N-diethylaminocyclohexyl, N-methyl-4-piperidinyl, N-ethyl-4-piperidinyl, N-isopropyl-4-piperidinyl, 1,3-dimethyl-5-pyrazolyl, 1-methyl-4-pyrazolyl, 3-methyl-5-isoxazolinyl, 1-(N-methyl-4-piperidinyl)-4-pyrazolyl, 1-(N-t-butoxycarbonyl-4-piperidinyl)-4-pyrazolyl;

2)

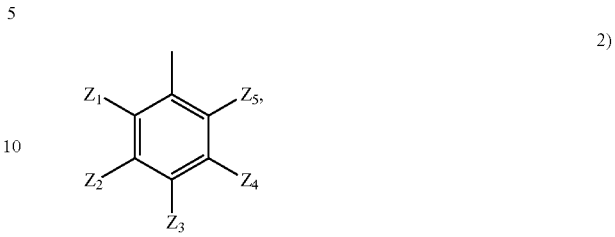

wherein $Z_1$, $Z_2$, $Z_3$, $Z_4$, $Z_5$ each are independently selected from:
(1) H, F, Cl, Br, I, nitro, cyano,
(2) C1-C6 alkyl, C1-C6 alkoxy, C1-C6 oxygen-containing alkyl, C1-C6 fluorine-containing alkyl, C1-C6 fluorine-containing alkoxy
(3) piperidinyl, N-methyl-4-piperidinyl, 4-N,N-dimethylaminopiperidinyl, 4-N,N-diethylaminopiperidinyl, 4-N,N-diisopropylaminopiperidinyl, 4-hydroxypiperidinyl, 4-(4-methylpiperazinyl)piperidinyl, 4-(N-ethylpiperazinyl) piperidinyl, 4-(4-isopropylpiperazinyl)piperidinyl, 4-(4-acetylpiperazinyl)piperidinyl, 4-(4-t-butoxycarbonylpiperazinyl)piperidinyl, 4-(4-methylsulfonylpiperazinyl)piperidinyl, 4-(4-(2-hydroxyethyl)piperazinyl)piperidinyl, 4-(4-(2-cyanoethyl) piperazinyl)piperidinyl, 4-(4-(3-hydroxypropyl)piperazinyl) piperidinyl, 4-(4-(2-N,N-dimethylaminoethyl)piperazinyl) piperidinyl, 4-(4-(2-N,N-diethylaminoethyl)piperazinyl) piperidinyl, 4-(4-(3-N,N-dimethylaminopropyl)piperazinyl) piperidinyl, 4-(4-(3-N,N-diethylaminopropyl)piperazinyl) piperidinyl, 4-(tetrahydropyrrolyl)piperidinyl, 4-(3-N,N-dimethylaminotetrahydropyrrolyl)piperidinyl,
(4) 4-methylpiperazinyl, 4-ethylpiperazinyl, 4-isopropylpiperazinyl, 4-acetylpiperazinyl, 4-t-butoxycarbonylpiperazinyl, 4-methylsulfonylpiperazinyl, 4-(2-hydroxyethyl)piperazinyl, 4-(2-cyanoethyl)piperazinyl, 4-(3-hydroxypropyl) piperazinyl, 4-(2-N,N-dimethylaminoethyl)piperazinyl, 4-(2-N,N-diethylaminoethyl)piperazinyl, 4-(3-N,N-dimethylaminopropyl)piperazinyl, 4-(3-N,N-diethylaminopropyl) piperazinyl, 4-(N-methyl-4-piperidinyl)piperazinyl, 4-(N-ethyl-4-piperidinyl)piperazinyl,
(5) N,N-dimethylamino, N,N-diethylamino, N,N-diisopropylamino, 2-N,N-dimethylaminoethylamino, 2-morpholinylethylamino, 2-(4-methylpiperazinyl)ethylamino, 3-N,N-dimethylaminopropylamino, 3-N,N-diethylaminopropylamino, 3-N,N-diisopropylaminopropylamino, 3-morpholinylpropylamino, 3-(4-methylpiperazinyl)propylamino, N-methylpiperidinyl-4-amino, N-ethylpiperidinyl-4-amino, N-isopropylpiperidinyl-4-amino,
(6) 2-N,N-dimethylaminoethoxy, 2-N,N-diethylaminoethoxy, 2-N,N-diisopropylaminoethoxy, 2-(4-methylpiperazinyl)ethoxy, 2-(4-acetylpiperazinyl)ethoxy, 2-morpholinylethoxy, 2-thiomorpholinylethoxy, 2-piperidinylethoxy, 3-N,N-dimethylaminopropoxy, 3-N,N-diethylaminopropoxy, 3-N,N-diisopropylaminopropoxy, 3-(4-methylpiperazinyl)propoxy, 3-(4-acetylpiperazinyl)propoxy, 3-morpholinylpropoxy, 3-thiomorpholinylpropoxy, 3-piperidinylpropoxy, pyridin-2-ylmethoxy, pyridin-3-ylmethoxy, pyridin-4-ylmethoxy, phenylmethoxy, monohalo-substituted phenylmethoxy, gem-dihalo-substituted phenylmethoxy, hetero-dihalo-substituted phenylmethoxy,
(7) hydroxysulfonyl, aminosulfonyl, methylaminosulfonyl, ethylaminosulfonyl, propylaminosulfonyl, isopropylaminosulfonyl, cyclopropylaminosulfonyl, cyclobutylaminosulfonyl, cyclopentylaminosulfonyl, piperidin-1-ylsulfonyl, 4-hydroxypiperidin-1-ylsulfonyl, 4-N,N-dimethylaminopiperidin-1-ylsulfonyl, 4-N,N-diethylaminopiperidin-1-ylsulfonyl, tetrahydropyrrolyl-1-sulfonyl, 3-N,N-dimethylaminotetrahydropyrrolyl-1-sulfonyl, 3-N,N-diethylaminotetrahydropyrrolyl-1-sulfonyl, 4-methylpiperazin-1-ylsulfonyl, 4-ethylpiperazinyl-1-sulfonyl, 4-acetylpiperazinyl-1-sulfonyl, 4-t-butoxycarbonylpiperazinyl-1-sulfonyl, 4-(2-hydroxyethyl)piperazinyl-1-sulfonyl, 4-(2-cyanoethyl)piperazinyl-1-sulfonyl, 4-(2-N,N-dimethylaminoethyl)piperazinyl-1-sulfonyl, 4-(2-N,N-diethylethyl)piperazinyl-1-sulfonyl, 4-(3-hydroxypropyl)piperazinyl-1-sulfonyl, 4-(3-N,N-dimethylaminopropyl)piperazinyl-1-sulfonyl, 4-(3-N,N-diethylaminopropyl)piperazinyl-1-sulfonyl, morpholinyl-1-sulfonyl, 3,5-dimethylmorpholinyl-1-sulfonyl, 4-(4-methyl-piperazin-1-yl)piperidin-1-ylsulfonyl, 4-(4-ethyl-1-piperazinyl)piperidin-1-ylsulfonyl, 4-(4-acetyl-1-piperazinyl)piperidin-1-ylsulfonyl, 4-(N-methyl-4-piperidinyl)piperazinyl-1-sulfonyl, (8) hydroxycarbonyl, aminocarbonyl, methylaminocarbonyl, ethylaminocarbonyl, propylaminocarbonyl, isopropylaminocarbonyl, cyclopropylaminocarbonyl, cyclobutylaminocarbonyl, cyclopentylaminocarbonyl, piperidin-1-carbonyl, 4-hydroxypiperidinyl-1-carbonyl, 4-N,N-dimethylaminopiperidinyl-1-carbonyl, 4-N,N-diethylaminopiperidinyl-1-carbonyl, tetrahydropyrrolyl-1-carbonyl, 3-N,N-dimethylaminotetrahydropyrrolyl-1-carbonyl, 3-N,N-diethylaminotetrahydropyrrolyl-1-carbonyl, 4-methylpiperazin-1-ylcarbonyl, 4-ethylpiperazinyl-1-carbonyl, 4-acetylpiperazinyl-1-carbonyl, 4-t-butoxycarbonylpiperazinyl-1-carbonyl, 4-(2-hydroxyethyl)piperazinyl-1-carbonyl, 4-(2-cyanoethyl)piperazinyl-1-carbonyl, 4-(2-N,N-dimethylaminoethyl)piperazinyl-1-carbonyl, 4-(2-N,N-diethylaminoethyl)piperazinyl-1-carbonyl, 4-(3-hydroxypropyl)piperazinyl-1-carbonyl, 4-(3-N,N-dimethylaminopropyl)piperazinyl-1-carbonyl, 4-(3-N,N-diethylaminopropyl)piperazinyl-1-carbonyl, morpholinyl-1-carbonyl, 3,5-dimethylmorpholinyl-1-carbonyl, 4-(4-methyl-piperazin-1-yl)piperidin-1-ylcarbonyl, 4-(4-ethyl-1-piperazinyl)piperidinyl-1-carbonyl, 4-(4-acetyl-1-piperazinyl)piperidinyl-1-carbonyl, 4-(N-methyl-4-piperidinyl)piperazinyl-1-carbonyl, methoxycarbonyl, ethoxycarbonyl, propoxycarbonyl, isopropoxycarbonyl, n-butoxycarbonyl, isobutoxycarbonyl, tert-butoxycarbonyl, (9) aminoformamido, methylaminoformamido, ethylaminoformamido, propylaminoformamido, isopropylaminoformamido, cyclopropylaminoformamido, cyclobutylaminoformamido, cyclopentylaminoformamido, piperidinyl-1-formamido, 4-hydroxypiperidinyl-1-formamido, 4-N,N-dimethylaminopiperidinyl-1-formamido, 4-N,N-diethylaminopiperidinyl-1-formamido, tetrahydropyrrolyl-1-formamido, 3-N,N-dimethylaminotetrahydropyrrolyl-1-formamido, 3-N,N-diethylaminotetrahydropyrrolyl-1-formamido, 4-methylpiperazinyl-1-formamido, 4-ethylpiperazinyl-1-formamido, 4-acetylpiperazinyl-1-formamido, 4-t-butoxycarbonylpiperazinyl-1-formamido, 4-(2-hydroxyethyl)piperazinyl-1-formamido, 4-(2-cyanoethyl)piperazinyl-1-formamido, 4-(2-N,N-dimethylaminoethyl)piperazinyl-1-formamido, 4-(2-N,N-diethylaminoethyl)piperazinyl-1-formamido, 4-(3-hydroxypropyl)piperazinyl-1-formamido, 4-(3-N,N-dimethylaminopropyl)piperazinyl-1-formamido, 4-(3-N,N-diethylaminopropyl)piperazinyl-1-formamido, morpholinyl-1-formamido, 3,5-dimethylmorpholinyl-1-formamido, 4-(4-methyl-piperazin-1-yl)piperidinyl-1-formamido, 4-(4-ethyl-1-piperazinyl)piperidinyl-1-formamido, 4-(4-acetyl-1-piperazinyl)piperidinyl-1-formamido, 4-(N-methyl-4-piperidinyl)piperazinyl-1-formamido; or

(10) $Z_2$ and $Z_3$ or $Z_3$ and $Z_4$ form a nitrogen- or oxygen-containing substituted or unsubstituted 5- or 6-membered ring, the substituent may be selected from the same substituents as described above for $Z_1$;

$R_2$ is selected from

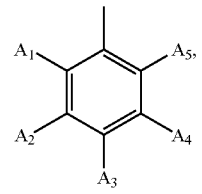

wherein $A_1$, $A_2$, $A_3$, $A_4$, $A_5$ each are independently selected from:

(1) H, F, Cl, Br, I, cyano, trifluoromethyl, trifluoromethoxy, nitro, (2) methylthio, ethylthio, isopropylthio, methylsulfinyl, ethylsulfinyl, isopropylsulfinyl, methylsulfonyl, ethylsulfonyl, isopropylsulfonyl, methylsulfonamido, methoxycarbonyl, ethoxycarbonyl, propoxycarbonyl, isopropoxycarbonyl, n-butoxycarbonyl, isobutoxycarbonyl, tert-butoxycarbonyl, methylaminocarbonyl, ethylaminocarbonyl, propylaminocarbonyl, isopropylaminocarbonyl, cyclopropylaminocarbonyl, cyclobutylaminocarbonyl, cyclopentylaminocarbonyl, dimethylphosphinyl, diethylphosphinyl, diisopropylphosphinyl.

In some embodiments, $R_1$ is selected from:

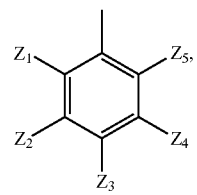

wherein $Z_1$, $Z_2$, $Z_3$, $Z_4$, $Z_5$ each are independently selected from:

(1) H, (2) C1-C6 alkoxy, (3) 4-methylpiperazinyl, 4-ethylpiperazinyl, 4-isopropylpiperazinyl, 4-acetylpiperazinyl, 4-t-butoxycarbonylpiperazinyl, 4-methylsulfonylpiperazinyl, 4-(2-hydroxyethyl)piperazinyl, 4-(2-cyanoethyl)piperazinyl, 4-(3-hydroxypropyl)piperazinyl, 4-(2-N,N-dimethylaminoethyl)piperazinyl, 4-(2-N,N-diethylaminoethyl)piperazinyl, 4-(3-N,N-dimethylaminopropyl)piperazinyl, 4-(3-N,N-diethylaminopropyl)piperazinyl, 4-(N-methyl-4-piperidinyl)piperazinyl, 4-(N-ethyl-4-piperidinyl)piperazinyl (4) piperidinyl, N-methyl-4-piperidinyl, 4-N,N-dimethylaminopiperidinyl, 4-N,N-diethylaminopiperidinyl, 4-N,N-diisopropylaminopiperidinyl, 4-hydroxypiperidinyl, 4-(4-methylpiperazinyl)piperidinyl, 4-(4-ethylpiperazinyl)piperidinyl, 4-(4-isopropylpiperazinyl)piperidinyl, 4-(4-acetylpiperazinyl)piperidinyl, 4-(4-t-butoxycarbonylpiperazinyl)piperidinyl, 4-(4-methylsulfonylpiperazinyl)piperidinyl, 4-(4-(2-hydroxyethyl)piperazinyl)piperidinyl, 4-(4-(2-cyanoethyl)piperazinyl)piperidinyl, 4-(4-(3-hydroxypropyl)piperazinyl)piperidinyl piperidinyl, 4-(4-(2-N,N-dimethylaminoethyl)piperazinyl)piperidinyl, 4-(4-(2-N,N-diethylaminoethyl)piperazinyl)piperidinyl, 4-(4-(3-N,N-dimethylaminopropyl)piperazinyl)piperidinyl, 4-(4-(3-N,N-diethylaminopropyl)piperazinyl)piperidinyl, 4-(tetrahydropyrrol-1-yl)piperidinyl, 4-(3-N,N-dimethylaminotetrahydropyrrolyl)piperidinyl, or (5) $Z_2$ and $Z_3$ or $Z_3$ and $Z_4$ form a nitrogen- or oxygen-containing substituted or unsubstituted 5-membered ring, the substituent may be selected from the same substituents as described above for $Z_1$.

In some embodiments, $R_1$ is selected from:

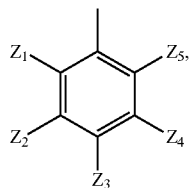

wherein $Z_1$, $Z_2$, $Z_3$, $Z_4$, $Z_5$ each are independently selected from:
(1) H,
(2) methoxy,
(3) 4-methylpiperazinyl,
(4) 4-(4-methylpiperazinyl)piperidinyl, or
(5) $Z_2$ and $Z_3$ or $Z_3$ and $Z_4$ form

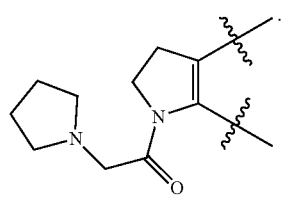 [SMILES: *C1=C(*)N(C(=O)CN2CCCC2)CC1]

In some embodiments, $R_1$ is selected from:

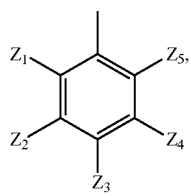

wherein one of $Z_1$ and $Z_5$ is H, the other is methoxy; $Z_4$ is H;
$Z_3$ is selected from: 4-methylpiperazinyl, 4-(4-methylpiperazinyl)piperidinyl, or
$Z_2$ and $Z_3$ form

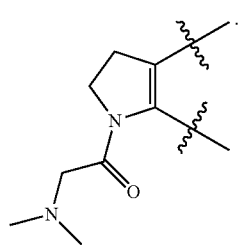 [SMILES: *C1=C(*)N(C(=O)CN(C)C)CC1]

In some embodiments, $R_2$ is selected from

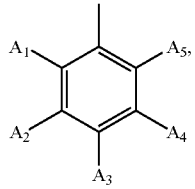

wherein $A_1$, $A_2$, $A_3$, $A_4$, $A_5$ each are independently selected from:
(1) H, (2) fluoro, (3) methylaminocarbonyl.

In some embodiments, $R_2$ is selected from:

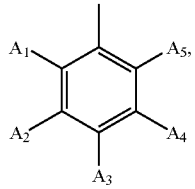

wherein one of $A_1$ and $A_5$ is H, the other is selected from: fluoro, methylaminocarbonyl; and one of $A_2$ and $A_4$ is H, the other is selected from: fluoro, methylaminocarbonyl; $A_3$ is H.

In some embodiments, $R_2$ is selected from:

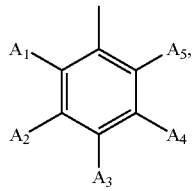

wherein, one of $A_1$ and $A_5$ is H, the other is methylaminocarbonyl; and one of $A_2$ and $A_4$ is H, the other is fluoro; $A_3$ is H.

In a tenth aspect, the present invention provides a compound of Formula IG, a stereoisomer thereof, a prodrug thereof, a pharmaceutically acceptable salt thereof or a pharmaceutically acceptable solvate thereof,

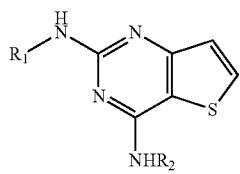

IG wherein, $R_1$ is selected from:
1) propylaminoethyl, 2-morpholinylethyl, 2-(4-methylpiperazinyl)ethyl, 3-N,N-dimethylaminopropyl, 3-N,N-diethylaminopropyl, 3-N,N-diisopropylaminopropyl, 3-morpholinylpropyl, 3-(4-methylpiperazinyl)propyl, C3-C6 cycloalkyl, 4-N,N-dimethylaminocyclohexyl, 4-N,N-diethylaminocyclohexyl, N-methyl-4-piperidinyl, N-ethyl-4-piperidinyl, N-isopropyl-4-piperidinyl, 1,3-dimethyl-5-pyrazolyl, 1-methyl-4-pyrazolyl, 3-methyl-5-isoxazolinyl, 1-(N-methyl-4-piperidinyl)-4-pyrazolyl, 1-(N-t-butoxycarbonyl-4-piperidinyl)-4-pyrazolyl;

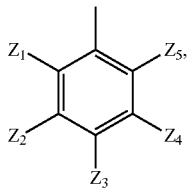

wherein $Z_1$, $Z_2$, $Z_3$, $Z_4$, $Z_5$ each are independently selected from:

(1) H, F, Cl, Br, I, nitro, cyano, (2) C1-C6 alkyl, C1-C6 alkoxy, C1-C6 oxygen-containing alkyl, C1-C6 fluorine-containing alkyl, C1-C6 fluorine-containing alkoxy, (3) piperidinyl, N-methyl-4-piperidinyl, 4-N,N-dimethylaminopiperidinyl, 4-N,N-diethylaminopiperidinyl, 4-N,N-diisopropylaminopiperidinyl, 4-hydroxypiperidinyl, 4-(4-methylpiperazinyl)piperidinyl, 4-(4-ethylpiperazinyl)piperidinyl, 4-(4-isopropylpiperazinyl)piperidinyl, 4-(4-acetylpiperazinyl)piperidinyl, 4-(4-t-butoxycarbonylpiperazinyl)piperidinyl, 4-(4-methylsulfonylpiperazinyl)piperidinyl, 4-(4-(2-hydroxyethyl)piperazinyl)piperidinyl, 4-(4-(2-cyanoethyl)piperazinyl)piperidinyl, 4-(4-(3-hydroxypropyl)piperazinyl)piperidinyl, 4-(4-(2-N,N-dimethylaminoethyl)piperazinyl)piperidinyl, 4-(4-(2-N,N-diethylaminoethyl)piperazinyl)piperidinyl, 4-(4-(3-N,N-dimethylaminopropyl)piperazinyl)piperidinyl, 4-(4-(3-N,N-diethylaminopropyl)piperazinyl)piperidinyl, 4-(tetrahydropyrrolyl)piperidinyl, 4-(3-N,N-dimethylaminotetrahydropyrrolyl)piperidinyl, (4) 4-methylpiperazinyl, 4-ethylpiperazinyl, 4-isopropylpiperazinyl, 4-acetylpiperazinyl, 4-t-butoxycarbonylpiperazinyl, 4-methylsulfonylpiperazinyl, 4-(2-hydroxyethyl)piperazinyl, 4-(2-cyanoethyl)piperazinyl, 4-(3-hydroxypropyl)piperazinyl, 4-(2-N,N-dimethylaminoethyl)piperazinyl, 4-(2-N,N-diethylaminoethyl)piperazinyl, 4-(3-N,N-dimethylaminopropyl)piperazinyl, 4-(3-N,N-diethylaminopropyl)piperazinyl, 4-(N-methyl-4-piperidinyl)piperazinyl, 4-(N-ethyl-4-piperidinyl)piperazinyl, (5) N,N-dimethylamino, N,N-diethylamino, N,N-diisopropylamino, 2-N,N-dimethylaminoethylamino, 2-morpholinylethylamino, 2-(4-methylpiperazinyl)ethylamino, 3-N,N-dimethylaminopropylamino, 3-N,N-diethylaminopropylamino, 3-N,N-diisopropylaminopropylamino, 3-morpholinylpropylamino, 3-(4-methylpiperazinyl)propylamino, N-methylpiperidinyl-4-amino, N-ethylpiperidinyl-4-amino, N-isopropylpiperidinyl-4-amino, (6) 2-N,N-dimethylaminoethoxy, 2-N,N-diethylaminoethoxy, 2-N,N-diisopropylaminoethoxy, 2-(4-methylpiperazinyl)ethoxy, 2-(4-acetylpiperazinyl)ethoxy, 2-morpholinylethoxy, 2-thiomorpholinylethoxy, 2-piperidinylethoxy, 3-N,N-dimethylaminopropoxy, 3-N,N-diethylaminopropoxy, 3-N,N-diisopropylaminopropoxy, 3-(4-methylpiperazinyl)propoxy, 3-(4-acetylpiperazinyl)propoxy, 3-morpholinylpropoxy, 3-thiomorpholinylpropoxy, 3-piperidinylpropoxy, pyridin-2-ylmethoxy, pyridin-3-ylmethoxy, pyridin-4-ylmethoxy, phenylmethoxy, monohalo-substituted phenylmethoxy, gem-dihalo-substituted phenylmethoxy, hetero-dihalo-substituted phenylmethoxy, (7) hydroxysulfonyl, aminosulfonyl, methylaminosulfonyl, ethylaminosulfonyl, propylaminosulfonyl, isopropylaminosulfonyl, cyclopropylaminosulfonyl, cyclobutylaminosulfonyl, cyclopentylaminosulfonyl, piperidinyl-1-ylsulfonyl, 4-hydroxypiperidin-1-ylsulfonyl, 4-N,N-dimethylaminopiperidin-1-ylsulfonyl, 4-N,N-diethylaminopiperidin-1-ylsulfonyl, tetrahydropyrrolyl-1-sulfonyl, 3-N,N-dimethylaminotetrahydropyrrolyl-1-sulfonyl, 3-N,N-diethylaminotetrahydropyrrolyl-1-sulfonyl, 4-methylpiperazin-1-ylsulfonyl, 4-ethylpiperazinyl-1-sulfonyl, 4-acetylpiperazinyl-1-sulfonyl, 4-t-butoxycarbonylpiperazinyl-1-sulfonyl, 4-(2-hydroxyethyl)piperazinyl-1-sulfonyl, 4-(2-cyanoethyl)piperazinyl-1-sulfonyl, 4-(2-N,N-dimethylaminoethyl)piperazinyl-1-sulfonyl, 4-(2-N,N-diethylethyl)piperazinyl-1-sulfonyl, 4-(3-hydroxypropyl)piperazinyl-1-sulfonyl, 4-(3-N,N-dimethylaminopropyl)piperazinyl-1-sulfonyl, 4-(3-N,N-diethylaminopropyl)piperazinyl-1-sulfonyl, morpholinyl-1-sulfonyl, 3,5-dimethylmorpholinyl-1-sulfonyl, 4-(4-methyl-piperazin-1-yl)piperidin-1-ylsulfonyl, 4-(4-ethyl-1-piperazinyl)piperidin-1-ylsulfonyl, 4-(4-acetyl-1-piperazinyl)piperidin-1-ylsulfonyl, 4-(N-methyl-4-piperidinyl)piperazinyl-1-sulfonyl, (8) hydroxycarbonyl, aminocarbonyl, methylaminocarbonyl, ethylaminocarbonyl, propylaminocarbonyl, isopropylaminocarbonyl, cyclopropylaminocarbonyl, cyclobutylaminocarbonyl, cyclopentylaminocarbonyl, piperidinyl-1-carbonyl, 4-hydroxypiperidinyl-1-carbonyl, 4-N,N-dimethylaminopiperidinyl-1-carbonyl, 4-N,N-diethylaminopiperidinyl-1-carbonyl, tetrahydropyrrolyl-1-carbonyl, 3-N,N-dimethylaminotetrahydropyrrolyl-1-carbonyl, 3-N,N-diethylaminotetrahydropyrrolyl-1-carbonyl, 4-methylpiperazin-1-ylcarbonyl, 4-ethylpiperazinyl-1-carbonyl, 4-acetylpiperazinyl-1-carbonyl, 4-t-butoxycarbonylpiperazinyl-1-carbonyl, 4-(2-hydroxyethyl)piperazinyl-1-carbonyl, 4-(2-cyanoethyl)piperazinyl-1-carbonyl, 4-(2-N,N-dimethylaminoethyl)piperazinyl-1-carbonyl, 4-(2-N,N-diethylaminoethyl)piperazinyl-1-carbonyl, 4-(3-hydroxypropyl)piperazinyl-1-carbonyl, 4-(3-N,N-dimethylaminopropyl)piperazinyl-1-carbonyl, 4-(3-N,N-diethylaminopropyl)piperazinyl-1-carbonyl, morpholinyl-1-carbonyl, 3,5-dimethylmorpholinyl-1-carbonyl, 4-(4-methyl-piperazin-1-yl)piperidin-1-ylcarbonyl, 4-(4-ethyl-1-piperazinyl)piperidinyl-1-carbonyl, 4-(4-acetyl-1-piperazinyl)piperidinyl-1-carbonyl, 4-(N-methyl-4-piperidinyl)piperazinyl-1-carbonyl, methoxycarbonyl, ethoxycarbonyl, propoxycarbonyl, isopropoxycarbonyl, n-butoxycarbonyl, isobutoxycarbonyl, tert-butoxycarbonyl, (9) aminoformamido, methylaminoformamido, ethylaminoformamido, propylaminoformamido, isopropylaminoformamido, cyclopropylaminoformamido, cyclobutylaminoformamido, cyclopentylaminoformamido, piperidinyl-1-formamido, 4-hydroxypiperidinyl-1-formamido, 4-N,N-dimethylaminopiperidinyl-1-formamido, 4-N,N-diethylaminopiperidinyl-1-formamido, tetrahydropyrrolyl-1-formamido, 3-N,N-dimethylaminotetrahydropyrrolyl-1-formamido, 3-N,N-diethylaminotetrahydropyrrolyl-1-formamido, 4-methylpiperazinyl-1-formamido, 4-ethylpiperazinyl-1-formamido, 4-acetylpiperazinyl-1-formamido, 4-t-butoxycarbonylpiperazinyl-1-formamido, 4-(2-hydroxyethyl)piperazinyl-1-formamido, 4-(2-cyanoethyl)piperazinyl-1-formamido, 4-(2-N,N-dimethylaminoethyl)piperazinyl-1-formamido, 4-(2-N,N-diethylaminoethyl)piperazinyl-1-formamido, 4-(3-hydroxypropyl)piperazinyl-1-formamido, 4-(3-N,N-dimethylaminopropyl)piperazinyl-1-formamido, 4-(3-N,N-diethylaminopropyl)piperazinyl-1-formamido, morpholinyl-1-formamido, 3,5-dimethylmorpholinyl-1-formamido, 4-(4-methyl-piperazin-1-yl)piperidinyl-1-formamido, 4-(4-ethyl-1-piperazinyl)piperidinyl-1-formamido, 4-(4-acetyl-1-piperazinyl)piperidinyl-1-formamido, 4-(N-methyl-4-piperidinyl)piperazinyl-1-formamido; or

(10) $Z_2$ and $Z_3$ or $Z_3$ and $Z_4$ form a nitrogen- or oxygen-containing substituted or unsubstituted 5- or 6-membered ring, the substituent may be selected from the same substituents as described above for $Z_1$;

$R_2$ is selected from:

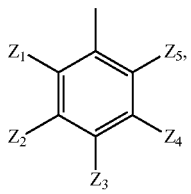

wherein $A_1$, $A_2$, $A_3$, $A_4$, $A_5$ each are independently selected from:
(1) H, F, Cl, Br, I, cyano, trifluoromethyl, trifluoromethoxy, nitro,
(2) methylthio, ethylthio, methylsulfinyl, ethylsulfinyl, methylsulfonyl, ethylsulfonyl, methylsulfonamido, methoxycarbonyl, ethoxycarbonyl, propoxycarbonyl, isopropoxycarbonyl, n-butoxycarbonyl, methylaminocarbonyl, ethylaminocarbonyl, propylaminocarbonyl, cyclopropylaminocarbonyl, cyclobutylaminocarbonyl, cyclopentylaminocarbonyl, dimethylphosphinyl.

In some embodiments, $R_1$ is selected from:

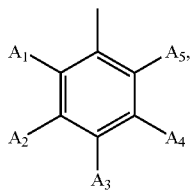

wherein $Z_1$, $Z_2$, $Z_3$, $Z_4$, $Z_5$ each are independently selected from:
(1) H,
(2) C1-C6 alkyl,
(3) C1-C6 alkoxy,
(4) piperidinyl, N-methyl-4-piperidinyl, 4-N,N-dimethylaminopiperidinyl, 4-N,N-diethylaminopiperidinyl, 4-N,N-diisopropylaminopiperidinyl, 4-hydroxypiperidinyl,
(5) 4-(4-methylpiperazinyl)piperidinyl, 4-(4-ethylpiperazinyl)piperidinyl, 4-(4-isopropylpiperazinyl)piperidinyl, 4-(4-acetylpiperazinyl)piperidinyl, 4-(4-t-butoxycarbonylpiperazinyl)piperidinyl, 4-(4-methylsulfonylpiperazinyl)piperidinyl, 4-(4-(2-hydroxyethyl)piperazinyl)piperidinyl, 4-(4-(2-cyanoethyl)piperazinyl)piperidinyl, 4-(4-(3-hydroxypropyl)piperazinyl)piperidinyl, 4-(4-(2-N,N-dimethylaminoethyl)piperazinyl)piperidinyl, 4-(4-(2-N,N-diethylaminoethyl)piperazinyl)piperidinyl, 4-(4-(3-N,N-dimethylaminopropyl)piperazinyl)piperidinyl, 4-(4-(3-N,N-diethylaminopropyl)piperazinyl)piperidinyl, 4-(tetrahydropyrrolyl)piperidinyl, 4-(3-N,N-dimethylaminotetrahydropyrrolyl)piperidinyl,
(6) 4-methylpiperazinyl, 4-ethylpiperazinyl, 4-isopropylpiperazinyl, 4-acetylpiperazinyl, 4-t-butoxycarbonylpiperazinyl, 4-methylsulfonylpiperazinyl, 4-(2-hydroxyethyl)piperazinyl, 4-(2-cyanoethyl)piperazinyl, 4-(3-hydroxypropyl)piperazinyl, 4-(2-N,N-dimethylaminoethyl)piperazinyl, 4-(2-N,N-diethylaminoethyl)piperazinyl, 4-(3-N,N-dimethylaminopropyl)piperazinyl, 4-(3-N,N-diethylaminopropyl)piperazinyl, 4-(N-methyl-4-piperidinyl)piperazinyl, 4-(N-ethyl-4-piperidinyl)piperazinyl,
(7) hydroxysulfonyl, aminosulfonyl, methylaminosulfonyl, ethylaminosulfonyl, propylaminosulfonyl, isopropylaminosulfonyl, cyclopropylaminosulfonyl, cyclobutylaminosulfonyl, cyclopentylaminosulfonyl, piperidin-1-ylsulfonyl, 4-hydroxypiperidin-1-ylsulfonyl, 4-N,N-dimethylaminopiperidin-1-ylsulfonyl, 4-N,N-diethylaminopiperidin-1-ylsulfonyl, tetrahydropyrrolyl-1-sulfonyl, 3-N,N-dimethylaminotetrahydropyrrolyl-1-sulfonyl, 3-N,N-diethylaminotetrahydropyrrolyl-1-sulfonyl, 4-methylpiperazin-1-ylsulfonyl, 4-ethylpiperazinyl-1-sulfonyl, 4-acetylpiperazinyl-1-sulfonyl, 4-t-butoxycarbonylpiperazinyl-1-sulfonyl, 4-(2-hydroxyethyl)piperazinyl-1-sulfonyl, 4-(2-cyanoethyl)piperazinyl-1-sulfonyl, 4-(2-N,N-dimethylaminoethyl)piperazinyl-1-sulfonyl, 4-(2-N,N-diethylethyl)piperazinyl-1-sulfonyl, 4-(3-hydroxypropyl)piperazinyl-1-sulfonyl, 4-(3-N,N-dimethylaminopropyl)piperazinyl-1-sulfonyl, 4-(3-N,N-diethylaminopropyl)piperazinyl-1-sulfonyl, morpholinyl-1-sulfonyl, 3,5-dimethylmorpholinyl-1-sulfonyl, 4-(4-methyl-piperazin-1-yl)piperidin-1-ylsulfonyl, 4-(4-ethyl-1-piperazinyl)piperidin-1-ylsulfonyl, 4-(4-acetyl-1-piperazinyl)piperidin-1-ylsulfonyl, 4-(N-methyl-4-piperidinyl)piperazinyl-1-sulfonyl, or
(8) $Z_2$ and $Z_3$ or $Z_3$ and $Z_4$ form a nitrogen- or oxygen-containing substituted or unsubstituted 5-membered ring, the substituent may be selected from the same substituents as described above for $Z_1$.

In some embodiments, $R_1$ is selected from:

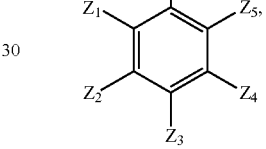

wherein $Z_1$, $Z_2$, $Z_3$, $Z_4$, $Z_5$ each are independently selected from:
(1) H,
(2) methyl, methoxy,
(3) N-methyl-4-piperidinyl, 4-hydroxypiperidinyl, 4-(4-methylpiperazinyl)piperidinyl, 4-(tetrahydropyrrol-1-yl)piperidinyl,
(4) aminosulfonyl, or
(5) $Z_2$ and $Z_3$ or $Z_3$ and $Z_4$ form

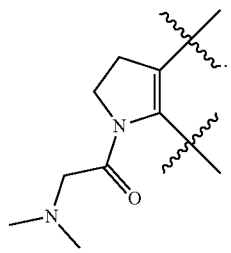

In some embodiments, $R_1$ is selected from:

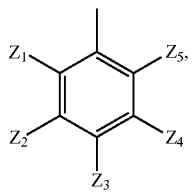

wherein one of $Z_1$ and $Z_5$ is H, the other is methoxy;
one of $Z_2$ and $Z_4$ is H, the other is methyl;

Z₃ is selected from: N-methyl-4-piperidinyl, 4-hydroxypiperidinyl, 4-(4-methylpiperazinyl)piperidinyl, 4-(tetrahydropyrrol-1-yl)piperidinyl, aminosulfonyl, or Z₂ and Z₃ or Z₃ and Z₄ form

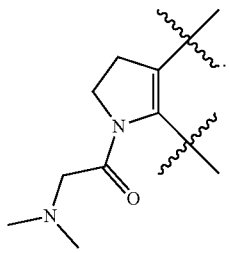 [SMILES: *C1=C(*)N(C(=O)CN(C)C)CC1]

In some embodiments, R₂ is selected from

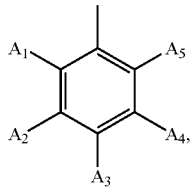

wherein A₁, A₂, A₃, A₄, A₅ each are independently selected from:
(1) H, (2) methylsulfonamido.

In some embodiments, R₂ is selected from:

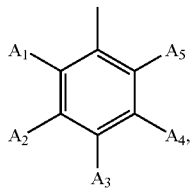

wherein one of A₂ and A₄ is H, the other is methylsulfonamido; A₁, A₃, A₅ are all H.

In an eleventh aspect, the present invention provides a compound of Formula IH, a stereoisomer thereof, a prodrug thereof, a pharmaceutically acceptable salt thereof or a pharmaceutically acceptable solvate thereof,

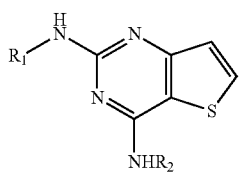

IH wherein, R₁ is selected from:
1) propylaminoethyl, 2-morpholinylethyl, 2-(4-4-methylpiperazinyl)ethyl, 3-N,N-dimethylaminopropyl, 3-N,N-diethylaminopropyl, 3-N,N-diisopropylaminopropyl, 3-morpholinylpropyl, 3-(4-methylpiperazinyl)propyl, C3-C6 cycloalkyl, 4-N,N-dimethylaminocyclohexyl, 4-N,N-diethylaminocyclohexyl, N-methyl-4-piperidinyl, N-ethyl-4-piperidinyl, N-isopropyl-4-piperidinyl, 1,3-dimethyl-5-pyrazolyl, 1-methyl-4-pyrazolyl, 3-methyl-5-isoxazolinyl, 1-(N-methyl-4-piperidinyl)-4-pyrazolyl, 1-(N-t-butoxycarbonyl-4-piperidinyl)-4-pyrazolyl;

2)

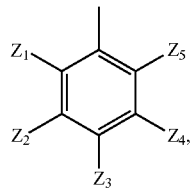

wherein Z₁, Z₂, Z₃, Z₄, Z₅ each are independently selected from:
(1) H, F, Cl, Br, I, nitro, cyano,
(2) C1-C6 alkyl, C1-C6 alkoxy, C1-C6 oxygen-containing alkyl, C1-C6 fluorine-containing alkyl, C1-C6 fluorine-containing alkoxy,
(3) piperidinyl, N-methyl-4-piperidinyl, 4-N,N-dimethylaminopiperidinyl, 4-N,N-diethylaminopiperidinyl, 4-N,N-diisopropylaminopiperidinyl, 4-hydroxypiperidinyl, 4-(4-methylpiperazinyl)piperidinyl, 4-(4-ethylpiperazinyl)piperidinyl, 4-(4-isopropylpiperazinyl)piperidinyl, 4-(4-acetylpiperazinyl)piperidinyl, 4-(4-t-butoxycarbonylpiperazinyl)piperidinyl, 4-(4-methylsulfonylpiperazinyl)piperidinyl, 4-(4-(2-hydroxyethyl)piperazinyl)piperidinyl, 4-(4-(2-cyanoethyl)piperazinyl)piperidinyl, 4-(4-(3-hydroxypropyl)piperazinyl)piperidinyl, 4-(4-(2-N,N-dimethylaminoethyl)piperazinyl)piperidinyl, 4-(4-(2-N,N-diethylaminoethyl)piperazinyl)piperidinyl, 4-(4-(3-N,N-dimethylaminopropyl)piperazinyl)piperidinyl, 4-(4-(3-N,N-diethylaminopropyl)piperazinyl)piperidinyl, 4-(tetrahydropyrrolyl)piperidinyl, 4-(3-N,N-dimethylaminotetrahydropyrrolyl)piperidinyl,
(4) 4-methylpiperazinyl, 4-ethylpiperazinyl, 4-isopropylpiperazinyl, 4-acetylpiperazinyl, 4-t-butoxycarbonylpiperazinyl, 4-methylsulfonylpiperazinyl, 4-(2-hydroxyethyl)piperazinyl, 4-(2-cyanoethyl)piperazinyl, 4-(3-hydroxypropyl)piperazinyl, 4-(2-N,N-dimethylaminoethyl)piperazinyl, 4-(2-N,N-diethylaminoethyl)piperazinyl, 4-(3-N,N-dimethylaminopropyl)piperazinyl, 4-(3-N,N-diethylaminopropyl)piperazinyl, 4-(N-methyl-4-piperidinyl)piperazinyl, 4-(N-ethyl-4-piperidinyl)piperazinyl,
(5) N,N-dimethylamino, N,N-diethylamino, N,N-diisopropylamino, 2-N,N-dimethylaminoethylamino, 2-morpholinylethylamino, 2-(4-methylpiperazinyl)ethylamino, 3-N,N-dimethylaminopropylamino, 3-N,N-diethylaminopropylamino, 3-N,N-diisopropylaminopropylamino, 3-morpholinylpropylamino, 3-(4-methylpiperazinyl)propylamino, N-methylpiperidinyl-4-amino, N-ethylpiperidinyl-4-amino, N-isopropylpiperidinyl-4-amino,
(6) 2-N,N-dimethylaminoethoxy, 2-N,N-diethylaminoethoxy, 2-N,N-diisopropylaminoethoxy, 2-(4-methylpiperazinyl)ethoxy, 2-(4-acetylpiperazinyl)ethoxy, 2-morpholinylethoxy, 2-thiomorpholinylethoxy, 2-piperidinylethoxy, 3-N,N-dimethylaminopropoxy, 3-N,N-diethylaminopropoxy, 3-N,N-diisopropylaminopropoxy, 3-(4-methylpiperazinyl)propoxy, 3-(4-acetylpiperazinyl)propoxy, 3-morpholinylpropoxy, 3-thiomorpholinylpropoxy, 3-piperidinylpropoxy, pyridin-2-ylmethoxy, pyridin-3-ylmethoxy, pyridin-4-ylmethoxy, phenylmethoxy, monohalo-substituted phenylmethoxy, gem-dihalo-substituted phenylmethoxy, hetero-dihalo-substituted phenylmethoxy,
(7) hydroxysulfonyl, aminosulfonyl, methylaminosulfonyl, ethylaminosulfonyl, propylaminosulfonyl, isopropylaminosulfonyl, cyclopropylaminosulfonyl, cyclobutylaminosulfonyl, cyclopentylaminosulfonyl, piperidin-1-ylsulfonyl, 4-hydroxypiperidin-1-ylsulfonyl, 4-N,N-dimethylaminopiperidin-1-ylsulfonyl, 4-N,N- diethylaminopiperidin-1-ylsulfonyl, tetrahydropyrrolyl-1-sulfonyl, 3-N,N-dimethylaminotetrahydropyrrolyl-1-sulfonyl, 3-N,N-diethylaminotetrahydropyrrolyl-1-sulfonyl, 4-methylpiperazin-1-ylsulfonyl, 4-ethylpiperazinyl-1-sulfonyl, 4-acetylpiperazinyl-1-sulfonyl, 4-t-butoxycarbonylpiperazinyl-1-sulfonyl, 4-(2-hydroxyethyl)piperazinyl-1-sulfonyl, 4-(2-cyanoethyl)piperazinyl-1-sulfonyl, 4-(2-N,N-dimethylaminoethyl)piperazinyl-1-sulfonyl, 4-(2-N,N-diethylethyl)piperazinyl-1-sulfonyl, 4-(3-hydroxypropyl)piperazinyl-1-sulfonyl, 4-(3-N,N-dimethylaminopropyl)piperazinyl-1-sulfonyl, 4-(3-N,N-diethylaminopropyl)piperazinyl-1-sulfonyl, morpholinyl-1-sulfonyl, 3,5-dimethylmorpholinyl-1-sulfonyl, 4-(4-methyl-piperazin-1-yl)piperidin-1-ylsulfonyl, 4-(4-ethyl-1-piperazinyl)piperidin-1-ylsulfonyl, 4-(4-acetyl-1-piperazinyl)piperidin-1-ylsulfonyl, 4-(N-methyl-4-piperidinyl)piperazinyl-1-sulfonyl, (8) hydroxycarbonyl, aminocarbonyl, methylaminocarbonyl, ethylaminocarbonyl, propylaminocarbonyl, isopropylaminocarbonyl, cyclopropylaminocarbonyl, cyclobutylaminocarbonyl, cyclopentylaminocarbonyl, piperidinyl-1-carbonyl, 4-hydroxypiperidinyl-1-carbonyl, 4-N,N-dimethylaminopiperidinyl-1-carbonyl, 4-N,N-diethylaminopiperidinyl-1-carbonyl, tetrahydropyrrolyl-1-carbonyl, 3-N,N-dimethylaminotetrahydropyrrolyl-1-carbonyl, 3-N,N-diethylaminotetrahydropyrrolyl-1-carbonyl, 4-methylpiperazin-1-ylcarbonyl, 4-ethylpiperazinyl-1-carbonyl, 4-acetylpiperazinyl-1-carbonyl, 4-t-butoxycarbonylpiperazinyl-1-carbonyl, 4-(2-hydroxyethyl)piperazinyl-1-carbonyl, 4-(2-cyanoethyl)piperazinyl-1-carbonyl, 4-(2-N,N-dimethylaminoethyl)piperazinyl-1-carbonyl, 4-(2-N,N-diethylaminoethyl)piperazinyl-1-carbonyl, 4-(3-hydroxypropyl)piperazinyl-1-carbonyl, 4-(3-N,N-dimethylaminopropyl)piperazinyl-1-carbonyl, 4-(3-N,N-diethylaminopropyl)piperazinyl-1-carbonyl, morpholinyl-1-carbonyl, 3,5-dimethylmorpholinyl-1-carbonyl, 4-(4-methyl-piperazin-1-yl)piperidin-1-ylcarbonyl, 4-(4-ethyl-1-piperazinyl)piperidinyl-1-carbonyl, 4-(4-acetyl-1-piperazinyl)piperidinyl-1-carbonyl, 4-(N-methyl-4-piperidinyl)piperazinyl-1-carbonyl, methoxycarbonyl, ethoxycarbonyl, propoxycarbonyl, isopropoxycarbonyl, n-butoxycarbonyl, isobutoxycarbonyl, tert-butoxycarbonyl, (9) aminoformamido, methylaminoformamido, ethylaminoformamido, propylaminoformamido, isopropylaminoformamido, cyclopropylaminoformamido, cyclobutylaminoformamido, cyclopentylaminoformamido, piperidinyl-1-formamido, 4-hydroxypiperidinyl-1-formamido, 4-N,N-dimethylaminopiperidinyl-1-formamido, 4-N,N-diethylaminopiperidinyl-1-formamido, tetrahydropyrrolyl-1-formamido, 3-N,N-dimethylaminotetrahydropyrrolyl-1-formamido, 3-N,N-diethylaminotetrahydropyrrolyl-1-formamido, 4-methylpiperazinyl-1-formamido, 4-ethylpiperazinyl-1-formamido, 4-acetylpiperazinyl-1-formamido, 4-t-butoxycarbonylpiperazinyl-1-formamido, 4-(2-hydroxyethyl)piperazinyl-1-formamido, 4-(2-cyanoethyl)piperazinyl-1-formamido, 4-(2-N,N-dimethylaminoethyl)piperazinyl-1-formamido, 4-(2-N,N-diethylaminoethyl)piperazinyl-1-formamido, 4-(3-hydroxypropyl)piperazinyl-1-formamido, 4-(3-N,N-dimethylaminopropyl)piperazinyl-1-formamido, 4-(3-N,N-diethylaminopropyl)piperazinyl-1-formamido, morpholinyl-1-formamido, 3,5-dimethylmorpholinyl-1-formamido, 4-(4-methyl-piperazin-1-yl)piperidinyl-1-formamido, 4-(4-ethyl-1-piperazinyl)piperidinyl-1-formamido, 4-(4-acetyl-1-piperazinyl)piperidinyl-1-formamido, 4-(N-methyl-4-piperidinyl)piperazinyl-1-formamido; or

(10) $Z_2$ and $Z_3$ or $Z_3$ and $Z_4$ form a nitrogen- or oxygen-containing substituted or unsubstituted 5- or 6-membered ring, the substituent may be selected from the same substituents as described above for $Z_1$;

$R_2$ is selected from:

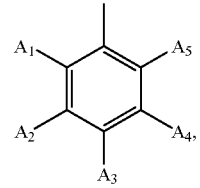

wherein $A_1$, $A_2$, $A_3$, $A_4$, $A_5$ each are independently selected from:

(1) H, F, Cl, Br, I, cyano, trifluoromethyl, trifluoromethoxy, nitro, (2) methylthio, ethylthio, methylsulfinyl, ethylsulfinyl, methylsulfonyl, ethylsulfonyl, methylsulfonamido, methoxycarbonyl, ethoxycarbonyl, propoxycarbonyl, isopropoxycarbonyl, n-butoxycarbonyl, methylaminocarbonyl, ethylaminocarbonyl, propylaminocarbonyl, cyclopropylaminocarbonyl, cyclobutylaminocarbonyl, cyclopentylaminocarbonyl, dimethylphosphinyl.

In some embodiments, $R_1$ is selected from:

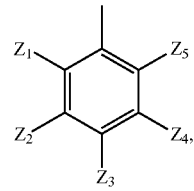

wherein $Z_1$, $Z_2$, $Z_3$, $Z_4$, $Z_5$ each are independently selected from:

(1) H, (2) C1-C6 alkoxy, (3) piperidinyl, N-methyl-4-piperidinyl, 4-N,N-dimethylaminopiperidinyl, 4-N,N-diethylaminopiperidinyl, 4-N,N-diisopropylaminopiperidinyl, 4-hydroxypiperidinyl (4) 4-(4-methylpiperazinyl)piperidinyl, 4-(4-ethylpiperazinyl)piperidinyl, 4-(4-isopropylpiperazinyl)piperidinyl, 4-(4-acetylpiperazinyl)piperidinyl, 4-(4-t-butoxycarbonylpiperazinyl)piperidinyl, 4-(4-methylsulfonylpiperazinyl)piperidinyl, 4-(4-(2-hydroxyethyl)piperazinyl)piperidinyl, 4-(4-(2-cyanoethyl)piperazinyl)piperidinyl, 4-(4-(3-hydroxypropyl)piperazinyl)piperidinyl, 4-(4-(2-N,N-dimethylaminoethyl)piperazinyl)piperidinyl, 4-(4-(2-N,N-diethylaminoethyl)piperazinyl)piperidinyl, 4-(4-(3-N,N-dimethylaminopropyl)piperazinyl)piperidinyl, 4-(4-(3-N,N-diethylaminopropyl)piperazinyl)piperidinyl, 4-(tetrahydropyrrolyl)piperidinyl, 4-(3-N,N-dimethylaminotetrahydropyrrolyl)piperidinyl, (5) 4-methylpiperazinyl, 4-ethylpiperazinyl, 4-isopropylpiperazinyl, 4-acetylpiperazinyl, 4-t-butoxycarbonylpiperazinyl, 4-methylsulfonylpiperazinyl, 4-(2-hydroxyethyl)piperazinyl, 4-(2-cyanoethyl)piperazinyl, 4-(3-hydroxypropyl)piperazinyl, 4-(2-N,N-dimethylaminoethyl)piperazinyl, 4-(2-N,N-diethylaminoethyl)piperazinyl, 4-(3-N,N-dimethylaminopropyl)piperazinyl, 4-(3-N,N-diethylaminopropyl)piperazinyl, 4-(N-methyl-4-piperidinyl)piperazinyl, 4-(N-ethyl-4-piperidinyl)piperazinyl, (6) hydroxysulfonyl, aminosulfonyl, methylaminosulfonyl, ethylaminosulfonyl, propylaminosulfonyl, isopropylaminosulfonyl, cyclopropylaminosulfonyl, cyclobutylaminosulfonyl, cyclopentylaminosulfonyl, piperidin-1-ylsulfonyl, 4-hydroxypiperidin-1-ylsulfonyl, 4-N,N-dimethylaminopiperidin-1-ylsulfonyl, 4-N,N-diethylaminopiperidin-1-ylsulfonyl, tetrahydropyrrolyl-1-sulfonyl, 3-N,N-dimethylaminotetrahydropyrrolyl-1-sulfonyl, 3-N,N-diethylaminotetrahydropyrrolyl-1-sulfonyl, 4-methylpiperazin-1-ylsulfonyl, 4-ethylpiperazinyl-1-sulfonyl, 4-acetylpiperazinyl-1-sulfonyl, 4-t-butoxycarbonylpiperazinyl-1-sulfonyl, 4-(2-hydroxyethyl)piperazinyl-1-sulfonyl, 4-(2-cyanoethyl)piperazinyl-1-sulfonyl, 4-(2-N,N-dimethylaminoethyl)piperazinyl-1-sulfonyl, 4-(2-N,N-diethylethyl)piperazinyl-1-sulfonyl, 4-(3-hydroxypropyl)piperazinyl-1-sulfonyl, 4-(3-N,N-dimethylaminopropyl)piperazinyl-1-sulfonyl, 4-(3-N,N-diethylaminopropyl)piperazinyl-1-sulfonyl, morpholinyl-1-sulfonyl, 3,5-dimethylmorpholinyl-1-sulfonyl, 4-(4-methyl-piperazin-1-yl)piperidin-1-ylsulfonyl, 4-(4-ethyl-1-piperazinyl)piperidin-1-ylsulfonyl, 4-(4-acetyl-1-piperazinyl)piperidin-1-ylsulfonyl, 4-(N-methyl-4-piperidinyl)piperazinyl-1-sulfonyl, or (7) $Z_2$ and $Z_3$ or $Z_3$ and $Z_4$ form a nitrogen- or oxygen-containing substituted or unsubstituted 5- or 6-membered ring, the substituent may be selected from the same substituents as described above for $Z_1$.

In some embodiments, $R_1$ is selected from:

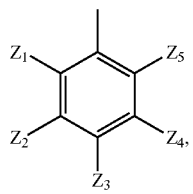

wherein $Z_1$, $Z_2$, $Z_3$, $Z_4$, $Z_5$ each are independently selected from:
(1) H,
(2) methoxy,
(3) N-methyl-4-piperidinyl, 4-hydroxypiperidinyl, 4-(4-methylpiperazinyl)piperidinyl, 4-(tetrahydropyrrol-1-yl)piperidinyl,
(4) 4-methylpiperazinyl,
(5) aminosulfonyl, or
(6) $Z_2$ and $Z_3$ or $Z_3$ and $Z_4$ form

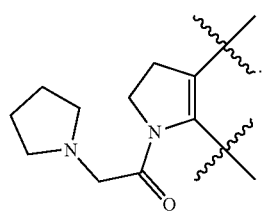 [SMILES: *C1=C(*)N(C(=O)CN2CCCC2)CC1]

In some embodiments, $R_1$ is selected from:

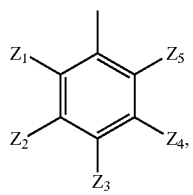

wherein one of $Z_1$ and $Z_5$ is H, the other is methoxy; $Z_4$ is H;

$Z_3$ is selected from: N-methyl-4-piperidinyl, 4-hydroxypiperidinyl, 4-methylpiperazinyl, 4-(4-methylpiperazinyl)piperidinyl, 4-(tetrahydropyrrol-1-yl)piperidinyl, aminosulfonyl, or $Z_2$ and $Z_3$ form

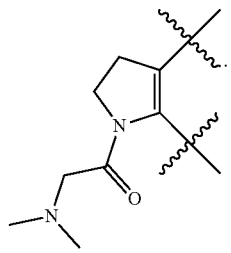

In some embodiments, $R_2$ is selected from:

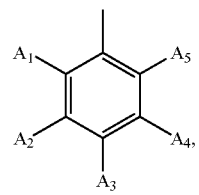

wherein $A_1$, $A_2$, $A_3$, $A_4$, $A_5$ each are independently selected from:
(1) H,
(2) methylsulfonamido.

In some embodiments, $R_2$ is selected from:

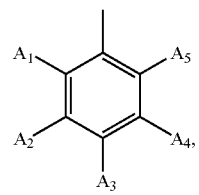

wherein one of $A_1$ and $A_5$ is H, the other is methylsulfonamido; $A_2$, $A_3$, $A_4$ are all H.

In a twelfth aspect, the present invention provides a compound of Formula II, a stereoisomer thereof, a prodrug thereof, a pharmaceutically acceptable salt thereof or a pharmaceutically acceptable solvate thereof,

II wherein, $R_1$ is selected from:
1) propylaminoethyl, 2-morpholinylethyl, 2-(4-methylpiperazinyl)ethyl, 3-N,N-dimethylaminopropyl, 3-N,N-diethylaminopropyl, 3-N,N-diisopropylaminopropyl, 3-morpholinylpropyl, 3-(4-methylpiperazinyl)propyl, C3-C6 cycloalkyl, 4-N,N-dimethylaminocyclohexyl, 4-N,N-diethylaminocyclohexyl, N-methyl-4-piperidinyl, N-ethyl-4-piperidinyl, N-isopropyl-4-piperidinyl, 1,3-dimethyl-5-pyrazolyl, 1-methyl-4-pyrazolyl, 3-methyl-5-isoxazolinyl, 1-(N-methyl-4-piperidinyl)-4-pyrazolyl, 1-(N-t-butoxycarbonyl-4-piperidinyl)-4-pyrazolyl;

2)

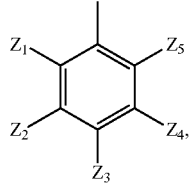

wherein $Z_1$, $Z_2$, $Z_3$, $Z_4$, $Z_5$ each are independently selected from:

(1) H, F, Cl, Br, I, nitro, cyano, (2) C1-C6 alkyl, C1-C6 alkoxy, C1-C6 oxygen-containing alkyl, C1-C6 fluorine-containing alkyl, C1-C6 fluorine-containing alkoxy, (3) piperidinyl, N-methyl-4-piperidinyl, 4-N,N-dimethylaminopiperidinyl, 4-N,N-diethylaminopiperidinyl, 4-N,N-diisopropylaminopiperidinyl, 4-hydroxypiperidinyl, 4-(4-methylpiperazinyl)piperidinyl, 4-(4-ethylpiperazinyl)piperidinyl, 4-(4-isopropylpiperazinyl)piperidinyl, 4-(4-acetylpiperazinyl)piperidinyl, 4-(4-t-butoxycarbonylpiperazinyl)piperidinyl, 4-(4-methylsulfonylpiperazinyl)piperidinyl, 4-(4-(2-hydroxyethyl)piperazinyl)piperidinyl, 4-(4-(2-cyanoethyl)piperazinyl)piperidinyl, 4-(4-(3-hydroxypropyl)piperazinyl)piperidinyl, 4-(4-(2-N,N-dimethylaminoethyl)piperazinyl)piperidinyl, 4-(4-(2-N,N-diethylaminoethyl)piperazinyl)piperidinyl, 4-(4-(3-N,N-dimethylaminopropyl)piperazinyl)piperidinyl, 4-(4-(3-N,N-diethylaminopropyl)piperazinyl)piperidinyl, 4-(tetrahydropyrrolyl)piperidinyl, 4-(3-N,N-dimethylaminotetrahydropyrrolyl)piperidinyl, (4) 4-methylpiperazinyl, 4-ethylpiperazinyl, 4-isopropylpiperazinyl, 4-acetylpiperazinyl, 4-t-butoxycarbonylpiperazinyl, 4-methylsulfonylpiperazinyl, 4-(2-hydroxyethyl)piperazinyl, 4-(2-cyanoethyl)piperazinyl, 4-(3-hydroxypropyl)piperazinyl, 4-(2-N,N-dimethylaminoethyl)piperazinyl, 4-(2-N,N-diethylaminoethyl)piperazinyl, 4-(3-N,N-dimethylaminopropyl)piperazinyl, 4-(3-N,N-diethylaminopropyl)piperazinyl, 4-(N-methyl-4-piperidinyl)piperazinyl, 4-(N-ethyl-4-piperidinyl)piperazinyl, (5) N,N-dimethylamino, N,N-diethylamino, N,N-diisopropylamino, 2-N,N-dimethylaminoethylamino, 2-morpholinylethylamino, 2-(4-methylpiperazinyl)ethylamino, 3-N,N-dimethylaminopropylamino, 3-N,N-diethylaminopropylamino, 3-N,N-diisopropylaminopropylamino, 3-morpholinylpropylamino, 3-(4-methylpiperazinyl)propylamino, N-methylpiperidinyl-4-amino, N-ethylpiperidinyl-4-amino, N-isopropylpiperidinyl-4-amino, (6) 2-N,N-dimethylaminoethoxy, 2-N,N-diethylaminoethoxy, 2-N,N-diisopropylaminoethoxy, 2-(4-methylpiperazinyl)ethoxy, 2-(4-acetylpiperazinyl)ethoxy, 2-morpholinylethoxy, 2-thiomorpholinylethoxy, 2-piperidinylethoxy, 3-N,N-dimethylaminopropoxy, 3-N,N-diethylaminopropoxy, 3-N,N-diisopropylaminopropoxy, 3-(4-methylpiperazinyl)propoxy, 3-(4-acetylpiperazinyl)propoxy, 3-morpholinylpropoxy, 3-thiomorpholinylpropoxy, 3-piperidinylpropoxy, pyridin-2-ylmethoxy, pyridin-3-ylmethoxy, pyridin-4-ylmethoxy, phenylmethoxy, monohalo-substituted phenylmethoxy, gem-dihalo-substituted phenylmethoxy, hetero-dihalo-substituted phenylmethoxy, (7) hydroxysulfonyl, aminosulfonyl, methylaminosulfonyl, ethylaminosulfonyl, propylaminosulfonyl, isopropylaminosulfonyl, cyclopropylaminosulfonyl, cyclobutylaminosulfonyl, cyclopentylaminosulfonyl, piperidin-1-ylsulfonyl, 4-hydroxypiperidin-1-ylsulfonyl, 4-N,N-dimethylaminopiperidin-1-ylsulfonyl, 4-N,N-diethylaminopiperidin-1-ylsulfonyl, tetrahydropyrrolyl-1-sulfonyl, 3-N,N-dimethylaminotetrahydropyrrolyl-1-sulfonyl, 3-N,N-diethylaminotetrahydropyrrolyl-1-sulfonyl, 4-methylpiperazin-1-ylsulfonyl, 4-ethylpiperazinyl-1-sulfonyl, 4-acetylpiperazinyl-1-sulfonyl, 4-t-butoxycarbonylpiperazinyl-1-sulfonyl, 4-(2-hydroxyethyl)piperazinyl-1-sulfonyl, 4-(2-cyanoethyl)piperazinyl-1-sulfonyl, 4-(2-N,N-dimethylaminoethyl)piperazinyl-1-sulfonyl, 4-(2-N,N-diethylethyl)piperazinyl-1-sulfonyl, 4-(3-hydroxypropyl)piperazinyl-1-sulfonyl, 4-(3-N,N-dimethylaminopropyl)piperazinyl-1-sulfonyl, 4-(3-N,N-diethylaminopropyl)piperazinyl-1-sulfonyl, morpholinyl-1-sulfonyl, 3,5-dimethylmorpholinyl-1-sulfonyl, 4-(4-methyl-piperazin-1-yl)piperidin-1-ylsulfonyl, 4-(4-ethyl-1-piperazinyl)piperidin-1-ylsulfonyl, 4-(4-acetyl-1-piperazinyl)piperidin-1-ylsulfonyl, 4-(N-methyl-4-piperidinyl)piperazinyl-1-sulfonyl, (8) hydroxycarbonyl, aminocarbonyl, methylaminocarbonyl, ethylaminocarbonyl, propylaminocarbonyl, isopropylaminocarbonyl, cyclopropylaminocarbonyl, cyclobutylaminocarbonyl, cyclopentylaminocarbonyl, piperidinyl-1-carbonyl, 4-hydroxypiperidinyl-1-carbonyl, 4-N,N-dimethylaminopiperidinyl-1-carbonyl, 4-N,N-diethylaminopiperidinyl-1-carbonyl, tetrahydropyrrolyl-1-carbonyl, 3-N,N-dimethylaminotetrahydropyrrolyl-1-carbonyl, 3-N,N-diethylaminotetrahydropyrrolyl-1-carbonyl, 4-methylpiperazin-1-ylcarbonyl, 4-ethylpiperazinyl-1-carbonyl, 4-acetylpiperazinyl-1-carbonyl, 4-t-butoxycarbonylpiperazinyl-1-carbonyl, 4-(2-hydroxyethyl)piperazinyl-1-carbonyl, 4-(2-cyanoethyl)piperazinyl-1-carbonyl, 4-(2-N,N-dimethylaminoethyl)piperazinyl-1-carbonyl, 4-(2-N,N-diethylaminoethyl)piperazinyl-1-carbonyl, 4-(3-hydroxypropyl)piperazinyl-1-carbonyl, 4-(3-N,N-dimethylaminopropyl)piperazinyl-1-carbonyl, 4-(3-N,N-diethylaminopropyl)piperazinyl-1-carbonyl, morpholinyl-1-carbonyl, 3,5-dimethylmorpholinyl-1-carbonyl, 4-(4-methyl-piperazin-1-yl)piperidinyl-1-ylcarbonyl, 4-(4-ethyl-1-piperazinyl)piperidinyl-1-carbonyl, 4-(4-acetyl-1-piperazinyl)piperidinyl-1-carbonyl, 4-(N-methyl-4-piperidinyl)piperazinyl-1-carbonyl, methoxycarbonyl, ethoxycarbonyl, propoxycarbonyl, isopropoxycarbonyl, n-butoxycarbonyl, isobutoxycarbonyl, tert-butoxycarbonyl, (9) aminoformamido, methylaminoformamido, ethylaminoformamido, propylaminoformamido, isopropylaminoformamido, cyclopropylaminoformamido, cyclobutylaminoformamido, cyclopentylaminoformamido, piperidinyl-1-formamido, 4-hydroxypiperidinyl-1-formamido, 4-N,N-dimethylaminopiperidinyl-1-formamido, 4-N,N-diethylaminopiperidinyl-1-formamido, tetrahydropyrrolyl-1-formamido, 3-N,N-dimethylaminotetrahydropyrrolyl-1-formamido, 3-N,N-diethylaminotetrahydropyrrolyl-1-formamido, 4-methylpiperazinyl-1-formamido, 4-ethylpiperazinyl-1-formamido, 4-acetylpiperazinyl-1-formamido, 4-t-butoxycarbonylpiperazinyl-1-formamido, 4-(2-hydroxyethyl)piperazinyl-1-formamido, 4-(2-cyanoethyl)piperazinyl-1-formamido, 4-(2-N,N-dimethylaminoethyl)piperazinyl-1-formamido, 4-(2-N,N-diethylaminoethyl)piperazinyl-1-formamido, 4-(3-hydroxypropyl)piperazinyl- 1-formamido, 4-(3-N,N-dimethylaminopropyl)piperazinyl-1-formamido, 4-(3-N,N-diethylaminopropyl)piperazinyl-1-formamido, morpholinyl-1-formamido, 3,5-dimethylmorpholinyl-1-formamido, 4-(4-methyl-piperazin-1-yl)piperidinyl-1-formamido, 4-(4-ethyl-1-piperazinyl)piperidinyl-1-formamido, 4-(4-acetyl-1-piperazinyl)piperidinyl-1-formamido, 4-(N-methyl-4-piperidinyl)piperazinyl-1-formamido;

R₂ is selected from:

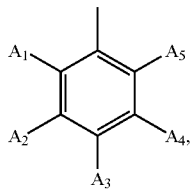

wherein A₁, A₂, A₃, A₄, A₅ each are independently selected from:
(1) H, F, C, Br, I, cyano, trifluoromethyl, trifluoromethoxy, nitro,
(2) methylthio, ethylthio, isopropylthio, methylsulfinyl, ethylsulfinyl, isopropylsulfinyl, methylsulfonyl, ethylsulfonyl, isopropylsulfonyl, methylsulfonamido, methoxycarbonyl, ethoxycarbonyl, propoxycarbonyl, isopropoxycarbonyl, n-butoxycarbonyl, isobutoxycarbonyl, tert-butoxycarbonyl, methylaminocarbonyl, ethylaminocarbonyl, propylaminocarbonyl, isopropylaminocarbonyl, cyclopropylaminocarbonyl, cyclobutylaminocarbonyl, cyclopentylaminocarbonyl, dimethylphosphinyl, diethylphosphinyl, diisopropylphosphinyl.

In some embodiments, R₁ is selected from:

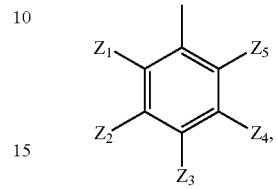

wherein Z₁, Z₂, Z₃, Z₄, Z₅ each are independently selected from:
(2) C1-C6 alkyl,
(3) C1-C6 alkoxy,
(4) piperidinyl, N-methyl-4-piperidinyl, 4-N,N-dimethylaminopiperidinyl, 4-N,N-diethylaminopiperidinyl, 4-N,N-diisopropylaminopiperidinyl, 4-hydroxypiperidinyl
(5) 4-(4-methylpiperazinyl)piperidinyl, 4-(4-ethylpiperazinyl)piperidinyl, 4-(4-isopropylpiperazinyl)piperidinyl, 4-(4-acetylpiperazinyl)piperidinyl, 4-(4-t-butoxycarbonylpiperazinyl)piperidinyl, 4-(4-methylsulfonylpiperazinyl)piperidinyl, 4-(4-2-hydroxyethyl)piperazinyl)piperidinyl, 4-(4-(2-cyanoethyl)piperazinyl)piperidinyl, 4-(4-(3-hydroxypropyl)piperazinyl)piperidinyl, 4-(4-(2-N,N-dimethylaminoethyl)piperazinyl)piperidinyl, 4-(4-(2-N,N-diethylaminoethyl)piperazinyl)piperidinyl, 4-(4-(3-N,N-dimethylaminopropyl)piperazinyl)piperidinyl, 4-(4-(3-N,N-diethylaminopropyl)piperazinyl)piperidinyl, 4-(tetrahydropyrrolyl)piperidinyl, 4-(3-N,N-dimethylaminotetrahydropyrrolyl)piperidinyl,
(6) 4-methylpiperazinyl, 4-ethylpiperazinyl, 4-isopropylpiperazinyl, 4-acetylpiperazinyl, 4-t-butoxycarbonylpiperazinyl, 4-methylsulfonylpiperazinyl, 4-(2-hydroxyethyl)piperazinyl, 4-(2-cyanoethyl)piperazinyl, 4-(3-hydroxypropyl)piperazinyl, 4-(2-N,N-dimethylaminoethyl)piperazinyl, 4-(2-N,N-diethylaminoethyl)piperazinyl, 4-(3-N,N-dimethylaminopropyl)piperazinyl, 4-(3-N,N-diethylaminopropyl)piperazinyl, 4-(N-methyl-4-piperidinyl)piperazinyl, 4-(N-ethyl-4-piperidinyl)piperazinyl.

In some embodiments, R₁ is selected from:

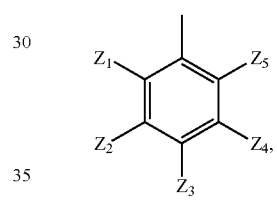

wherein Z₁, Z₂, Z₃, Z₄, Z₅ each are independently selected from:
(1) H,
(2) methyl, methoxy, ethoxy, isopropoxy;
(3) N-methyl-4-piperidinyl, 4-(4-methylpiperazinyl)piperidinyl, 4-(tetrahydropyrrol-1-yl)piperidinyl, 4-hydroxypiperidinyl;
(4) 4-methylpiperazinyl.

In some embodiments, R₁ is selected from:

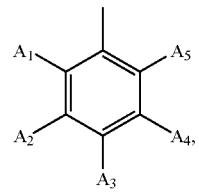

wherein one of Z₁ and Z₅ is H, the other is selected from: methoxy, ethoxy, isopropoxy;
one of Z₂ and Z₄ is H, the other is methyl;
Z₃ is selected from: N-methyl-4-piperidinyl, 4-methylpiperazinyl, 4-hydroxypiperidinyl, 4-(4-methylpiperazinyl)piperidinyl, 4-(tetrahydropyrrol-1-yl)piperidinyl.

In some embodiments, R₂ is selected from:

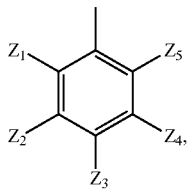

wherein A₁, A₂, A₃, A₄, A₅ each are independently selected from: (1) H; (2) methylaminocarbonyl.

In some embodiments, R₂ is selected from

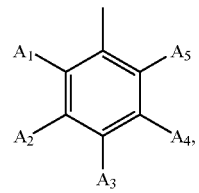

wherein one of $A_1$ and $A_5$ is H, the other is methylaminocarbonyl; $A_2$, $A_3$, $A_4$ are all H.

In a thirteenth aspect, the present invention provides a compound of Formula IPQ, a stereoisomer thereof, a prodrug thereof, a pharmaceutically acceptable salt thereof or a pharmaceutically acceptable solvate thereof,

IPQ

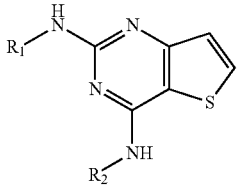

wherein, $R_1$ is selected from:

1) C1-C6 alkyl, 2-N,N-dimethylaminoethyl, 2-hydroxyethyl, 2-N,N-diethylaminoethyl, 2-N,N-diisopropylaminoethyl, 2-morpholinylethyl, 2-(4-methylpiperazinyl)ethyl, 3-N,N-dimethylaminopropyl, 3-N,N-diethylaminopropyl, 3-N,N-diisopropylaminopropyl, 3-morpholinylpropyl, 3-(4-methylpiperazinyl)propyl, C3-C6 cycloalkyl, 4-N,N-dimethylaminocyclohexyl, 4-N,N-diethylaminocyclohexyl, N-methyl-4-piperidinyl, N-ethyl-4-piperidinyl, N-isopropyl-4-piperidinyl, 1,3-dimethyl-5-pyrazolyl, 1-methyl-4-pyrazolyl, 3-methyl-5-isoxazolinyl, 1-(N-methyl-4-piperidinyl)-4-pyrazolyl, 1-(N-t-butoxycarbonyl-4-piperidinyl)-4-pyrazolyl;

2)

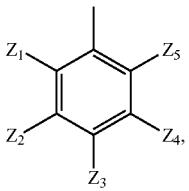

wherein $Z_1$, $Z_2$, $Z_3$, $Z_4$, $Z_5$ each are independently selected from:

(1) H, F, Cl, Br, I, nitro, cyano, (2) C1-C6 alkyl, C1-C6 alkoxy, C1-C6 oxygen-containing alkyl, C1-C6 fluorine-containing alkyl, C1-C6 fluorine-containing alkoxy, (3) piperidinyl, N-methyl-4-piperidinyl, 4-dimethylaminopiperidinyl, 4-N,N-diethylaminopiperidinyl, 4-N,N-diisopropylaminopiperidinyl, 4-hydroxypiperidinyl, 4-(4-methylpiperazinyl)piperidinyl, 4-(4-ethylpiperazinyl)piperidinyl, 4-(4-isopropylpiperazinyl)piperidinyl, 4-(4-acetylpiperazinyl)piperidinyl, 4-(4-t-butoxycarbonylpiperazinyl)piperidinyl, 4-(4-methylsulfonylpiperazinyl)piperidinyl, 4-(4-(2-hydroxyethyl)piperazinyl)piperidinyl, 4-(4-(2-cyanoethyl)piperazinyl)piperidinyl, 4-(4-(3-hydroxypropyl)piperazinyl)piperidinyl, 4-(4-(2-N,N-dimethylaminoethyl)piperazinyl)piperidinyl, 4-(4-(2-N,N-diethylaminoethyl)piperazinyl)piperidinyl, 4-(4-(3-N,N-dimethylaminopropyl)piperazinyl)piperidinyl, 4-(4-(3-N,N-diethylaminopropyl)piperazinyl)piperidinyl, 4-(tetrahydropyrrolyl)piperidinyl, 4-(3-N,N-dimethylaminotetrahydropyrrolyl)piperidinyl, (4) 4-methylpiperazinyl, 4-ethylpiperazinyl, 4-isopropylpiperazinyl, 4-acetylpiperazinyl, 4-t-butoxycarbonylpiperazinyl, 4-methylsulfonylpiperazinyl, 4-(2-hydroxyethyl)piperazinyl, 4-(2-cyanoethyl)piperazinyl, 4-(3-hydroxypropyl)piperazinyl, 4-(2-N,N-dimethylaminoethyl)piperazinyl, 4-(2-N,N-diethylaminoethyl)piperazinyl, 4-(3-N,N-dimethylaminopropyl)piperazinyl, 4-(3-N,N-diethylaminopropyl)piperazinyl, 4-(N-methyl-4-piperidinyl)piperazinyl, 4-(N-ethyl-4-piperidinyl)piperazinyl, (5) N,N-dimethylamino, N,N-diethylamino, N,N-diisopropylamino, 2-N,N-dimethylaminoethylamino, 2-morpholinylethylamino, 2-(4-methylpiperazinyl)ethylamino, 3-N,N-dimethylaminopropylamino, 3-N,N-diethylaminopropylamino, 3-N,N-diisopropylaminopropylamino, 3-morpholinylpropylamino, 3-(4-methylpiperazinyl)propylamino, N-methylpiperidinyl-4-amino, N-ethylpiperidinyl-4-amino, N-isopropylpiperidinyl-4-amino, (6) 2-N,N-dimethylaminoethoxy, 2-N,N-diethylaminoethoxy, 2-N,N-diisopropylaminoethoxy, 2-(4-methylpiperazinyl)ethoxy, 2-(4-acetylpiperazinyl)ethoxy, 2-morpholinylethoxy, 2-thiomorpholinylethoxy, 2-piperidinylethoxy, 3-N,N-dimethylaminopropoxy, 3-N,N-diethylaminopropoxy, 3-N,N-diisopropylaminopropoxy, 3-(4-methylpiperazinyl)propoxy, 3-(4-acetylpiperazinyl)propoxy, 3-morpholinylpropoxy, 3-thiomorpholinylpropoxy, 3-piperidinylpropoxy, pyridin-2-ylmethoxy, pyridin-3-ylmethoxy, pyridin-4-ylmethoxy, phenylmethoxy, monohalo-substituted phenylmethoxy, gem-dihalo-substituted phenylmethoxy, hetero-dihalo-substituted phenylmethoxy, (7) hydroxysulfonyl, aminosulfonyl, methylaminosulfonyl, ethylaminosulfonyl, propylaminosulfonyl, isopropylaminosulfonyl, cyclopropylaminosulfonyl, cyclobutylaminosulfonyl, cyclopentylaminosulfonyl, piperidin-1-ylsulfonyl, 4-hydroxypiperidin-1-ylsulfonyl, 4-N,N-dimethylaminopiperidin-1-ylsulfonyl, 4-N,N-diethylaminopiperidin-1-ylsulfonyl, tetrahydropyrrolyl-1-sulfonyl, 3-N,N-dimethylaminotetrahydropyrrolyl-1-sulfonyl, 3-N,N-diethylaminotetrahydropyrrolyl-1-sulfonyl, 4-methylpiperazin-1-ylsulfonyl, 4-ethylpiperazinyl-1-sulfonyl, 4-acetylpiperazinyl-1-sulfonyl, 4-t-butoxycarbonylpiperazinyl-1-sulfonyl, 4-(2-hydroxyethyl)piperazinyl-1-sulfonyl, 4-(2-cyanoethyl)piperazinyl-1-sulfonyl, 4-(2-N,N-dimethylaminoethyl)piperazinyl-1-sulfonyl, 4-(2-N,N-diethylethyl)piperazinyl-1-sulfonyl, 4-(3-hydroxypropyl)piperazinyl-1-sulfonyl, 4-(3-N,N-dimethylaminopropyl)piperazinyl-1-sulfonyl, 4-(3-N,N-diethylaminopropyl)piperazinyl-1-sulfonyl, morpholinyl-1-sulfonyl, 3,5-dimethylmorpholinyl-1-sulfonyl, 4-(4-methyl-piperazin-1-yl)piperidin-1-ylsulfonyl, 4-(4-ethyl-1-piperazinyl)piperidin-1-ylsulfonyl, 4-(4-acetyl-1-piperazinyl)piperidin-1-ylsulfonyl, 4-(N-methyl-4-piperidinyl)piperazinyl-1-sulfonyl, (8) hydroxycarbonyl, aminocarbonyl, methylaminocarbonyl, ethylaminocarbonyl, propylaminocarbonyl, isopropylaminocarbonyl, cyclopropylaminocarbonyl, cyclobutylaminocarbonyl, cyclopentylaminocarbonyl, piperidinyl-1-carbonyl, 4-hydroxypiperidinyl-1-carbonyl, 4-N,N-dimethylaminopiperidinyl-1-carbonyl, 4-N,N-diethylaminopiperidinyl-1-carbonyl, tetrahydropyrrolyl-1-carbonyl, 3-N,N-dimethylaminotetrahydropyrrolyl-1-carbonyl, 3-N,N-diethylaminotetrahydropyrrolyl-1-carbonyl, 4-methylpiperazin-1-ylcarbonyl, 4-ethylpiperazinyl-1-carbonyl, 4-acetylpiperazinyl-1-carbonyl, 4-t-butoxycarbonylpiperazinyl-1-carbonyl, 4-(2-hydroxyethyl)piperazinyl-1-carbonyl, 4-(2-cyanoethyl)piperazinyl-1-carbonyl, 4-(2-N,N-dimethylaminoethyl)piperazinyl-1-carbonyl, 4-(2-N,N-diethylaminoethyl)piperazinyl-1-carbonyl, 4-(3-hydroxypropyl)piperazinyl-1-carbonyl, 4-(3-N,N-dimethylaminopropyl)piperazinyl-1-carbonyl, 4-(3-N,N-diethylaminopropyl)piperazinyl-1-carbonyl, morpholinyl-1-carbonyl, 3,5-dimethylmorpholinyl-1-carbonyl, 4-(4-methyl-piperazin-1-yl)piperidin-1-ylcarbonyl, 4-(4-ethyl-1-piperazinyl)piperidinyl-1-carbonyl, 4-(4-acetyl-1-piperazinyl)piperidinyl-1-carbonyl, 4-(N-methyl-4-piperidinyl)piperazinyl-1-carbonyl, methoxycarbonyl, ethoxycarbonyl, propoxycarbonyl, isopropoxycarbonyl, n-butoxycarbonyl, isobutoxycarbonyl, tert-butoxycarbonyl, (9) aminoformamido, methylaminoformamido, ethylaminoformamido, propylaminoformamido, isopropylaminoformamido, cyclopropylaminoformamido, cyclobutylaminoformamido, cyclopentylaminoformamido, piperidinyl-1-formamido, 4-hydroxypiperidinyl-1-formamido, 4-N,N-dimethylaminopiperidinyl-1-formamido, 4-N,N-diethylaminopiperidinyl-1-formamido, tetrahydropyrrolyl-1-formamido, 3-N,N-dimethylaminotetrahydropyrrolyl-1-formamido, 3-N,N-diethylaminotetrahydropyrrolyl-1-formamido, 4-methylpiperazinyl-1-formamido, 4-ethylpiperazinyl-1-formamido, 4-acetylpiperazinyl-1-formamido, 4-t-butoxycarbonylpiperazinyl-1-formamido, 4-(2-hydroxyethyl)piperazinyl-1-formamido, 4-(2-cyanoethyl)piperazinyl-1-formamido, 4-(2-N,N-dimethylaminoethyl)piperazinyl-1-formamido, 4-(2-N,N-diethylaminoethyl)piperazinyl-1-formamido, 4-(3-hydroxypropyl)piperazinyl-1-formamido, 4-(3-N,N-dimethylaminopropyl)piperazinyl-1-formamido, 4-(3-N,N-diethylaminopropyl)piperazinyl-1-formamido, morpholinyl-1-formamido, 3,5-dimethylmorpholinyl-1-formamido, 4-(4-methyl-piperazin-1-yl)piperidinyl-1-formamido, 4-(4-ethyl-1-piperazinyl)piperidinyl-1-formamido, 4-(4-acetyl-1-piperazinyl)piperidinyl-1-formamido, 4-(N-methyl-4-piperidinyl)piperazinyl-1-formamido; or

(10) $Z_2$ and $Z_3$ or $Z_3$ and $Z_4$ form a nitrogen- or oxygen-containing substituted or unsubstituted 5- or 6-membered ring, the substituent may be selected from the same substituents as described above for $Z_1$;

$R_2$ is selected from

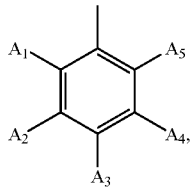

wherein $A_1$, $A_2$, $A_3$, $A_4$, $A_5$ each are independently selected from:

(1) H, F, Cl, Br, I, cyano, trifluoromethyl, trifluoromethoxy, nitro, (2) methylthio, ethylthio, isopropylthio, methylsulfinyl, ethylsulfinyl, isopropylsulfinyl, methylsulfonyl, ethylsulfonyl, isopropylsulfonyl, tert-butyl sulfonyl, methylsulfonamido, methoxycarbonyl, ethoxycarbonyl, propoxycarbonyl, isopropoxycarbonyl, n-butoxycarbonyl, isobutoxycarbonyl, tert-butoxycarbonyl, methylaminocarbonyl, ethylaminocarbonyl, propylaminocarbonyl, isopropylaminocarbonyl, dimethylaminocarbonyl, cyclopropylaminocarbonyl, cyclobutylaminocarbonyl, cyclopentylaminocarbonyl, dimethylphosphinyl, diethylphosphinyl, diisopropylphosphinyl.

In some embodiments, $R_1$ is selected from

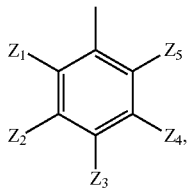

wherein $Z_1$, $Z_2$, $Z_3$, $Z_4$, $Z_5$ each are independently selected from:

(1) H, (2) C1-C6 alkoxy, (3) piperidinyl, N-methyl-4-piperidinyl, 4-dimethylaminopiperidinyl, 4-N,N-diethylaminopiperidinyl, 4-N,N-diisopropylaminopiperidinyl, 4-hydroxypiperidinyl, 4-(4-methylpiperazinyl)piperidinyl, 4-(4-ethylpiperazinyl)piperidinyl, 4-(4-isopropylpiperazinyl)piperidinyl, 4-(4-acetylpiperazinyl)piperidinyl, 4-(4-t-butoxycarbonylpiperazinyl)piperidinyl, 4-(4-methylsulfonylpiperazinyl)piperidinyl, 4-(4-(2-hydroxyethyl)piperazinyl)piperidinyl, 4-(4-(2-cyanoethyl)piperazinyl)piperidinyl, 4-(4-(3-hydroxypropyl)piperazinyl)piperidinyl, 4-(4-(2-N,N-dimethylaminoethyl)piperazinyl)piperidinyl, 4-(4-(2-N,N-diethylaminoethyl)piperazinyl)piperidinyl, 4-(4-(3-N,N-dimethylaminopropyl)piperazinyl)piperidinyl, 4-(4-(3-N,N-diethylaminopropyl)piperazinyl)piperidinyl, 4-(tetrahydropyrrolyl)piperidinyl, 4-(3-N,N-dimethylaminotetrahydropyrrolyl)piperidinyl, (4) 4-methylpiperazinyl, 4-ethylpiperazinyl, 4-isopropylpiperazinyl, 4-acetylpiperazinyl, 4-t-butoxycarbonylpiperazinyl, 4-methylsulfonylpiperazinyl, 4-(2-hydroxyethyl)piperazinyl, 4-(2-cyanoethyl)piperazinyl, 4-(3-hydroxypropyl)piperazinyl, 4-(2-N,N-dimethylaminoethyl)piperazinyl, 4-(2-N,N-diethylaminoethyl)piperazinyl, 4-(3-N,N-dimethylaminopropyl)piperazinyl, 4-(3-N,N-diethylaminopropyl)piperazinyl, 4-(N-methyl-4-piperidinyl)piperazinyl, 4-(N-ethyl-4-piperidinyl)piperazinyl or (5) $Z_2$ and $Z_3$ or $Z_3$ and $Z_4$ form a nitrogen- or oxygen-containing substituted or unsubstituted 5-membered ring, the substituent may be selected from the same substituents as described above for $Z_1$.

In some embodiments, $R_1$ is selected from:

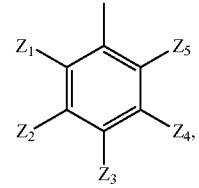

wherein $Z_1$, $Z_2$, $Z_3$, $Z_4$, $Z_5$ each are independently selected from:

(1) H, (2) C1-C6 alkoxy, (3) 4-(4-methylpiperazinyl)piperidinyl, 4-methylpiperazinyl, 4-dimethylamino-piperidinyl.

In some embodiments, $R_1$ is selected from:

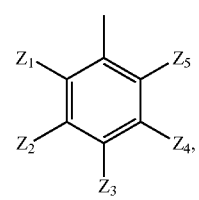

wherein, $Z_1$ is methoxy, and $Z_3$ is selected from: 4-dimethylamino-piperidinyl, 4-methylpiperazinyl 4-(4-methylpiperazinyl)piperidinyl, the rest being H; or $Z_3$ and $Z_4$ form

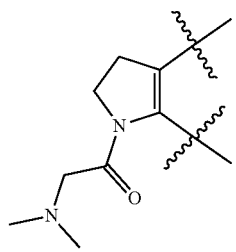

and $Z_1$ is methoxy, the rest being H.

In some embodiments, $R_2$ is selected from:

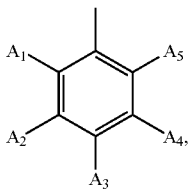

wherein $A_1$, $A_2$, $A_3$, $A_4$, $A_5$ each are independently selected from:
(1) H, (2) isopropylaminocarbonyl, dimethylaminocarbonyl.

In some embodiments, $R_2$ is selected from:

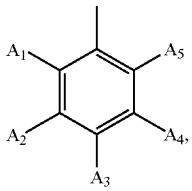

wherein one of $A_1$ and $A_5$ is H, the other is isopropylaminocarbonyl or dimethylaminocarbonyl; $A_2$, $A_3$, $A_4$ are all H.

In a fourteenth aspect, the present invention provides a compound of Formula IJ, a stereoisomer thereof, a prodrug thereof, a pharmaceutically acceptable salt thereof or a pharmaceutically acceptable solvate thereof,

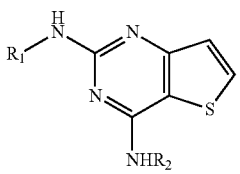

IJ wherein, $R_1$ is selected from:
1) propylaminoethyl, 2-morpholinylethyl, 2-(4-methylpiperazinyl)ethyl, 3-N,N-dimethylaminopropyl, 3-N,N-diethylaminopropyl, 3-N,N-diisopropylaminopropyl, 3-morpholinylpropyl, 3-(4-methylpiperazinyl)propyl, C3-C6 cycloalkyl, 4-N,N-dimethylaminocyclohexyl, 4-N,N-diethylaminocyclohexyl, N-methyl-4-piperidinyl, N-ethyl-4-piperidinyl, N-isopropyl-4-piperidinyl, 1,3-dimethyl-5-pyrazolyl, 1-methyl-4-pyrazolyl, 3-methyl-5-isoxazolinyl, 1-(N-methyl-4-piperidinyl)-4-pyrazolyl, 1-(N-t-butoxycarbonyl-4-piperidinyl)-4-pyrazolyl;

2)

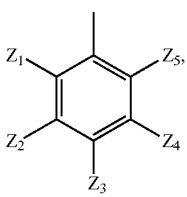

wherein $Z_1$, $Z_2$, $Z_3$, $Z_4$, $Z_5$ each are independently selected from:
(1) H, F, Cl, Br, I, nitro, cyano,
(2) C1-C6 alkyl, C1-C6 alkoxy, C1-C6 oxygen-containing alkyl, C1-C6 fluorine-containing alkyl, C1-C6 fluorine-containing alkoxy, (3) piperidinyl, N-methyl-4-piperidinyl, 4-N,N-dimethylaminopiperidinyl, 4-N,N-diethylaminopiperidinyl, 4-N,N-diisopropylaminopiperidinyl, 4-hydroxypiperidinyl, 4-(4-methylpiperazinyl)piperidinyl, 4-(N-ethylpiperazinyl)piperidinyl, 4-(4-isopropylpiperazinyl)piperidinyl, 4-(4-acetylpiperazinyl)piperidinyl, 4-(4-t-butoxycarbonylpiperazinyl)piperidinyl, 4-(4-methylsulfonylpiperazinyl)piperidinyl, 4-(4-(2-hydroxyethyl)piperazinyl)piperidinyl, 4-(4-(2-cyanoethyl)piperazinyl)piperidinyl, 4-(4-(3-hydroxypropyl)piperazinyl)piperidinyl, 4-(4-(2-N,N-dimethylaminoethyl)piperazinyl)piperidinyl, 4-(4-(2-N,N-diethylaminoethyl)piperazinyl)piperidinyl, 4-(4-(3-N,N-dimethylaminopropyl)piperazinyl)piperidinyl, 4-(4-(3-N,N-diethylaminopropyl)piperazinyl)piperidinyl, 4-(tetrahydropyrrolyl)piperidinyl, 4-(3-N,N-dimethylaminotetrahydropyrrolyl)piperidinyl, (4) 4-methylpiperazinyl, 4-ethylpiperazinyl, 4-isopropylpiperazinyl, 4-acetylpiperazinyl, 4-t-butoxycarbonylpiperazinyl, 4-methylsulfonylpiperazinyl, 4-(2-hydroxyethyl)piperazinyl, 4-(2-cyanoethyl)piperazinyl, 4-(3-hydroxypropyl)piperazinyl, 4-(2-N,N-dimethylaminoethyl)piperazinyl, 4-(2-N,N-diethylaminoethyl)piperazinyl, 4-(3-N,N-dimethylaminopropyl)piperazinyl, 4-(3-N,N-diethylaminopropyl)piperazinyl, 4-(N-methyl-4-piperidinyl)piperazinyl, 4-(N-ethyl-4-piperidinyl)piperazinyl, (5) N,N-dimethylamino, N,N-diethylamino, N,N-diisopropylamino, 2-N,N-dimethylaminoethylamino, 2-morpholinylethylamino, 2-(4-methylpiperazinyl)ethylamino, 3-N,N-dimethylaminopropylamino, 3-N,N-diethylaminopropylamino, 3-N,N-diisopropylaminopropylamino, 3-morpholinylpropylamino, 3-(4-methylpiperazinyl)propylamino, N-methylpiperidinyl-4-amino, N-ethylpiperidinyl-4-amino, N-isopropylpiperidinyl-4-amino, (6) 2-N,N-dimethylaminoethoxy, 2-N,N-diethylaminoethoxy, 2-N,N-diisopropylaminoethoxy, 2-(4-methylpiperazinyl)ethoxy, 2-(4-acetylpiperazinyl)ethoxy, 2-morpholinylethoxy, 2-thiomorpholinylethoxy, 2-piperidinylethoxy, 3-N,N-dimethylaminopropoxy, 3-N,N-diethylaminopropoxy, 3-N,N-diisopropylaminopropoxy, 3-(4-methylpiperazinyl)propoxy, 3-(4-acetylpiperazinyl)propoxy, 3-morpholinylpropoxy, 3-thiomorpholinylpropoxy, 3-piperidinylpropoxy, pyridin-2-ylmethoxy, pyridin-3-ylmethoxy, pyridin-4-ylmethoxy, phenylmethoxy, monohalo-substituted phenylmethoxy, gem-dihalo-substituted phenylmethoxy, hetero-dihalo-substituted phenylmethoxy, (7) hydroxysulfonyl, aminosulfonyl, methylaminosulfonyl, ethylaminosulfonyl, propylaminosulfonyl, isopropylaminosulfonyl, cyclopropylaminosulfonyl, cyclobutylaminosulfonyl, cyclopentylaminosulfonyl, piperidin-1-ylsulfonyl, 4-hydroxypiperidin-1-ylsulfonyl, 4-N,N-dimethylaminopiperidin-1-ylsulfonyl, 4-N,N-diethylaminopiperidin-1-ylsulfonyl, tetrahydropyrrolyl-1-sulfonyl, 3-N,N-dimethylaminotetrahydropyrrolyl-1-sulfonyl, 3-N,N-diethylaminotetrahydropyrrolyl-1-sulfonyl, 4-methylpiperazin-1-ylsulfonyl, 4-ethylpiperazinyl-1-sulfonyl, 4-acetylpiperazinyl-1-sulfonyl, 4-t-butoxycarbonylpiperazinyl-1-sulfonyl, 4-(2-hydroxyethyl)piperazinyl-1-sulfonyl, 4-(2-cyanoethyl)piperazinyl-1-sulfonyl, 4-(2-N,N-dimethylaminoethyl)piperazinyl-1-sulfonyl, 4-(2-N,N-diethylethyl)piperazinyl-1-sulfonyl, 4-(3-hydroxypropyl)piperazinyl-1-sulfonyl, 4-(3-N,N-dimethylaminopropyl)piperazinyl-1-sulfonyl, 4-(3-N,N-diethylaminopropyl)piperazinyl-1-sulfonyl, morpholinyl-1-sulfonyl, 3,5-dimethylmorpholinyl-1-sulfonyl, 4-(4-methyl-piperazin-1-yl)piperidin-1-ylsulfonyl, 4-(4-ethyl-1-piperazinyl)piperidin-1-ylsulfonyl, 4-(4-acetyl-1-piperazinyl)piperidin-1-ylsulfonyl, 4-(N-methyl-4-piperidinyl)piperazinyl-1-sulfonyl, (8) hydroxycarbonyl, aminocarbonyl, methylaminocarbonyl, ethylaminocarbonyl, propylaminocarbonyl, isopropylaminocarbonyl, cyclopropylaminocarbonyl, cyclobutylaminocarbonyl, cyclopentylaminocarbonyl, piperidinyl-1-carbonyl, 4-hydroxypiperidinyl-1-carbonyl, 4-N,N-dimethylaminopiperidinyl-1-carbonyl, 4-N,N-diethylaminopiperidinyl-1-carbonyl, tetrahydropyrrolyl-1-carbonyl, 3-N,N-dimethylaminotetrahydropyrrolyl-1-carbonyl, 3-N,N-diethylaminotetrahydropyrrolyl-1-carbonyl, 4-methylpiperazin-1-ylcarbonyl, 4-ethylpiperazinyl-1-carbonyl, 4-acetylpiperazinyl-1-carbonyl, 4-t-butoxycarbonylpiperazinyl-1-carbonyl, 4-(2-hydroxyethyl)piperazinyl-1-carbonyl, 4-(2-cyanoethyl)piperazinyl-1-carbonyl, 4-(2-N,N-dimethylaminoethyl)piperazinyl-1-carbonyl, 4-(2-N,N-diethylaminoethyl)piperazinyl-1-carbonyl, 4-(3-hydroxypropyl)piperazinyl-1-carbonyl, 4-(3-N,N-dimethylaminopropyl)piperazinyl-1-carbonyl, 4-(3-N,N-diethylaminopropyl)piperazinyl-1-carbonyl, morpholinyl-1-carbonyl, 3,5-dimethylmorpholinyl-1-carbonyl, 4-(4-methyl-piperazin-1-yl)piperidin-1-ylcarbonyl, 4-(4-ethyl-1-piperazinyl)piperidinyl-1-carbonyl, 4-(4-acetyl-1-piperazinyl)piperidinyl-1-carbonyl, 4-(N-methyl-4-piperidinyl)piperazinyl-1-carbonyl, methoxycarbonyl, ethoxycarbonyl, propoxycarbonyl, isopropoxycarbonyl, n-butoxycarbonyl, isobutoxycarbonyl, tert-butoxycarbonyl, (9) aminoformamido, methylaminoformamido, ethylaminoformamido, propylaminoformamido, isopropylaminoformamido, cyclopropylaminoformamido, cyclobutylaminoformamido, cyclopentylaminoformamido, piperidinyl-1-formamido, 4-hydroxypiperidinyl-1-formamido, 4-N,N-dimethylaminopiperidinyl-1-formamido, 4-N,N-diethylaminopiperidinyl-1-formamido, tetrahydropyrrolyl-1-formamido, 3-N,N-dimethylaminotetrahydropyrrolyl-1-formamido, 3-N,N-diethylaminotetrahydropyrrolyl-1-formamido, 4-methylpiperazinyl-1-formamido, 4-ethylpiperazinyl-1-formamido, 4-acetylpiperazinyl-1-formamido, 4-t-butoxycarbonylpiperazinyl-1-formamido, 4-(2-hydroxyethyl)piperazinyl-1-formamido, 4-(2-cyanoethyl)piperazinyl-1-formamido, 4-(2-N,N-dimethylaminoethyl)piperazinyl-1-formamido, 4-(2-N,N-diethylaminoethyl)piperazinyl-1-formamido, 4-(3-hydroxypropyl)piperazinyl-1-formamido, 4-(3-N,N-dimethylaminopropyl)piperazinyl-1-formamido, 4-(3-N,N-diethylaminopropyl)piperazinyl-1-formamido, morpholinyl-1-formamido, 3,5-dimethylmorpholinyl-1-formamido, 4-(4-methyl-piperazin-1-yl)piperidinyl-1-formamido, 4-(4-ethyl-1-piperazinyl)piperidinyl-1-formamido, 4-(4-acetyl-1-piperazinyl)piperidinyl-1-formamido, 4-(N-methyl-4-piperidinyl)piperazinyl-1-formamido; or

(10) $Z_2$ and $Z_3$ or $Z_3$ and $Z_4$ form a nitrogen- or oxygen-containing substituted or unsubstituted 5- or 6-membered ring, the substituent may be selected from the same substituents as described above for $Z_1$;

$R_2$ is selected from:

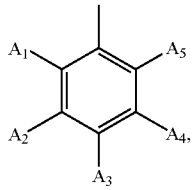

wherein $A_1$, $A_2$, $A_3$, $A_4$, $A_5$ each are independently selected from:
(1) H, F, C, Br, I, cyano, trifluoromethyl, trifluoromethoxy, nitro,
(2) methylthio, ethylthio, isopropylthio, methylsulfinyl, ethylsulfinyl, isopropylsulfinyl, methylsulfonyl, ethylsulfonyl, isopropylsulfonyl, methylsulfonamido, methoxycarbonyl, ethoxycarbonyl, propoxycarbonyl, isopropoxycarbonyl, n-butoxycarbonyl, isobutoxycarbonyl, tert-butoxycarbonyl, methylaminocarbonyl, ethylaminocarbonyl, propylaminocarbonyl, isopropylaminocarbonyl, cyclopropylaminocarbonyl, cyclobutylaminocarbonyl, cyclopentylaminocarbonyl, dimethylphosphinyl, diethylphosphinyl, diisopropylphosphinyl.

In some embodiments, $R_1$ is selected from:

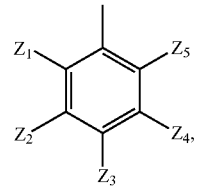

wherein $Z_1$, $Z_2$, $Z_3$, $Z_4$, $Z_5$ each are independently selected from:
(1) H,
(2) C1-C6 alkyl,
(3) C1-C6 alkoxy,
(4) piperidinyl, N-methyl-4-piperidinyl, 4-N,N-dimethylaminopiperidinyl, 4-N,N-diethylaminopiperidinyl, 4-N,N-diisopropylaminopiperidinyl, 4-hydroxypiperidinyl,
(5) 4-(4-methylpiperazinyl)piperidinyl, 4-(4-ethylpiperazinyl)piperidinyl, 4-(4-isopropylpiperazinyl)piperidinyl, 4-(4-acetylpiperazinyl)piperidinyl, 4-(4-t-butoxycarbonylpiperazinyl)piperidinyl, 4-(4-methylsulfonylpiperazinyl)piperidinyl, 4-(4-(2-hydroxyethyl)piperazinyl)piperidinyl, 4-(4-(2-cyanoethyl)piperazinyl)piperidinyl, 4-(4-(3-hydroxypropyl)piperazinyl)piperidinyl, 4-(4-(2-N,N-dimethylaminoethyl)piperazinyl)piperidinyl, 4-(4-(2-N,N-diethylaminoethyl)piperazinyl)piperidinyl, 4-(4-(3-N,N-dimethylaminopropyl)piperazinyl)piperidinyl, 4-(4-(3-N,N-diethylaminopropyl)piperazinyl)piperidinyl, 4-(tetrahydropyrrolyl)piperidinyl, 4-(3-N,N-dimethylaminotetrahydropyrrolyl)piperidinyl,
(6) 4-methylpiperazinyl, 4-ethylpiperazinyl, 4-isopropylpiperazinyl, 4-acetylpiperazinyl, 4-t-butoxycarbonylpiperazinyl, 4-methylsulfonylpiperazinyl, 4-(2-hydroxyethyl)piperazinyl, 4-(2-cyanoethyl)piperazinyl, 4-(3-hydroxypropyl)piperazinyl, 4-(2-N,N-dimethylaminoethyl)piperazinyl, 4-(2-N,N-diethylaminoethyl)piperazinyl, 4-(3-N,N-dimethylaminopropyl)piperazinyl, 4-(3-N,N-diethylaminopropyl)piperazinyl, 4-(N-methyl-4-piperidinyl)piperazinyl, 4-(N-ethyl-4-piperidinyl)piperazinyl, or
(7) $Z_2$ and $Z_3$ or $Z_3$ and $Z_4$ form a nitrogen- or oxygen-containing substituted or unsubstituted 5-membered ring, the substituent may be selected from the same substituents as described above for $Z_1$.

In some embodiments, $R_1$ is selected from:

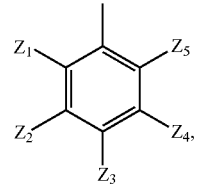

wherein $Z_1$, $Z_2$, $Z_3$, $Z_4$, $Z_5$ each are independently selected from:
(1) H,
(2) methyl, methoxy,
(3) N-methyl-4-piperidinyl, 4-N,N-dimethylaminopiperidinyl, 4-(4-methylpiperazinyl)piperidinyl, 4-(tetrahydropyrrol-1-yl)piperidinyl, (4) 4-methylpiperazinyl, or
(5) $Z_2$ and $Z_3$ or $Z_3$ and $Z_4$ form

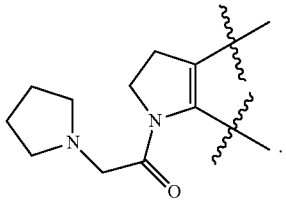 [SMILES: *C1=C(*)N(C(=O)CN2CCCC2)CC1]

In some embodiments, $R_1$ is selected from:

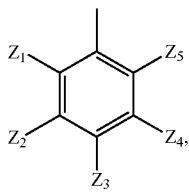

wherein one of $Z_1$ and $Z_5$ is H, the other is methoxy, one of $Z_2$ and $Z_4$ is H, the other is methyl, $Z_3$ is selected from: N-methyl-4-piperidinyl, 4-N,N-dimethylaminopiperidinyl, 4-methylpiperazinyl, 4-(4-methylpiperazinyl)piperidinyl, 4-(tetrahydropyrrol-1-yl)piperidin, or $Z_2$ and $Z_3$ or $Z_3$ and $Z_4$ form

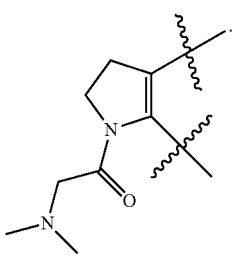 [SMILES: *C1=C(*)N(C(=O)CN(C)C)CC1]

In some embodiments, $R_2$ is selected from:

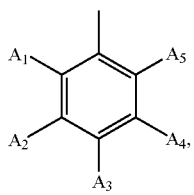

wherein $A_1$, $A_2$, $A_3$, $A_4$, $A_5$ each are independently selected from:
(1) H, (2) isopropylsulfinyl.

In some embodiments, $R_2$ is selected from:

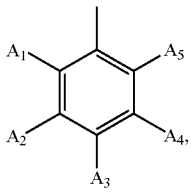

wherein one of $A_1$ and $A_5$ is H, the other is isopropylsulfinyl; $A_2$, $A_3$, $A_4$ are all H.

In a fifteenth aspect, the present invention provides a compound of Formula IK, a stereoisomer thereof, a prodrug thereof, a pharmaceutically acceptable salt thereof or a pharmaceutically acceptable solvate thereof,

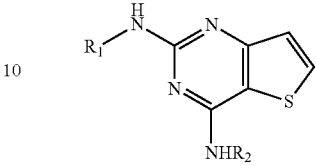

IK wherein, $R_1$ is selected from:
1) C1-C6 alkyl, 2-N,N-dimethylaminoethyl, 2-hydroxyethyl, 2-N,N-diethylaminoethyl, 2-N,N-diisopropylaminoethyl, 2-morpholinylethyl, 2-(4-methylpiperazinyl)ethyl, 3-N,N-dimethylaminopropyl, 3-N,N-diethylaminopropyl, 3-N,N-diisopropylaminopropyl, 3-morpholinylpropyl, 3-(4-methylpiperazinyl)propyl, C3-C6 cycloalkyl, 4-N,N-dimethylaminocyclohexyl, 4-N,N-diethylaminocyclohexyl, N-methyl-4-piperidinyl, N-ethyl-4-piperidinyl, N-isopropyl-4-piperidinyl, 1,3-dimethyl-5-pyrazolyl, 1-methyl-4-pyrazolyl, 3-methyl-5-isoxazolinyl, 1-(N-methyl-4-piperidinyl)-4-pyrazolyl, 1-(N-t-butoxycarbonyl-4-piperidinyl)-4-pyrazolyl;

2)

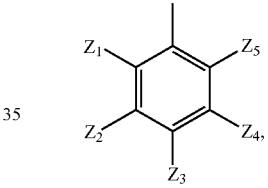

wherein $Z_1$, $Z_2$, $Z_3$, $Z_4$, $Z_5$ each are independently selected from:
(1) H, F, Cl, Br, I, nitro, cyano,
(2) C1-C6 alkyl, C1-C6 alkoxy, C1-C6 oxygen-containing alkyl, C1-C6 fluorine-containing alkyl, C1-C6 fluorine-containing alkoxy,
(3) piperidinyl, N-methyl-4-piperidinyl, 4-N,N-dimethylaminopiperidinyl, 4-N,N-diethylaminopiperidinyl, 4-N,N-diisopropylaminopiperidinyl, 4-hydroxypiperidinyl, 4-(4-methylpiperazinyl)piperidinyl, 4-(4-ethylpiperazinyl)piperidinyl, 4-(4-isopropylpiperazinyl)piperidinyl, 4-(4-acetylpiperazinyl)piperidinyl, 4-(4-t-butoxycarbonylpiperazinyl)piperidinyl, 4-(4-methylsulfonylpiperazinyl)piperidinyl, 4-(4-(2-hydroxyethyl)piperazinyl)piperidinyl, 4-(4-(2-cyanoethyl)piperazinyl)piperidinyl, 4-(4-(3-hydroxypropyl)piperazinyl)piperidinyl, 4-(4-(2-N,N-dimethylaminoethyl)piperazinyl)piperidinyl, 4-(4-(2-N,N-diethylaminoethyl)piperazinyl)piperidinyl, 4-(4-(3-N,N-dimethylaminopropyl)piperazinyl)piperidinyl, 4-(4-(3-N,N-diethylaminopropyl)piperazinyl)piperidinyl, 4-(tetrahydropyrrolyl)piperidinyl, 4-(3-N,N-dimethylaminotetrahydropyrrolyl)piperidinyl,
(4) 4-methylpiperazinyl, 4-ethylpiperazinyl, 4-isopropylpiperazinyl, 4-acetylpiperazinyl, 4-t-butoxycarbonylpiperazinyl, 4-methylsulfonylpiperazinyl, 4-(2-hydroxyethyl)piperazinyl, 4-(2-cyanoethyl)piperazinyl, 4-(3-hydroxypropyl)piperazinyl, 4-(2-N,N-dimethylaminoethyl)piperazinyl, 4-(2-N,N-diethylaminoethyl)piperazinyl, 4-(3-N,N-dimethylaminopropyl)piperazinyl, 4-(3-N,N-diethylaminopropyl)

piperazinyl, 4-(N-methyl-4-piperidinyl)piperazinyl, 4-(N-ethyl-4-piperidinyl)piperazinyl, (5) N,N-dimethylamino, N,N-diethylamino, N,N-diisopropylamino, 2-N,N-dimethylaminoethylamino, 2-morpholinylethylamino, 2-(4-methylpiperazinyl)ethylamino, 3-N,N-dimethylaminopropylamino, 3-N,N-diethylaminopropylamino, 3-N,N-diisopropylaminopropylamino, 3-morpholinylpropylamino, 3-(4-methylpiperazinyl)propylamino, N-methylpiperidinyl-4-amino, N-ethylpiperidinyl-4-amino, N-isopropylpiperidinyl-4-amino, (6) 2-N,N-dimethylaminoethoxy, 2-N,N-diethylaminoethoxy, 2-N,N-diisopropylaminoethoxy, 2-(4-methylpiperazinyl)ethoxy, 2-(4-acetylpiperazinyl)ethoxy, 2-morpholinylethoxy, 2-thiomorpholinylethoxy, 2-piperidinylethoxy, 3-N,N-dimethylaminopropoxy, 3-N,N-diethylaminopropoxy, 3-N,N-diisopropylaminopropoxy, 3-(4-methylpiperazinyl)propoxy, 3-(4-acetylpiperazinyl)propoxy, 3-morpholinylpropoxy, 3-thiomorpholinylpropoxy, 3-piperidinylpropoxy, pyridin-2-ylmethoxy, pyridin-3-ylmethoxy, pyridin-4-ylmethoxy, phenylmethoxy, monohalo-substituted phenylmethoxy, gem-dihalo-substituted phenylmethoxy, hetero-dihalo-substituted phenylmethoxy, (7) hydroxysulfonyl, aminosulfonyl, methylaminosulfonyl, ethylaminosulfonyl, propylaminosulfonyl, isopropylaminosulfonyl, cyclopropylaminosulfonyl, cyclobutylaminosulfonyl, cyclopentylaminosulfonyl, piperidin-1-ylsulfonyl, 4-hydroxypiperidin-1-ylsulfonyl, 4-N,N-dimethylaminopiperidin-1-ylsulfonyl, 4-N,N-diethylaminopiperidin-1-ylsulfonyl, tetrahydropyrrolyl-1-sulfonyl, 3-N,N-dimethylaminotetrahydropyrrolyl-1-sulfonyl, 3-N,N-diethylaminotetrahydropyrrolyl-1-sulfonyl, 4-methylpiperazin-1-ylsulfonyl, 4-ethylpiperazinyl-1-sulfonyl, 4-acetylpiperazinyl-1-sulfonyl, 4-t-butoxycarbonylpiperazinyl-1-sulfonyl, 4-(2-hydroxyethyl)piperazinyl-1-sulfonyl, 4-(2-cyanoethyl)piperazinyl-1-sulfonyl, 4-(2-N,N-dimethylaminoethyl)piperazinyl-1-sulfonyl, 4-(2-N,N-diethylethyl)piperazinyl-1-sulfonyl, 4-(3-hydroxypropyl)piperazinyl-1-sulfonyl, 4-(3-N,N-dimethylaminopropyl)piperazinyl-1-sulfonyl, 4-(3-N,N-diethylaminopropyl)piperazinyl-1-sulfonyl, morpholinyl-1-sulfonyl, 3,5-dimethylmorpholinyl-1-sulfonyl, 4-(4-methyl-piperazin-1-yl)piperidin-1-ylsulfonyl, 4-(4-ethyl-1-piperazinyl)piperidin-1-ylsulfonyl, 4-(4-acetyl-1-piperazinyl)piperidin-1-ylsulfonyl, 4-(N-methyl-4-piperidinyl)piperazinyl-1-sulfonyl, (8) hydroxycarbonyl, aminocarbonyl, methylaminocarbonyl, ethylaminocarbonyl, propylaminocarbonyl, isopropylaminocarbonyl, cyclopropylaminocarbonyl, cyclobutylaminocarbonyl, cyclopentylaminocarbonyl, piperidinyl-1-carbonyl, 4-hydroxypiperidinyl-1-carbonyl, 4-N,N-dimethylaminopiperidinyl-1-carbonyl, 4-N,N-diethylaminopiperidinyl-1-carbonyl, tetrahydropyrrolyl-1-carbonyl, 3-N,N-dimethylaminotetrahydropyrrolyl-1-carbonyl, 3-N,N-diethylaminotetrahydropyrrolyl-1-carbonyl, 4-methylpiperazin-1-ylcarbonyl, 4-ethylpiperazinyl-1-carbonyl, 4-acetylpiperazinyl-1-carbonyl, 4-t-butoxycarbonylpiperazinyl-1-carbonyl, 4-(2-hydroxyethyl)piperazinyl-1-carbonyl, 4-(2-cyanoethyl)piperazinyl-1-carbonyl, 4-(2-N,N-dimethylaminoethyl)piperazinyl-1-carbonyl, 4-(2-N,N-diethylaminoethyl)piperazinyl-1-carbonyl, 4-(3-hydroxypropyl)piperazinyl-1-carbonyl, 4-(3-N,N-dimethylaminopropyl)piperazinyl-1-carbonyl, 4-(3-N,N-diethylaminopropyl)piperazinyl-1-carbonyl, morpholinyl-1-carbonyl, 3,5-dimethylmorpholinyl-1-carbonyl, 4-(4-methyl-piperazin-1-yl)piperidin-1-ylcarbonyl, 4-(4-ethyl-1-piperazinyl)piperidinyl-1-carbonyl, 4-(4-acetyl-1-piperazinyl)piperidinyl-1-carbonyl, 4-(N-methyl-4-piperidinyl)piperazinyl-1-carbonyl, methoxycarbonyl, ethoxycarbonyl, propoxycarbonyl, isopropoxycarbonyl, n-butoxycarbonyl, isobutoxycarbonyl, tert-butoxycarbonyl, (9) aminoformamido, methylaminoformamido, ethylaminoformamido, propylaminoformamido, isopropylaminoformamido, cyclopropylaminoformamido, cyclobutylaminoformamido, cyclopentylaminoformamido, piperidinyl-1-formamido, 4-hydroxypiperidinyl-1-formamido, 4-N,N-dimethylaminopiperidinyl-1-formamido, 4-N,N-diethylaminopiperidinyl-1-formamido, tetrahydropyrrolyl-1-formamido, 3-N,N-dimethylaminotetrahydropyrrolyl-1-formamido, 3-N,N-diethylaminotetrahydropyrrolyl-1-formamido, 4-methylpiperazinyl-1-formamido, 4-ethylpiperazinyl-1-formamido, 4-acetylpiperazinyl-1-formamido, 4-t-butoxycarbonylpiperazinyl-1-formamido, 4-(2-hydroxyethyl)piperazinyl-1-formamido, 4-(2-cyanoethyl)piperazinyl-1-formamido, 4-(2-N,N-dimethylaminoethyl)piperazinyl-1-formamido, 4-(2-N,N-diethylaminoethyl)piperazinyl-1-formamido, 4-(3-hydroxypropyl)piperazinyl-1-formamido, 4-(3-N,N-dimethylaminopropyl)piperazinyl-1-formamido, 4-(3-N,N-diethylaminopropyl)piperazinyl-1-formamido, morpholinyl-1-formamido, 3,5-dimethylmorpholinyl-1-formamido, 4-(4-methyl-piperazin-1-yl)piperidinyl-1-formamido, 4-(4-ethyl-1-piperazinyl)piperidinyl-1-formamido, 4-(4-acetyl-1-piperazinyl)piperidinyl-1-formamido, 4-(N-methyl-4-piperidinyl)piperazinyl-1-formamido; or

(10) $Z_2$ and $Z_3$ or $Z_3$ and $Z_4$ form a nitrogen- or oxygen-containing substituted or unsubstituted 5- or 6-membered ring, the substituent may be selected from the same substituents as described above for $Z_1$;

$R_2$ is selected from:

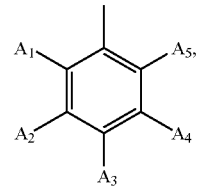

wherein $A_1$, $A_2$, $A_3$, $A_4$, $A_5$ each are independently selected from:

(1) H, F, Cl, Br, I, cyano, trifluoromethyl, trifluoromethoxy, nitro, (2) methylthio, ethylthio, isopropylthio, methylsulfinyl, ethylsulfinyl, isopropylsulfinyl, methylsulfonyl, ethylsulfonyl, isopropylsulfonyl, methylsulfonamido, methoxycarbonyl, ethoxycarbonyl, propoxycarbonyl, isopropoxycarbonyl, n-butoxycarbonyl, isobutoxycarbonyl, tert-butoxycarbonyl, methylaminocarbonyl, ethylaminocarbonyl, propylaminocarbonyl, isopropylaminocarbonyl, cyclopropylaminocarbonyl, cyclobutylaminocarbonyl, cyclopentylaminocarbonyl, dimethylphosphinyl, diethylphosphinyl, diisopropylphosphinyl.

In some embodiments, $R_1$ is selected from:

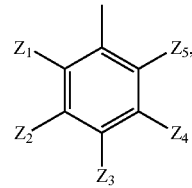

wherein $Z_1$, $Z_2$, $Z_3$, $Z_4$, $Z_5$ each are independently selected from:

(1) H,
(2) C1-C6 alkyl,
(3) C1-C6 alkoxy
(4) piperidinyl, N-methyl-4-piperidinyl, 4-N,N-dimethylaminopiperidinyl, 4-N,N-diethylaminopiperidinyl, 4-N,N-diisopropylaminopiperidinyl, 4-hydroxypiperidinyl
(5) 4-(4-methylpiperazinyl)piperidinyl, 4-(4-ethylpiperazinyl)piperidinyl, 4-(4-isopropylpiperazinyl)piperidinyl, 4-(4-acetylpiperazinyl)piperidinyl, 4-(4-t-butoxycarbonylpiperazinyl)piperidinyl, 4-(4-methylsulfonylpiperazinyl)piperidinyl, 4-(4-(2-hydroxyethyl)piperazinyl)piperidinyl, 4-(4-(2-cyanoethyl)piperazinyl)piperidinyl, 4-(4-(3-hydroxypropyl)piperazinyl)piperidinyl, 4-(4-(2-N,N-dimethylaminoethyl)piperazinyl)piperidinyl, 4-(4-(2-N,N-diethylaminoethyl)piperazinyl)piperidinyl, 4-(4-(3-N,N-dimethylaminopropyl)piperazinyl)piperidinyl, 4-(4-(3-N,N-diethylaminopropyl)piperazinyl)piperidinyl, 4-(tetrahydropyrrolyl)piperidinyl, 4-(3-N,N-dimethylaminotetrahydropyrrolyl)piperidinyl,
(6) 4-methylpiperazinyl, 4-ethylpiperazinyl, 4-isopropylpiperazinyl, 4-acetylpiperazinyl, 4-t-butoxycarbonylpiperazinyl, 4-methylsulfonylpiperazinyl, 4-(2-hydroxyethyl)piperazinyl, 4-(2-cyanoethyl)piperazinyl, 4-(3-hydroxypropyl)piperazinyl, 4-(2-N,N-dimethylaminoethyl)piperazinyl, 4-(2-N,N-diethylaminoethyl)piperazinyl, 4-(3-N,N-dimethylaminopropyl)piperazinyl, 4-(3-N,N-diethylaminopropyl)piperazinyl, 4-(N-methyl-4-piperidinyl)piperazinyl, 4-(N-ethyl-4-piperidinyl)piperazinyl, or
(7) $Z_2$ and $Z_3$ or $Z_3$ and $Z_4$ form a nitrogen- or oxygen-containing substituted or unsubstituted 5- or 6-membered ring, the substituent may be selected from the same substituents as described above for $Z_1$.

In some embodiments, $R_1$ is selected from:

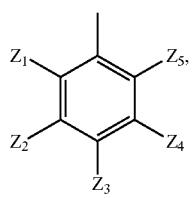

wherein $Z_1$, $Z_2$, $Z_3$, $Z_4$, $Z_5$ each are independently selected from:

(1) H,
(2) methyl, methoxy,
(3) 4-methylpiperazinyl,
(4) N-methyl-4-piperidinyl, 4-(4-methylpiperazinyl)piperidinyl, 4-(tetrahydropyrrol-1-yl)piperidinyl, 4-N,N-dimethylaminopiperidinyl, or
(5) $Z_2$ and $Z_3$ or $Z_3$ and $Z_4$ form

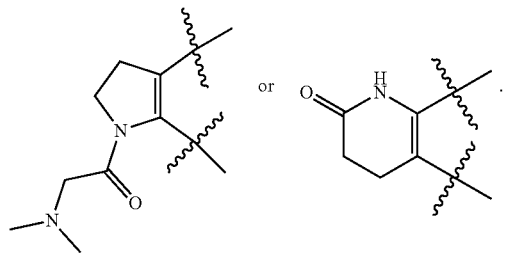 [SMILES: *C1=C(*)N(C(=O)CN(C)C)CC1 ; *C1=C(*)NC(=O)CC1]

In some embodiments, $R_1$ is selected from

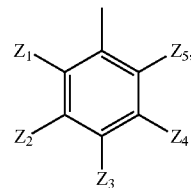

wherein one of $Z_2$ and $Z_4$ is H, the other is methyl, one of $Z_1$ and $Z_5$ is H, the other is methoxy, $Z_3$ is selected from: N-methyl-4-piperidinyl, 4-methylpiperazinyl, 4-(4-methylpiperazinyl)piperidinyl, 4-(tetrahydropyrrol-1-yl)piperidinyl, 4-N,N-dimethylaminopiperidinyl, or $Z_2$ and $Z_3$ or $Z_3$ and $Z_4$ form

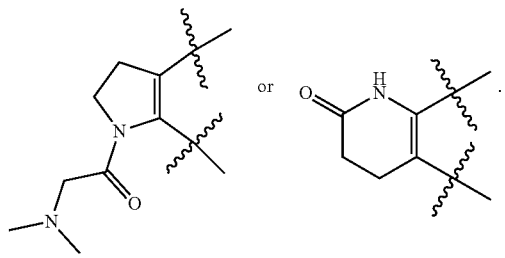 [SMILES: *C1=C(*)N(C(=O)CN(C)C)CC1 ; *C1=C(*)NC(=O)CC1]

In some embodiments, $R_2$ is selected from:

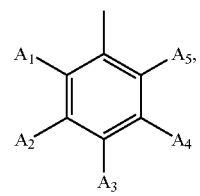

wherein $A_1$, $A_2$, $A_3$, $A_4$, $A_5$ each are independently selected from:

(1) H, (2) dimethylphosphinyl.

In some embodiments, $R_2$ is selected from:

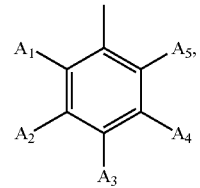

wherein one of $A_1$ and $A_5$ is H, the other is dimethylphosphinyl; $A_2$, $A_3$, $A_4$ are all H.

In a sixteenth aspect, the present invention provides a compound of Formula IRS, a stereoisomer thereof, a prodrug thereof, a pharmaceutically acceptable salt thereof or a pharmaceutically acceptable solvate thereof,

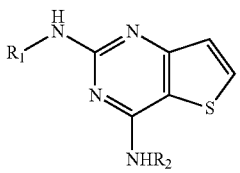

wherein, $R_1$ is selected from:

1) C1-C6 alkyl, 2-N,N-dimethylaminoethyl, 2-hydroxyethyl, 2-N,N-diethylaminoethyl, 2-N,N-diisopropylaminoethyl, 2-morpholinylethyl, 2-(4-methylpiperazinyl)ethyl, 3-N,N-dimethylaminopropyl, 3-N,N-diethylaminopropyl, 3-N,N-diisopropylaminopropyl, 3-morpholinylpropyl, 3-(4-methylpiperazinyl)propyl, C3-C6 cycloalkyl, 4-N,N-dimethylaminocyclohexyl, 4-N,N-diethylaminocyclohexyl, N-methyl-4-piperidinyl, N-ethyl-4-piperidinyl, N-isopropyl-4-piperidinyl, 1,3-dimethyl-5-pyrazolyl, 1-methyl-4-pyrazolyl, 3-methyl-5-isoxazolinyl, 1-(N-methyl-4-piperidinyl)-4-pyrazolyl, 1-(N-t-butoxycarbonyl-4-piperidinyl)-4-pyrazolyl;

2)

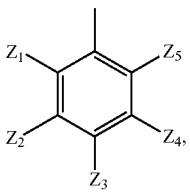

wherein $Z_1$, $Z_2$, $Z_3$, $Z_4$, $Z_5$ each are independently selected from:

(1) H, F, Cl, Br, I, nitro, cyano, (2) C1-C6 alkyl, C1-C6 alkoxy, C1-C6 oxygen-containing alkyl, C1-C6 fluorine-containing alkyl, C1-C6 fluorine-containing alkoxy, (3) piperidinyl, N-methyl-4-piperidinyl, 4-dimethylaminopiperidinyl, 4-N,N-diethylaminopiperidinyl, 4-N,N-diisopropylaminopiperidinyl, 4-hydroxypiperidinyl, 4-(4-methylpiperazinyl)piperidinyl, 4-(4-ethylpiperazinyl)piperidinyl, 4-(4-isopropylpiperazinyl)piperidinyl, 4-(4-acetylpiperazinyl)piperidinyl, 4-(4-t-butoxycarbonylpiperazinyl)piperidinyl, 4-(4-methylsulfonylpiperazinyl)piperidinyl, 4-(4-(2-hydroxyethyl)piperazinyl)piperidinyl, 4-(4-(2-cyanoethyl)piperazinyl)piperidinyl, 4-(4-(3-hydroxypropyl)piperazinyl)piperidinyl, 4-(4-(2-N,N-dimethylaminoethyl)piperazinyl)piperidinyl, 4-(4-(2-N,N-diethylaminoethyl)piperazinyl)piperidinyl, 4-(4-(3-N,N-dimethylaminopropyl)piperazinyl)piperidinyl, 4-(4-(3-N,N-diethylaminopropyl)piperazinyl)piperidinyl, 4-(tetrahydropyrrolyl)piperidinyl, 4-(3-N,N-dimethylaminotetrahydropyrrolyl)piperidinyl, 4-(tetrahydropyrrol-1-yl)piperidinyl (4) 4-methylpiperazinyl, 4-ethylpiperazinyl, 4-isopropylpiperazinyl, 4-acetylpiperazinyl, 4-t-butoxycarbonylpiperazinyl, 4-methylsulfonylpiperazinyl, 4-(2-hydroxyethyl)piperazinyl, 4-(2-cyanoethyl)piperazinyl, 4-(3-hydroxypropyl)piperazinyl, 4-(2-N,N-dimethylaminoethyl)piperazinyl, 4-(2-N,N-diethylaminoethyl)piperazinyl, 4-(3-N,N-dimethylaminopropyl)piperazinyl, 4-(3-N,N-diethylaminopropyl)piperazinyl, 4-(N-methyl-4-piperidinyl)piperazinyl, 4-(N-ethyl-4-piperidinyl)piperazinyl, (5) N,N-dimethylamino, N,N-diethylamino, N,N-diisopropylamino, 2-N,N-dimethylaminoethylamino, 2-morpholinylethylamino, 2-(4-methylpiperazinyl)ethylamino, 3-N,N-dimethylaminopropylamino, 3-N,N-diethylaminopropylamino, 3-N,N-diisopropylaminopropylamino, 3-morpholinylpropylamino, 3-(4-methylpiperazinyl)propylamino, N-methylpiperidinyl-4-amino, N-ethylpiperidinyl-4-amino, N-isopropylpiperidinyl-4-amino, (6) 2-N,N-dimethylaminoethoxy, 2-N,N-diethylaminoethoxy, 2-N,N-diisopropylaminoethoxy, 2-(4-methylpiperazinyl)ethoxy, 2-(4-acetylpiperazinyl)ethoxy, 2-morpholinylethoxy, 2-thiomorpholinylethoxy, 2-piperidinylethoxy, 3-N,N-dimethylaminopropoxy, 3-N,N-diethylaminopropoxy, 3-N,N-diisopropylaminopropoxy, 3-(4-methylpiperazinyl)propoxy, 3-(4-acetylpiperazinyl)propoxy, 3-morpholinylpropoxy, 3-thiomorpholinylpropoxy, 3-piperidinylpropoxy, pyridin-2-ylmethoxy, pyridin-3-ylmethoxy, pyridin-4-ylmethoxy, phenylmethoxy, monohalo-substituted phenylmethoxy, gem-dihalo-substituted phenylmethoxy, hetero-dihalo-substituted phenylmethoxy, (7) hydroxysulfonyl, aminosulfonyl, methylaminosulfonyl, ethylaminosulfonyl, propylaminosulfonyl, isopropylaminosulfonyl, cyclopropylaminosulfonyl, cyclobutylaminosulfonyl, cyclopentylaminosulfonyl, piperidin-1-ylsulfonyl, 4-hydroxypiperidin-1-ylsulfonyl, 4-N,N-dimethylaminopiperidin-1-ylsulfonyl, 4-N,N-diethylaminopiperidin-1-ylsulfonyl, tetrahydropyrrolyl-1-sulfonyl, 3-N,N-dimethylaminotetrahydropyrrolyl-1-sulfonyl, 3-N,N-diethylaminotetrahydropyrrolyl-1-sulfonyl, 4-methylpiperazin-1-ylsulfonyl, 4-ethylpiperazinyl-1-sulfonyl, 4-acetylpiperazinyl-1-sulfonyl, 4-t-butoxycarbonylpiperazinyl-1-sulfonyl, 4-(2-hydroxyethyl)piperazinyl-1-sulfonyl, 4-(2-cyanoethyl)piperazinyl-1-sulfonyl, 4-(2-N,N-dimethylaminoethyl)piperazinyl-1-sulfonyl, 4-(2-N,N-diethylethyl)piperazinyl-1-sulfonyl, 4-(3-hydroxypropyl)piperazinyl-1-sulfonyl, 4-(3-N,N-dimethylaminopropyl)piperazinyl-1-sulfonyl, 4-(3-N,N-diethylaminopropyl)piperazinyl-1-sulfonyl, morpholinyl-1-sulfonyl, 3,5-dimethylmorpholinyl-1-sulfonyl, 4-(4-methyl-piperazin-1-yl)piperidin-1-ylsulfonyl, 4-(4-ethyl-1-piperazinyl)piperidin-1-ylsulfonyl, 4-(4-acetyl-1-piperazinyl)piperidin-1-ylsulfonyl, 4-(N-methyl-4-piperidinyl)piperazinyl-1-sulfonyl, (8) hydroxycarbonyl, aminocarbonyl, methylaminocarbonyl, ethylaminocarbonyl, propylaminocarbonyl, isopropylaminocarbonyl, cyclopropylaminocarbonyl, cyclobutylaminocarbonyl, cyclopentylaminocarbonyl, piperidinyl-1-carbonyl, 4-hydroxypiperidinyl-1-carbonyl, 4-N,N-dimethylaminopiperidinyl-1-carbonyl, 4-N,N-diethylaminopiperidinyl-1-carbonyl, tetrahydropyrrolyl-1-carbonyl, 3-N,N-dimethylaminotetrahydropyrrolyl-1-carbonyl, 3-N,N-diethylaminotetrahydropyrrolyl-1-carbonyl, 4-methylpiperazin-1-ylcarbonyl, 4-ethylpiperazinyl-1-carbonyl, 4-acetylpiperazinyl-1-carbonyl, 4-t-butoxycarbonylpiperazinyl-1-carbonyl, 4-(2-hydroxyethyl)piperazinyl-1-carbonyl, 4-(2-cyanoethyl)piperazinyl-1-carbonyl, 4-(2-N,N-dimethylaminoethyl)piperazinyl-1-carbonyl, 4-(2-N,N-diethylaminoethyl)piperazinyl-1-carbonyl, 4-(3-hydroxypropyl)piperazinyl-1-carbonyl, 4-(3-N,N-dimethylaminopropyl)piperazinyl-1-carbonyl, 4-(3-N,N-diethylaminopropyl)piperazinyl-1-carbonyl, morpholinyl-1-carbonyl, 3,5-dimethylmorpholinyl-1-carbonyl, 4-(4-methyl-piperazin-1-yl)piperidin-1-ylcarbonyl, 4-(4-ethyl-1-piperazinyl)piperidinyl-1-carbonyl, 4-(4-acetyl-1-piperazinyl)piperidinyl-1-carbonyl, 4-(N-methyl-4-piperidinyl)piperazinyl-1-carbonyl, methoxycarbonyl, ethoxycarbonyl, propoxycarbonyl, isopropoxycarbonyl, n-butoxycarbonyl, isobutoxycarbonyl, tert-butoxycarbonyl, (9) aminoformamido, methylaminoformamido, ethylaminoformamido, propylaminoformamido, isopropylaminoformamido, cyclopropylaminoformamido, cyclobutylaminoformamido, cyclopentylaminoformamido, piperidinyl-1-formamido, 4-hydroxypiperidinyl-1-formamido, 4-N,N-dimethylaminopiperidinyl-1-formamido, 4-N,N-diethylaminopiperidinyl-1-formamido, tetrahydropyrrolyl-1-formamido, 3-N,N-dimethylaminotetrahydropyrrolyl-1-formamido, 3-N,N-diethylaminotetrahydropyrrolyl-1-formamido, 4-methylpiperazinyl-1-formamido, 4-ethylpiperazinyl-1-formamido, 4-acetylpiperazinyl-1-formamido, 4-t-butoxycarbonylpiperazinyl-1-formamido, 4-(2-hydroxyethyl)piperazinyl-1-formamido, 4-(2-cyanoethyl)piperazinyl-1-formamido, 4-(2-N,N-dimethylaminoethyl)piperazinyl-1-formamido, 4-(2-N,N-diethylaminoethyl)piperazinyl-1-formamido, 4-(3-hydroxypropyl)piperazinyl-1-formamido, 4-(3-N,N-dimethylaminopropyl)piperazinyl-1-formamido, 4-(3-N,N-diethylaminopropyl)piperazinyl-1-formamido, morpholinyl-1-formamido, 3,5-dimethylmorpholinyl-1-formamido, 4-(4-methyl-piperazin-1-yl)piperidinyl-1-formamido, 4-(4-ethyl-1-piperazinyl)piperidinyl-1-formamido, 4-(4-acetyl-1-piperazinyl)piperidinyl-1-formamido, 4-(N-methyl-4-piperidinyl)piperazinyl-1-formamido; or

(10) $Z_2$ and $Z_3$ or $Z_3$ and $Z_4$ form a nitrogen- or oxygen-containing substituted or unsubstituted 5- or 6-membered ring, the substituent may be selected from the same substituents as described above for $Z_1$;

$R_2$ is selected from

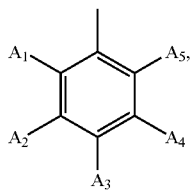

wherein $A_1$, $A_2$, $A_3$, $A_4$, $A_5$ each are independently selected from:

(1) H, F, Cl, Br, I, cyano, trifluoromethyl, trifluoromethoxy, nitro, (2) methylthio, ethylthio, isopropylthio, methylsulfinyl, ethylsulfinyl, isopropylsulfinyl, methylsulfonyl, ethylsulfonyl, isopropylsulfonyl, tert-butyl sulfonyl, methylsulfonamido, methoxycarbonyl, ethoxycarbonyl, propoxycarbonyl, isopropoxycarbonyl, n-butoxycarbonyl, isobutoxycarbonyl, tert-butoxycarbonyl, methylaminocarbonyl, ethylaminocarbonyl, propylaminocarbonyl, isopropylaminocarbonyl, dimethylaminocarbonyl, cyclopropylaminocarbonyl, cyclobutylaminocarbonyl, cyclopentylaminocarbonyl, dimethylphosphinyl, diethylphosphinyl, diisopropylphosphinyl.

In some embodiments, $R_1$ is selected from

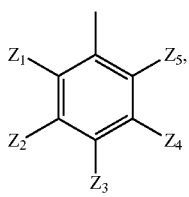

wherein $Z_1$, $Z_2$, $Z_3$, $Z_4$, $Z_5$ each are independently selected from:

(1) H, (2) C1-C6 alkoxy, (3) piperidinyl, N-methyl-4-piperidinyl, 4-dimethylaminopiperidinyl, 4-N,N-diethylaminopiperidinyl, 4-N,N-diisopropylaminopiperidinyl, 4-hydroxypiperidinyl, 4-(4-methylpiperazinyl)piperidinyl, 4-(4-ethylpiperazinyl)piperidinyl, 4-(4-isopropylpiperazinyl)piperidinyl, 4-(4-acetylpiperazinyl)piperidinyl, 4-(4-t-butoxycarbonylpiperazinyl)piperidinyl, 4-(4-methylsulfonylpiperazinyl)piperidinyl, 4-(4-(2-hydroxyethyl)piperazinyl)piperidinyl, 4-(4-(2-cyanoethyl)piperazinyl)piperidinyl, 4-(4-(3-hydroxypropyl)piperazinyl)piperidinyl, 4-(4-(2-N,N-dimethylaminoethyl)piperazinyl)piperidinyl, 4-(4-(2-N,N-diethylaminoethyl)piperazinyl)piperidinyl, 4-(4-(3-N,N-dimethylaminopropyl)piperazinyl)piperidinyl, 4-(4-(3-N,N-diethylaminopropyl)piperazinyl)piperidinyl, 4-(tetrahydropyrrolyl)piperidinyl, 4-(3-N,N-dimethylaminotetrahydropyrrolyl)piperidinyl, 4-(tetrahydropyrrol-1-yl)piperidinyl;

(4) 4-methylpiperazinyl, 4-ethylpiperazinyl, 4-isopropylpiperazinyl, 4-acetylpiperazinyl, 4-t-butoxycarbonylpiperazinyl, 4-methylsulfonylpiperazinyl, 4-(2-hydroxyethyl)piperazinyl, 4-(2-cyanoethyl)piperazinyl, 4-(3-hydroxypropyl)piperazinyl, 4-(2-N,N-dimethylaminoethyl)piperazinyl, 4-(2-N,N-diethylaminoethyl)piperazinyl, 4-(3-N,N-dimethylaminopropyl)piperazinyl, 4-(3-N,N-diethylaminopropyl)piperazinyl, 4-(N-methyl-4-piperidinyl)piperazinyl, 4-(N-ethyl-4-piperidinyl)piperazinyl or (5) $Z_2$ and $Z_3$ or $Z_3$ and $Z_4$ form a nitrogen- or oxygen-containing substituted or unsubstituted 5-membered ring, the substituent may be selected from the same substituents as described above for $Z_1$.

In some embodiments, $R_1$ is selected from

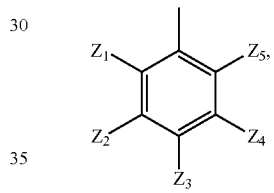

wherein $Z_1$, $Z_2$, $Z_3$, $Z_4$, $Z_5$ each are independently selected from:

(1) H, (2) C1-C6 alkoxy, (3) 4-(tetrahydropyrrol-1-yl)piperidinyl, 4-methylpiperazinyl, 4-(4-methylpiperazinyl)piperidinyl, 4-dimethylamino-piperidinyl;

(4) $Z_2$ and $Z_3$ may form a nitrogen-containing substituted or unsubstituted 5-membered ring

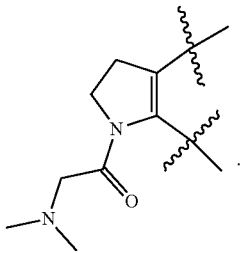 [SMILES: *C1=C(*)N(C(=O)CN(C)C)CC1]

In some embodiments, $R_1$ is selected from:

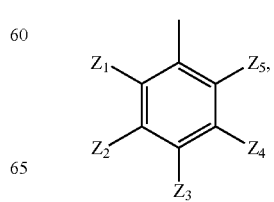

wherein
one of $Z_1$ and $Z_5$ is H, the other is methoxy;
$Z_3$ is selected from: 4-dimethylamino-piperidinyl, 4-methylpiperazinyl, 4-(4-methylpiperazinyl)piperidinyl, 4-(tetrahydropyrrol-1-yl)piperidinyl, or
$Z_2$ and $Z_3$ or $Z_3$ and $Z_4$ form

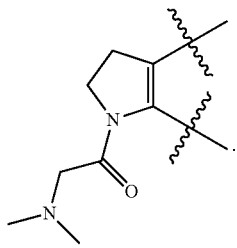 [SMILES: *C1=C(*)N(C(=O)CN(C)C)CC1]

In some embodiments, $R_2$ is selected from:

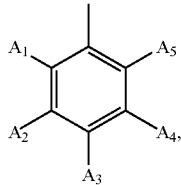

wherein $A_1$, $A_2$, $A_3$, $A_4$, $A_5$ each are independently selected from:
(1) H; (2) diisopropylphosphinyl, diethylphosphinyl.
In some embodiments, $R_2$ is selected from:

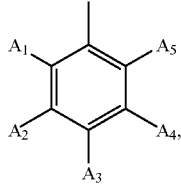

wherein one of $A_1$ and $A_5$ is H, the other is diisopropylphosphinyl or diethylphosphinyl; $A_2$, $A_3$, $A_4$ are all H.

In a seventeenth aspect, the present invention provides a compound of Formula IL, a stereoisomer thereof, a prodrug thereof, a pharmaceutically acceptable salt thereof or a pharmaceutically acceptable solvate thereof,

IL

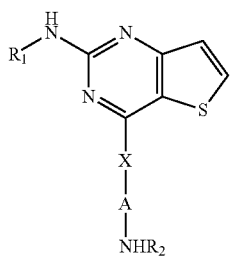

wherein, A is methylene; X is NH;

$R_1$ is selected from:
1) C1-C6 alkyl, 2-N,N-dimethylaminoethyl, 2-hydroxyethyl, 2-N,N-diethylaminoethyl, 2-N,N-diisopropylaminoethyl, 2-morpholinylethyl, 2-(4-methylpiperazinyl)ethyl, 3-N,N-dimethylaminopropyl, 3-N,N-diethylaminopropyl, 3-N,N-diisopropylaminopropyl, 3-morpholinylpropyl, 3-(4-methylpiperazinyl)propyl, C3-C6 cycloalkyl, 4-N,N-dimethylaminocyclohexyl, 4-N,N-diethylaminocyclohexyl, N-methyl-4-piperidinyl, N-ethyl-4-piperidinyl, N-isopropyl-4-piperidinyl, 1,3-dimethyl-5-pyrazolyl, 1-methyl-4-pyrazolyl, 3-methyl-5-isoxazolinyl, 1-(N-methyl-4-piperidinyl)-4-pyrazolyl, 1-(N-t-butoxycarbonyl-4-piperidinyl)-4-pyrazolyl;

2)

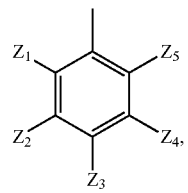

wherein $Z_1$, $Z_2$, $Z_3$, $Z_4$, $Z_5$ each are independently selected from:
(1) H, F, Cl, Br, I, nitro, cyano,
(2) C1-C6 alkyl, C1-C6 alkoxy, C1-C6 oxygen-containing alkyl, C1-C6 fluorine-containing alkyl, C1-C6 fluorine-containing alkoxy,
(3) piperidinyl, N-methyl-4-piperidinyl, 4-N,N-dimethylaminopiperidinyl, 4-N,N-diethylaminopiperidinyl, 4-N,N-diisopropylaminopiperidinyl, 4-hydroxypiperidinyl, 4-(4-methylpiperazinyl)piperidinyl, 4-(4-ethylpiperazinyl)piperidinyl, 4-(4-isopropylpiperazinyl)piperidinyl, 4-(4-acetylpiperazinyl)piperidinyl, 4-(4-t-butoxycarbonylpiperazinyl)piperidinyl, 4-(4-methylsulfonylpiperazinyl)piperidinyl, 4-(4-(2-hydroxyethyl)piperazinyl)piperidinyl, 4-(4-(2-cyanoethyl)piperazinyl)piperidinyl, 4-(4-(3-hydroxypropyl)piperazinyl)piperidinyl, 4-(4-(2-N,N-dimethylaminoethyl)piperazinyl)piperidinyl, 4-(4-(2-N,N-diethylaminoethyl)piperazinyl)piperidinyl, 4-(4-(3-N,N-dimethylaminopropyl)piperazinyl)piperidinyl, 4-(4-(3-N,N-diethylaminopropyl)piperazinyl)piperidinyl, 4-(tetrahydropyrrolyl)piperidinyl, 4-(3-N,N-dimethylaminotetrahydropyrrolyl)piperidinyl,
(4) 4-methylpiperazinyl, 4-ethylpiperazinyl, 4-isopropylpiperazinyl, 4-acetylpiperazinyl, 4-t-butoxycarbonylpiperazinyl, 4-methylsulfonylpiperazinyl, 4-(2-hydroxyethyl)piperazinyl, 4-(2-cyanoethyl)piperazinyl, 4-(3-hydroxypropyl)piperazinyl, 4-(2-N,N-dimethylaminoethyl)piperazinyl, 4-(2-N,N-diethylaminoethyl)piperazinyl, 4-(3-N,N-dimethylaminopropyl)piperazinyl, 4-(3-N,N-diethylaminopropyl)piperazinyl, 4-(N-methyl-4-piperidinyl)piperazinyl, 4-(N-ethyl-4-piperidinyl)piperazinyl,
(5) N,N-dimethylamino, N,N-diethylamino, N,N-diisopropylamino, 2-N,N-dimethylaminoethylamino, 2-morpholinylethylamino, 2-(4-methylpiperazinyl)ethylamino, 3-N,N-dimethylaminopropylamino, 3-N,N-diethylaminopropylamino, 3-N,N-diisopropylaminopropylamino, 3-morpholinylpropylamino, 3-(4-methylpiperazinyl)propylamino, N-methylpiperidinyl-4-amino, N-ethylpiperidinyl-4-amino, N-isopropylpiperidinyl-4-amino,
(6) 2-N,N-dimethylaminoethoxy, 2-N,N-diethylaminoethoxy, 2-N,N-diisopropylaminoethoxy, 2-(4-methylpiperazinyl)ethoxy, 2-(4-acetylpiperazinyl)ethoxy, 2-morpholinylethoxy, 2-thiomorpholinylethoxy, 2-piperidinylethoxy, 3-N,N-dimethylaminopropoxy, 3-N,N-diethylaminopropoxy, 3-N,N-diisopropylaminopropoxy, 3-(4-methylpiperazinyl)propoxy, 3-(4-acetylpiperazinyl)propoxy, 3-morpholinylpropoxy, 3-thiomorpholinylpropoxy, 3-piperidinylpropoxy, pyridin-2-ylmethoxy, pyridin-3-ylmethoxy, pyridin-4-ylmethoxy, phenylmethoxy, monohalo-substituted phenylmethoxy, gem-dihalo-substituted phenylmethoxy, hetero-dihalo-substituted phenylmethoxy, (7) hydroxysulfonyl, aminosulfonyl, methylaminosulfonyl, ethylaminosulfonyl, propylaminosulfonyl, isopropylaminosulfonyl, cyclopropylaminosulfonyl, cyclobutylaminosulfonyl, cyclopentylaminosulfonyl, piperidin-1-ylsulfonyl, 4-hydroxypiperidin-1-ylsulfonyl, 4-N,N-dimethylaminopiperidin-1-ylsulfonyl, 4-N,N-diethylaminopiperidin-1-ylsulfonyl, tetrahydropyrrolyl-1-sulfonyl, 3-N,N-dimethylaminotetrahydropyrrolyl-1-sulfonyl, 3-N,N-diethylaminotetrahydropyrrolyl-1-sulfonyl, 4-methylpiperazin-1-ylsulfonyl, 4-ethylpiperazinyl-1-sulfonyl, 4-acetylpiperazinyl-1-sulfonyl, 4-t-butoxycarbonylpiperazinyl-1-sulfonyl, 4-(2-hydroxyethyl)piperazinyl-1-sulfonyl, 4-(2-cyanoethyl)piperazinyl-1-sulfonyl, 4-(2-N,N-dimethylaminoethyl)piperazinyl-1-sulfonyl, 4-(2-N,N-diethylethyl)piperazinyl-1-sulfonyl, 4-(3-hydroxypropyl)piperazinyl-1-sulfonyl, 4-(3-N,N-dimethylaminopropyl)piperazinyl-1-sulfonyl, 4-(3-N,N-diethylaminopropyl)piperazinyl-1-sulfonyl, morpholinyl-1-sulfonyl, 3,5-dimethylmorpholinyl-1-sulfonyl, 4-(4-methyl-piperazin-1-yl)piperidin-1-ylsulfonyl, 4-(4-ethyl-1-piperazinyl)piperidin-1-ylsulfonyl, 4-(4-acetyl-1-piperazinyl)piperidin-1-ylsulfonyl, 4-(N-methyl-4-piperidinyl)piperazinyl-1-sulfonyl, (8) hydroxycarbonyl, aminocarbonyl, methylaminocarbonyl, ethylaminocarbonyl, propylaminocarbonyl, isopropylaminocarbonyl, cyclopropylaminocarbonyl, cyclobutylaminocarbonyl, cyclopentylaminocarbonyl, piperidinyl-1-carbonyl, 4-hydroxypiperidinyl-1-carbonyl, 4-N,N-dimethylaminopiperidinyl-1-carbonyl, 4-N,N-diethylaminopiperidinyl-1-carbonyl, tetrahydropyrrolyl-1-carbonyl, 3-N,N-dimethylaminotetrahydropyrrolyl-1-carbonyl, 3-N,N-diethylaminotetrahydropyrrolyl-1-carbonyl, 4-methylpiperazin-1-ylcarbonyl, 4-ethylpiperazinyl-1-carbonyl, 4-acetylpiperazinyl-1-carbonyl, 4-t-butoxycarbonylpiperazinyl-1-carbonyl, 4-(2-hydroxyethyl)piperazinyl-1-carbonyl, 4-(2-cyanoethyl)piperazinyl-1-carbonyl, 4-(2-N,N-dimethylaminoethyl)piperazinyl-1-carbonyl, 4-(2-N,N-diethylaminoethyl)piperazinyl-1-carbonyl, 4-(3-hydroxypropyl)piperazinyl-1-carbonyl, 4-(3-N,N-dimethylaminopropyl)piperazinyl-1-carbonyl, 4-(3-N,N-diethylaminopropyl)piperazinyl-1-carbonyl, morpholinyl-1-carbonyl, 3,5-dimethylmorpholinyl-1-carbonyl, 4-(4-methyl-piperazin-1-yl)piperidin-1-ylcarbonyl, 4-(4-ethyl-1-piperazinyl)piperidinyl-1-carbonyl, 4-(4-acetyl-1-piperazinyl)piperidinyl-1-carbonyl, 4-(N-methyl-4-piperidinyl)piperazinyl-1-carbonyl, methoxycarbonyl, ethoxycarbonyl, propoxycarbonyl, isopropoxycarbonyl, n-butoxycarbonyl, isobutoxycarbonyl, tert-butoxycarbonyl, (9) aminoformamido, methylaminoformamido, ethylaminoformamido, propylaminoformamido, isopropylaminoformamido, cyclopropylaminoformamido, cyclobutylaminoformamido, cyclopentylaminoformamido, piperidinyl-1-formamido, 4-hydroxypiperidinyl-1-formamido, 4-N,N-dimethylaminopiperidinyl-1-formamido, 4-N,N-diethylaminopiperidinyl-1-formamido, tetrahydropyrrolyl-1-formamido, 3-N,N-dimethylaminotetrahydropyrrolyl-1-formamido, 3-N,N-diethylaminotetrahydropyrrolyl-1-formamido, 4-methylpiperazinyl-1-formamido, 4-ethylpiperazinyl-1-formamido, 4-acetylpiperazinyl-1-formamido, 4-t-butoxycarbonylpiperazinyl-1-formamido, 4-(2-hydroxyethyl)piperazinyl-1-formamido, 4-(2-cyanoethyl)piperazinyl-1-formamido, 4-(2-N,N-dimethylaminoethyl)piperazinyl-1-formamido, 4-(2-N,N-diethylaminoethyl)piperazinyl-1-formamido, 4-(3-hydroxypropyl)piperazinyl-1-formamido, 4-(3-N,N-dimethylaminopropyl)piperazinyl-1-formamido, 4-(3-N,N-diethylaminopropyl)piperazinyl-1-formamido, morpholinyl-1-formamido, 3,5-dimethylmorpholinyl-1-formamido, 4-(4-methyl-piperazin-1-yl)piperidinyl-1-formamido, 4-(4-ethyl-1-piperazinyl)piperidinyl-1-formamido, 4-(4-acetyl-1-piperazinyl)piperidinyl-1-formamido, 4-(N-methyl-4-piperidinyl)piperazinyl-1-formamido; or

(10) $Z_2$ and $Z_3$ or $Z_3$ and $Z_4$ form a nitrogen- or oxygen-containing substituted or unsubstituted 5- or 6-membered ring, the substituent may be selected from the same substituents as described above for $Z_1$;

$R_2$ is selected from

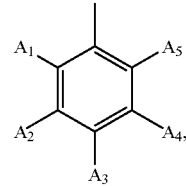

wherein $A_1$, $A_2$, $A_3$, $A_4$, $A_5$ each are independently selected from:
(1) H, F, C, Br, I, cyano, trifluoromethyl, trifluoromethoxy, nitro,
(2) methylthio, ethylthio, isopropylthio, methylsulfinyl, ethylsulfinyl, isopropylsulfinyl, methylsulfonyl, ethylsulfonyl, isopropylsulfonyl, methylsulfonamido, methoxycarbonyl, ethoxycarbonyl, propoxycarbonyl, isopropoxycarbonyl, n-butoxycarbonyl, isobutoxycarbonyl, tert-butoxycarbonyl, methylaminocarbonyl, ethylaminocarbonyl, propylaminocarbonyl, isopropylaminocarbonyl, cyclopropylaminocarbonyl, cyclobutylaminocarbonyl, cyclopentylaminocarbonyl, dimethylphosphinyl, diethylphosphinyl, diisopropylphosphinyl.

In some embodiments, $R_1$ is selected from:

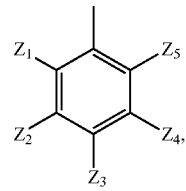

wherein $Z_1$, $Z_2$, $Z_3$, $Z_4$, $Z_5$ each are independently selected from:
(1) H,
(2) C1-C6 alkoxy,
(3) piperidinyl, N-methyl-4-piperidinyl, 4-N,N-dimethylaminopiperidinyl, 4-N,N-diethylaminopiperidinyl, 4-N,N-diisopropylaminopiperidinyl, 4-hydroxypiperidinyl
(4) 4-(4-methylpiperazinyl)piperidinyl, 4-(4-ethylpiperazinyl)piperidinyl, 4-(4-isopropylpiperazinyl)piperidinyl, 4-(4-acetylpiperazinyl)piperidinyl, 4-(4-t-butoxycarbonylpiperazinyl)piperidinyl, 4-(4-methylsulfonylpiperazinyl)

piperidinyl, 4-(4-(2-hydroxyethyl)piperazinyl)piperidinyl, 4-(4-(2-cyanoethyl)piperazinyl)piperidinyl, 4-(4-(3-hydroxypropyl)piperazinyl)piperidinyl, 4-(4-(2-N,N-dimethylaminoethyl)piperazinyl)piperidinyl, 4-(4-(2-N,N-diethylaminoethyl)piperazinyl)piperidinyl, 4-(4-(3-N,N-dimethylaminopropyl)piperazinyl)piperidinyl, 4-(4-(3-N,N-diethylaminopropyl)piperazinyl)piperidinyl, 4-(tetrahydropyrrol-1-yl)piperidinyl, 4-(3-N,N-dimethylaminotetrahydropyrrolyl)piperidinyl, (5) 4-methylpiperazinyl, 4-ethylpiperazinyl, 4-isopropylpiperazinyl, 4-acetylpiperazinyl, 4-t-butoxycarbonylpiperazinyl, 4-methylsulfonylpiperazinyl, 4-(2-hydroxyethyl)piperazinyl, 4-(2-cyanoethyl)piperazinyl, 4-(3-hydroxypropyl)piperazinyl, 4-(2-N,N-dimethylaminoethyl)piperazinyl, 4-(2-N,N-diethylaminoethyl)piperazinyl, 4-(3-N,N-dimethylaminopropyl)piperazinyl, 4-(3-N,N-diethylaminopropyl)piperazinyl, 4-(N-methyl-4-piperidinyl)piperazinyl, 4-(N-ethyl-4-piperidinyl)piperazinyl, or (6) $Z_2$ and $Z_3$ or $Z_3$ and $Z_4$ form a nitrogen- or oxygen-containing substituted or unsubstituted 5-membered ring, the substituent may be selected from the same substituents as described above for $Z_1$.

In some embodiments, $R_1$ is selected from:

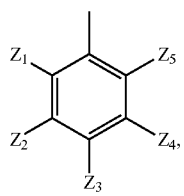

wherein $Z_1$, $Z_2$, $Z_3$, $Z_4$, $Z_5$ each are independently selected from:
(1) H,
(2) methoxy,
(3) 4-hydroxypiperidinyl, 4-(4-methylpiperazinyl)piperidinyl,
(4) 4-methylpiperazinyl, or
(5) $Z_2$ and $Z_3$ or $Z_3$ and $Z_4$ form

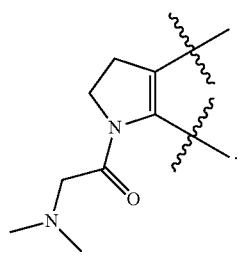 [SMILES: *C1=C(*)N(C(=O)CN(C)C)CC1]

In some embodiments, $R_1$ is selected from:

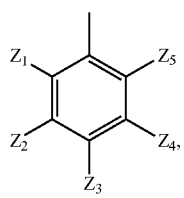

wherein one of $Z_1$ and $Z_5$ is H, the other is methoxy; $Z_4$ is H;
$Z_3$ is selected from: 4-hydroxypiperidinyl, 4-methylpiperazinyl, 4-(4-methylpiperazinyl)piperidinyl, or $Z_2$ and $Z_3$ form

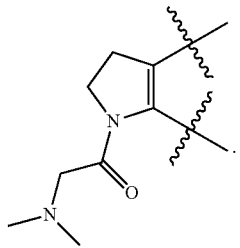 [SMILES: *C1=C(*)N(C(=O)CN(C)C)CC1]

In some embodiments, $R_2$ is selected from:

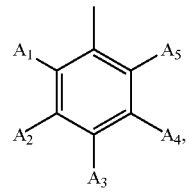

wherein $A_1$, $A_2$, $A_3$, $A_4$, $A_5$ each are independently selected from:
(1) H, (2) methylsulfonyl.

In some embodiments, $R_2$ is selected from:

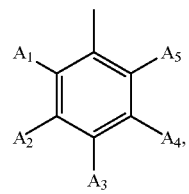

wherein one of $A_1$ and $A_5$ is H, the other is methylsulfonyl; $A_2$, $A_3$, $A_4$ are all H.

In a eighteenth aspect, the present invention provides a compound of Formula IM, a stereoisomer thereof, a prodrug thereof, a pharmaceutically acceptable salt thereof or a pharmaceutically acceptable solvate thereof,

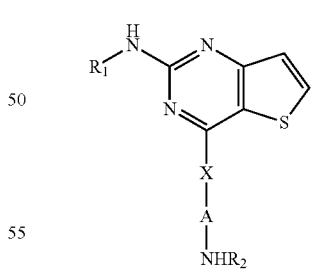

IM wherein, A is methylene; X is NH;
$R_1$ is selected from:
1) C1-C6 alkyl, 2-N,N-dimethylaminoethyl, 2-hydroxyethyl, 2-N,N-diethylaminoethyl, 2-N,N-diisopropylaminoethyl, 2-morpholinylethyl, 2-(4-methylpiperazinyl)ethyl, 3-N,N-dimethylaminopropyl, 3-N,N-diethylaminopropyl, 3-N,N-diisopropylaminopropyl, 3-morpholinylpropyl, 3-(4-methylpiperazinyl)propyl, C3-C6 cycloalkyl, 4-N,N-dimethylaminocyclohexyl, 4-N,N-diethylaminocyclohexyl, N-methyl-4-piperidinyl, N-ethyl-4-piperidinyl, N-isopropyl-4-piperidinyl, 1,3-dimethyl-5-pyrazolyl, 1-methyl-4-pyrazolyl, 3-methyl-5-isoxazolinyl, 1-(N-methyl-4-piperidinyl)-4-pyrazolyl, 1-(N-t-butoxycarbonyl-4-piperidinyl)-4-pyrazolyl;

2)

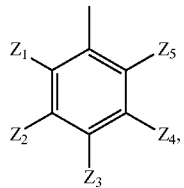

wherein $Z_1$, $Z_2$, $Z_3$, $Z_4$, $Z_5$ each are independently selected from:

(1) H, F, Cl, Br, I, nitro, cyano, (2) C1-C6 alkyl, C1-C6 alkoxy, C1-C6 oxygen-containing alkyl, C1-C6 fluorine-containing alkyl, C1-C6 fluorine-containing alkoxy, (3) piperidinyl, N-methyl-4-piperidinyl, 4-N,N-dimethylaminopiperidinyl, 4-N,N-diethylaminopiperidinyl, 4-N,N-diisopropylaminopiperidinyl, 4-hydroxypiperidinyl, 4-(4-methylpiperazinyl)piperidinyl, 4-(4-ethylpiperazinyl)piperidinyl, 4-(4-isopropylpiperazinyl)piperidinyl, 4-(4-acetylpiperazinyl)piperidinyl, 4-(4-t-butoxycarbonylpiperazinyl)piperidinyl, 4-(4-methylsulfonylpiperazinyl)piperidinyl, 4-(4-(2-hydroxyethyl)piperazinyl)piperidinyl, 4-(4-(2-cyanoethyl)piperazinyl)piperidinyl, 4-(4-(3-hydroxypropyl)piperazinyl)piperidinyl, 4-(4-(2-N,N-dimethylaminoethyl)piperazinyl)piperidinyl, 4-(4-(2-N,N-diethylaminoethyl)piperazinyl)piperidinyl, 4-(4-(3-N,N-dimethylaminopropyl)piperazinyl)piperidinyl, 4-(4-(3-N,N-diethylaminopropyl)piperazinyl)piperidinyl, 4-(tetrahydropyrrolyl)piperidinyl, 4-(3-N,N-dimethylaminotetrahydropyrrolyl)piperidinyl, (4) 4-methylpiperazinyl, 4-ethylpiperazinyl, 4-isopropylpiperazinyl, 4-acetylpiperazinyl, 4-t-butoxycarbonylpiperazinyl, 4-methylsulfonylpiperazinyl, 4-(2-hydroxyethyl)piperazinyl, 4-(2-cyanoethyl)piperazinyl, 4-(3-hydroxypropyl)piperazinyl, 4-(2-N,N-dimethylaminoethyl)piperazinyl, 4-(2-N,N-diethylaminoethyl)piperazinyl, 4-(3-N,N-dimethylaminopropyl)piperazinyl, 4-(3-N,N-diethylaminopropyl)piperazinyl, 4-(N-methyl-4-piperidinyl)piperazinyl, 4-(N-ethyl-4-piperidinyl)piperazinyl, (5) N,N-dimethylamino, N,N-diethylamino, N,N-diisopropylamino, 2-N,N-dimethylaminoethylamino, 2-morpholinylethylamino, 2-(4-methylpiperazinyl)ethylamino, 3-N,N-dimethylaminopropylamino, 3-N,N-diethylaminopropylamino, 3-N,N-diisopropylaminopropylamino, 3-morpholinylpropylamino, 3-(4-methylpiperazinyl)propylamino, N-methylpiperidinyl-4-amino, N-ethylpiperidinyl-4-amino, N-isopropylpiperidinyl-4-amino, (6) 2-N,N-dimethylaminoethoxy, 2-N,N-diethylaminoethoxy, 2-N,N-diisopropylaminoethoxy, 2-(4-methylpiperazinyl)ethoxy, 2-(4-acetylpiperazinyl)ethoxy, 2-morpholinylethoxy, 2-thiomorpholinylethoxy, 2-piperidinylethoxy, 3-N,N-dimethylaminopropoxy, 3-N,N-diethylaminopropoxy, 3-N,N-diisopropylaminopropoxy, 3-(4-methylpiperazinyl)propoxy, 3-(4-acetylpiperazinyl)propoxy, 3-morpholinylpropoxy, 3-thiomorpholinylpropoxy, 3-piperidinylpropoxy, pyridin-2-ylmethoxy, pyridin-3-ylmethoxy, pyridin-4-ylmethoxy, phenylmethoxy, monohalo-substituted phenylmethoxy, gem-dihalo-substituted phenylmethoxy, hetero-dihalo-substituted phenylmethoxy, (7) hydroxysulfonyl, aminosulfonyl, methylaminosulfonyl, ethylaminosulfonyl, propylaminosulfonyl, isopropylaminosulfonyl, cyclopropylaminosulfonyl, cyclobutylaminosulfonyl, cyclopentylaminosulfonyl, piperidin-1-ylsulfonyl, 4-hydroxypiperidin-1-ylsulfonyl, 4-N,N-dimethylaminopiperidin-1-ylsulfonyl, 4-N,N-diethylaminopiperidin-1-ylsulfonyl, tetrahydropyrrolyl-1-sulfonyl, 3-N,N-dimethylaminotetrahydropyrrolyl-1-sulfonyl, 3-N,N-diethylaminotetrahydropyrrolyl-1-sulfonyl, 4-methylpiperazin-1-ylsulfonyl, 4-ethylpiperazinyl-1-sulfonyl, 4-acetylpiperazinyl-1-sulfonyl, 4-t-butoxycarbonylpiperazinyl-1-sulfonyl, 4-(2-hydroxyethyl)piperazinyl-1-sulfonyl, 4-(2-cyanoethyl)piperazinyl-1-sulfonyl, 4-(2-N,N-dimethylaminoethyl)piperazinyl-1-sulfonyl, 4-(2-N,N-diethylethyl)piperazinyl-1-sulfonyl, 4-(3-hydroxypropyl)piperazinyl-1-sulfonyl, 4-(3-N,N-dimethylaminopropyl)piperazinyl-1-sulfonyl, 4-(3-N,N-diethylaminopropyl)piperazinyl-1-sulfonyl, morpholinyl-1-sulfonyl, 3,5-dimethylmorpholinyl-1-sulfonyl, 4-(4-methyl-piperazin-1-yl)piperidin-1-ylsulfonyl, 4-(4-ethyl-1-piperazinyl)piperidin-1-ylsulfonyl, 4-(4-acetyl-1-piperazinyl)piperidin-1-ylsulfonyl, 4-(N-methyl-4-piperidinyl)piperazinyl-1-sulfonyl, (8) hydroxycarbonyl, aminocarbonyl, methylaminocarbonyl, ethylaminocarbonyl, propylaminocarbonyl, isopropylaminocarbonyl, cyclopropylaminocarbonyl, cyclobutylaminocarbonyl, cyclopentylaminocarbonyl, piperidinyl-1-carbonyl, 4-hydroxypiperidinyl-1-carbonyl, 4-N,N-dimethylaminopiperidinyl-1-carbonyl, 4-N,N-diethylaminopiperidinyl-1-carbonyl, tetrahydropyrrolyl-1-carbonyl, 3-N,N-dimethylaminotetrahydropyrrolyl-1-carbonyl, 3-N,N-diethylaminotetrahydropyrrolyl-1-carbonyl, 4-methylpiperazin-1-ylcarbonyl, 4-ethylpiperazinyl-1-carbonyl, 4-acetylpiperazinyl-1-carbonyl, 4-t-butoxycarbonylpiperazinyl-1-carbonyl, 4-(2-hydroxyethyl)piperazinyl-1-carbonyl, 4-(2-cyanoethyl)piperazinyl-1-carbonyl, 4-(2-N,N-dimethylaminoethyl)piperazinyl-1-carbonyl, 4-(2-N,N-diethylaminoethyl)piperazinyl-1-carbonyl, 4-(3-hydroxypropyl)piperazinyl-1-carbonyl, 4-(3-N,N-dimethylaminopropyl)piperazinyl-1-carbonyl, 4-(3-N,N-diethylaminopropyl)piperazinyl-1-carbonyl, morpholinyl-1-carbonyl, 3,5-dimethylmorpholinyl-1-carbonyl, 4-(4-methyl-piperazin-1-yl)piperidin-1-ylcarbonyl, 4-(4-ethyl-1-piperazinyl)piperidinyl-1-carbonyl, 4-(4-acetyl-1-piperazinyl)piperidinyl-1-carbonyl, 4-(N-methyl-4-piperidinyl)piperazinyl-1-carbonyl, methoxycarbonyl, ethoxycarbonyl, propoxycarbonyl, isopropoxycarbonyl, n-butoxycarbonyl, isobutoxycarbonyl, tert-butoxycarbonyl, (9) aminoformamido, methylaminoformamido, ethylaminoformamido, propylaminoformamido, isopropylaminoformamido, cyclopropylaminoformamido, cyclobutylaminoformamido, cyclopentylaminoformamido, piperidinyl-1-formamido, 4-hydroxypiperidinyl-1-formamido, 4-N,N-dimethylaminopiperidinyl-1-formamido, 4-N,N-diethylaminopiperidinyl-1-formamido, tetrahydropyrrolyl-1-formamido, 3-N,N-dimethylaminotetrahydropyrrolyl-1-formamido, 3-N,N-diethylaminotetrahydropyrrolyl-1-formamido, 4-methylpiperazinyl-1-formamido, 4-ethylpiperazinyl-1-formamido, 4-acetylpiperazinyl-1-formamido, 4-t-butoxycarbonylpiperazinyl-1-formamido, 4-(2-hydroxyethyl)piperazinyl-1-formamido, 4-(2-cyanoethyl)piperazinyl-1-formamido, 4-(2-N,N-dimethylaminoethyl)piperazinyl-1-formamido, 4-(2-N,N-diethylaminoethyl)piperazinyl-1-formamido, 4-(3-hydroxypropyl)piperazinyl-1-formamido, 4-(3-N,N-dimethylaminopropyl)piperazinyl-1-formamido, 4-(3-N,N-diethylaminopropyl)piperazinyl-1- formamido, morpholinyl-1-formamido, 3,5-dimethylmorpholinyl-1-formamido, 4-(4-methyl-piperazin-1-yl)piperidinyl-1-formamido, 4-(4-ethyl-1-piperazinyl)piperidinyl-1-formamido, 4-(4-acetyl-1-piperazinyl)piperidinyl-1-formamido, 4-(N-methyl-4-piperidinyl)piperazinyl-1-formamido; or

(10) $Z_2$ and $Z_3$ or $Z_3$ and $Z_4$ form a nitrogen- or oxygen-containing substituted or unsubstituted 5- or 6-membered ring, the substituent may be selected from the same substituents as described above for $Z_1$;

$R_2$ is selected from:

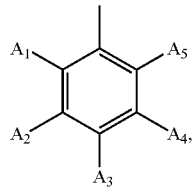

wherein $A_1$, $A_2$, $A_3$, $A_4$, $A_5$ each are independently selected from:

(1) H, F, Cl, Br, I, cyano, trifluoromethyl, trifluoromethoxy, nitro, (2) methylthio, ethylthio, isopropylthio, methylsulfinyl, ethylsulfinyl, isopropylsulfinyl, methylsulfonyl, ethylsulfonyl, isopropylsulfonyl, methylsulfonamido, methoxycarbonyl, ethoxycarbonyl, propoxycarbonyl, isopropoxycarbonyl, n-butoxycarbonyl, isobutoxycarbonyl, tert-butoxycarbonyl, methylaminocarbonyl, ethylaminocarbonyl, propylaminocarbonyl, isopropylaminocarbonyl, cyclopropylaminocarbonyl, cyclobutylaminocarbonyl, cyclopentylaminocarbonyl, dimethylphosphinyl, diethylphosphinyl, diisopropylphosphinyl.

In some embodiments, $R_1$ is selected from:

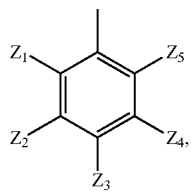

wherein $Z_1$, $Z_2$, $Z_3$, $Z_4$, $Z_5$ each are independently selected from:

(1) H, (2) C1-C6 alkoxy, (3) piperidinyl, N-methyl-4-piperidinyl, 4-N,N-dimethylaminopiperidinyl, 4-N,N-diethylaminopiperidinyl, 4-N,N-diisopropylaminopiperidinyl, 4-hydroxypiperidinyl (4) 4-(4-methylpiperazinyl)piperidinyl, 4-(4-ethylpiperazinyl)piperidinyl, 4-(4-isopropylpiperazinyl)piperidinyl, 4-(4-acetylpiperazinyl)piperidinyl, 4-(4-t-butoxycarbonylpiperazinyl)piperidinyl, 4-(4-methylsulfonylpiperazinyl)piperidinyl, 4-(4-(2-hydroxyethyl)piperazinyl)piperidinyl, 4-(4-(2-cyanoethyl)piperazinyl)piperidinyl, 4-(4-(3-hydroxypropyl)piperazinyl)piperidinyl, 4-(4-(2-N,N-dimethylaminoethyl)piperazinyl)piperidinyl, 4-(4-(2-N,N-diethylaminoethyl)piperazinyl)piperidinyl, 4-(4-(3-N,N-dimethylaminopropyl)piperazinyl)piperidinyl, 4-(4-(3-N,N-diethylaminopropyl)piperazinyl)piperidinyl, 4-(tetrahydropyrrol-1-yl)piperidinyl, 4-(3-N,N-dimethylaminotetrahydropyrrolyl)piperidinyl, (5) 4-methylpiperazinyl, 4-ethylpiperazinyl, 4-isopropylpiperazinyl, 4-acetylpiperazinyl, 4-t-butoxycarbonylpiperazinyl, 4-methylsulfonylpiperazinyl, 4-(2-hydroxyethyl)piperazinyl, 4-(2-cyanoethyl)piperazinyl, 4-(3-hydroxypropyl)piperazinyl, 4-(2-N,N-dimethylaminoethyl)piperazinyl, 4-(2-N,N-diethylaminoethyl)piperazinyl, 4-(3-N,N-dimethylaminopropyl)piperazinyl, 4-(3-N,N-diethylaminopropyl)piperazinyl, 4-(N-methyl-4-piperidinyl)piperazinyl, 4-(N-ethyl-4-piperidinyl)piperazinyl or (6) $Z_2$ and $Z_3$ or $Z_3$ and $Z_4$ form a nitrogen- or oxygen-containing substituted or unsubstituted 5-membered ring, the substituent may be selected from the same substituents as described above for $Z_1$.

In some embodiments, $R_1$ is selected from:

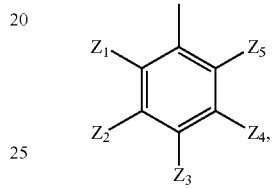

wherein $Z_1$, $Z_2$, $Z_3$, $Z_4$, $Z_5$ each are independently selected from:

(1) H, (2) methoxy, (3) 4-hydroxypiperidinyl, 4-(4-methylpiperazinyl)piperidinyl, (4) 4-methylpiperazinyl, or (5) $Z_2$ and $Z_3$ or $Z_3$ and $Z_4$ form

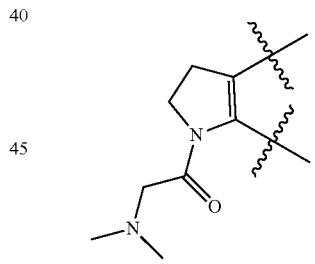

In some embodiments, $R_1$ is selected from:

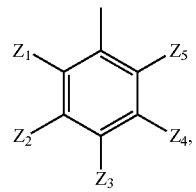

wherein one of $Z_1$ and $Z_5$ is H, the other is methoxy; $Z_4$ is H;

$Z_3$ is selected from: 4-hydroxypiperidinyl, 4-methylpiperazinyl, 4-(4-methylpiperazinyl)piperidinyl, or $Z_2$ and $Z_3$ form

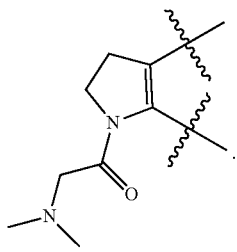 [SMILES: *C1=C(*)N(C(=O)CN(C)C)CC1]

In some embodiments, $R_2$ is selected from:

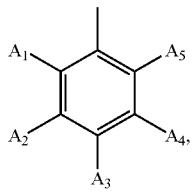

wherein $A_1$, $A_2$, $A_3$, $A_4$, $A_5$ each are independently selected from:
(1) H, (2) isopropylsulfonyl.

In some embodiments, $R_2$ is selected from:

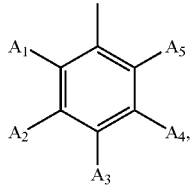

wherein one of $A_1$ and $A_5$ is H, the other is isopropylsulfonyl; $A_2$, $A_3$, $A_4$ are all H.

In a nineteenth aspect, the present invention provides a compound of Formula IT, a stereoisomer thereof, a prodrug thereof, a pharmaceutically acceptable salt thereof or a pharmaceutically acceptable solvate thereof,

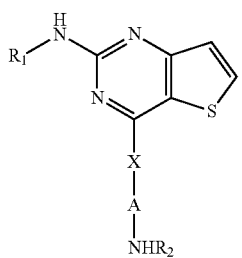

IT wherein, A is methylene; X is O;
$R_1$ is selected from:
1) C1-C6 alkyl, 2-N,N-dimethylaminoethyl, 2-hydroxyethyl, 2-N,N-diethylaminoethyl, 2-N,N-diisopropylaminoethyl, 2-morpholinylethyl, 2-(4-methylpiperazinyl)ethyl, 3-N,N-dimethylaminopropyl, 3-N,N-diethylaminopropyl, 3-N,N-diisopropylaminopropyl, 3-morpholinylpropyl, 3-(4-methylpiperazinyl)propyl, C3-C6 cycloalkyl, 4-N,N-dimethylaminocyclohexyl, 4-N,N-diethylaminocyclohexyl, N-methyl-4-piperidinyl, N-ethyl-4-piperidinyl, N-isopropyl-4-piperidinyl, 1,3-dimethyl-5-pyrazolyl, 1-methyl-4-pyrazolyl, 3-methyl-5-isoxazolinyl, 1-(N-methyl-4-piperidinyl)-4-pyrazolyl, 1-(N-t-butoxycarbonyl-4-piperidinyl)-4-pyrazolyl;

2)

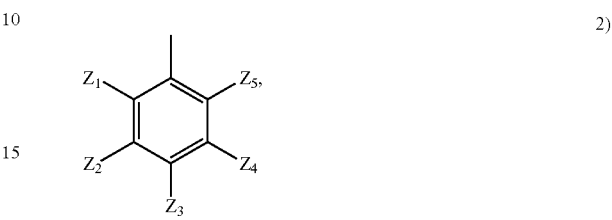

wherein $Z_1$, $Z_2$, $Z_3$, $Z_4$, $Z_5$ each are independently selected from:
(1) H, F, Cl, Br, I, nitro, cyano,
(2) C1-C6 alkyl, C1-C6 alkoxy, C1-C6 oxygen-containing alkyl, C1-C6 fluorine-containing alkyl, C1-C6 fluorine-containing alkoxy,
(3) piperidinyl, N-methyl-4-piperidinyl, 4-dimethylaminopiperidinyl, 4-N,N-diethylaminopiperidinyl, 4-N,N-diisopropylaminopiperidinyl, 4-hydroxypiperidinyl, 4-(4-methylpiperazinyl)piperidinyl, 4-(4-ethylpiperazinyl)piperidinyl, 4-(4-isopropylpiperazinyl)piperidinyl, 4-(4-acetylpiperazinyl)piperidinyl, 4-(4-t-butoxycarbonylpiperazinyl)piperidinyl, 4-(4-methylsulfonylpiperazinyl)piperidinyl, 4-(4-(2-hydroxyethyl)piperazinyl)piperidinyl, 4-(4-(2-cyanoethyl)piperazinyl)piperidinyl, 4-(4-(3-hydroxypropyl)piperazinyl) piperidinyl, 4-(4-(2-N,N-dimethylaminoethyl)piperazinyl) piperidinyl, 4-(4-(2-N,N-diethylaminoethyl)piperazinyl) piperidinyl, 4-(4-(3-N,N-dimethylaminopropyl)piperazinyl) piperidinyl, 4-(4-(3-N,N-diethylaminopropyl)piperazinyl) piperidinyl, 4-(tetrahydropyrrolyl)piperidinyl, 4-(3-N,N-dimethylaminotetrahydropyrrolyl)piperidinyl, 4-(tetrahydropyrrol-1-yl)piperidinyl
(4) 4-methylpiperazinyl, 4-ethylpiperazinyl, 4-isopropylpiperazinyl, 4-acetylpiperazinyl, 4-t-butoxycarbonylpiperazinyl, 4-methylsulfonylpiperazinyl, 4-(2-hydroxyethyl)piperazinyl, 4-(2-cyanoethyl)piperazinyl, 4-(3-hydroxypropyl) piperazinyl, 4-(2-N,N-dimethylaminoethyl)piperazinyl, 4-(2-N,N-diethylaminoethyl)piperazinyl, 4-(3-N,N-dimethylaminopropyl)piperazinyl, 4-(3-N,N-diethylaminopropyl)piperazinyl, 4-(N-methyl-4-piperidinyl)piperazinyl, 4-(N-ethyl-4-piperidinyl)piperazinyl,
(5) N,N-dimethylamino, N,N-diethylamino, N,N-diisopropylamino, 2-N,N-dimethylaminoethylamino, 2-morpholinylethylamino, 2-(4-methylpiperazinyl)ethylamino, 3-N,N-dimethylaminopropylamino, 3-N,N-diethylaminopropylamino, 3-N,N-diisopropylaminopropylamino, 3-morpholinylpropylamino, 3-(4-methylpiperazinyl)propylamino, N-methylpiperidinyl-4-amino, N-ethylpiperidinyl-4-amino, N-isopropylpiperidinyl-4-amino,
(6) 2-N,N-dimethylaminoethoxy, 2-N,N-diethylaminoethoxy, 2-N,N-diisopropylaminoethoxy, 2-(4-methylpiperazinyl)ethoxy, 2-(4-acetylpiperazinyl)ethoxy, 2-morpholinylethoxy, 2-thiomorpholinylethoxy, 2-piperidinylethoxy, 3-N,N-dimethylaminopropoxy, 3-N,N-diethylaminopropoxy, 3-N,N-diisopropylaminopropoxy, 3-(4-methylpiperazinyl)propoxy, 3-(4-acetylpiperazinyl)propoxy, 3-morpholinylpropoxy, 3-thiomorpholinylpropoxy, 3-piperidinylpropoxy, pyridin-2-ylmethoxy, pyridin-3-ylmethoxy, pyridin-4-ylmethoxy, phenylmethoxy, monohalo-substituted phenylmethoxy, gem-dihalo-substituted phenylmethoxy, hetero-dihalo-substituted phenylmethoxy, (7) hydroxysulfonyl, aminosulfonyl, methylaminosulfonyl, ethylaminosulfonyl, propylaminosulfonyl, isopropylaminosulfonyl, cyclopropylaminosulfonyl, cyclobutylaminosulfonyl, cyclopentylaminosulfonyl, piperidin-1-ylsulfonyl, 4-hydroxypiperidin-1-ylsulfonyl, 4-N,N-dimethylaminopiperidin-1-ylsulfonyl, 4-N,N-diethylaminopiperidin-1-ylsulfonyl, tetrahydropyrrolyl-1-sulfonyl, 3-N,N-dimethylaminotetrahydropyrrolyl-1-sulfonyl, 3-N,N-diethylaminotetrahydropyrrolyl-1-sulfonyl, 4-methylpiperazin-1-ylsulfonyl, 4-ethylpiperazinyl-1-sulfonyl, 4-acetylpiperazinyl-1-sulfonyl, 4-t-butoxycarbonylpiperazinyl-1-sulfonyl, 4-(2-hydroxyethyl)piperazinyl-1-sulfonyl, 4-(2-cyanoethyl)piperazinyl-1-sulfonyl, 4-(2-N,N-dimethylaminoethyl)piperazinyl-1-sulfonyl, 4-(2-N,N-diethylethyl)piperazinyl-1-sulfonyl, 4-(3-hydroxypropyl)piperazinyl-1-sulfonyl, 4-(3-N,N-dimethylaminopropyl)piperazinyl-1-sulfonyl, 4-(3-N,N-diethylaminopropyl)piperazinyl-1-sulfonyl, morpholinyl-1-sulfonyl, 3,5-dimethylmorpholinyl-1-sulfonyl, 4-(4-methyl-piperazin-1-yl)piperidin-1-ylsulfonyl, 4-(4-ethyl-1-piperazinyl)piperidin-1-ylsulfonyl, 4-(4-acetyl-1-piperazinyl)piperidin-1-ylsulfonyl, 4-(N-methyl-4-piperidinyl)piperazinyl-1-sulfonyl, (8) hydroxycarbonyl, aminocarbonyl, methylaminocarbonyl, ethylaminocarbonyl, propylaminocarbonyl, isopropylaminocarbonyl, cyclopropylaminocarbonyl, cyclobutylaminocarbonyl, cyclopentylaminocarbonyl, piperidinyl-1-carbonyl, 4-hydroxypiperidinyl-1-carbonyl, 4-N,N-dimethylaminopiperidinyl-1-carbonyl, 4-N,N-diethylaminopiperidinyl-1-carbonyl, tetrahydropyrrolyl-1-carbonyl, 3-N,N-dimethylaminotetrahydropyrrolyl-1-carbonyl, 3-N,N-diethylaminotetrahydropyrrolyl-1-carbonyl, 4-methylpiperazin-1-ylcarbonyl, 4-ethylpiperazinyl-1-carbonyl, 4-acetylpiperazinyl-1-carbonyl, 4-t-butoxycarbonylpiperazinyl-1-carbonyl, 4-(2-hydroxyethyl)piperazinyl-1-carbonyl, 4-(2-cyanoethyl)piperazinyl-1-carbonyl, 4-(2-N,N-dimethylaminoethyl)piperazinyl-1-carbonyl, 4-(2-N,N-diethylaminoethyl)piperazinyl-1-carbonyl, 4-(3-hydroxypropyl)piperazinyl-1-carbonyl, 4-(3-N,N-dimethylaminopropyl)piperazinyl-1-carbonyl, 4-(3-N,N-diethylaminopropyl)piperazinyl-1-carbonyl, morpholinyl-1-carbonyl, 3,5-dimethylmorpholinyl-1-carbonyl, 4-(4-methyl-piperazin-1-yl)piperidin-1-ylcarbonyl, 4-(4-ethyl-1-piperazinyl)piperidinyl-1-carbonyl, 4-(4-acetyl-1-piperazinyl)piperidinyl-1-carbonyl, 4-(N-methyl-4-piperidinyl)piperazinyl-1-carbonyl, methoxycarbonyl, ethoxycarbonyl, propoxycarbonyl, isopropoxycarbonyl, n-butoxycarbonyl, isobutoxycarbonyl, tert-butoxycarbonyl, (9) aminoformamido, methylaminoformamido, ethylaminoformamido, propylaminoformamido, isopropylaminoformamido, cyclopropylaminoformamido, cyclobutylaminoformamido, cyclopentylaminoformamido, piperidinyl-1-formamido, 4-hydroxypiperidinyl-1-formamido, 4-N,N-dimethylaminopiperidinyl-1-formamido, 4-N,N-diethylaminopiperidinyl-1-formamido, tetrahydropyrrolyl-1-formamido, 3-N,N-dimethylaminotetrahydropyrrolyl-1-formamido, 3-N,N-diethylaminotetrahydropyrrolyl-1-formamido, 4-methylpiperazinyl-1-formamido, 4-ethylpiperazinyl-1-formamido, 4-acetylpiperazinyl-1-formamido, 4-t-butoxycarbonylpiperazinyl-1-formamido, 4-(2-hydroxyethyl)piperazinyl-1-formamido, 4-(2-cyanoethyl)piperazinyl-1-formamido, 4-(2-N,N-dimethylaminoethyl)piperazinyl-1-formamido, 4-(2-N,N-diethylaminoethyl)piperazinyl-1-formamido, 4-(3-hydroxypropyl)piperazinyl-1-formamido, 4-(3-N,N-dimethylaminopropyl)piperazinyl-1-formamido, 4-(3-N,N-diethylaminopropyl)piperazinyl-1-formamido, morpholinyl-1-formamido, 3,5-dimethylmorpholinyl-1-formamido, 4-(4-methyl-piperazin-1-yl)piperidinyl-1-formamido, 4-(4-ethyl-1-piperazinyl)piperidinyl-1-formamido, 4-(4-acetyl-1-piperazinyl)piperidinyl-1-formamido, 4-(N-methyl-4-piperidinyl)piperazinyl-1-formamido; or

(10) $Z_2$ and $Z_3$ or $Z_3$ and $Z_4$ form a nitrogen- or oxygen-containing substituted or unsubstituted 5- or 6-membered ring, the substituent may be selected from the same substituents as described above for $Z_1$;

$R_2$ is selected from

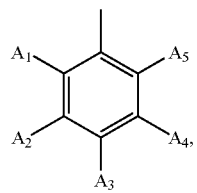

wherein $A_1$, $A_2$, $A_3$, $A_4$, $A_5$ each are independently selected from:

(1) H, F, Cl, Br, I, cyano, trifluoromethyl, trifluoromethoxy, nitro, (2) methylthio, ethylthio, isopropylthio, methylsulfinyl, ethylsulfinyl, isopropylsulfinyl, methylsulfonyl, ethylsulfonyl, isopropylsulfonyl, tert-butyl sulfonyl, methylsulfonamido, methoxycarbonyl, ethoxycarbonyl, propoxycarbonyl, isopropoxycarbonyl, n-butoxycarbonyl, isobutoxycarbonyl, tert-butoxycarbonyl, methylaminocarbonyl, ethylaminocarbonyl, propylaminocarbonyl, isopropylaminocarbonyl, dimethylaminocarbonyl, cyclopropylaminocarbonyl, cyclobutylaminocarbonyl, cyclopentylaminocarbonyl, dimethylphosphinyl, diethylphosphinyl, diisopropylphosphinyl.

In some embodiments, $R_1$ is selected from

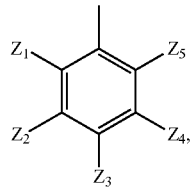

wherein $Z_1$, $Z_2$, $Z_3$, $Z_4$, $Z_5$ each are independently selected from:

(1) H, (2) C1-C6 alkoxy, (3) piperidinyl, N-methyl-4-piperidinyl, 4-dimethylaminopiperidinyl, 4-N,N-diethylaminopiperidinyl, 4-N,N-diisopropylaminopiperidinyl, 4-hydroxypiperidinyl, 4-(4-methylpiperazinyl)piperidinyl, 4-(4-ethylpiperazinyl)piperidinyl, 4-(4-isopropylpiperazinyl)piperidinyl, 4-(4-acetylpiperazinyl)piperidinyl, 4-(4-t-butoxycarbonylpiperazinyl)piperidinyl, 4-(4-methylsulfonylpiperazinyl)piperidinyl, 4-(4-(2-hydroxyethyl)piperazinyl)piperidinyl, 4-(4-(2-cyanoethyl)piperazinyl)piperidinyl, 4-(4-(3-hydroxypropyl)piperazinyl)piperidinyl, 4-(4-(2-N,N-dimethylaminoethyl)piperazinyl)piperidinyl, 4-(4-(2-N,N-diethylaminoethyl)piperazinyl)piperidinyl, 4-(4-(3-N,N-dimethylaminopropyl)piperazinyl)

piperidinyl, 4-(4-(3-N,N-diethylaminopropyl)piperazinyl) piperidinyl, 4-(tetrahydropyrrolyl)piperidinyl, 4-(3-N,N-dimethylaminotetrahydropyrrolyl)piperidinyl, 4-(tetrahydropyrrol-1-yl)piperidinyl;

(4) 4-methylpiperazinyl, 4-ethylpiperazinyl, 4-isopropylpiperazinyl, 4-acetylpiperazinyl, 4-t-butoxycarbonylpiperazinyl, 4-methylsulfonylpiperazinyl, 4-(2-hydroxyethyl)piperazinyl, 4-(2-cyanoethyl)piperazinyl, 4-(3-hydroxypropyl) piperazinyl, 4-(2-N,N-dimethylaminoethyl)piperazinyl, 4-(2-N,N-diethylaminoethyl)piperazinyl, 4-(3-N,N-dimethylaminopropyl)piperazinyl, 4-(3-N,N-diethylaminopropyl) piperazinyl, 4-(N-methyl-4-piperidinyl)piperazinyl, 4-(N-ethyl-4-piperidinyl)piperazinyl or (5) $Z_2$ and $Z_3$ or $Z_3$ and $Z_4$ form a nitrogen- or oxygen-containing substituted or unsubstituted 5-membered ring, the substituent may be selected from the same substituents as described above for $Z_1$.

In some embodiments, $R_1$ is selected from:

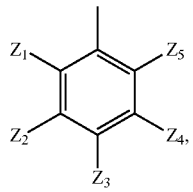

wherein $Z_1$, $Z_2$, $Z_3$, $Z_4$, $Z_5$ each are independently selected from:
(1) H,
(2) C1-C6 alkoxy,
(3) 4-methylpiperazinyl, 4-(4-methylpiperazinyl)piperidinyl, morpholinyl, 4-dimethylamino-piperidinyl,
(4) $Z_2$ and $Z_3$ may form a nitrogen-containing substituted or unsubstituted 5-membered ring

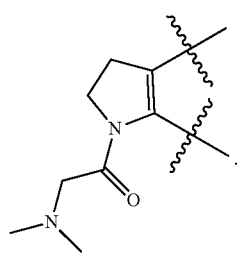 [SMILES: *C1=C(*)N(C(=O)CN(C)C)CC1]

In some embodiments, $R_1$ is selected from:

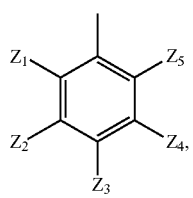

wherein
one of $Z_1$ and $Z_5$ is H, the other is methoxy;
$Z_3$ is selected from: 4-dimethylamino-piperidinyl, 4-methylpiperazinyl, 4-(4-methylpiperazinyl)piperidinyl, 4-methylpiperazinyl or morpholinyl, or $Z_2$ and $Z_3$ or $Z_3$ and $Z_4$ form

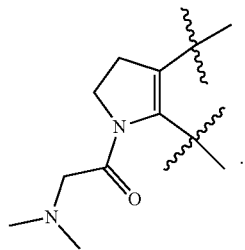 [SMILES: *C1=C(*)N(C(=O)CN(C)C)CC1]

In some embodiments, $R_2$ is selected from:

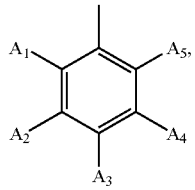

wherein $A_1$, $A_2$, $A_3$, $A_4$, $A_5$ each are independently selected from:
(1) H
(2) isopropylsulfonyl.

In some embodiments, $R_2$ is selected from:

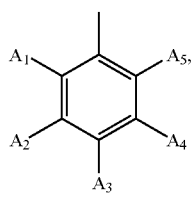

wherein one of $A_1$ and $A_5$ is H, the other is isopropylsulfonyl; $A_2$, $A_3$, $A_4$ are all H.

In a twentieth aspect, the present invention provides a compound of Formula IN, a stereoisomer thereof, a prodrug thereof, a pharmaceutically acceptable salt thereof or a pharmaceutically acceptable solvate thereof,

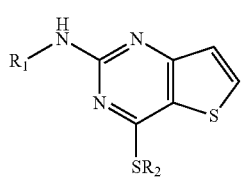

IN wherein, $R_1$ is selected from:
1) propylaminoethyl, 2-morpholinylethyl, 2-(4-methylpiperazinyl)ethyl, 3-N,N-dimethylaminopropyl, 3-N,N-diethylaminopropyl, 3-N,N-diisopropylaminopropyl, 3-morpholinylpropyl, 3-(4-methylpiperazinyl)propyl, C3-C6 cycloalkyl, 4-N,N-dimethylaminocyclohexyl, 4-N,N-diethylaminocyclohexyl, N-methyl-4-piperidinyl, N-ethyl-4-piperidinyl, N-isopropyl-4-piperidinyl, 1,3-dimethyl-5-pyrazolyl, 1-methyl-4-pyrazolyl, 3-methyl-5-isoxazolinyl, 1-(N-methyl-4-piperidinyl)-4-pyrazolyl, 1-(N-t-butoxycarbonyl-4-piperidinyl)-4-pyrazolyl;

2)

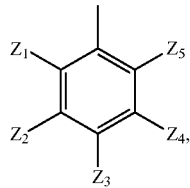

wherein $Z_1$, $Z_2$, $Z_3$, $Z_4$, $Z_5$ each are independently selected from:

(1) H, F, Cl, Br, I, nitro, cyano, (2) C1-C6 alkyl, C1-C6 alkoxy, C1-C6 oxygen-containing alkyl, C1-C6 fluorine-containing alkyl, C1-C6 fluorine-containing alkoxy, (3) piperidinyl, N-methyl-4-piperidinyl, 4-N,N-dimethylaminopiperidinyl, 4-N,N-diethylaminopiperidinyl, 4-N,N-diisopropylaminopiperidinyl, 4-hydroxypiperidinyl, 4-(4-methylpiperazinyl)piperidinyl, 4-(4-ethylpiperazinyl)piperidinyl, 4-(4-isopropylpiperazinyl)piperidinyl, 4-(4-acetylpiperazinyl)piperidinyl, 4-(4-t-butoxycarbonylpiperazinyl)piperidinyl, 4-(4-methylsulfonylpiperazinyl)piperidinyl, 4-(4-(2-hydroxyethyl)piperazinyl)piperidinyl, 4-(4-(2-cyanoethyl)piperazinyl)piperidinyl, 4-(4-(3-hydroxypropyl)piperazinyl)piperidinyl, 4-(4-(2-N,N-dimethylaminoethyl)piperazinyl)piperidinyl, 4-(4-(2-N,N-diethylaminoethyl)piperazinyl)piperidinyl, 4-(4-(3-N,N-dimethylaminopropyl)piperazinyl)piperidinyl, 4-(4-(3-N,N-diethylaminopropyl)piperazinyl)piperidinyl, 4-(tetrahydropyrrolyl)piperidinyl, 4-(3-N,N-dimethylaminotetrahydropyrrolyl)piperidinyl, (4) 4-methylpiperazinyl, 4-ethylpiperazinyl, 4-isopropylpiperazinyl, 4-acetylpiperazinyl, 4-t-butoxycarbonylpiperazinyl, 4-methylsulfonylpiperazinyl, 4-(2-hydroxyethyl)piperazinyl, 4-(2-cyanoethyl)piperazinyl, 4-(3-hydroxypropyl)piperazinyl, 4-(2-N,N-dimethylaminoethyl)piperazinyl, 4-(2-N,N-diethylaminoethyl)piperazinyl, 4-(3-N,N-dimethylaminopropyl)piperazinyl, 4-(3-N,N-diethylaminopropyl)piperazinyl, 4-(N-methyl-4-piperidinyl)piperazinyl, 4-(N-ethyl-4-piperidinyl)piperazinyl, (5) N,N-dimethylamino, N,N-diethylamino, N,N-diisopropylamino, 2-N,N-dimethylaminoethylamino, 2-morpholinylethylamino, 2-(4-methylpiperazinyl)ethylamino, 3-N,N-dimethylaminopropylamino, 3-N,N-diethylaminopropylamino, 3-N,N-diisopropylaminopropylamino, 3-morpholinylpropylamino, 3-(4-methylpiperazinyl)propylamino, N-methylpiperidinyl-4-amino, N-ethylpiperidinyl-4-amino, N-isopropylpiperidinyl-4-amino, (6) 2-N,N-dimethylaminoethoxy, 2-N,N-diethylaminoethoxy, 2-N,N-diisopropylaminoethoxy, 2-(4-methylpiperazinyl)ethoxy, 2-(4-acetylpiperazinyl)ethoxy, 2-morpholinylethoxy, 2-thiomorpholinylethoxy, 2-piperidinylethoxy, 3-N,N-dimethylaminopropoxy, 3-N,N-diethylaminopropoxy, 3-N,N-diisopropylaminopropoxy, 3-(4-methylpiperazinyl)propoxy, 3-(4-acetylpiperazinyl)propoxy, 3-morpholinylpropoxy, 3-thiomorpholinylpropoxy, 3-piperidinylpropoxy, pyridin-2-ylmethoxy, pyridin-3-ylmethoxy, pyridin-4-ylmethoxy, phenylmethoxy, monohalo-substituted phenylmethoxy, gem-dihalo-substituted phenylmethoxy, hetero-dihalo-substituted phenylmethoxy, (7) hydroxysulfonyl, aminosulfonyl, methylaminosulfonyl, ethylaminosulfonyl, propylaminosulfonyl, isopropylaminosulfonyl, cyclopropylaminosulfonyl, cyclobutylaminosulfonyl, cyclopentylaminosulfonyl, piperidin-1-ylsulfonyl, 4-hydroxypiperidin-1-ylsulfonyl, 4-N,N-dimethylaminopiperidin-1-ylsulfonyl, 4-N,N-diethylaminopiperidin-1-ylsulfonyl, tetrahydropyrrolyl-1-sulfonyl, 3-N,N-dimethylaminotetrahydropyrrolyl-1-sulfonyl, 3-N,N-diethylaminotetrahydropyrrolyl-1-sulfonyl, 4-methylpiperazin-1-ylsulfonyl, 4-ethylpiperazinyl-1-sulfonyl, 4-acetylpiperazinyl-1-sulfonyl, 4-t-butoxycarbonylpiperazinyl-1-sulfonyl, 4-(2-hydroxyethyl)piperazinyl-1-sulfonyl, 4-(2-cyanoethyl)piperazinyl-1-sulfonyl, 4-(2-N,N-dimethylaminoethyl)piperazinyl-1-sulfonyl, 4-(2-N,N-diethylethyl)piperazinyl-1-sulfonyl, 4-(3-hydroxypropyl)piperazinyl-1-sulfonyl, 4-(3-N,N-dimethylaminopropyl)piperazinyl-1-sulfonyl, 4-(3-N,N-diethylaminopropyl)piperazinyl-1-sulfonyl, morpholinyl-1-sulfonyl, 3,5-dimethylmorpholinyl-1-sulfonyl, 4-(4-methyl-piperazin-1-yl)piperidin-1-ylsulfonyl, 4-(4-ethyl-1-piperazinyl)piperidin-1-ylsulfonyl, 4-(4-acetyl-1-piperazinyl)piperidin-1-ylsulfonyl, 4-(N-methyl-4-piperidinyl)piperazinyl-1-sulfonyl, (8) hydroxycarbonyl, aminocarbonyl, methylaminocarbonyl, ethylaminocarbonyl, propylaminocarbonyl, isopropylaminocarbonyl, cyclopropylaminocarbonyl, cyclobutylaminocarbonyl, cyclopentylaminocarbonyl, piperidinyl-1-carbonyl, 4-hydroxypiperidinyl-1-carbonyl, 4-N,N-dimethylaminopiperidinyl-1-carbonyl, 4-N,N-diethylaminopiperidinyl-1-carbonyl, tetrahydropyrrolyl-1-carbonyl, 3-N,N-dimethylaminotetrahydropyrrolyl-1-carbonyl, 3-N,N-diethylaminotetrahydropyrrolyl-1-carbonyl, 4-methylpiperazin-1-ylcarbonyl, 4-ethylpiperazinyl-1-carbonyl, 4-acetylpiperazinyl-1-carbonyl, 4-t-butoxycarbonylpiperazinyl-1-carbonyl, 4-(2-hydroxyethyl)piperazinyl-1-carbonyl, 4-(2-cyanoethyl)piperazinyl-1-carbonyl, 4-(2-N,N-dimethylaminoethyl)piperazinyl-1-carbonyl, 4-(2-N,N-diethylaminoethyl)piperazinyl-1-carbonyl, 4-(3-hydroxypropyl)piperazinyl-1-carbonyl, 4-(3-N,N-dimethylaminopropyl)piperazinyl-1-carbonyl, 4-(3-N,N-diethylaminopropyl)piperazinyl-1-carbonyl, morpholinyl-1-carbonyl, 3,5-dimethylmorpholinyl-1-carbonyl, 4-(4-methyl-piperazin-1-yl)piperidin-1-ylcarbonyl, 4-(4-ethyl-1-piperazinyl)piperidinyl-1-carbonyl, 4-(4-acetyl-1-piperazinyl)piperidinyl-1-carbonyl, 4-(N-methyl-4-piperidinyl)piperazinyl-1-carbonyl, methoxycarbonyl, ethoxycarbonyl, propoxycarbonyl, isopropoxycarbonyl, n-butoxycarbonyl, isobutoxycarbonyl, tert-butoxycarbonyl, (9) aminoformamido, methylaminoformamido, ethylaminoformamido, propylaminoformamido, isopropylaminoformamido, cyclopropylaminoformamido, cyclobutylaminoformamido, cyclopentylaminoformamido, piperidinyl-1-formamido, 4-hydroxypiperidinyl-1-formamido, 4-N,N-dimethylaminopiperidinyl-1-formamido, 4-N,N-diethylaminopiperidinyl-1-formamido, tetrahydropyrrolyl-1-formamido, 3-N,N-dimethylaminotetrahydropyrrolyl-1-formamido, 3-N,N-diethylaminotetrahydropyrrolyl-1-formamido, 4-methylpiperazinyl-1-formamido, 4-ethylpiperazinyl-1-formamido, 4-acetylpiperazinyl-1-formamido, 4-t-butoxycarbonylpiperazinyl-1-formamido, 4-(2-hydroxyethyl)piperazinyl-1-formamido, 4-(2-cyanoethyl)piperazinyl-1-formamido, 4-(2-N,N-dimethylaminoethyl)piperazinyl-1-formamido, 4-(2-N,N-diethylaminoethyl)piperazinyl-1-formamido, 4-(3-hydroxypropyl)piperazinyl-1-formamido, 4-(3-N,N-dimethylaminopropyl)piperazinyl-1-formamido, 4-(3-N,N-diethylaminopropyl)piperazinyl-1-formamido, morpholinyl-1-formamido, 3,5-dimethylmorpholinyl-1-formamido, 4-(4-methyl-piperazin-1-yl)piperidinyl-1-formamido, 4-(4-ethyl-1-piperazinyl)piperidinyl-1-formamido, 4-(4-acetyl-1-piperazinyl)piperidinyl-1-formamido, 4-(N-methyl-4-piperidinyl)piperazinyl-1-formamido; or

(10) $Z_2$ and $Z_3$ or $Z_3$ and $Z_4$ form a nitrogen- or oxygen-containing substituted or unsubstituted 5- or 6-membered ring, the substituent may be selected from the same substituents as described above for $Z_1$;

$R_2$ is selected from

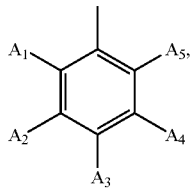

wherein $A_1$, $A_2$, $A_3$, $A_4$, $A_5$ each are independently selected from:

(1) H, F, Cl, Br, I, cyano, trifluoromethyl, trifluoromethoxy, nitro, (2) methylthio, ethylthio, isopropylthio, methylsulfinyl, ethylsulfinyl, isopropylsulfinyl, methylsulfonyl, ethylsulfonyl, isopropylsulfonyl, methylsulfonamido, methoxycarbonyl, ethoxycarbonyl, propoxycarbonyl, isopropoxycarbonyl, n-butoxycarbonyl, isobutoxycarbonyl, tert-butoxycarbonyl, methylaminocarbonyl, ethylaminocarbonyl, propylaminocarbonyl, isopropylaminocarbonyl, cyclopropylaminocarbonyl, cyclobutylaminocarbonyl, cyclopentylaminocarbonyl, dimethylphosphinyl, diethylphosphinyl, diisopropylphosphinyl.

In some embodiments, $R_1$ is selected from:

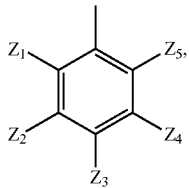

wherein $Z_1$, $Z_2$, $Z_3$, $Z_4$, $Z_5$ each are independently selected from:

(1) H,
(2) C1-C6 alkyl,
(3) C1-C6 alkoxy,
(4) piperidinyl, N-methyl-4-piperidinyl, 4-N,N-dimethylaminopiperidinyl, 4-N,N-diethylaminopiperidinyl, 4-N,N-diisopropylaminopiperidinyl, 4-hydroxypiperidinyl (5) 4-(4-methylpiperazinyl)piperidinyl, 4-(4-ethylpiperazinyl)piperidinyl, 4-(4-isopropylpiperazinyl)piperidinyl, 4-(4-acetylpiperazinyl)piperidinyl, 4-(4-t-butoxycarbonylpiperazinyl)piperidinyl, 4-(4-methylsulfonylpiperazinyl)piperidinyl, 4-(4-(2-hydroxyethyl)piperazinyl)piperidinyl, 4-(4-(2-cyanoethyl)piperazinyl)piperidinyl, 4-(4-(3-hydroxypropyl)piperazinyl)piperidinyl, 4-(4-(2-N,N-dimethylaminoethyl)piperazinyl)piperidinyl, 4-(4-(2-N,N-diethylaminoethyl)piperazinyl)piperidinyl, 4-(4-(3-N,N-dimethylaminopropyl)piperazinyl)piperidinyl, 4-(4-(3-N,N-diethylaminopropyl)piperazinyl)piperidinyl, 4-(tetrahydropyrrolyl)piperidinyl, 4-(3-N,N-dimethylaminotetrahydropyrrolyl)piperidinyl, (6) 4-methylpiperazinyl, 4-ethylpiperazinyl, 4-isopropylpiperazinyl, 4-acetylpiperazinyl, 4-t-butoxycarbonylpiperazinyl, 4-methylsulfonylpiperazinyl, 4-(2-hydroxyethyl)piperazinyl, 4-(2-cyanoethyl)piperazinyl, 4-(3-hydroxypropyl)piperazinyl, 4-(2-N,N-dimethylaminoethyl)piperazinyl, 4-(2-N,N-diethylaminoethyl)piperazinyl, 4-(3-N,N-dimethylaminopropyl)piperazinyl, 4-(3-N,N-diethylaminopropyl)piperazinyl, 4-(N-methyl-4-piperidinyl)piperazinyl, 4-(N-ethyl-4-piperidinyl)piperazinyl, (7) hydroxysulfonyl, aminosulfonyl, methylaminosulfonyl, ethylaminosulfonyl, propylaminosulfonyl, isopropylaminosulfonyl, cyclopropylaminosulfonyl, cyclobutylaminosulfonyl, cyclopentylaminosulfonyl, piperidin-1-ylsulfonyl, 4-hydroxypiperidin-1-ylsulfonyl, 4-N,N-dimethylaminopiperidin-1-ylsulfonyl, 4-N,N-diethylaminopiperidin-1-ylsulfonyl, tetrahydropyrrolyl-1-sulfonyl, 3-N,N-dimethylaminotetrahydropyrrolyl-1-sulfonyl, 3-N,N-diethylaminotetrahydropyrrolyl-1-sulfonyl, 4-methylpiperazin-1-ylsulfonyl, 4-ethylpiperazinyl-1-sulfonyl, 4-acetylpiperazinyl-1-sulfonyl, 4-t-butoxycarbonylpiperazinyl-1-sulfonyl, 4-(2-hydroxyethyl)piperazinyl-1-sulfonyl, 4-(2-cyanoethyl)piperazinyl-1-sulfonyl, 4-(2-N,N-dimethylaminoethyl)piperazinyl-1-sulfonyl, 4-(2-N,N-diethylethyl)piperazinyl-1-sulfonyl, 4-(3-hydroxypropyl)piperazinyl-1-sulfonyl, 4-(3-N,N-dimethylaminopropyl)piperazinyl-1-sulfonyl, 4-(3-N,N-diethylaminopropyl)piperazinyl-1-sulfonyl, morpholinyl-1-sulfonyl, 3,5-dimethylmorpholinyl-1-sulfonyl, 4-(4-methyl-piperazin-1-yl)piperidin-1-ylsulfonyl, 4-(4-ethyl-1-piperazinyl)piperidin-1-ylsulfonyl, 4-(4-acetyl-1-piperazinyl)piperidin-1-ylsulfonyl, 4-(N-methyl-4-piperidinyl)piperazinyl-1-sulfonyl, or (8) $Z_2$ and $Z_3$ or $Z_3$ and $Z_4$ form a nitrogen- or oxygen-containing substituted or unsubstituted 5- or 6-membered ring, the substituent may be selected from the same substituents as described above for $Z_1$.

In some embodiments, $R_1$ is selected from:

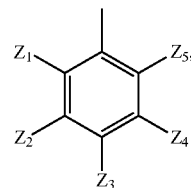

wherein $Z_1$, $Z_2$, $Z_3$, $Z_4$, $Z_5$ each are independently selected from:

(1) H,
(2) methyl, methoxy,
(3) 4-hydroxypiperidinyl, 4-methylpiperazinyl, N-methyl-4-piperidinyl,
(4) 4-(4-methylpiperazinyl)piperidinyl, 4-(tetrahydropyrrol-1-yl)piperidinyl, aminosulfonyl, or
(5) $Z_2$ and $Z_3$ or $Z_3$ and $Z_4$ form

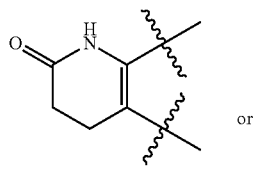

or

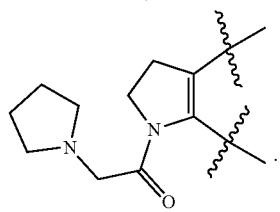

.

In some embodiments, $R_1$ is selected from:

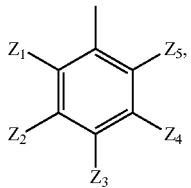

wherein one of $Z_1$ and $Z_5$ is H, the other is methoxy; one of $Z_2$ and $Z_4$ is H, the other is methyl, $Z_3$ is selected from: 4-hydroxypiperidinyl, 4-methylpiperazinyl, N-methyl-4-piperidinyl, 4-(4-methylpiperazinyl)piperidinyl, 4-(tetrahydropyrrol-1-yl)piperidinyl, aminosulfonyl, or $Z_2$ and $Z_3$ or $Z_3$ and $Z_4$ form

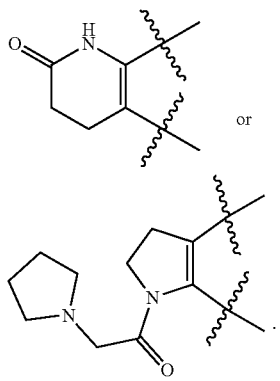

In some embodiments, $R_2$ is selected from:

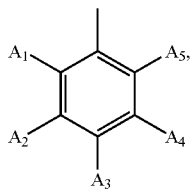

wherein $A_1$, $A_2$, $A_3$, $A_4$, $A_5$ each are independently selected from:
(1) H, F, Cl, Br, I, cyano, trifluoromethyl, trifluoromethoxy, nitro,
(2) methylthio, ethylthio, methylsulfinyl, ethylsulfinyl, methylsulfonyl, ethylsulfonyl, methylsulfonamido, methoxycarbonyl, ethoxycarbonyl, propoxycarbonyl, isopropoxycarbonyl, n-butoxycarbonyl, methylaminocarbonyl, ethylaminocarbonyl, propylaminocarbonyl, cyclopropylaminocarbonyl, cyclobutylaminocarbonyl, cyclopentylaminocarbonyl, dimethylphosphinyl.

In some embodiments, $R_2$ is selected from:

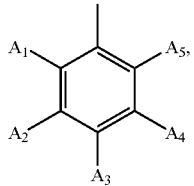

wherein $A_1$, $A_2$, $A_3$, $A_4$, $A_5$ each are independently selected from:
(1) H, (2) methoxycarbonyl.

In some embodiments, $R_2$ is selected from:

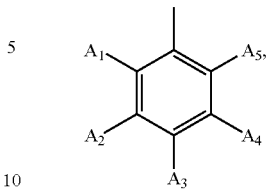

wherein one of $A_1$ and $A_5$ is H, the other is methoxycarbonyl; $A_2$, $A_3$, $A_4$ are all H.

In a twenty-first aspect, the present invention provides a compound of Formula IU, a stereoisomer thereof, a prodrug thereof, a pharmaceutically acceptable salt thereof or a pharmaceutically acceptable solvate thereof,

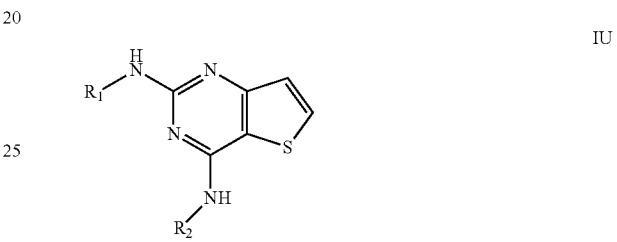

IU wherein, $R_1$ is selected from:
1) C1-C6 alkyl, 2-N,N-dimethylaminoethyl, 2-hydroxyethyl, 2-N,N-diethylaminoethyl, 2-N,N-diisopropylaminoethyl, 2-morpholinylethyl, 2-(4-methylpiperazinyl)ethyl, 3-N,N-dimethylaminopropyl, 3-N,N-diethylaminopropyl, 3-N,N-diisopropylaminopropyl, 3-morpholinylpropyl, 3-(4-methylpiperazinyl)propyl, C3-C6 cycloalkyl, 4-N,N-dimethylaminocyclohexyl, 4-N,N-diethylaminocyclohexyl, N-methyl-4-piperidinyl, N-ethyl-4-piperidinyl, N-isopropyl-4-piperidinyl, 1,3-dimethyl-5-pyrazolyl, 1-methyl-4-pyrazolyl, 3-methyl-5-isoxazolinyl, 1-(N-methyl-4-piperidinyl)-4-pyrazolyl, 1-(N-t-butoxycarbonyl-4-piperidinyl)-4-pyrazolyl;

2)

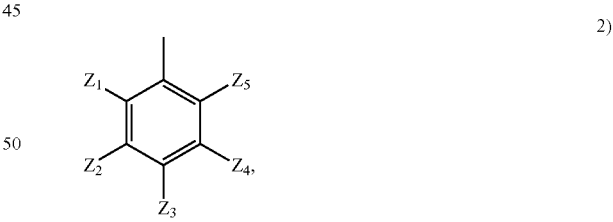

wherein $Z_1$, $Z_2$, $Z_3$, $Z_4$, $Z_5$ each are independently selected from:
(1) H, F, Cl, Br, I, nitro, cyano,
(2) C1-C6 alkyl, C1-C6 alkoxy, C1-C6 oxygen-containing alkyl, C1-C6 fluorine-containing alkyl, C1-C6 fluorine-containing alkoxy,
(3) piperidinyl, N-methyl-4-piperidinyl, 4-N,N-dimethylaminopiperidinyl, 4-N,N-diethylaminopiperidinyl, 4-N,N-diisopropylaminopiperidinyl, 4-hydroxypiperidinyl, 4-(4-methylpiperazinyl)piperidinyl, 4-(4-ethylpiperazinyl)piperidinyl, 4-(4-isopropylpiperazinyl)piperidinyl, 4-(4-acetylpiperazinyl)piperidinyl, 4-(4-t-butoxycarbonylpiperazinyl)piperidinyl, 4-(4- methylsulfonylpiperazinyl)piperidinyl, 4-(4-(2-hydroxyethyl)piperazinyl)piperidinyl, 4-(4-(2-cyanoethyl)piperazinyl)piperidinyl, 4-(4-(3-hydroxypropyl)piperazinyl)piperidinyl, 4-(4-(2-N,N-dimethylaminoethyl)piperazinyl)piperidinyl, 4-(4-(2-N,N-diethylaminoethyl)piperazinyl)piperidinyl, 4-(4-(3-N,N-dimethylaminopropyl)piperazinyl)piperidinyl, 4-(4-(3-N,N-diethylaminopropyl)piperazinyl)piperidinyl, 4-(tetrahydropyrrolyl)piperidinyl, 4-(3-N,N-dimethylaminotetrahydropyrrolyl)piperidinyl, (4) 4-methylpiperazinyl, 4-ethylpiperazinyl, 4-isopropylpiperazinyl, 4-acetylpiperazinyl, 4-t-butoxycarbonylpiperazinyl, 4-methylsulfonylpiperazinyl, 4-(2-hydroxyethyl)piperazinyl, 4-(2-cyanoethyl)piperazinyl, 4-(3-hydroxypropyl)piperazinyl, 4-(2-N,N-dimethylaminoethyl)piperazinyl, 4-(2-N,N-diethylaminoethyl)piperazinyl, 4-(3-N,N-dimethylaminopropyl)piperazinyl, 4-(3-N,N-diethylaminopropyl)piperazinyl, 4-(N-methyl-4-piperidinyl)piperazinyl, 4-(N-ethyl-4-piperidinyl)piperazinyl, (5) N,N-dimethylamino, N,N-diethylamino, N,N-diisopropylamino, 2-N,N-dimethylaminoethylamino, 2-morpholinylethylamino, 2-(4-methylpiperazinyl)ethylamino, 3-N,N-dimethylaminopropylamino, 3-N,N-diethylaminopropylamino, 3-N,N-diisopropylaminopropylamino, 3-morpholinylpropylamino, 3-(4-methylpiperazinyl)propylamino, N-methylpiperidinyl-4-amino, N-ethylpiperidinyl-4-amino, N-isopropylpiperidinyl-4-amino, (6) 2-N,N-dimethylaminoethoxy, 2-N,N-diethylaminoethoxy, 2-N,N-diisopropylaminoethoxy, 2-(4-methylpiperazinyl)ethoxy, 2-(4-acetylpiperazinyl)ethoxy, 2-morpholinylethoxy, 2-thiomorpholinylethoxy, 2-piperidinylethoxy, 3-N,N-dimethylaminopropoxy, 3-N,N-diethylaminopropoxy, 3-N,N-diisopropylaminopropoxy, 3-(4-methylpiperazinyl)propoxy, 3-(4-acetylpiperazinyl)propoxy, 3-morpholinylpropoxy, 3-thiomorpholinylpropoxy, 3-piperidinylpropoxy, pyridin-2-ylmethoxy, pyridin-3-ylmethoxy, pyridin-4-ylmethoxy, phenylmethoxy, monohalo-substituted phenylmethoxy, gem-dihalo-substituted phenylmethoxy, hetero-dihalo-substituted phenylmethoxy, (7) hydroxysulfonyl, aminosulfonyl, methylaminosulfonyl, ethylaminosulfonyl, propylaminosulfonyl, isopropylaminosulfonyl, cyclopropylaminosulfonyl, cyclobutylaminosulfonyl, cyclopentylaminosulfonyl, piperidin-1-ylsulfonyl, 4-hydroxypiperidin-1-ylsulfonyl, 4-N,N-dimethylaminopiperidin-1-ylsulfonyl, 4-N,N-diethylaminopiperidin-1-ylsulfonyl, tetrahydropyrrolyl-1-sulfonyl, 3-N,N-dimethylaminotetrahydropyrrolyl-1-sulfonyl, 3-N,N-diethylaminotetrahydropyrrolyl-1-sulfonyl, 4-methylpiperazin-1-ylsulfonyl, 4-ethylpiperazinyl-1-sulfonyl, 4-acetylpiperazinyl-1-sulfonyl, 4-t-butoxycarbonylpiperazinyl-1-sulfonyl, 4-(2-hydroxyethyl)piperazinyl-1-sulfonyl, 4-(2-cyanoethyl)piperazinyl-1-sulfonyl, 4-(2-N,N-dimethylaminoethyl)piperazinyl-1-sulfonyl, 4-(2-N,N-diethylethyl)piperazinyl-1-sulfonyl, 4-(3-hydroxypropyl)piperazinyl-1-sulfonyl, 4-(3-N,N-dimethylaminopropyl)piperazinyl-1-sulfonyl, 4-(3-N,N-diethylaminopropyl)piperazinyl-1-sulfonyl, morpholinyl-1-sulfonyl, 3,5-dimethylmorpholinyl-1-sulfonyl, 4-(4-methyl-piperazin-1-yl)piperidin-1-ylsulfonyl, 4-(4-ethyl-1-piperazinyl)piperidin-1-ylsulfonyl, 4-(4-acetyl-1-piperazinyl)piperidin-1-ylsulfonyl, 4-(N-methyl-4-piperidinyl)piperazinyl-1-sulfonyl, (8) hydroxycarbonyl, aminocarbonyl, methylaminocarbonyl, ethylaminocarbonyl, propylaminocarbonyl, isopropylaminocarbonyl, cyclopropylaminocarbonyl, cyclobutylaminocarbonyl, cyclopentylaminocarbonyl, piperidinyl-1-carbonyl, 4-hydroxypiperidinyl-1-carbonyl, 4-N,N-dimethylaminopiperidinyl-1-carbonyl, 4-N,N-diethylaminopiperidinyl-1-carbonyl, tetrahydropyrrolyl-1-carbonyl, 3-N,N-dimethylaminotetrahydropyrrolyl-1-carbonyl, 3-N,N-diethylaminotetrahydropyrrolyl-1-carbonyl, 4-methylpiperazin-1-ylcarbonyl, 4-ethylpiperazinyl-1-carbonyl, 4-acetylpiperazinyl-1-carbonyl, 4-t-butoxycarbonylpiperazinyl-1-carbonyl, 4-(2-hydroxyethyl)piperazinyl-1-carbonyl, 4-(2-cyanoethyl)piperazinyl-1-carbonyl, 4-(2-N,N-dimethylaminoethyl)piperazinyl-1-carbonyl, 4-(2-N,N-diethylaminoethyl)piperazinyl-1-carbonyl, 4-(3-hydroxypropyl)piperazinyl-1-carbonyl, 4-(3-N,N-dimethylaminopropyl)piperazinyl-1-carbonyl, 4-(3-N,N-diethylaminopropyl)piperazinyl-1-carbonyl, morpholinyl-1-carbonyl, 3,5-dimethylmorpholinyl-1-carbonyl, 4-(4-methyl-piperazin-1-yl)piperidin-1-ylcarbonyl, 4-(4-ethyl-1-piperazinyl)piperidinyl-1-carbonyl, 4-(4-acetyl-1-piperazinyl)piperidinyl-1-carbonyl, 4-(N-methyl-4-piperidinyl)piperazinyl-1-carbonyl, methoxycarbonyl, ethoxycarbonyl, propoxycarbonyl, isopropoxycarbonyl, n-butoxycarbonyl, isobutoxycarbonyl, tert-butoxycarbonyl, (9) aminoformamido, methylaminoformamido, ethylaminoformamido, propylaminoformamido, isopropylaminoformamido, cyclopropylaminoformamido, cyclobutylaminoformamido, cyclopentylaminoformamido, piperidinyl-1-formamido, 4-hydroxypiperidinyl-1-formamido, 4-N,N-dimethylaminopiperidinyl-1-formamido, 4-N,N-diethylaminopiperidinyl-1-formamido, tetrahydropyrrolyl-1-formamido, 3-N,N-dimethylaminotetrahydropyrrolyl-1-formamido, 3-N,N-diethylaminotetrahydropyrrolyl-1-formamido, 4-methylpiperazinyl-1-formamido, 4-ethylpiperazinyl-1-formamido, 4-acetylpiperazinyl-1-formamido, 4-t-butoxycarbonylpiperazinyl-1-formamido, 4-(2-hydroxyethyl)piperazinyl-1-formamido, 4-(2-cyanoethyl)piperazinyl-1-formamido, 4-(2-N,N-dimethylaminoethyl)piperazinyl-1-formamido, 4-(2-N,N-diethylaminoethyl)piperazinyl-1-formamido, 4-(3-hydroxypropyl)piperazinyl-1-formamido, 4-(3-N,N-dimethylaminopropyl)piperazinyl-1-formamido, 4-(3-N,N-diethylaminopropyl)piperazinyl-1-formamido, morpholinyl-1-formamido, 3,5-dimethylmorpholinyl-1-formamido, 4-(4-methyl-piperazin-1-yl)piperidinyl-1-formamido, 4-(4-ethyl-1-piperazinyl)piperidinyl-1-formamido, 4-(4-acetyl-1-piperazinyl)piperidinyl-1-formamido, 4-(N-methyl-4-piperidinyl)piperazinyl-1-formamido; or

(10) $Z_2$ and $Z_3$ or $Z_3$ and $Z_4$ form a nitrogen- or oxygen-containing substituted or unsubstituted 5- or 6-membered ring, the substituent may be selected from the same substituents as described above for $Z_1$;

$R_2$ is selected from

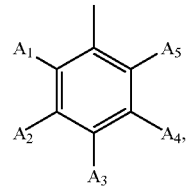

wherein $A_1$, $A_2$, $A_3$, $A_4$, $A_5$ each are independently selected from:

(1) H, F, Cl, Br, I, cyano, trifluoromethyl, trifluoromethoxy, nitro, (2) methylthio, ethylthio, isopropylthio, methylsulfinyl, ethylsulfinyl, isopropylsulfinyl, methylsulfonyl, ethylsulfonyl, isopropylsulfonyl, tert-butyl sulfonyl, dimethylaminosulfonyl, methylsulfonamido, methoxycarbonyl, ethoxycarbonyl, propoxycarbonyl, isopropoxycarbonyl, n-butoxycarbonyl, isobutoxycarbonyl, tert-butoxycarbonyl, methylaminocarbonyl, ethylaminocarbonyl, propylaminocarbonyl, isopropylaminocarbonyl, dimethylaminocarbonyl, cyclopropylaminocarbonyl, cyclobutylaminocarbonyl, cyclopentylaminocarbonyl, dimethylphosphinyl, diethylphosphinyl, diisopropylphosphinyl.

In some embodiments, $R_1$ is selected from:

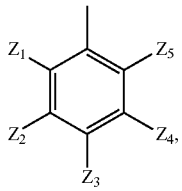

wherein $Z_1$, $Z_2$, $Z_3$, $Z_4$, $Z_5$ each are independently selected from:

(1) H, (2) C1-C6 alkoxy, (3) piperidinyl, N-methyl-4-piperidinyl, 4-N,N-dimethylaminopiperidinyl, 4-N,N-diethylaminopiperidinyl, 4-N,N-diisopropylaminopiperidinyl, 4-hydroxypiperidinyl (4) 4-(4-methylpiperazinyl)piperidinyl, 4-(4-ethylpiperazinyl)piperidinyl, 4-(4-isopropylpiperazinyl)piperidinyl, 4-(4-acetylpiperazinyl)piperidinyl, 4-(4-t-butoxycarbonylpiperazinyl)piperidinyl, 4-(4-methylsulfonylpiperazinyl) piperidinyl, 4-(4-(2-hydroxyethyl)piperazinyl)piperidinyl, 4-(4-(2-cyanoethyl)piperazinyl)piperidinyl, 4-(4-(3-hydroxypropyl)piperazinyl)piperidinyl, 4-(4-(2-N,N-dimethylaminoethyl)piperazinyl)piperidinyl, 4-(4-(2-N,N-diethylaminoethyl)piperazinyl)piperidinyl, 4-(4-(3-N,N-dimethylaminopropyl)piperazinyl)piperidinyl, 4-(4-(3-N,N-diethylaminopropyl)piperazinyl)piperidinyl, 4-(tetrahydropyrrol-1-yl)piperidinyl, 4-(3-N,N-dimethylaminotetrahydropyrrolyl)piperidinyl, (5) 4-methylpiperazinyl, 4-ethylpiperazinyl, 4-isopropylpiperazinyl, 4-acetylpiperazinyl, 4-t-butoxycarbonylpiperazinyl, 4-methylsulfonylpiperazinyl, 4-(2-hydroxyethyl)piperazinyl, 4-(2-cyanoethyl)piperazinyl, 4-(3-hydroxypropyl)piperazinyl, 4-(2-N,N-dimethylaminoethyl)piperazinyl, 4-(2-N,N-diethylaminoethyl)piperazinyl, 4-(3-N,N-dimethylaminopropyl)piperazinyl, 4-(3-N,N-diethylaminopropyl)piperazinyl, 4-(N-methyl-4-piperidinyl)piperazinyl, 4-(N-ethyl-4-piperidinyl)piperazinyl, or (6) $Z_2$ and $Z_3$ or $Z_3$ and $Z_4$ form a nitrogen- or oxygen-containing substituted or unsubstituted 5-membered ring, the substituent may be selected from the same substituents as described above for $Z_1$.

In some embodiments, $R_1$ is selected from:

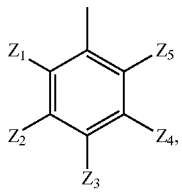

wherein $Z_1$, $Z_2$, $Z_3$, $Z_4$, $Z_5$ each are independently selected from:

(1) H, (2) C1-C6 alkoxy, (3) 4-(4-methylpiperazinyl)piperidinyl, 4-methylpiperazinyl, (4) $Z_2$ and $Z_3$ may form a nitrogen-containing substituted or unsubstituted 5-membered ring

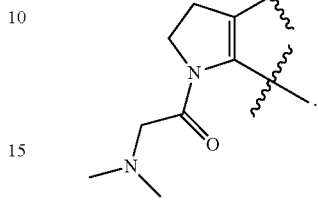

In some embodiments, $R_1$ is selected from:

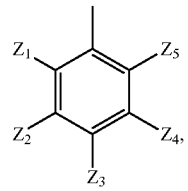

wherein one of $Z_1$ and $Z_5$ is H, the other is methoxy;

$Z_3$ is selected from: 4-methylpiperazinyl, 4-(4-methylpiperazinyl)piperidinyl, or $Z_2$ and $Z_3$ or $Z_3$ and $Z_4$ form

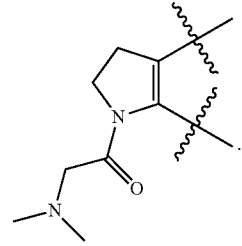 [SMILES: *C1=C(*)N(C(=O)CN(C)C)CC1]

In some embodiments, $R_2$ is selected from:

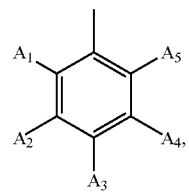

wherein $A_1$, $A_2$, $A_3$, $A_4$, $A_5$ each are independently selected from:

(1) H (2) dimethylaminosulfonyl.

In some embodiments, R₂ is selected from:

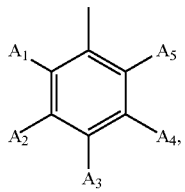

wherein one of A₁ and A₅ is H, the other is dimethylaminosulfonyl; A₂, A₃, A₄ are all H.

Unless otherwise indicated, the above groups and substituents have the ordinary meanings in the field of medicinal chemistry.

It should be noted that C1-C6 oxygen-containing alkyl refers to a group in which C1-C6 alkyl skeleton is substituted by one or more C1-C6 alkoxy groups, for example, methoxyethyl, methoxyethoxymethyl and the like.

The term "C1-C6 alkyl" refers to any straight-chain or branched-chain group having 1 to 6 carbon atoms, such as methyl, ethyl, n-propyl, isopropyl, n-butyl, isobutyl, t-butyl, sec-butyl, n-pentyl, tert-amyl, n-hexyl and the like.

The term "C2-C6 alkenyl" refers to any straight-chain or branched-chain group containing 2 to 6 carbon atoms and containing at least one alkenyl, such as vinyl, allyl, 1-propenyl, isopropenyl, 1-butenyl, 2-butenyl, 3-butenyl, 2-pentenyl, 1-hexenyl and the like.

The term "C2-C6 alkynyl" refers to any straight-chain or branched-chain group containing 2 to 6 carbon atoms and containing at least one alkynyl, such as ethynyl, 2-propynyl, 4-pentynyl and the like.

According to the invention, unless otherwise indicated, any of the above groups may be optionally substituted by one or more groups at any free position thereof, for example by 1-6 groups, which are independently selected from: halogen atom, nitro, oxo (═O), cyano, C1-C6 alkyl, polyfluoroalkyl, polyfluoroalkoxy, alkenyl, alkynyl, hydroxyalkyl, hydroxyalkylamino, hydroxyheterocyclyl, aryl, aryl-alkyl, heteroaryl, heteroaryl-alkyl, heterocyclyl, heterocyclyl-alkyl, C3-C7 cycloalkyl, cycloalkyl-alkyl, alkyl-aryl, alkyl-heteroaryl, alkyl-heterocyclyl, alkyl-cycloalkyl, alkyl-aryl-alkyl, alkyl-heteroaryl-alkyl, alkyl-heterocyclyl-alkyl, alkyl-cycloalkyl-alkyl, alkyl-heterocyclyl-heterocyclyl, heterocyclyl-heterocyclyl, heterocyclyl-alkyl-heterocyclyl, heterocyclyl-alkylamino, alkyl-heterocyclyl-alkyl-amino, hydroxy, alkoxy, aryloxy, heterocyclyloxy, alkyl-heterocyclyloxy, methylenedioxy, alkylcarbonyloxy, arylcarbonyloxy, cycloalkenyloxy, heterocyclyl carbonyloxy, alkylene aminooxy, carboxy, alkoxycarbonyl, aryloxycarbonyl, cycloalkyloxycarbonyl, heterocyclyl oxycarbonyl, amino, ureido, alkylamino, amino-alkylamino, dialkylamino, dialkylamino-heterocyclyl, dialkylamino-alkylamino, arylamino, arylalkylamino, diarylamino, heterocyclylamino, alkyl-heterocyclylamino, alkyl-heterocyclylcarbonyl, carbonylamino, alkylcarbonylamino, arylcarbonylamino, heterocyclyl carbonylamino, alkyl-heterocyclyl carbonylamino, aminocarbonyl, alkylaminocarbonyl, dialkylaminocarbonyl, arylaminocarbonyl, heterocyclyl aminocarbonyl, alkoxycarbonylamino, alkoxycarbonylamino-alkylamino, alkoxycarbonyl heterocyclyl-alkylamino, alkoxy-aryl-alkyl, hydroxyamino-carbonyl, alkoxyimino, alkylsulfonylamino, arylsulfonylamino, heterocyclylsulfonylamino, formyl, alkylcarbonyl, arylcarbonyl, cycloalkylcarbonyl, heterocyclylcarbonyl, alkylsulfonyl, arylsulfonyl, aminosulfonyl, alkylaminosulfonyl, dialkylaminosulfonyl, arylaminosulfonyl, heterocyclyl aminosulfonyl, arylthio, alkylthio, phosphonate and alkylphosphonate.

Further, if appropriate, each of the above substituents may be further substituted by one or more of the above-exemplified groups.

In this respect, the term "halogen atom" refers to a fluoro (F), chloro (Cl), bromo (Br) or iodine (I) atom.

The term "cyano" refers to —CN residue.

The term "nitro" refers to —NO₂ group.

The terms "alkoxy", "cycloalkoxy", "aryloxy", "heterocyclyloxy" and derivatives thereof refer to any of the above C1-C6 alkyl, C3-C7 cycloalkyl, aryl or heterocyclyl, which is attached to the remainder of molecules through oxygen atom (—O—).

The term "aryl" refers to a mono-, di- or poly-carbocyclic hydrocarbon having from 1 to 2 ring systems which are optionally further fused or attached to each other by a single bond, wherein at least one of the carbon rings is "aromatic", and the term "aromatic" refers to a fully conjugated 7-electron bond system. The aryl ring may be optionally further fused or attached to aromatic or non-aromatic carbocyclic rings or heterocyclic rings. Non-limiting examples of the aryl group are phenyl, α- or β-naphthyl.

The term "heteroaryl" refers to an aromatic heterocyclic ring, which is usually a 5- to 8-membered heterocyclic ring having from 1 to 3 heteroatoms selected from N, O or S; a heteroaryl ring may be optionally further fused or attached to aromatic or non-aromatic carbocyclic rings or heterocyclic rings.

Non-limiting examples of the heteroaryl group are, for example, pyridyl, pyrazinyl, pyrimidinyl, pyridazinyl, indolyl, imidazolyl, thiazolyl, isothiazolyl, thioxazolyl, pyrrolyl, phenyl-pyrrolyl, furyl, phenyl-furyl, oxazolyl, isoxazolyl, pyrazolyl, thienyl, benzothienyl, isoindolinyl, benzoimidazolyl, indazolyl, quinolyl, isoquinolyl, 1,2,3-triazolyl, 1-phenyl-1,2,3-triazolyl, 2,3-indolinyl, 2,3-dihydrobenzofuryl, 2,3-dihydrobenzothienyl, benzopyranyl, 2,3-dihydrobenzoxazinyl, 2,3-dihydroquinoxalinyl and the like.

The term "heterocyclyl" (also referred to as "heterocloalkyl") refers to 3-, 4-, 5-, 6- and 7-membered saturated or partially unsaturated carbocyclic rings, wherein one or more carbon atoms are substituted by heteroatoms such as nitrogen, oxygen and sulfur. Non-limiting examples of the heterocyclic group are, for example, pyranyl, pyrrolidinyl, pyrrolinyl, imidazolinyl, imidazolidinyl, pyrazolidinyl, pyrazolinyl, thiazolinyl, thiazolidinyl, dihydrofuryl, tetrahydrofuryl, 1,3-dioxolanyl, piperidinyl, piperazinyl, morpholinyl, tetrahydropyrrolyl, thiomorpholinyl and the like.

The term "nitrogen-containing or oxygen-containing substituted or unsubstituted five-membered ring or six-membered ring" refers to 5- or 6-membered saturated or partially unsaturated carbocyclic rings, wherein one or more carbon atoms are substituted by heteroatoms such as nitrogen, oxygen. The nitrogen-containing or oxygen-containing substituted or unsubstituted five-membered ring or six-membered ring is selected from pyrrolidine, pyrroline, pyrrole, imidazoline, imidazolidine, imidazole, pyrazolidine, pyrazoline, pyrazole, dihydrofuran, tetrahydrofuran, furan, 1,3-dioxolane, oxazole, dihydrooxazole; pyridine, pyrazine, pyrimidine, pyridazine, pyran, piperidine, piperazine, morpholine and the like.

From all of the above description, it will be apparent to those skilled in the art that any group whose name is a compound name, such as "arylamino", shall mean to conventionally construct from the moiety that is derived, such as the amino substituted by the aryl, wherein the aryl is as defined above.

Similarly, any term such as alkylthio, alkylamino, dialkylamino, alkoxycarbonyl, alkoxycarbonylamino, heterocyclylcarbonyl, heterocyclyl carbonylamino, cycloalkyloxycarbonyl and the like includes groups, wherein alkyl, alkoxy, aryl, C3-C7 cycloalkyl and heterocyclyl moieties are as defined above.

As used herein, unless otherwise indicated, the term "prodrug" refers to a derivative that can be hydrolyzed, oxidized or otherwise reacted under biological conditions (in vitro or in vivo) to provide a compound of the invention. Prodrugs can become active compounds only by carrying out the reaction under biological conditions, or they are inactive in their non-reacted form. Prodrugs can be generally prepared using known methods, for example, those methods described in 1 Burger's Medicinal Chemistry and Drug Discovery (1995) 172-178, 949-982 (Manfred E. Wolff, ed. 5th edition).

Pharmaceutically acceptable salts can be obtained using standard procedures well known in the art, for example, by reacting a sufficient amount of a basic compound with a suitable acid that provides a pharmaceutically acceptable anion.

The term "treatment" as used herein generally refers to obtaining the desired pharmacological and/or physiological effect. The effect may be preventive according to complete or partial prevention of disease or its symptoms; and/or may be therapeutic according to partial or complete stabilization or cure of disease and/or side effects due to the disease. The term "treatment" as used herein encompasses any treatment on a patient's disease, including: (a) preventing the disease or symptom that occurs in a patient who is susceptible to the disease or symptom but not yet diagnosed to suffer from the disease; (b) suppressing symptoms of the disease, i.e., stopping its development; or (c) relieving symptoms of the disease, i.e., causing degeneration of the disease or symptom.

According to a specific embodiment of the present invention relating to the compound, a stereoisomer thereof, a prodrug thereof, or a pharmaceutically acceptable salt thereof or a pharmaceutically acceptable solvate thereof, the compound is one of the compounds described in the examples below.

In another aspect, the present invention provides a pharmaceutical composition comprising the compound, a stereoisomer thereof, a prodrug thereof, or a pharmaceutically acceptable salt thereof or pharmaceutically acceptable solvate thereof according to any one of the above embodiments, and a pharmaceutically acceptable carrier, diluent or excipient.

Methods for preparing a pharmaceutical composition comprising a certain amount of an active ingredient, are known or are obvious for a person skilled in the art according to the contents as disclosed in the invention. For example, as described in REMINGTON'S PHARMACEUTICAL SCIENCES, Martin, E. W., ed., Mack Publishing Company, 19th ed. (1995), methods for preparing a pharmaceutical composition comprise incorporating a suitable pharmaceutically acceptable excipient, carrier, diluent, etc.

The known methods for preparing a pharmaceutical preparation according to the invention include the conventional mixing, dissolving or freeze-drying methods. The compound according to the invention can be used to prepare into a pharmaceutical composition, which is administered to a patient by various routes suitable for the selected administration mode, for example, oral, or parenteral route (intravenous, intramuscular, topical, or subcutaneous route).

Therefore, the compound of the invention in combination with a pharmaceutically acceptable carrier (such as an inert diluent or an assimilable edible carrier) can be administered systemically, e.g., orally. They can be encapsulated into a hard or soft shell gelatin capsule, or pressed into a table. For the treatment by oral administration, an active compound may be combined with one or more excipients, and be used in a form of a deglutible tablet, a buccal tablet, a troche, a capsule, an elixir, a suspension, a syrup, a wafer, etc. The composition and preparation shall comprise at least 0.1% of an active compound. The ratio of the composition to the preparation can be varied certainly, and the composition may account for about 1 wt % to about 99 wt % of a given unit dosage form. In such a therapeutically active composition, the active compound is in an amount sufficient to obtain an effective dosage level.

A tablet, a troche, a pill, a capsule, and the like may include: a binder, such as tragacanth gum, arabic gum, maize starch or gelatin; an excipient, such as dicalcium phosphate; a disintegrant, such as maize starch, potato starch, and alginic acid etc; a lubricant, such as magnesium stearate; and a sweeting agent, such as sucrose, fructose, lactose or aspartame; or a flavoring agent, such as peppermint, winter green oil or cherry flavor. When the unit dosage form is a capsule, in addition to the above types of materials, it may comprise a liquid carrier, such as vegetable oil or polyethylene glycol. Various other materials may be present as a coating or change the physical form of a solid unit dosage form in other manners. For example, a tablet, a pill or a capsule may be coated with gelatin, wax, shellac or sugar etc. A syrup or elixir may comprise an active compound, sucrose or fructose as a sweeting agent, methyl p-hydroxybenzoate or propyl p-hydroxybenzoate as preservative, a dye and a flavoring agent (such as a cherry flavor or an orange flavor). Certainly, any material for preparing any unit dosage form should be pharmaceutically acceptable and be substantively not toxic in its applied amount. In addition, an active compound may be incorporated into a sustained release preparation and a sustained release device.

An active compound may also be administered intravenously or intraperitoneally by infusion or injection. An aqueous solution of an active compound or a salt thereof may be prepared, optionally, by mixing it with a non-toxic surfactant. A dispersible formulation in glycerol, liquid polyethylene glycol, glycerin triacetate and a mixture thereof and in oil may also be prepared. Under the common conditions of storage and use, the preparations may comprise a preservative in order to suppress the growth of microbes.

A pharmaceutical dosage form suitable for injection or infusion may include a sterile aqueous solution or a dispersible formulation or a sterile powder comprising an active ingredient (optionally encapsulated into a liposome) of an immediate preparation such as a solution or a dispersible formulation suitable for sterile injection or infusion. Under all the conditions, the final dosage form shall be sterile, liquid and stable under the production and storage conditions. A liquid carrier may be a solution or a liquid disperse medium, including, for example, water, ethanol, polyols (such as glycerol, propylene glycol, and liquid macrogol, etc), vegetable oil, a non-toxic glyceride and a suitable mixture thereof. A suitable fluidity may be retained, for example, by the formation of liposome, by retaining the desired particle size in the presence of a dispersing agent, or by using a surfactant. The effect of suppressing microbes can be obtained by various antibacterial agents and antifungal agents (such as paraben, chlorbutol, phenol, sorbic acid, and thiomersal, etc). In many conditions, an isotonizing agent, such as sugar, buffer agent or NaCl, is preferably comprised. By the use of a composition of delayed absorbents (e.g., aluminium monostearate and gelatin), an extended absorption of an injectable composition can be obtained.

A sterile injectable solution can be prepared by mixing a desired amount of an active compound in a suitable solvent with the desired various other ingredients as listed above, and then performing filtration and sterilization. In the case of a sterile powder for the preparation of a sterile injectable solution, the preferred preparation method is vacuum drying and freeze drying techniques, which will result in the production of the powder of the active ingredient and any other desired ingredient present in the previous sterile filtration solution.

A useful solid carrier includes crushed solid (such as talc, clay, microcrystalline cellulose, silicon dioxide, and aluminum oxide etc). A useful liquid carrier includes water, ethanol or ethylene glycol or water-ethanol/ethylene glycol mixture, in which the compound of the invention may be dissolved or dispersed in an effective amount, optionally, with the aid of a non-toxic surfactant. An adjuvant (such as a flavor) and an additional antimicrobial agent may be added to optimize the property for a given use.

A thickener (such as synthetic polymer, fatty acid, fatty acid salt and ester, fatty alcohol, modified cellulose or modified inorganic material) may also be used with a liquid carrier to form a coatable paste, gel, ointment, soap and the like, and be directly applied to the skin of a user.

A therapeutically effective amount of a compound or an active salt or derivative thereof not only depends on the specific salt selected, but also depends on the administration mode, the nature of the disease to be treated and the age and state of a patient, and finally depends on the decision made by an attending physician or a clinical physician.

Above preparation may be present in a unit dosage form, which is a physical dispersion unit comprising a unit dose, suitable for administration to a human body and other mammalian body. A unit dosage form may be capsule(s) or tablet(s).

Depending on the particular treatment involved, the amount of an active ingredient in a unit dose may be varied or adjusted between about 0.1 and about 1000 mg or more.

In addition, the present invention further includes use of various new drug dosage forms such as milk liposomes, microspheres and nanospheres, for example, medicaments prepared with the use of a particulate dispersion system including polymeric micelles, nanoemulsions, submicroemulsions, microcapsules, microspheres, liposomes and niosomes (also known as nonionic surfactant vesicles), etc.

In another aspect, the present invention further provides a preparation method of the compound according to any of the above embodiments, comprising the following steps:

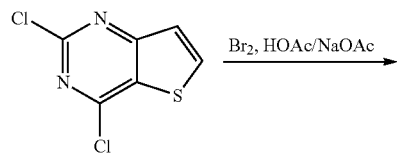

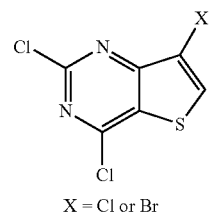

The starting materials for this reaction are commercially available.

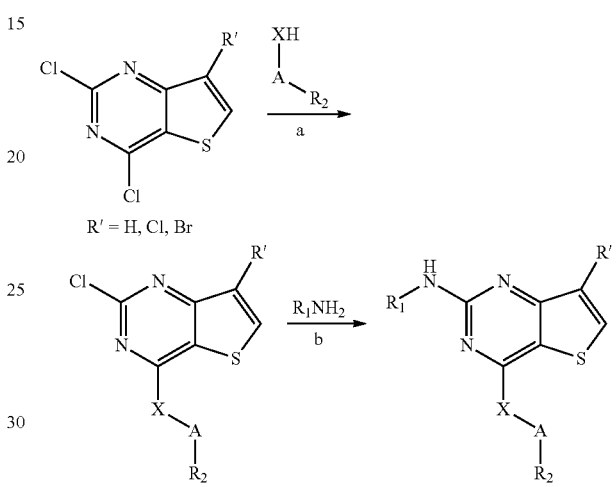

Reaction conditions: (a) substitution reaction under basic conditions (such as diisopropylethylamine, triethylamine, potassium carbonate, etc.) or acidic conditions (trifluoroacetic acid, hydrochloric acid, etc.); (b) amination reaction under acidic conditions (trifluoroacetic acid, hydrochloric acid, etc.) or under catalysis of palladium.

In another aspect, the present invention further provides use of the compound according to any one of the above embodiments, a stereoisomer thereof, a prodrug thereof, or a pharmaceutically acceptable salt thereof or a pharmaceutically acceptable solvate thereof in the manufacture of a medicament for preventing or treating tumor. Preferably, the tumor is any one selected from the group consisting of anaplastic large cell lymphoma, inflammatory myofibroblastic tumor, non-small cell lung cancer, neuroblastoma, small cell lung cancer, lung adenocarcinoma, pancreatic cancer, breast cancer, prostate cancer, liver cancer, skin cancer, epithelial cell carcinoma, gastrointestinal stromal tumor, leukemia, histiocytic lymphoma and nasopharyngeal carcinoma; more preferably, the tumor is anaplastic large cell lymphoma, inflammatory myofibroblastic tumor, non-small cell lung cancer or neuroblastoma.

MODE OF CARRYING OUT THE INVENTION

The embodiments of the present invention are described in detail below by way of specific examples, but in any case they cannot be construed as limiting the present invention.

General Methods of Purification and Analysis

Thin layer chromatography was carried out on a silica gel GF254 precoated plate (Qingdao Marine Chemical Plant). Column chromatography was carried out by silica gel (300-400 mesh, Yantai Zhihuangwu Silica Gel Development Reagent Factory) under medium pressure or by a pre-packed silica gel cartridge (ISCO or Welch) with the use of an ISCO Combiflash Rf200 rapid purification system. The ingredient was developed by UV light (λ: 254 nm) or iodine vapor. When necessary, the compound was prepared by preparative HPLC and purified by a Waters Symmetry C18 (19×50 mm, 5 m) column or a Waters X Terra RP 18 (30×150 mm, 5 μm) column, wherein a Waters preparative HPLC 600 equipped with a 996 Waters PDA detector and Micromass mod. ZMD single quadrupole mass spectrometry (electrospray ionization, cationic mode) were used. Method 1: Phase A: 0.1% TFA/MeOH 95/5; Phase B: MeOH/H$_2$O 95/5. Gradient: proceeding at 10 to 90% B for 8 min, keeping at 90% B for 2 min; flow rate 20 mL/min. Method 2: Phase A: 0.05% NH$_4$OH/MeOH 95/5; Phase B: MeOH/H$_2$O 95/5. Gradient: proceeding at 10 to 100% B for 8 min, keeping at 100% B for 2 min. Flow rate 20 mL/min.

$^1$H-NMR spectra were recorded in DMSO-d$_6$ or CDCl$_3$ via a Bruker Avance 600 spectrometer (for 1H) operated at 600 MHz. The residual solvent signal was used as a reference (δ=2.50 or 7.27 ppm). Chemical shift (δ) was reported in parts per million (ppm) and coupling constant (J) in Hz. The following abbreviations were used for peak splitting: s=single; br. s.=wide signal; d=double; t=triple; m=multiple; dd=double double.

Electrospray (ESI) mass spectra were obtained via Finnigan LCQ ion trap.

Unless otherwise indicated, all final compounds were homogeneous (with purity not less than 95%), as determined by high performance liquid chromatography (HPLC). HPLC-UV-MS analysis for evaluation of compound purity was performed by combining an ion trap MS device and an HPLC system SSP4000 (Thermo Separation Products) equipped with an autosampler LC Pal (CTC Analytics) and a UV6000LP diode array detector (UV detection 215-400 nm). Device control, data acquisition and processing were performed with Xcalibur 1.2 software (Finnigan). HPLC chromatography was carried out at room temperature and a flow rate of 1 mL/min using a Waters X Terra RP 18 column (4.6×50 mm; 3.5 μm). Mobile phase A was ammonium acetate 5 mM buffer (pH 5.5 with acetic acid):acetonitrile 90:10, mobile phase B was ammonium acetate 5 mM buffer (pH 5.5 with acetic acid):acetonitrile 10:90; proceeding at a gradient of 0 to 100% B for 7 min and then keeping at 100% B for 2 min before rebalancing.

Reagent purification was carried out in accordance with the book Purification of Laboratory Chemicals (Perrin, D. D., Armarego, W. L. F. and Perrins Eds, D. R.; Pergamon Press: Oxford, 1980). Petroleum ether was 60-90° C. fraction, ethyl acetate, methanol, dichloromethane were all analytically pure.

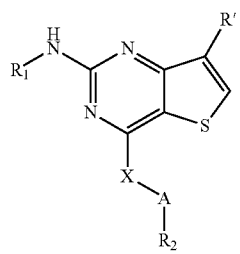

The above compound of formula was divided into several types for preparation.

The compound of formula I:

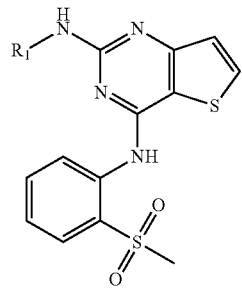

IA

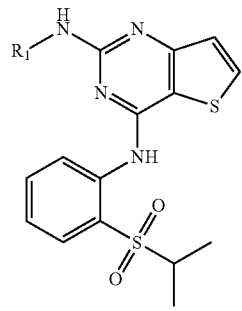

IB

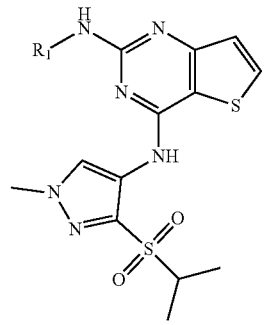

IC

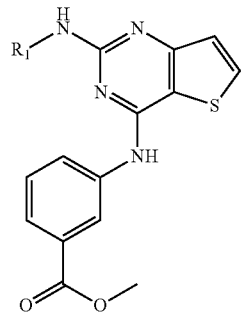

ID

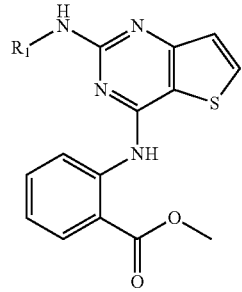

IE

-continued
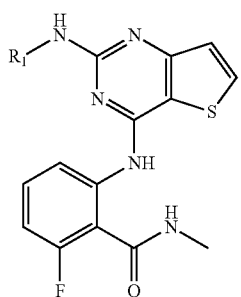
IF
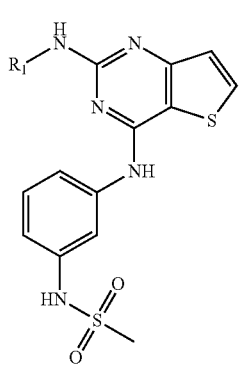
IG
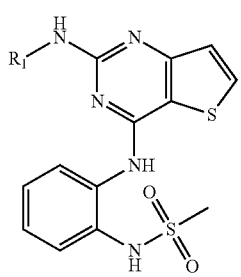
IH
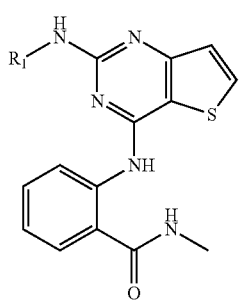
II
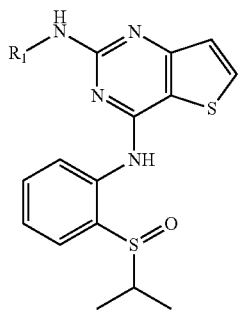
IJ
-continued
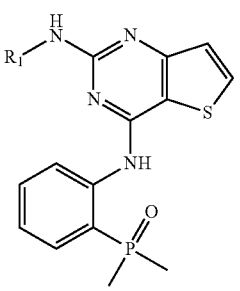
IK
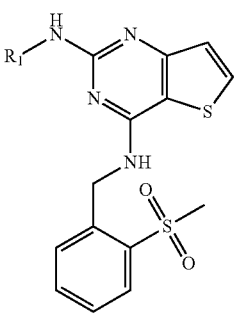
IL
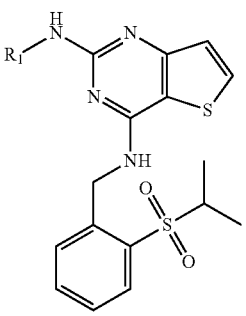
IM
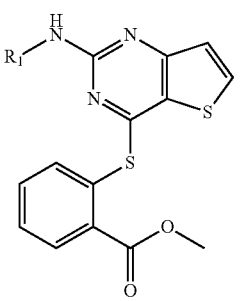
IN
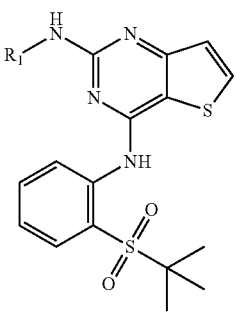
IO -continued
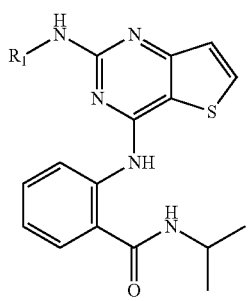
IP
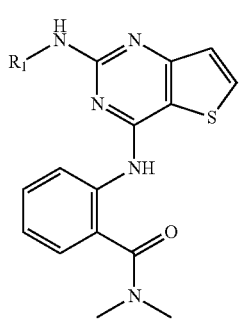
IQ
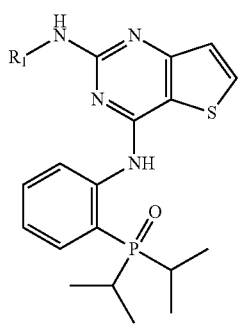
IR
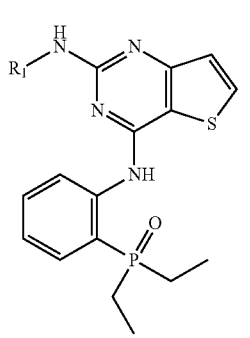
IS
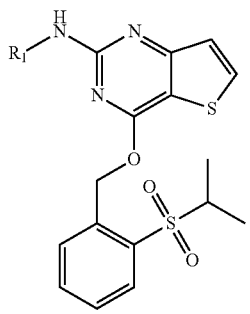
IT
-continued
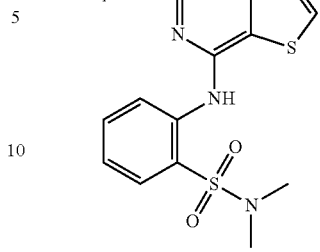
IU
Example 1
Synthetic Scheme of Compound IA
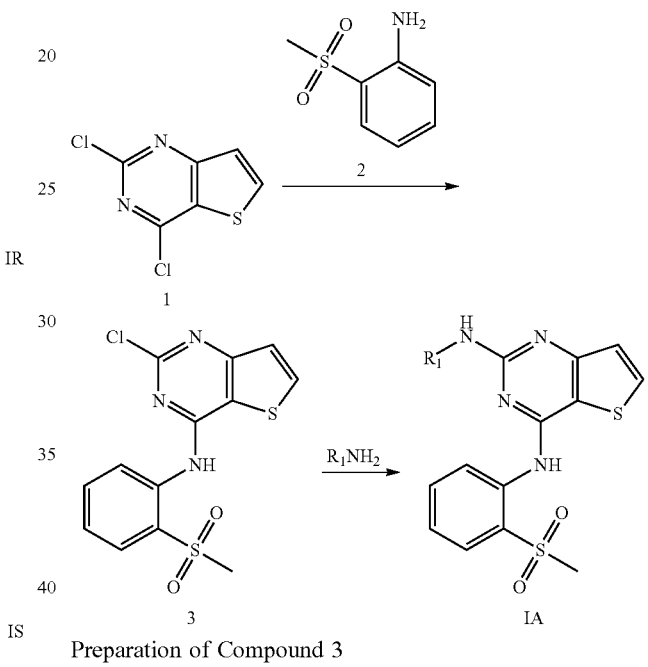
Preparation of Compound 3
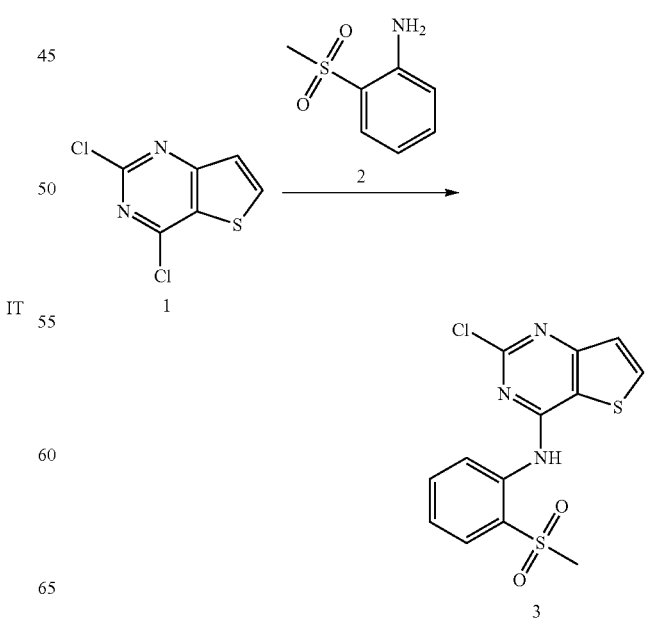

Compound 2 (200 mg, 1.17 mmol) was dissolved in N,N-dimethylformamide (4 mL), and, under the condition of ice bath, sodium hydride (93.6 mg, 2.34 mmol) was added and stirred for 5-10 min; next, compound 1 (240.0 mg, 1.17 mmol) was added and stirred at room temperature for 1.0 h (TLC tracking), then the reaction was stopped. Ice water was added to the system to quench sodium hydride, and ethyl acetate was added to separate the solution; the organic phase was washed twice with saturated sodium chloride solution, dried over anhydrous sodium sulfate, concentrated and separated by silica gel column chromatography (petroleum ether/ethyl acetate=5/1) to obtain compound 3 (solid, 270.0 mg, yield: 79.5%), which was directly used for the next step reaction.

MS (ESI) m/z: 340 [M+H]$^+$.

Preparation of Compound IA

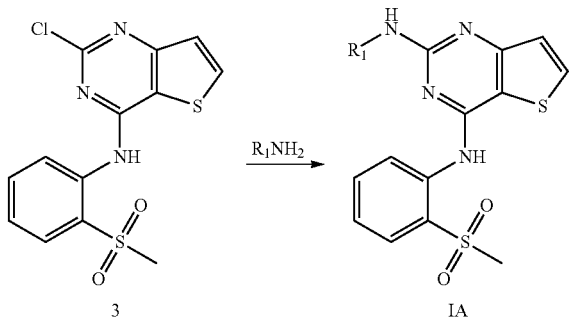

Method A:

Compound 3 (30.0 mg, 0.09 mmol), arylamine (0.072 mmol) were dissolved in 1 mL of tert-butanol, then to the solution were added 2-dicyclohexylphosphino-2,4,6-triisopropylbiphenyl (7.7 mg, 0.016 mmol), tris(dibenzylideneacetone)dipalladium (9.9 mg, 0.011 mmol), potassium carbonate (37 mg, 0.27 mmol); under the protection of nitrogen, the resulting reaction solution was heated and stirred in an oil bath preheated to 110° C. until complete reaction of the arylamine (LC-MS and TLC tracking), then the reaction was stopped. Methanol and dichloromethane were added to the reaction solution, and the system was filtered, concentrated and separated by silica gel chromatograph (dichloromethane/methanol) to obtain compound IA.

Method B:

Compound 3 (30.0 mg, 0.09 mmol), arylamine (0.072 mmol) were dissolved in 1 mL of tert-butanol, then to the solution were added 2-dicyclohexylphosphino-2,4,6-triisopropylbiphenyl (7.7 mg, 0.016 mmol), tris(dibenzylideneacetone)dipalladium (9.9 mg, 0.011 mmol), potassium carbonate (37 mg, 0.27 mmol); under the protection of nitrogen, the resulting reaction solution was heated and stirred in an oil bath preheated to 110° C. until complete reaction of the arylamine (LC-MS and TLC tracking), then the reaction was stopped. Methanol and dichloromethane were added to the reaction solution, and the system was filtered, concentrated, purified by reverse-phase preparative HPLC (aqueous solution containing 0.35% trifluoroacetic acid and methanol as mobile phase), and then concentrated in vacuo to obtain compound IA.

Compounds IB, IC both could be synthesized by a similar method.

The table below lists the specific compounds and structure identification data.

TABLE 1

Structure and characterization of compounds IA-IC

| No. | Structure | $^1$H NMR and/or MS data |
|---|---|---|
| IA-1 | 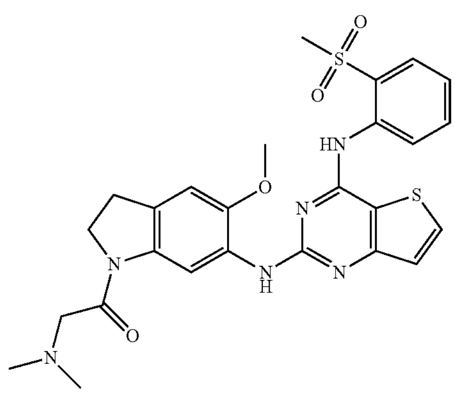 [SMILES: COc1cc2c(cc1Nc1nc(Nc3ccccc3S(C)(=O)=O)c3sccc3n1)N(C(=O)CN(C)C)CC2] | $^1$H NMR (600 MHz, Methanol-d$_4$) δ 8.21 (d, J = 5.4 Hz, 1H), 8.15 (s, 1H), 8.05 (dd, J = 8.0, 1.5 Hz, 1H), 8.00 (d, J = 8.0 Hz, 1H), 7.68 (s, 1H), 7.57 (t, J = 7.7 Hz, 1H), 7.31 (d, J = 5.4 Hz, 1H), 7.10 (s, 1H), 4.34 (s, 2H), 4.13 (t, J = 8.3 Hz, 2H), 3.82 (s, 3H), 3.37-3.30 (m, 2H), 3.17 (s, 3H), 3.01 (s, 6H). MS (ESI) m/z: 553 [M + H]$^+$. |
| IA-2 | TFA salt | $^1$H NMR (600 MHz, Methanol-d$_4$) δ 8.23 (d, J = 5.4 Hz, 1H), 8.12 (dd, J = 8.0, 1.6 Hz, 1H), 7.97 (d, J = 8.0 Hz, 1H), 7.81 (td, J = 7.8, 1.6 Hz, 1H), 7.66 (td, J = 7.7, 1.2 Hz, 1H), 7.41 (d, J = 8.7 Hz, 1H), 7.31 (d, J = 5.4 Hz, 1H), 6.94 (d, J = 2.5 Hz, 1H), 6.70 (dd, J = 8.8, 2.5 Hz, 1H), 3.87 (s, 3H), 3.85 (s, 1H), 3.58 (s, 4H), 3.47 (s, 4H), 3.21-3.16 (m, 2H), 3.14 (s, 3H), 2.97 (s, 3H), 2.26 (dt, J = 13.1, 2.8 Hz, 2H), 2.01 (qd, J = 12.3, 4.0 Hz, 2H). MS (ESI) m/z: 608 [M + H]$^+$. |

TABLE 1-continued

Structure and characterization of compounds IA-IC

| No. | Structure | ¹H NMR and/or MS data |
|---|---|---|
| IA-3 | 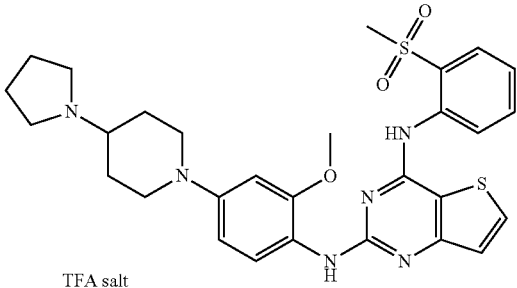 TFA salt | ¹H NMR (600 MHz, Methanol-$d_4$) δ 8.22 (d, J = 5.4 Hz, 1H), 8.11 (dd, J = 7.9, 1.6 Hz, 1H), 8.00 (s, 1H), 7.80 (td, J = 7.8, 1.6 Hz, 1H), 7.64 (td, J = 7.7, 1.2 Hz, 1H), 7.32 (d, J = 8.3 Hz, 1H), 7.30 (d, J = 5.4 Hz, 1H), 6.82 (d, J = 2.5 Hz, 1H), 6.61 (d, J = 8.6 Hz, 1H), 3.88 (d, J = 12.9 Hz, 2H), 3.85 (s, 3H), 3.71 (s, 2H), 3.38 (tt, J = 11.7, 4.0 Hz, 1H), 3.20 (q, J = 13.9, 11.5 Hz, 2H), 3.15 (s, 3H), 3.01 (t, J = 12.4 Hz, 2H), 2.36-2.26 (m, 2H), 2.18 (s, 2H), 2.04 (s, 2H), 1.95 (qd, J = 12.0, 3.7 Hz, 2H). MS (ESI) m/z: 693 [M + H]⁺. |
| IA-4 | 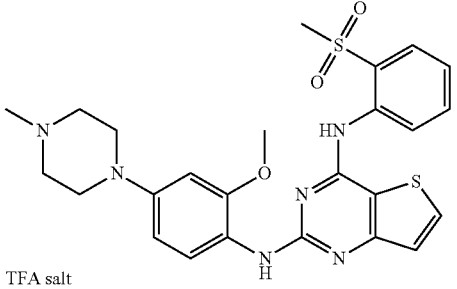 [SMILES: COc1cc(N2CCN(C)CC2)ccc1Nc1nc(Nc2ccccc2S(C)(=O)=O)c2sccc2n1] TFA salt | ¹H NMR (600 MHz, Methanol-$d_4$) δ 8.22 (d, J = 5.4 Hz, 1H), 8.12 (dd, J = 8.0, 1.6 Hz, 1H), 8.00 (s, 1H), 7.80 (t, J = 7.7 Hz, 1H), 7.64 (t, J = 7.8 Hz, 1H), 7.31 (d, J = 8.9 Hz, 1H), 7.28 (d, J = 5.4 Hz, 1H), 6.75 (d, J = 2.4 Hz, 1H), 6.55 (s, 1H), 3.90 (s, 2H), 3.85 (s, 3H), 3.64 (s, 2H), 3.15 (s, 3H), 2.99 (s, 3H). MS (ESI) m/z: 525 [M + H]⁺. |
| IA-5 | 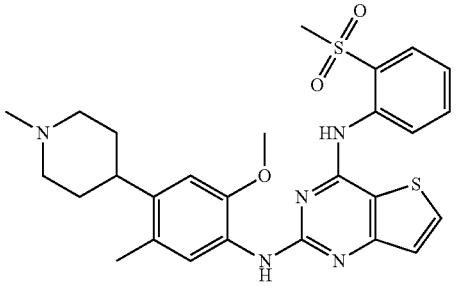 [SMILES: COc1cc(C2CCN(C)CC2)c(C)cc1Nc1nc(Nc2ccccc2S(C)(=O)=O)c2sccc2n1] | ¹H NMR (600 MHz, Methanol-$d_4$) δ 8.47 (dd, J = 8.3, 1.2 Hz, 1H), 8.02 (dd, J = 8.0, 1.6 Hz, 1H), 8.00 (d, J = 5.3 Hz, 1H), 7.92 (s, 1H), 7.71 (ddd, J = 8.7, 7.4, 1.6 Hz, 1H), 7.40 (td, J = 7.7, 1.1 Hz, 1H), 7.21 (d, J = 5.4 Hz, 1H), 6.80 (s, 1H), 3.89 (s, 3H), 3.44 (dd, J = 9.5, 6.1 Hz, 2H), 3.13 (s, 3H), 2.98 (ddd, J = 15.9, 10.6, 6.6 Hz, 1H), 2.90 (td, J = 11.9, 5.8 Hz, 2H), 2.76 (s, 3H), 2.20 (s, 3H). MS (ESI) m/z: 538 [M + H]⁺. |
| IA-6 | 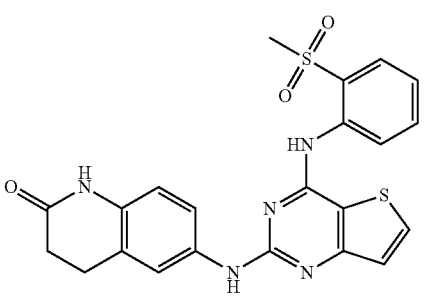 TFA salt | MS (ESI) m/z: 466 [M + H]⁺. |

TABLE 1-continued

Structure and characterization of compounds IA-IC

| No. | Structure | ¹H NMR and/or MS data |
|---|---|---|
| IB-1 | 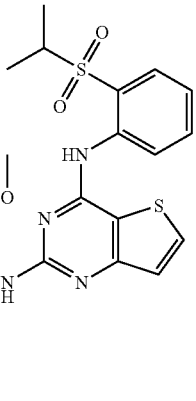 TFA salt | 1H NMR (600 MHz, Methanol-d4) δ 8.27-8.19 (m, 3H), 7.98 (dd, J = 7.9, 1.6 Hz, 1H), 7.69 (s, 1H), 7.53 (t, J = 7.7 Hz, 1H), 7.31 (d, J = 5.4 Hz, 1H), 7.15 (s, 1H), 4.34 (s, 2H), 4.15 (t, J = 8.3 Hz, 2H), 3.83 (s, 3H), 3.41-3.33 (m, 3H), 3.00 (s, 6H), 1.23 (d, J = 6.8 Hz, 6H). MS (ESI) m/z: 581 [M + H]⁺. |
| IB-2 | 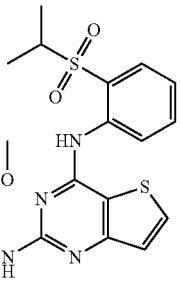 TFA salt | ¹H NMR (600 MHz, Methanol-d₄) δ 8.25 (d, J = 5.4 Hz, 1H), 8.19 (s, 1H), 8.04 (dd, J = 7.9, 1.6 Hz, 1H), 7.81 (td, J = 7.8, 1.6 Hz, 1H), 7.64-7.58 (m, 1H), 7.39 (d, J = 8.7 Hz, 1H), 7.31 (d, J = 5.4 Hz, 1H), 6.88 (d, J = 2.4 Hz, 1H), 6.68 (dd, J = 8.5, 2.5 Hz, 1H), 3.87 (s, 3H), 3.86 (s, 1H), 3.41 (s, 4H), 3.38-3.34 (m, 1H), 3.25 (s, 4H), 3.06 (t, J = 12.2 Hz, 3H), 2.90 (s, 3H), 2.17 (d, J = 12.7 Hz, 2H), 1.89 (tt, J = 13.8, 7.0 Hz, 2H), 1.22 (d, J = 6.8 Hz, 6H). MS (ESI) m/z: 636 [M + H]⁺. |
| IB-3 | 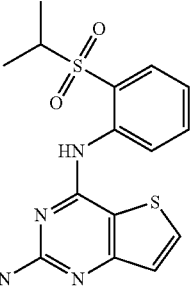 TFA salt | ¹H NMR (600 MHz, Chloroform-d) δ 11.94 (s, 1H), 10.37 (s, 1H), 8.50 (dd, J = 8.4, 1.1 Hz, 1H), 7.94 (d, J = 5.3 Hz, 1H), 7.92 (dd, J = 8.0, 1.6 Hz, 1H), 7.55-7.47 (m, 3H), 7.43 (d, J = 5.4 Hz, 1H), 7.40 (td, J = 7.6, 1.1 Hz, 1H), 6.94-6.88 (m, 2H), 3.67 (dd, J = 46.3, 12.3 Hz, 4H), 3.36 (t, J = 12.7 Hz, 2H), 3.22 (p, J = 6.9 Hz, 1H), 3.09 (d, J = 12.2 Hz, 2H), 2.91 (s, 3H), 1.31 (d, J = 6.9 Hz, 6H). MS (ESI) m/z: 523 [M + H]⁺. |
| IB-4 | 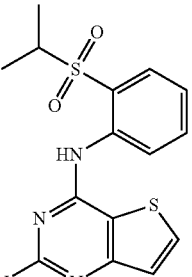 TFA salt | ¹H NMR (600 MHz, Methanol-d₄) δ 8.33 (d, J = 8.1 Hz, 1H), 8.19 (d, J = 5.4 Hz, 1H), 8.01 (dd, J = 8.0, 1.6 Hz, 1H), 7.82 (td, J = 7.8, 1.7 Hz, 1H), 7.64 (d, J = 8.4 Hz, 2H), 7.56 (t, J = 7.7 Hz, 1H), 7.35 (dd, J = 15.4, 6.9 Hz, 3H), 4.02 (s, 1H), 3.75 (s, 2H), 3.46-3.37 (m, 2H), 3.35 (s, 1H), 2.16 (s, 2H), 1.92 (s, 2H), 1.21 (d, J = 6.8 Hz, 6H). MS (ESI) m/z: 524 [M + H]⁺. |

TABLE 1-continued

Structure and characterization of compounds IA-IC

| No. | Structure | ¹H NMR and/or MS data |
|---|---|---|
| IB-5 | 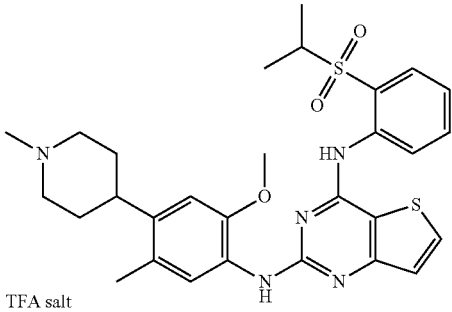 [SMILES: COc1cc(C2CCN(C)CC2)c(C)cc1Nc1nc(Nc2ccccc2S(=O)(=O)C(C)C)c2sccc2n1] TFA salt | ¹H NMR (600 MHz, Methanol-$d_4$) δ 8.27 (d, J = 5.4 Hz, 1H), 8.11 (s, 1H), 8.03 (dd, J = 8.0, 1.5 Hz, 1H), 7.78 (t, J = 7.8 Hz, 1H), 7.61 (t, J = 7.7 Hz, 1H), 7.33 (d, J = 5.4 Hz, 1H), 7.29 (s, 1H), 6.90 (s, 1H), 3.86 (s, 3H), 3.65 (d, J = 12.7 Hz, 2H), 3.38-3.32 (m, 1H), 3.20 (td, J = 12.3, 4.1 Hz, 2H), 3.12 (ddd, J = 12.7, 7.3, 4.4 Hz, 1H), 2.94 (s, 3H), 2.20 (s, 3H), 2.03 (h, J = 10.5, 9.1 Hz, 4H), 1.19 (d, J = 6.8 Hz, 6H). MS (ESI) m/z: 566 [M + H]⁺. |
| IB-6 | 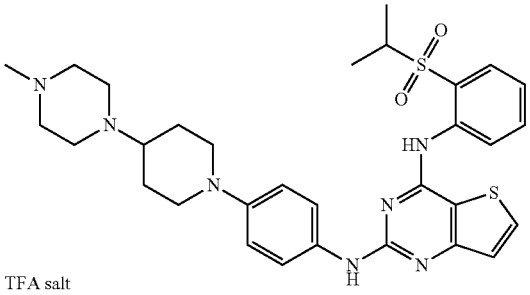 [SMILES: CC(C)S(=O)(=O)c1ccccc1Nc1nc(Nc2ccc(N3CCC(N4CCN(C)CC4)CC3)cc2)nc2ccsc12] TFA salt | ¹H NMR (600 MHz, Methanol-$d_4$) δ 8.26 (d, J = 5.4 Hz, 1H), 8.08 (d, J = 8.1 Hz, 1H), 8.04 (dd, J = 7.9, 1.5 Hz, 1H), 7.83 (td, J = 7.8, 1.6 Hz, 1H), 7.65 (td, J = 7.7, 1.2 Hz, 1H), 7.44 (d, J = 9.0 Hz, 2H), 7.37 (d, J = 5.4 Hz, 1H), 7.24 (d, J = 9.0 Hz, 2H), 3.80 (d, J = 12.5 Hz, 2H), 3.49 (s, 4H), 3.23 (t, J = 12.3 Hz, 2H), 3.20-3.12 (m, 1H), 2.95 (s, 3H), 2.23 (d, J = 12.3 Hz, 2H), 2.05-1.95 (m, 2H), 1.17 (d, J = 6.8 Hz, 6H). MS (ESI) m/z: 606 [M + H]⁺. |
| IB-7 | 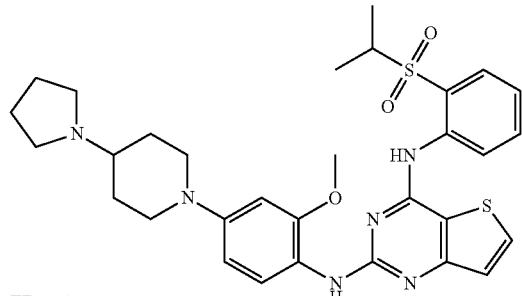 TFA salt | ¹H NMR (600 MHz, Methanol-$d_4$) δ 8.23 (d, J = 5.4 Hz, 2H), 8.01 (dd, J = 7.9, 1.6 Hz, 1H), 7.78 (t, J = 7.8 Hz, 1H), 7.58 (t, J = 7.7 Hz, 1H), 7.30 (t, J = 7.7 Hz, 2H), 6.78 (d, J = 2.5 Hz, 1H), 6.60 (d, J = 8.7 Hz, 1H), 3.90 (d, J = 12.8 Hz, 2H), 3.85 (s, 3H), 3.71 (s, 2H), 3.40-3.32 (m, 2H), 3.19 (q, J = 7.7 Hz, 2H), 2.93 (td, J = 12.6, 2.3 Hz, 2H), 2.30 (d, J = 12.9 Hz, 2H), 2.18 (d, J = 7.8 Hz, 2H), 2.09-1.98 (m, 2H), 1.91 (qd, J = 12.2, 4.0 Hz, 2H), 1.21 (d, J = 6.8 Hz, 6H). MS (ESI) m/z: 607 [M + H]⁺. |
| IB-8 | 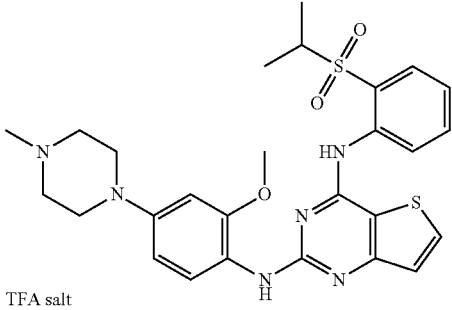 [SMILES: COc1cc(N2CCN(C)CC2)ccc1Nc1nc(Nc2ccccc2S(=O)(=O)C(C)C)c2sccc2n1] TFA salt | ¹H NMR (600 MHz, Methanol-$d_4$) δ 8.24 (d, J = 5.4 Hz, 2H), 8.00 (dd, J = 7.9, 1.5 Hz, 1H), 7.77 (s, 1H), 7.58 (t, J = 7.7 Hz, 1H), 7.31 (t, J = 6.2 Hz, 2H), 6.81-6.70 (m, 1H), 6.56 (s, 1H), 3.91 (d, J = 13.4 Hz, 2H), 3.85 (s, 3H), 3.65 (d, J = 12.1 Hz, 2H), 3.35 (m, 1H), 3.30-3.25 (m, 2H), 3.12 (t, J = 12.8 Hz, 2H), 2.99 (s, 3H), 1.21 (d, J = 6.8 Hz, 6H). MS (ESI) m/z: 553 [M + H]⁺. |

TABLE 1-continued

Structure and characterization of compounds IA-IC

| No. | Structure | ¹H NMR and/or MS data |
|---|---|---|
| IB-9 | 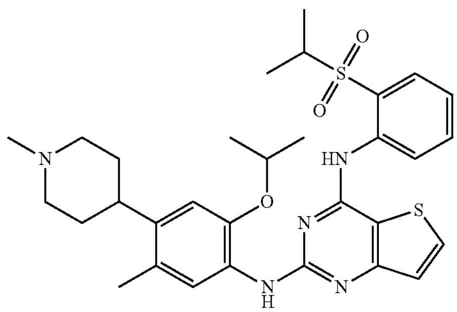 [SMILES: Cc1cc(Nc2nc(Nc3ccccc3S(=O)(=O)C(C)C)c3sccc3n2)c(OC(C)C)cc1C1CCN(C)CC1] | ¹H NMR (600 MHz, Methanol-d$_4$) δ 8.52 (dd, J = 8.4, 1.2 Hz, 1H), 7.98 (d, J = 5.3 Hz, 1H), 7.91 (dd, J = 8.0, 1.6 Hz, 1H), 7.87 (s, 1H), 7.68 (ddd, J = 8.5, 7.3, 1.6 Hz, 1H), 7.39-7.33 (m, 1H), 7.19 (d, J = 5.4 Hz, 1H), 6.84 (s, 1H), 4.59 (p, J = 6.0 Hz, 1H), 3.05-2.98 (m, 2H), 2.75-2.66 (m, 1H), 2.35 (s, 3H), 2.23-2.16 (m, 2H), 2.14 (s, 3H), 1.75 (tt, J = 7.1, 3.3 Hz, 4H), 1.33 (d, J = 6.1 Hz, 6H), 1.22 (d, J = 6.8 Hz, 6H). MS (ESI) m/z: 594 [M + H]⁺. |
| IB-10 TFA salt | | ¹H NMR (600 MHz, Methanol-d$_4$) δ 8.24 (d, J = 5.4 Hz, 2H), 8.02 (dd, J = 8.0, 1.6 Hz, 1H), 7.79 (t, J = 7.9 Hz, 1H), 7.59 (td, J = 7.8, 1.2 Hz, 1H), 7.34-7.25 (m, 2H), 6.78 (d, J = 2.6 Hz, 1H), 6.63-6.55 (m, 1H), 3.90-3.87 (m, 4H), 3.85 (s, 3H), 3.37 (dd, J = 13.5, 6.6 Hz, 1H), 3.29-3.25 (m, 4H), 1.21 (d, J = 6.8 Hz, 6H). MS (ESI) m/z: 510 [M + H]⁺. |
| IB-11 TFA salt | | ¹H NMR (600 MHz, Methanol-d$_4$) δ 8.22 (dd, J = 12.5, 6.8 Hz, 2H), 8.02 (dd, J = 8.0, 1.5 Hz, 1H), 7.85 (td, J = 7.7, 1.6 Hz, 1H), 7.71 (d, J = 8.5 Hz, 2H), 7.62-7.56 (m, 3H), 7.37 (d, J = 5.4 Hz, 1H), 7.14 (tt, J = 7.8, 3.7 Hz, 1H), 3.30-3.27 (m, 2H), 2.76 (ddd, J = 12.2, 8.8, 3.3 Hz, 2H), 1.89 (ddd, J = 13.2, 6.9, 3.5 Hz, 2H), 1.59 (dtd, J = 12.4, 8.3, 3.7 Hz, 2H), 1.16 (d, J = 6.8 Hz, 6H). MS (ESI) m/z: 588 [M + H]⁺. |
| IB-12 | 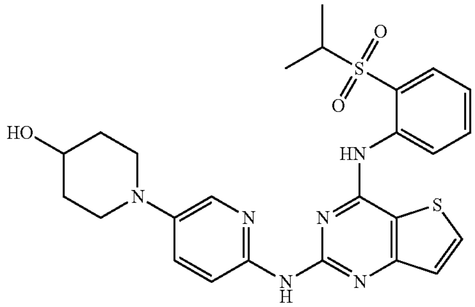 [SMILES: CC(C)S(=O)(=O)c1ccccc1Nc1nc(Nc2ccc(N3CCC(O)CC3)cn2)nc2ccsc12] | ¹H NMR (600 MHz, DMSO-d$_6$) δ 9.59 (s, 1H), 9.42 (s, 1H), 8.98 (d, J = 8.4 Hz, 1H), 8.16 (d, J = 5.3 Hz, 1H), 8.07 (d, J = 9.0 Hz, 1H), 7.99 (d, J = 3.0 Hz, 1H), 7.86 (dd, J = 7.9, 1.6 Hz, 1H), 7.80-7.74 (m, 1H), 7.39 (t, J = 7.6 Hz, 1H), 7.36 (dd, J = 9.2, 3.0 Hz, 1H), 7.32 (d, J = 5.3 Hz, 1H), 4.71 (d, J = 4.2 Hz, 1H), 4.11 (q, J = 5.2 Hz, 1H), 3.53-3.48 (m, 1H), 3.46 (dd, J = 11.6, 5.6 Hz, 2H), 2.81 (ddd, J = 12.7, 10.1, 3.0 Hz, 2H), 1.89-1.73 (m, 2H), 1.56-1.40 (m, 2H), 1.17 (d, J = 6.8 Hz, 6H). MS (ESI) m/z: 525 [M + H]⁺. |

TABLE 1-continued

Structure and characterization of compounds IA-IC

| No. | Structure | ¹H NMR and/or MS data |
|---|---|---|
| IB-13 | 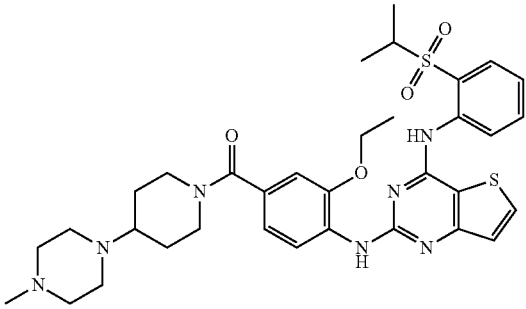<br>TFA salt | ¹H NMR (600 MHz, Methanol-d₄) δ 8.31 (d, J = 5.4 Hz, 1H), 8.06 (dd, J = 8.0, 1.6 Hz, 1H), 8.02 (d, J = 8.0 Hz, 1H), 7.86 (td, J = 7.8, 1.6 Hz, 1H), 7.68 (td, J = 7.7, 1.2 Hz, 1H), 7.63 (d, J = 8.1 Hz, 1H), 7.36 (d, J = 5.4 Hz, 1H), 7.11 (d, J = 1.8 Hz, 1H), 6.82 (d, J = 8.3 Hz, 1H), 4.75 (s, 1H), 4.16 (q, J = 7.0 Hz, 2H), 3.87 (s, 1H), 3.59 (s, 4H), 3.51 (s, 4H), 3.40 (tt, J = 12.4, 4.4 Hz, 1H), 3.37-3.31 (m, 1H), 3.21 (s, 1H), 2.96 (s, 3H), 2.15 (d, J = 76.2 Hz, 2H), 1.73 (s, 2H), 1.39 (t, J = 7.0 Hz, 3H), 1.18 (d, J = 6.8 Hz, 6H). MS (ESI) m/z: 678 [M + H]⁺. |
| IB-14 | 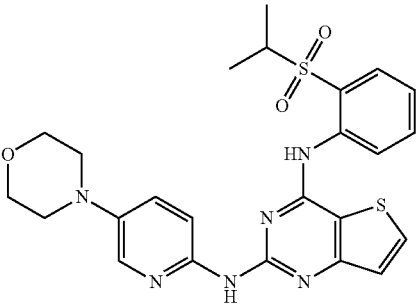 | ¹H NMR (600 MHz, DMSO-d₆) δ 9.59 (s, 1H), 9.48 (s, 1H), 8.99 (d, J = 8.4 Hz, 1H), 8.17 (d, J = 5.3 Hz, 1H), 8.12 (d, J = 9.0 Hz, 1H), 8.00 (d, J = 3.1 Hz, 1H), 7.86 (dd, J = 7.9, 1.5 Hz, 1H), 7.82-7.74 (m, 1H), 7.39 (q, J = 7.9 Hz, 2H), 7.33 (d, J = 5.3 Hz, 1H), 3.76 (t, J = 4.8 Hz, 4H), 3.54-3.45 (m, 1H), 3.09 (dd, J = 5.8, 3.7 Hz, 4H), 1.17 (d, J = 6.8 Hz, 6H). MS (ESI) m/z: 678 [M + H]⁺. |
| IB-15 | 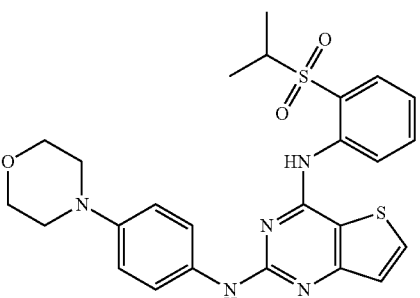<br>TFA salt | ¹H NMR (600 MHz, Methanol-d₄) δ 8.26 (d, J = 5.4 Hz, 1H), 8.12 (s, 1H), 8.04 (dd, J = 7.9, 1.6 Hz, 1H), 7.81 (td, J = 7.8, 1.6 Hz, 1H), 7.66-7.60 (m, 1H), 7.34 (dd, J = 7.2, 1.8 Hz, 3H), 7.10 (d, J = 8.5 Hz, 2H), 3.93-3.89 (m, 4H), 3.34 (d, J = 9.7 Hz, 1H), 3.28 (t, J = 4.8 Hz, 4H), 1.18 (d, J = 6.8 Hz, 6H). MS (ESI) m/z: 510 [M + H]⁺. |
| IB-16 | 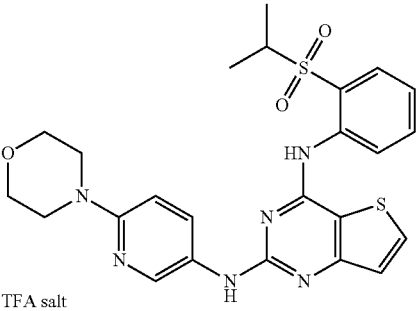 [SMILES: CC(C)S(=O)(=O)c1ccccc1Nc1nc(Nc2ccc(N3CCOCC3)nc2)nc2ccsc12]<br>TFA salt | ¹H NMR (600 MHz, Methanol-d₄) δ 8.48 (s, 1H), 8.32 (s, 1H), 8.18 (d, J = 5.3 Hz, 1H), 8.02-7.93 (m, 2H), 7.81 (td, J = 7.8, 1.6 Hz, 1H), 7.54 (t, J = 7.7 Hz, 1H), 7.30 (d, J = 5.4 Hz, 1H), 7.17 (d, J = 9.7 Hz, 1H), 3.90-3.83 (m, 4H), 3.64-3.57 (m, 4H), 3.35 (p, J = 6.9 Hz, 1H), 1.21 (d, J = 6.8 Hz, 6H). MS (ESI) m/z: 511 [M + H]⁺. |

TABLE 1-continued

Structure and characterization of compounds IA-IC

| No. | Structure | ¹H NMR and/or MS data |
|---|---|---|
| IB-17 | 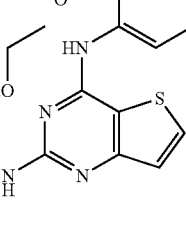 TFA salt | 1H NMR (600 MHz, Methanol-d4) δ 8.29 (d, J = 5.5 Hz, 1H), 8.06 (dd, J = 7.9, 1.6 Hz, 1H), 8.01 (d, J = 8.0 Hz, 1H), 7.85 (td, J = 7.8, 1.6 Hz, 1H), 7.73 (d, J = 8.7 Hz, 1H), 7.68 (td, J = 7.7, 1.2 Hz, 1H), 7.37 (d, J = 5.4 Hz, 1H), 7.30 (d, J = 2.5 Hz, 1H), 6.99 (dd, J = 8.8, 2.5 Hz, 1H), 4.19 (q, J = 7.0 Hz, 2H), 4.08 (tt, J = 7.1, 3.5 Hz, 1H), 3.79 (ddd, J = 11.9, 8.1, 3.6 Hz, 2H), 3.55 (ddd, J = 11.8, 7.7, 3.7 Hz, 2H), 3.37-3.31 (m, 1H), 2.24 (ddt, J = 14.8, 7.6, 3.6 Hz, 2H), 2.01 (dtd, J = 14.6, 7.5, 3.6 Hz, 2H), 1.42 (t, J = 7.0 Hz, 3H), 1.17 (d, J = 6.8 Hz, 6H). MS (ESI) m/z: 568 [M + H]⁺. |
| IB-18 | 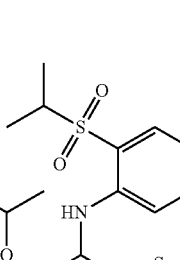 TFA salt | ¹H NMR (600 MHz, Methanol-d₄) δ 8.30 (d, J = 5.4 Hz, 1H), 8.06 (dd, J = 7.9, 1.5 Hz, 1H), 8.01 (d, J = 8.0 Hz, 1H), 7.75 (d, J = 8.7 Hz, 1H), 7.68 (td, J = 7.7, 1.2 Hz, 1H), 7.37 (d, J = 5.4 Hz, 1H), 7.35 (d, J = 2.5 Hz, 1H), 6.99 (dd, J = 8.8, 2.5 Hz, 1H), 4.77 (hept, J = 6.1 Hz, 1H), 4.09 (tt, J = 7.1, 3.4 Hz, 1H), 3.79 (ddd, J = 11.9, 8.1, 3.6 Hz, 2H), 3.57 (ddd, J = 11.7, 7.6, 3.7 Hz, 2H), 3.37-3.30 (m, 1H), 2.25 (ddt, J = 14.8, 7.6, 3.6 Hz, 2H), 2.02 (dtd, J = 14.6, 7.4, 3.6 Hz, 2H), 1.35 (d, J = 6.0 Hz, 6H), 1.17 (d, J = 6.8 Hz, 6H). MS (ESI) m/z: 582 [M + H]⁺. |
| IB-19 | 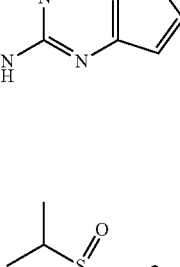 TFA salt | ¹H NMR (600 MHz, Methanol-d₄) δ 8.29 (d, J = 5.4 Hz, 1H), 8.05 (dd, J = 7.9, 1.6 Hz, 1H), 8.00 (d, J = 8.1 Hz, 1H), 7.84 (td, J = 7.7, 1.6 Hz, 1H), 7.72 (d, J = 8.7 Hz, 1H), 7.67 (td, J = 7.7, 1.2 Hz, 1H), 7.37 (d, J = 5.4 Hz, 1H), 7.33 (d, J = 2.5 Hz, 1H), 7.01 (dd, J = 8.7, 2.5 Hz, 1H), 4.09 (tt, J = 7.1, 3.4 Hz, 1H), 3.95 (s, 3H), 3.80 (ddd, J = 12.0, 8.1, 3.6 Hz, 2H), 3.57 (ddd, J = 11.7, 7.6, 3.7 Hz, 2H), 3.34-3.32 (m, 1H), 2.25 (ddt, J = 14.7, 7.6, 3.6 Hz, 2H), 2.02 (dtd, J = 14.5, 7.4, 3.6 Hz, 2H), 1.17 (d, J = 6.8 Hz, 6H). MS (ESI) m/z: 554 [M + H]⁺. |
| IB-20 | 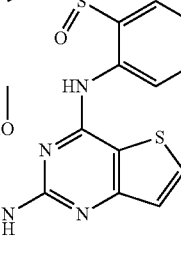 TFA salt | ¹H NMR (600 MHz, Methanol-d₄) δ 8.79 (dd, J = 5.6, 1.5 Hz, 1H), 8.41 (td, J = 7.9, 1.7 Hz, 1H), 8.27 (d, J = 5.4 Hz, 1H), 8.07 (s, 1H), 8.04-7.99 (m, 2H), 7.87-7.83 (m, 1H), 7.78 (t, J = 7.8 Hz, 1H), 7.64-7.58 (m, 1H), 7.41-7.29 (m, 3H), 7.06 (s, 1H), 5.42 (s, 2H), 3.35-3.32 (m, 1H), 1.16 (d, J = 6.8 Hz, 6H). MS (ESI) m/z: 532 [M + H]⁺. |

TABLE 1-continued

Structure and characterization of compounds IA-IC

| No. | Structure | ¹H NMR and/or MS data |
|---|---|---|
| IB-21 | 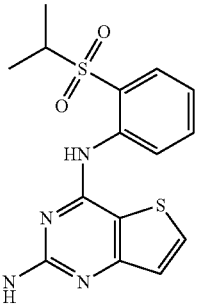<br>TFA salt | ¹H NMR (600 MHz, Methanol-$d_4$) δ 8.23 (d, J = 5.4 Hz, 1H), 8.10 (d, J = 8.0 Hz, 1H), 8.04 (dd, J = 8.0, 1.6 Hz, 1H), 7.86 (td, J = 7.7, 1.6 Hz, 1H), 7.72 (d, J = 8.4 Hz, 2H), 7.68-7.63 (m, 1H), 7.59-7.54 (m, 2H), 7.37 (d, J = 5.3 Hz, 1H), 3.89 (s, 2H), 3.59 (s, 2H), 3.37-3.32 (m, 1H), 3.22 (s, 2H), 2.90 (s, 3H), 2.63 (s, 2H), 1.16 (d, J = 6.8 Hz, 6H). MS (ESI) m/z: 587 [M + H]⁺. |
| IB-22 | 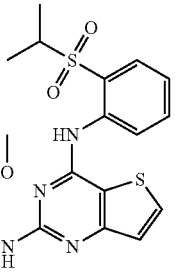<br>TFA salt | MS (ESI) m/z: 664 [M + H]⁺. |
| IB-23 | 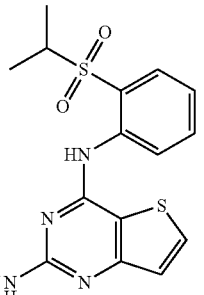<br>TFA salt | 1H NMR (600 MHz, Methanol-d4) δ 8.43 (s, 2H), 8.14 (d, J = 5.3 Hz, 1H), 7.96 (ddd, J = 7.7, 6.5, 2.1 Hz, 2H), 7.80 (td, J = 7.8, 1.6 Hz, 1H), 7.51 (t, J = 7.7 Hz, 1H), 7.26 (d, J = 5.3 Hz, 1H), 7.22 (d, J = 9.8 Hz, 1H), 4.00 (ddt, J = 12.6, 8.6, 4.2 Hz, 1H), 3.94 (ddd, J = 13.5, 6.8, 3.9 Hz, 2H), 3.50 (ddd, J = 13.5, 8.8, 3.5 Hz, 2H), 3.35 (p, J = 6.8 Hz, 1H), 2.03 (ddt, J = 13.7, 7.3, 3.7 Hz, 2H), 1.68 (dtd, J = 12.7, 8.4, 3.8 Hz, 2H), 1.20 (d, J = 6.8 Hz, 6H). MS (ESI) m/z: 525 [M + H]⁺. |
| IB-24 | 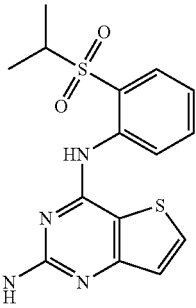<br>TFA salt | ¹H NMR (600 MHz, Methanol-$d_4$) δ 8.28 (s, 1H), 8.24 (d, J = 5.4 Hz, 1H), 8.08 (s, 1H), 8.00 (dd, J = 7.9, 1.5 Hz, 1H), 7.78 (td, J = 7.8, 1.6 Hz, 1H), 7.72 (dd, J = 9.1, 2.7 Hz, 1H), 7.60 (t, J = 7.7 Hz, 1H), 7.34 (d, J = 5.4 Hz, 1H), 6.94 (d, J = 9.0 Hz, 1H), 4.44 (s, 2H), 3.62 (d, J = 21.4 Hz, 2H), 3.36-3.32 (m, 1H), 2.98 (s, 3H), 1.17 (d, J = 6.8 Hz, 6H). MS (ESI) m/z: 524 [M + H]⁺. |

TABLE 1-continued

Structure and characterization of compounds IA-IC

| No. | Structure | ¹H NMR and/or MS data |
|---|---|---|
| IB-25 | 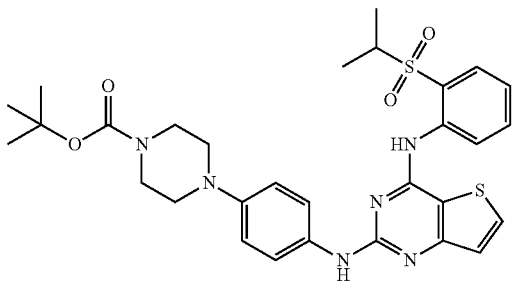 [SMILES: CC(C)S(=O)(=O)c1ccccc1Nc1nc(Nc2ccc(N3CCN(C(=O)OC(C)(C)C)CC3)cc2)nc2ccsc12] | ¹H NMR (600 MHz, DMSO-d₆) δ 9.44 (s, 1H), 9.13 (s, 1H), 8.71 (s, 1H), 8.13 (d, J = 5.3 Hz, 1H), 7.87 (dd, J = 8.0, 1.6 Hz, 1H), 7.82-7.74 (m, 1H), 7.58 (d, J = 8.3 Hz, 2H), 7.40 (t, J = 7.7 Hz, 1H), 7.26 (d, J = 5.3 Hz, 1H), 6.89 (d, J = 8.8 Hz, 2H), 3.53-3.47 (m, 1H), 3.46 (s, 4H), 3.01 (t, J = 5.1 Hz, 4H), 1.42 (s, 9H), 1.16 (d, J = 6.8 Hz, 6H). MS (ESI) m/z: 609 [M + H]⁺. |
| IB-26 | 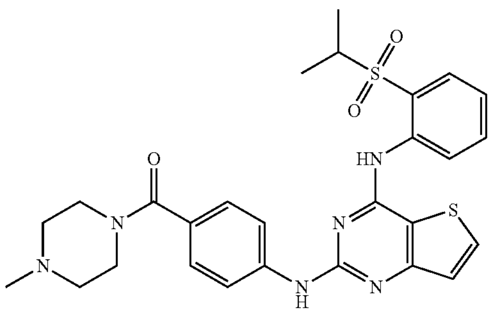 [SMILES: CC(C)S(=O)(=O)c1ccccc1Nc1nc(Nc2ccc(C(=O)N3CCN(C)CC3)cc2)nc2ccsc12] | ¹H NMR (600 MHz, DMSO-d₆) δ 9.57 (s, 1H), 9.52 (s, 1H), 8.55 (d, J = 8.2 Hz, 1H), 8.17 (d, J = 5.3 Hz, 1H), 7.91 (dd, J = 7.9, 1.6 Hz, 1H), 7.83 (td, J = 7.8, 1.6 Hz, 1H), 7.78 (d, J = 8.2 Hz, 2H), 7.47 (t, J = 7.7 Hz, 1H), 7.32 (d, J = 5.3 Hz, 1H), 7.26 (d, J = 8.4 Hz, 2H), 3.48 (p, J = 6.7 Hz, 1H), 2.31 (s, 4H), 2.20 (s, 3H), 1.14 (d, J = 6.8 Hz, 6H). MS (ESI) m/z: 551 [M + H]⁺. |
| IB-27 TFA salt | | ¹H NMR (600 MHz, Chloroform-d) δ 11.94 (s, 1H), 10.37 (s, 1H), 8.50 (dd, J = 8.4, 1.1 Hz, 1H), 7.94 (d, J = 5.3 Hz, 1H), 7.92 (dd, J = 8.0, 1.6 Hz, 1H), 7.55-7.47 (m, 3H), 7.43 (d, J = 5.4 Hz, 1H), 7.40 (td, J = 7.6, 1.1 Hz, 1H), 6.94-6.88 (m, 2H), 3.67 (dd, J = 46.3, 12.3 Hz, 4H), 3.36 (t, J = 12.7 Hz, 2H), 3.22 (p, J = 6.9 Hz, 1H), 3.09 (d, J = 12.2 Hz, 2H), 2.91 (s, 3H), 1.31 (d, J = 6.9 Hz, 6H). MS (ESI) m/z: 523 [M + H]⁺. |
| IB-28 | 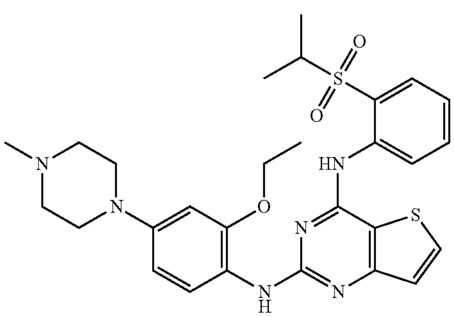 [SMILES: CCOc1cc(N2CCN(C)CC2)ccc1Nc1nc(Nc2ccccc2S(=O)(=O)C(C)C)c2sccc2n1] | ¹H NMR (600 MHz, Chloroform-d) δ 9.74 (s, 1H), 8.60 (d, J = 8.4 Hz, 1H), 8.03 (s, 1H), 7.88 (dd, J = 8.0, 1.6 Hz, 1H), 7.80 (d, J = 5.4 Hz, 1H), 7.54 (t, J = 7.8 Hz, 1H), 7.33 (d, J = 5.3 Hz, 1H), 7.28 (ddd, J = 8.2, 7.4, 1.1 Hz, 1H), 6.53-6.47 (m, 2H), 4.07 (q, J = 7.0 Hz, 2H), 3.46 (d, J = 18.0 Hz, 4H), 3.33 (s, 4H), 3.23 (hept, J = 6.8 Hz, 1H), 2.87 (s, 3H), 1.43 (t, J = 7.0 Hz, 3H), 1.30 (d, J = 6.9 Hz, 6H). MS (ESI) m/z: 567 [M + H]⁺. |
| IB-29 | 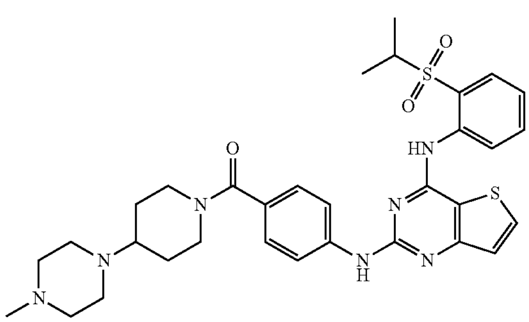 [SMILES: CC(C)S(=O)(=O)c1ccccc1Nc1nc(Nc2ccc(C(=O)N3CCC(N4CCN(C)CC4)CC3)cc2)nc2ccsc12] | ¹H NMR (600 MHz, Methanol-d₄) δ 8.29 (d, J = 5.4 Hz, 1H), 8.06 (dd, J = 8.0, 1.6 Hz, 1H), 8.01 (d, J = 8.0 Hz, 1H), 7.86 (td, J = 7.7, 1.6 Hz, 1H), 7.68 (td, J = 7.7, 1.2 Hz, 1H), 7.50 (d, J = 8.4 Hz, 2H), 7.40 (d, J = 5.4 Hz, 1H), 7.33-7.27 (m, 2H), 3.83 (s, 1H), 3.50 (s, 4H), 2.94 (s, 3H), 2.09 (d, J = 76.7 Hz, 2H), 1.66 (s, 2H), 1.15 (d, J = 6.8 Hz, 6H). MS (ESI) m/z: 634 [M + H]⁺. |

TABLE 1-continued

Structure and characterization of compounds IA-IC

| No. | Structure | ¹H NMR and/or MS data |
|---|---|---|
| IB-30 | 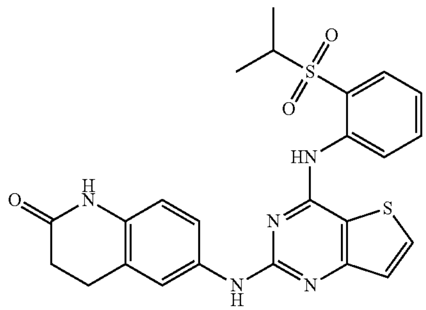 [SMILES: CC(C)S(=O)(=O)c1ccccc1Nc1nc(Nc2ccc3c(c2)CCC(=O)N3)nc2ccsc12] | MS (ESI) m/z: 494 [M + H]⁺. |
| IB-31 | 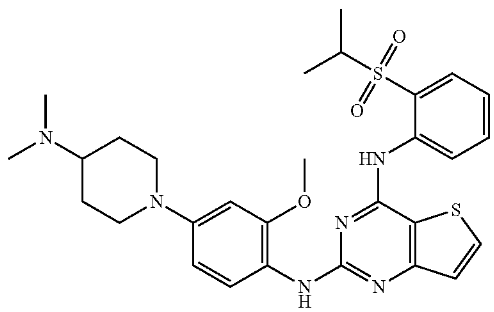 [SMILES: COc1cc(N2CCC(N(C)C)CC2)ccc1Nc1nc(Nc2ccccc2S(=O)(=O)C(C)C)c2sccc2n1] | MS (ESI) m/z: 581 [M + H]⁺. |
| IB-32 (TFA salt) | | ¹H NMR (600 MHz, Methanol-d4) δ 8.24 (d, J = 5.4 Hz, 1H), 8.20 (d, J = 8.2 Hz, 1H), 7.99 (dd, J = 7.9, 1.5 Hz, 1H), 7.85 (d, J = 2.6 Hz, 1H), 7.73-7.69 (m, 1H), 7.53 (td, J = 7.7, 1.2 Hz, 1H), 7.50 (dd, J = 8.9, 2.6 Hz, 1H), 7.33 (d, J = 5.4 Hz, 1H), 7.13 (d, J = 8.9 Hz, 1H), 4.14 (s, 2H), 3.85 (s, 3H), 3.43-3.33 (m, 1H), 3.00 (s, 6H), 1.23 (d, J = 6.8 Hz, 6H). MS (ESI) m/z: 555 [M + H]⁺. |
| IB-33 (TFA salt) | | ¹H NMR (600 MHz, Methanol-d4) δ 8.24 (d, J = 5.4 Hz, 2H), 8.20 (s, 1H), 7.97 (dd, J = 7.9, 1.6 Hz, 1H), 7.73-7.62 (m, 1H), 7.53 (t, J = 7.7 Hz, 1H), 7.32 (d, J = 5.4 Hz, 1H), 7.14 (s, 1H), 4.42 (s, 2H), 4.15 (t, J = 8.4 Hz, 2H), 3.83 (s, 3H), 3.79 (s, 2H), 3.40-3.32 (m, 3H), 3.21 (m, 2H), 2.12 (d, J = 63.9 Hz, 4H), 1.23 (d, J = 6.9 Hz, 6H). MS (ESI) m/z: 607 [M + H]⁺. |

TABLE 1-continued

Structure and characterization of compounds IA-IC

| No. | Structure | ¹H NMR and/or MS data |
|---|---|---|
| IB-34 | 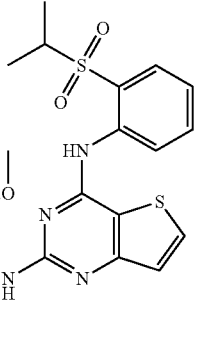 TFA salt | ¹H NMR (600 MHz, Methanol-d4) δ 8.30 (d, J = 8.1 Hz, 1H), 8.21 (d, J = 5.4 Hz, 1H), 8.03 (dd, J = 8.0, 1.5 Hz, 1H), 7.86-7.82 (m, 1H), 7.58 (td, J = 7.6, 1.2 Hz, 1H), 7.31 (d, J = 5.4 Hz, 1H), 7.19 (s, 1H), 7.01 (d, J = 8.8 Hz, 1H), 6.71 (dd, J = 8.8, 2.8 Hz, 1H), 4.01 (s, 2H), 3.82 (s, 3H), 3.38 (p, J = 6.8 Hz, 1H), 3.07 (s, 3H), 2.99 (s, 3H), 1.24 (d, J = 6.8 Hz, 6H). MS (ESI) m/z: 555 [M + H]⁺. |
| IB-35 | 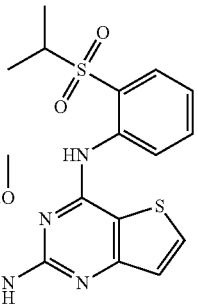 TFA salt | ¹H NMR (600 MHz, Methanol-d4) δ 8.25 (d, J = 5.4 Hz, 1H), 8.12 (d, J = 8.1 Hz, 1H), 8.03-7.97 (m, 2H), 7.73 (t, J = 7.6 Hz, 1H), 7.56 (td, J = 7.7, 1.2 Hz, 1H), 7.32 (d, J = 5.4 Hz, 1H), 7.09 (d, J = 12.1 Hz, 1H), 4.20 (s, 2H), 3.84 (s, 3H), 3.38 (p, J = 6.8 Hz, 1H), 2.99 (s, 6H), 1.23 (d, J = 6.8 Hz, 6H). MS (ESI) m/z: 573 [M + H]⁺. |
| IC-1 | 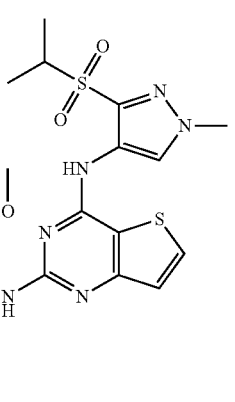 | ¹H NMR (600 MHz, DMSO-d₆) δ 8.61 (s, 1H), 8.48 (s, 1H), 8.39 (s, 1H), 8.16 (s, 1H), 8.08 (d, J = 5.3 Hz, 1H), 7.16 (d, J = 5.3 Hz, 1H), 7.03 (s, 1H), 4.18 (t, J = 8.4 Hz, 2H), 3.90 (s, 3H), 3.77 (s, 3H), 3.50 (h, J = 6.8 Hz, 1H), 3.23 (s, 2H), 3.15 (t, J = 8.4 Hz, 2H), 2.28 (s, 6H), 1.22 (d, J = 7.1 Hz, 6H). MS (ESI) m/z: 585 [M + H]⁺. |
| IC-2 | 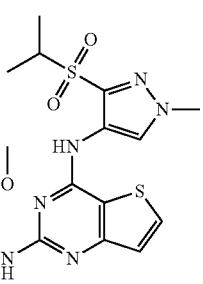 TFA salt | ¹H NMR (600 MHz, Methanol-d₄) δ 8.21 (d, J = 5.4 Hz, 2H), 7.38 (s, 1H), 7.30 (d, J = 5.4 Hz, 1H), 6.88 (s, 1H), 6.78 (d, J = 8.7 Hz, 1H), 3.98 (s, 2H), 3.97 (s, 4H), 3.85 (s, 3H), 3.56 (s, 4H), 3.48 (d, J = 14.4 Hz, 4H), 3.03 (t, J = 12.5 Hz, 2H), 2.95 (s, 3H), 2.24 (d, J = 12.2 Hz, 2H), 1.97-1.86 (m, 2H), 1.32 (d, J = 6.8 Hz, 6H). MS (ESI) m/z: 640 [M + H]⁺. |

TABLE 1-continued

Structure and characterization of compounds IA-IC

| No. | Structure | ¹H NMR and/or MS data |
|---|---|---|
| IC-3 | 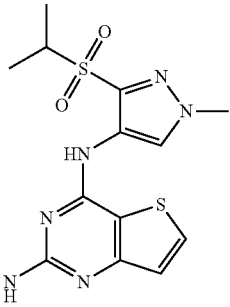<br>TFA salt | ¹H NMR (600 MHz, Chloroform-d) δ 11.84 (s, 1H), 9.23 (s, 1H), 7.90 (d, J = 5.3 Hz, 1H), 7.80 (s, 1H), 7.42 (d, J = 8.2 Hz, 2H), 7.38 (d, J = 5.3 Hz, 1H), 7.01 (d, J = 8.2 Hz, 2H), 3.78 (s, 3H), 3.70 (s, 4H), 3.44 (p, J = 6.8 Hz, 1H), 3.39 (s, 2H), 3.08 (s, 2H), 2.91 (s, 3H), 1.38 (d, J = 6.9 Hz, 6H). MS (ESI) m/z: 527 [M + H]⁺. |
| IC-4 | 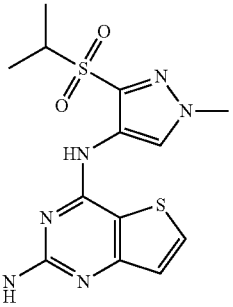<br>TFA salt | 1H NMR (600 MHz, Chloroform-d) δ 12.36 (s, 1H), 9.42 (s, 1H), 8.10 (s, 1H), 7.97 (d, J = 5.1 Hz, 1H), 7.84-7.68 (m, 4H), 7.44 (d, J = 5.4 Hz, 1H), 4.27 (s, 1H), 3.93 (s, 3H), 3.82 (t, J = 11.3 Hz, 2H), 3.50 (s, 2H), 3.48 (q, J = 6.9 Hz, 1H), 2.44 (t, J = 13.3 Hz, 2H), 2.08 (d, J = 14.5 Hz, 2H), 1.42 (d, J = 6.8 Hz, 6H). MS (ESI) m/z: 528 [M + H]⁺. |

Example 2

Synthetic Scheme of Compound ID

Preparation of Compound 5

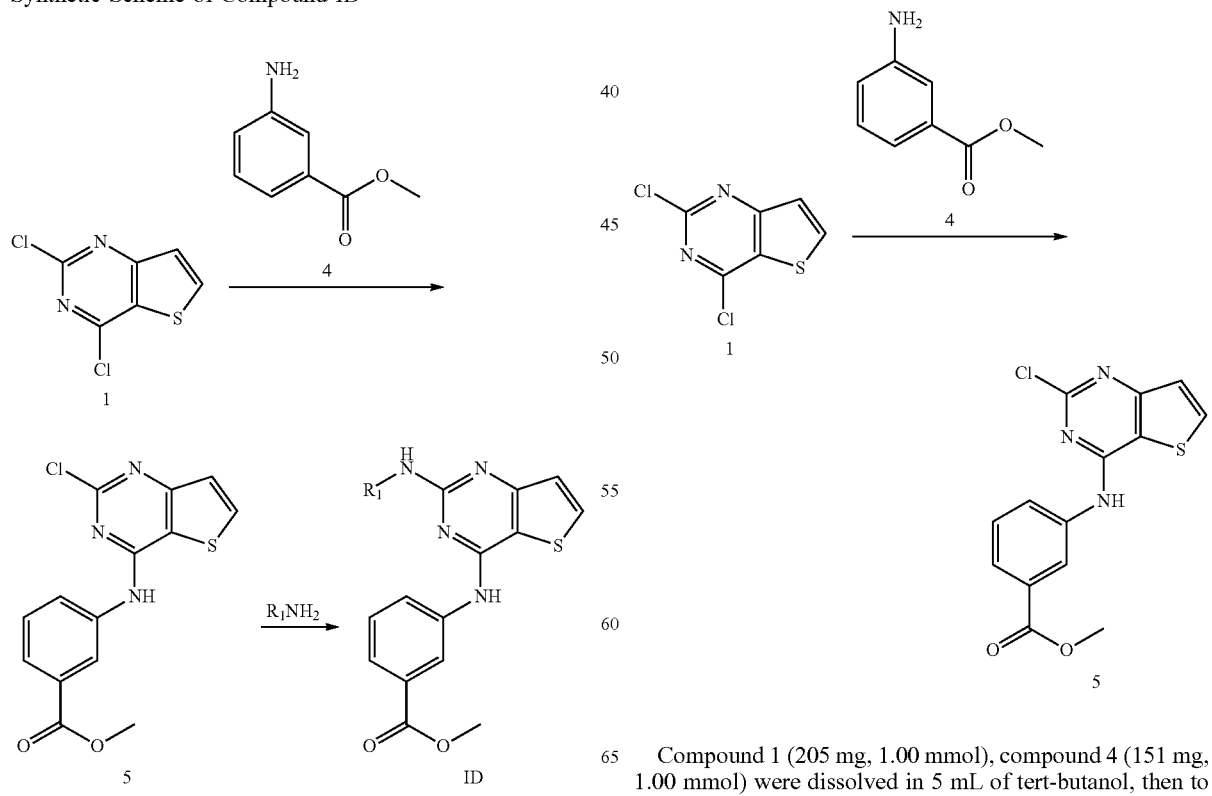

Compound 1 (205 mg, 1.00 mmol), compound 4 (151 mg, 1.00 mmol) were dissolved in 5 mL of tert-butanol, then to the solution were added 2-dicyclohexylphosphino-2,4,6-triisopropylbiphenyl (56 mg, 0.12 mmol), tris(dibenzylideneacetone)dipalladium (37 mg, 0.04 mmol), potassium carbonate (415 mg, 3.00 mmol); under the protection of nitrogen, the resulting reaction solution was heated and stirred in an oil bath preheated to 110° C. until complete reaction of compound 1 (LC-MS and TLC tracking). Methanol and dichloromethane were added to the reaction solution, the system was filtered, the filtrate was concentrated and then diluted with dichloromethane, washed twice with saturated sodium chloride solution, dried over anhydrous sodium sulfate, concentrated and separated by silica gel column chromatography (dichloromethane/aminomethanol=10/1) to obtain compound 5 (white solid, 293.5 mg, yield 92.0%), which was directly used for the next step reaction.

MS (ESI) m/z: 320 [M+H]$^+$

Preparation of Compound ID

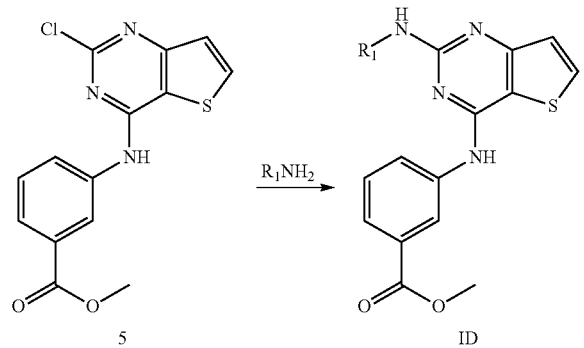

Method A:

Compound 5 (31.8 mg, 0.10 mmol), arylamine (0.09 mmol) were dissolved in 1 mL of tert-butanol, then to the solution were added 2-dicyclohexylphosphino-2,4,6-triisopropylbiphenyl (0.018 mmol), tris(dibenzylideneacetone)dipalladium (0.012 mmol), potassium carbonate (0.30 mmol); under the protection of nitrogen, the resulting reaction solution was heated and stirred in an oil bath preheated to 110° C. until complete reaction of compound 5 (LC-MS and TLC tracking), then the reaction was stopped. Methanol and dichoromethane were added to the reaction solution, and the system was filtered, concentrated and separated by silica gel chromatograph (dichloromethane/methanol) to obtain compound ID.

Method B:

Compound (31.8 mg, 0.10 mmol), arylamine (0.09 mmol) were dissolved in mL of tert-butanol, then to the solution were added 2-dicyclohexylphosphino-2,4,6-triisopropylbiphenyl (0.018 mmol), tris(dibenzylideneacetone)dipalladium (0.012 mmol), potassium carbonate 0.30 mmol); under the protection of nitrogen, the resulting reaction solution was heated and stirred in an oil bath preheated to 1100 until complete reaction of compound 5 (LC-MS and TLC tracking), then the reaction was stopped. Methanol and dichloromethane were added to the reaction solution, and the system was filtered, concentrated, purified by reverse-phase preparative HPLC (aqueous solution containing 0.35% trifluoroacetic acid and methanol as mobile phase), and then concentrated in vacuo to obtain compound ID.

Compounds IE, IF, IG, IH, II, IJ, and IK all could be synthesized by a similar method.

TABLE 2

| No. | Structure | $^1$H NMR and/or MS data |
|---|---|---|
| ID-1 | (structure, TFA salt) | $^1$H NMR (600 MHz, DMSO-d$_6$) δ 10.86 (s, 1H), 9.83 (s, 1H), 8.33 (d, J = 5.4 Hz, 1H), 8.25-8.06 (m, 3H), 7.72 (d, J = 7.5 Hz, 1H), 7.36 (s, 1H), 7.31 (d, J = 5.3 Hz, 1H), 7.19 (S, 1H), 4.34 (s, 2H), 4.09 (t, J = 8.4 Hz, 2H), 3.84 (s, 3H), 3.77 (s, 3H), 3.28 (t, J = 8.4 Hz, 2H), 2.84 (s, 6H). MS (ESI) m/z: 533 [M + H]$^+$. |
| ID-2 | (structure, TFA salt) | $^1$H NMR (600 MHz, DMSO-d$_6$) δ 10.92 (s, 1H), 10.20 (s, 1H), 8.33 (d, J = 5.4 Hz, 1H), 8.15 (s, 1H), 7.77 (d, J = 7.3 Hz, 1H), 7.51-7.25 (m, 3H), 6.77 (d, J = 2.6 Hz, 1H), 6.54 (s, 1H), 3.97-3.88 (m, 2H), 3.87 (s, 3H), 3.79 (s, 3H), 3.62-3.44 (m, 2H), 3.25-3.11 (m, 2H), 3.05-2.97 (m, 2H), 2.89 (s, 3H). MS (ESI) m/z: 505 [M + H]$^+$ |

Structure and characterization of compounds ID-IK

TABLE 2-continued

Structure and characterization of compounds ID-IK

| No. | Structure | ¹H NMR and/or MS data |
|---|---|---|
| ID-3 <br> TFA salt | 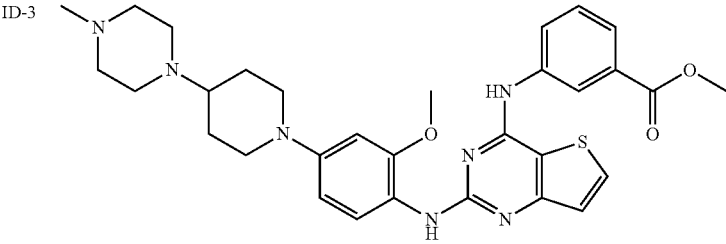 | ¹H NMR (600 MHz, DMSO-d$_6$) δ 10.71 (s, 1H), 10.23 (s, 1H), 8.29 (d, J = 5.4 Hz, 1H), 8.19 (s, 1H), 8.14 (s, 1H), 7.79 (d, J = 7.7 Hz, 1H), 7.53 t, J = 7.9 Hz, 1H), 7.43 (s, 2H), 7.30 (d, J = 5.3 Hz, 1H), 7.01 (s, 2H), 3.86 (s, 3H), 3.77 (d, J = 12.4 Hz, 2H), 2.84 (s, 3H), 2.55 (s, 1H), 2.10 (d, J = 11.9 Hz, 2H), 1.71 (d, J = 12.5 Hz, 2H). MS (ESI) m/z: 558 [M + H]⁺ |
| ID-4 <br> TFA salt | 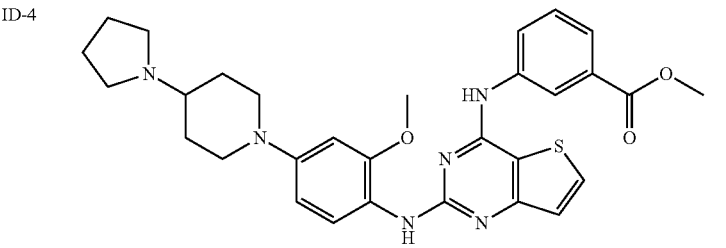 | ¹H NMR (600 MHz, DMSO-d$_6$) δ 10.97 (s, 1H), 10.10 (s, 1H), 8.33 (d, J = 5.4 Hz, 1H), 8.15 (s, 1H), 7.78 (d, J = 7.6 Hz, 1H), 7.47 (s, 1H), 7.32 (d, J = 5.4 Hz, 2H), 6.72 (d, J = 2.5 Hz, 1H), 6.51 (s, 1H), 3.89 (s, 2H), 3.86 (s, 3H), 3.78 (s, 3H), 3.62-3.53 (m, 2H), 3.35-3.24 (m, 1H), 3.16-3.06 (m, 2H), 2.73 (t, J = 12.3 Hz, 2H), 2.16 (dd, J = 11.7, 3.6 Hz, 2H), 2.07-1.98 (m, 2H), 1.93-1.81 (m, 2H), 1.71 (qd, J = 12.2, 4.0 Hz, 2H). MS (ESI) m/z: 559 [M + H]⁺. |
| ID-5 <br> TFA salt | 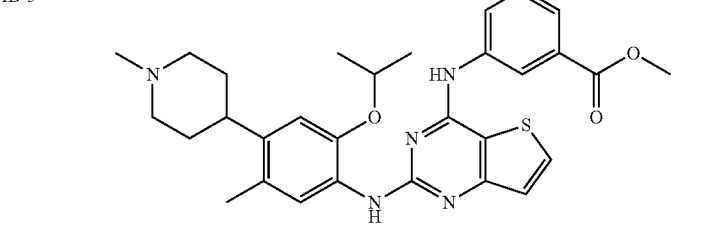 | ¹H NMR (600 MHz, DMSO-d$_6$) δ 10.85 (s, 1H), 9.96 (s, 1H), 8.33 (d, J = 5.4 Hz, 1H), 8.20 (d, J = 2.1 Hz, 1H), 8.10 (s, 1H), 7.79 (d, J = 7.7 Hz, 1H), 7.52 (s, 1H), 7.47 (t, J = 7.9 Hz, 1H), 7.35 (d, J = 5.4 Hz, 1H), 6.84 (s, 1H), 4.57 (p, J = 6.1 Hz, 1H), 3.83 (s, 3H), 3.52 (d, J = 11.9 Hz, 2H), 3.19-3.06 (m, 2H), 2.99- 2.91 (m, 1H), 2.82 (d, J = 4.5 Hz, 3H), 2.11 (s, 3H), 1.97-1.92 (m, 2H), 1.88 (d, J = 13.3 Hz, 2H), 1.21 (d, J = 6.0 Hz, 6H). MS (ESI) m/z: 546 [M + H]⁺. |
| IE-6 <br> TFA salt | 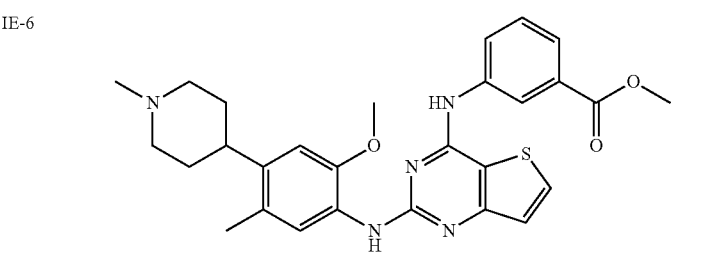 | ¹H NMR (600 MHz, DMSO-d$_6$) δ 10.83 (s, 1H), 9.93 (s, 1H), 8.32 (d, J = 5.3 Hz, 1H), 8.16 (s, 1H), 8.11 (s, 1H), 7.77 (d, J = 7.7 Hz, 1H), 7.45 (d, J = 9.9 Hz, 2H), 7.34 (d, J = 5.4 Hz, 1H), 6.85 (s, 1H), 3.84 (s, 3H), 3.80 (s, 3H), 3.53 (d, J = 12.0 Hz, 2H), 3.17-3.09 (m, 2H), 3.03-2.94 (m, 1H), 2.83 (d, J = 4.3 Hz, 3H), 2.14 (s, 3H), 1.96 (dd, J = 13.7, 10.3 Hz, 2H), 1.90 (d. J = 13.6 Hz, 2H). MS (ESI) m/z: 518 [M + H]⁺. |
| IE-1 | 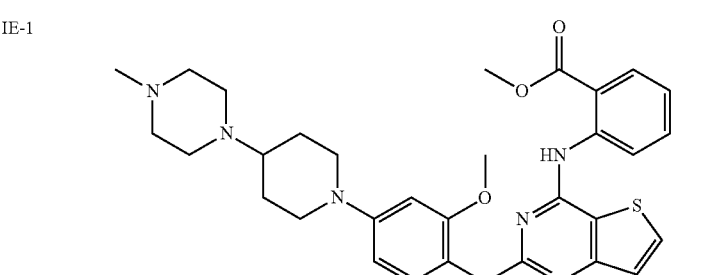 | ¹H NMR (600 MHz, DMSO-d$_6$) δ 10.80 (s, 1H), 8.74 (d, J = 8.5 Hz, 1H), 8.11 (d, J = 5.3 Hz, 1H), 7.99 (dd, J = 8.0, 1.7 Hz, 1H), 7.83 (s, 1H), 7.71 (s, 1H), 7.54 (t, J = 7.9 Hz, 1H), 7.22 (d, J = 5.3 Hz, 1H), 7.18-7.11 (m, 1H), 6.65 (s, 1H), 6.52 (dd, J = 8.8, 2.6 Hz, 1H), 3.88 (s, 3H), 3.79 (s, 3H), 3.74 (d, J = 12.1 Hz, 2H), 3.16 (s, 1H), 2.67 (td, J = 12.2, 2.4 Hz, 3H), 2.49-2.43 (m, 2H), 1.92-1.86 (m, 2H), 1.61-1.51 (m, 2H). MS (ESI) m/z: 588 [M + H]⁺. |

TABLE 2-continued

Structure and characterization of compounds ID-IK

| No. | Structure | ¹H NMR and/or MS data |
|---|---|---|
| IE-2 | 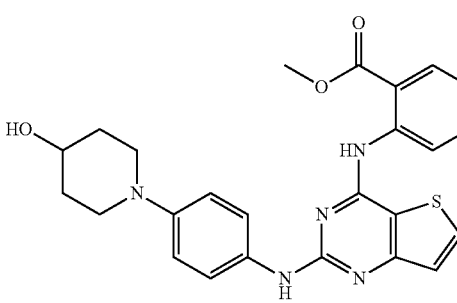 TFA salt | ¹H NMR (600 MHz, DMSO-d$_6$) δ 10.99 (s, 1H), 9.95 (s, 1H), 8.58 (s, 1H), 8.24 (d, J = 5.3 Hz, 1H), 8.02 (dd, J = 7.9, 1.6 Hz, 1H), 7.85-7.60 (m, 3H), 7.42 (s, 2H), 7.33 (d, J = 5.3 Hz, 1H), 7.30 (t, J = 7.6 Hz, 1H), 3.84 (s, 4H), 3.60 (s, 2H), 3.36 (s, 2H), 2.01 (s, 2H), 1.76 (s, 2H). MS (ESI) m/z: 476 (M + H)⁺. |
| IE-3 | 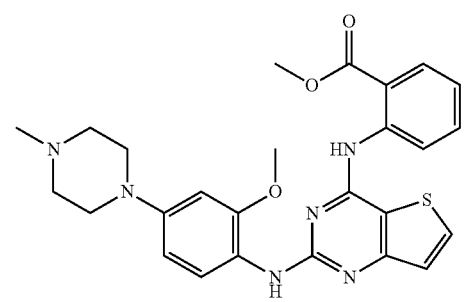 TFA salt | ¹H NMR (600 MHz, DMSO-d$_6$) δ 11.23 (s, 1H), 10.22 (s, 1H), 8.32 (d, J = 5.5 Hz, 1H), 8.04 (s, 1H), 7.98 (dd, J = 7.9, 1.6 Hz, 1H), 7.65 (s, 1H), 7.40 (s, 1H), 7.32 (d, J = 5.4 Hz, 2H), 6.76 (d, J = 2.6 Hz, 1H), 6.56 (s, 1H), 3.93 (d, J = 13.3 Hz, 2H), 3.80 (d, J = 10.7 Hz, 6H), 3.56 (d, J = 11.9 Hz, 2H), 3.17 (d, J = 10.2 Hz, 2H), 3.00 (t, J = 12.6 Hz, 2H), 2.89 (s, 3H). MS (ESI) m/z: 505 [M + H]⁺. |
| IE-4 | 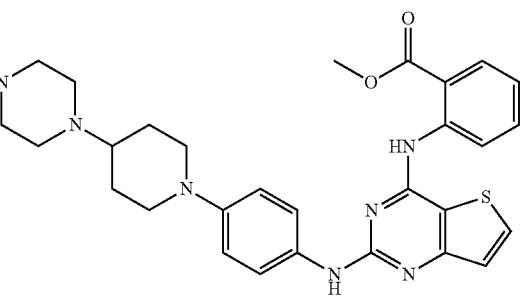 TFA salt | ¹H NMR (600 MHz, DMSO-d$_6$) δ 10.98 (s, 1H), 9.57 (s, 1H), 8.74 (s, 1H), 8.20 (d, J = 5.3 Hz, 1H), 8.03 (dd, J = 7.9, 1.7 Hz, 1H), 7.69-7.64 (m, 1H), 7.59 (s, 2H), 7.29 (d, J = 5.4 Hz, 1H), 7.27-7.23 (m, 1H), 7.06 (s, 2H), 3.87 (s, 3H), 3.16 (s, 1H), 2.77 (s, 3H). MS (ESI) m/z: 558 [M + H]⁺ |
| IE-5 | 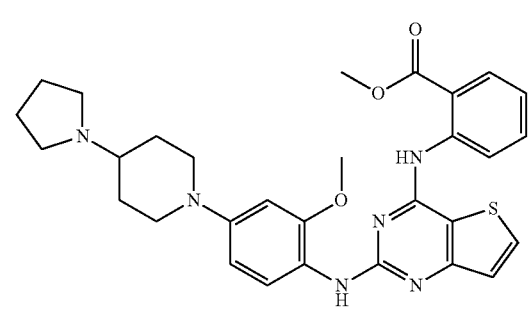 TFA salt | ¹H NMR (600 MHz, DMSO-d$_6$) δ 11.24 (s, 1H), 10.16 (s, 1H), 8.32 (d, J = 5.3 Hz, 1H), 8.05 (s, 1H), 7.99 (dd, J = 7.9, 1.6 Hz, 1H), 7.65 (s, 1H), 7.41 (t, J = 7.6 Hz, 1H), 7.32 (d, J = 5.4 Hz, 1H), 7.25 (s, 1H), 6.74 (s, 1H), 6.55 (s, 1H), 3.90 (d, J = 12.4 Hz, 2H), 3.81 (s, 3H), 3.78 (s, 3H), 3.62-3.53 (m, 2H), 3.34-3.24 (m, 1H), 3.10 (dd, J = 13.4, 5.4 Hz, 2H), 2.76 (t, J = 12.4 Hz, 2H), 2.15 (d, J = 12.1 Hz, 2H), 2.08-1.97 (m, 2H), 1.90-1.81 (m, 2H), 1.73 (tt, J = 12.8, 6.4 Hz, 2H). MS (ESI) m/z: 559 [M + H]⁺. |

TABLE 2-continued

Structure and characterization of compounds ID-IK

| No. | Structure | ¹H NMR and/or MS data |
|---|---|---|
| IE-6 | 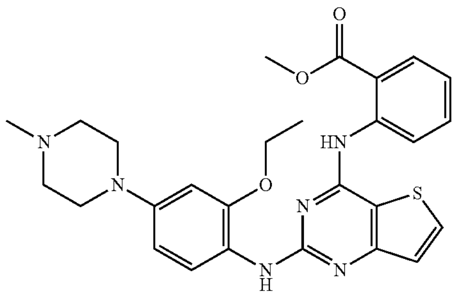 [SMILES: CCOc1cc(N2CCN(C)CC2)ccc1Nc1nc(Nc2ccccc2C(=O)OC)c2sccc2n1] | ¹H NMR (600 MHz, Chloroform-d) δ 11.10 (s, 1H), 9.06 (d, J = 1.1 Hz, 1H), 8.30 (d, J = 9.3 Hz, 1H), 8.10 (dd, J = 7.9, 1.7 Hz, 1H), 7.73 (d, J = 5.3 Hz, 1H), 7.55 (ddd, J = 8.7, 7.1, 1.7 Hz, 1H), 7.35 (s, 1H), 7.27 (d, J = 5.4 Hz, 1H), 7.09-7.05 (m, 1H), 6.63-6.58 (m, 2H), 4.13 (q, J = 6.9 Hz, 2H), 4.01 (s, 3H), 3.22 (t, J = 4.9 Hz, 4H), 2.67 (t, J = 4.9 Hz, 4H), 2.42 (s, 3H), 1.49 (t, J = 7.0 Hz, 3H). MS (ESI) m/z: 519 [M + H]⁺ |
| IE-7 | TFA salt | ¹H NMR (600 MHz, DMSO-d₆) δ 11.12 (s, 1H), 9.81 (s, 1H), 8.33 (d, J = 5.4 Hz, 1H), 8.03 (d, J = 8.1 Hz, 1H), 7.98 (dd, J = 7.9, 1.6 Hz, 1H), 7.65 (t, J = 7.7 Hz, 1H), 7.47 (s, 1H), 7.40 (t, J = 7.6 Hz, 1H), 7.35 (d, J = 5.3 Hz, 1H), 6.82 (s, 1H), 4.57 (p, J = 6.0 Hz, 1H), 3.76 (s, 3H), 3.52 (d, J = 11.9 Hz, 2H), 3.12 (q, J = 13.2, 11.0 Hz, 2H), 2.98-2.91 (m, 1H), 2.82 (d, J = 4.6 Hz, 3H), 2.15 (s, 3H), 1.98-1.70 (m, 4H), 1.22 (d, J = 6.0 Hz, 6H). MS (ESI) m/z: 546 [M + H]⁺. |
| IE-8 | TFA salt | ¹H NMR (600 MHz, DMSO-d₆) δ 11.23 (s, 1H), 10.06 (s, 1H), 8.34 (d, J = 5.4 Hz, 1H), 7.98 (t, J = 10.6 Hz, 2H), 7.62 (d, J = 7.8 Hz, 1H), 7.43-7.38 (m, 1H), 7.36 (d, J = 5.4 Hz, 2H), 6.85 (s, 1H), 3.77 (d, J = 6.4 Hz, 6H), 3.53 (d, J = 11.8 Hz, 2H), 3.13 (q, J = 11.1 Hz, 2H), 2.99 (ddd, J = 14.7, 10.9, 6.3 Hz, 1H), 2.83 (d, J = 4.4 Hz, 3H), 2.16 (s, 3H), 1.98 (dd, J = 14.8, 10.3 Hz, 2H), 1.89 (d, J = 14.0 Hz, 2H). MS (ESI) m/z: 518 [M + H]⁺. |
| IF-1 | TFA salt | MS (ESI) m/z: 550 [M + H]⁺. |

TABLE 2-continued
Structure and characterization of compounds ID-IK
| No. | Structure | ¹H NMR and/or MS data |
|---|---|---|
| IF-2 | 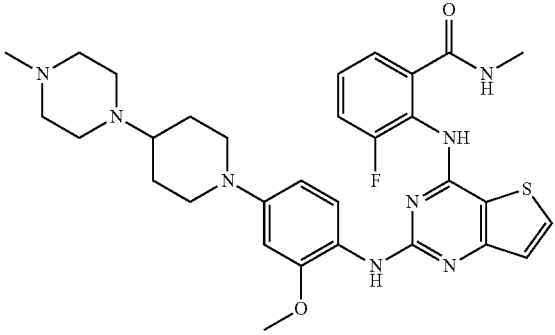<br>TFA salt | MS (ESI) m/z: 605 [M + H]⁺. |
| IF-3 | 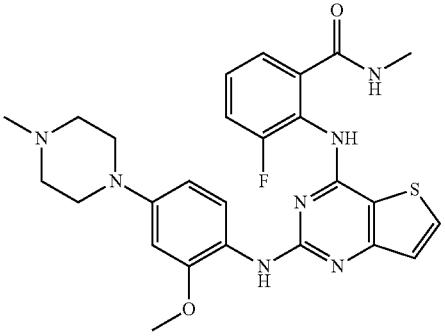<br>TFA salt | MS (ESI) m/z: 522 [M + H]⁺. |
| IG-1 | 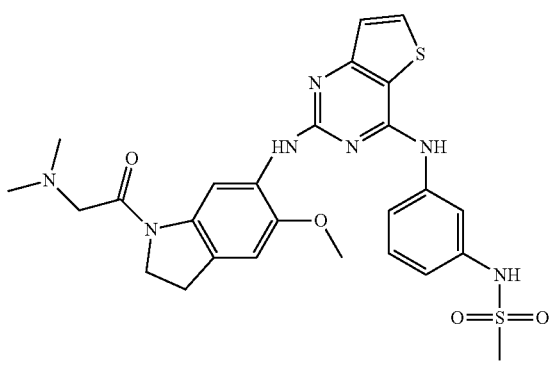<br>TFA salt | ¹H NMR (600 MHz, DMSO-d$_6$) δ 10.64 (s, 1H), 9.87 (s, 2H), 8.30 (d, J = 5.5 Hz, 2H), 7.55 (d, J = 28.6 Hz, 2H), 7.28 (d, J = 5.4 Hz, 1H), 7.18 (s, 2H), 6.98 (s, 1H), 4.37 (s, 2H), 4.10 (t, J = 8.4 Hz, 2H), 3.78 (s, 3H), 3.28 (t, J = 8.4 Hz, 2H), 3.02 (s, 3H), 2.87 (s, 6H). MS (ESI) m/z: 568 [M + H]⁺ |

TABLE 2-continued

Structure and characterization of compounds ID-IK

| No. | Structure | ¹H NMR and/or MS data |
|---|---|---|
| IG-2 | 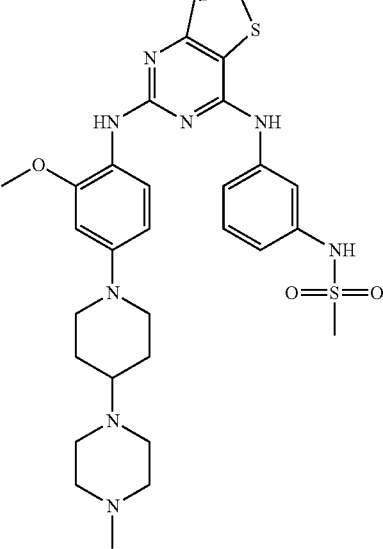 TFA salt | ¹H NMR (600 MHz, DMSO-d$_6$) δ 10.90 (s, 1H), 9.93 (s, 1H), 9.80 (s, 1H), 8.32 (s, 1H), 7.59 (s, 1H), 7.43 (s, 1H), 7.31 (d, J = 5.4 Hz, 3H), 7.07 (s, 1H), 6.77 (d, J = 2.5 Hz, 1H), 6.61 (d, J = 8.7 Hz, 1H), 3.96 (d, J = 12.2 Hz, 2H), 3.80 (s, 4H), 3.41 (s, 2H), 3.03 (s, 3H), 2.89 (s, 3H), 2.78 (t, J = 12.2 Hz, 2H), 2.55 (s, 1H), 2.16 (d, J = 11.7 Hz, 2H), 1.72 (dd, J = 12.0, 3.9 Hz, 2H). MS (ESI) m/z: 623 [M + H]⁺ |
| IG-3 | 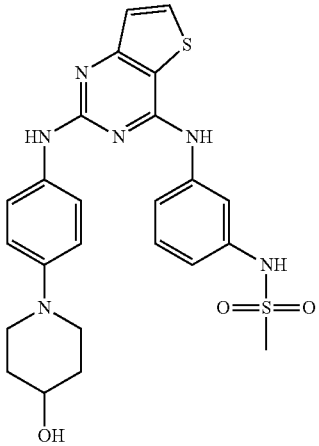 TFA salt | ¹H NMR (600 MHz, DMSO-d$_6$) δ 10.57 (s, 1H), 10.31 (s, 1H), 9.93 (s, 1H), 8.27 (d, J = 5.4 Hz, 1H), 7.65 (s, 2H), 7.58 (d, J = 8.1 Hz, 1H), 7.44 (s, 1H), 7.37 (t, J = 8.1 Hz, 3H), 7.30 (d, J = 5.4 Hz, 1H), 7.07 (d, 1H), 3.82 (s, 1H), 3.62-3.55 (m, 2H), 3.30 (s, 2H), 3.03 (s, 3H), 1.99 (s, 2H), 1.73 (s. 2H). MS (ESI) m/z: 511 [M + H]⁺. |
| IG-4 | 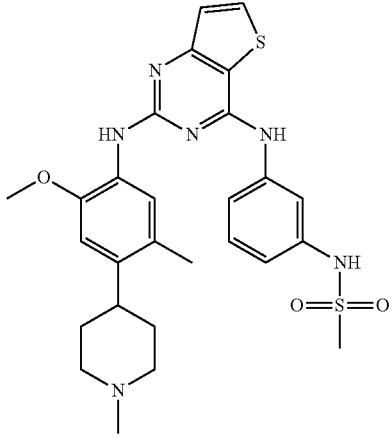 TFA salt | ¹H NMR (600 MHz, DMSO-d$_6$) δ 10.01 (s, 1H), 9.94 (s, 1H), 8.31 (d, J = 5.4 Hz, 1H), 7.53 (s, 3H), 7.47 (s, 1H), 7.34 (d, J = 5.5 Hz, 1H), 7.27 (d, 1H), 7.04 (d, J = 8.1 Hz, 1H), 6.86 (s, 1H), 3.81 (s, 3H), 3.17 (s, 1H), 3.02 (t, 6H), 2.82 (d, J = 4.3 Hz, 3H), 2.55 (s, 3H), 2.19 (s, 3H), 1.91 (d, J = 13.9 Hz, 2H). MS (ESI) m/z: 553 [M + H]⁺ |

TABLE 2-continued

Structure and characterization of compounds ID-IK

| No. | Structure | ¹H NMR and/or MS data |
|---|---|---|
| IG-5 | 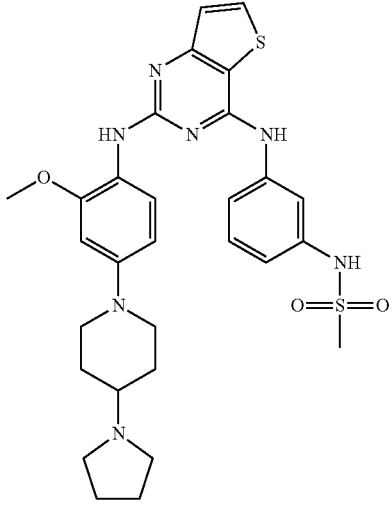 TFA salt | ¹H NMR (600 MHz, DMSO-$d_6$) δ 10.86 (s, 1H), 10.04 (s, 1H), 9.93 (s, 1H), 8.31 (s, 1H), 7.58 (s, 1H), 7.44 (s, 1H), 7.31 (d, J = 5.5 Hz, 3H), 7.06 (s, 1H), 6.73 (d, J = 2.5 Hz, 1H), 6.58 (d, J = 8.7 Hz, 1H), 3.91 (d, J = 13.0 Hz, 4H), 3.59-3.57 (m, 3H), 3.33-3.28 (m, 1H), 3.15-3.08 (m, 2H), 3.03 (s, 3H), 2.75 (d, J = 2.0 Hz, 2H), 2.15 (d, J = 11.3 Hz, 2H), 2.03 (s, 2H), 1.87 (d, J = 5.7 Hz, 2H), 1.71 (dd, J = 12.2, 4.0 Hz, 2H). MS (ESI) m/z: 594 [M + H]⁺ |
| IG-6 | 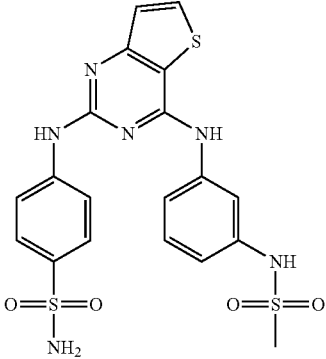 TFA salt | ¹H NMR (600 MHz, DMSO-$d_6$) δ 10.31 (s, 1H), 10.09 (s, 1H), 9.91 (s, 1H), 8.25 (d, J = 5.4 Hz, 1H), 7.85 (d, J = 8.6 Hz, 2H), 7.70 (d, J = 8.8 Hz, 2H), 7.64 (d, J = 8.1 Hz, 1H), 7.45 (s, 1H), 7.38 (t, J = 8.1 Hz, 1H), 7.33 (d, J = 5.4 Hz, 1H), 7.24 (s, 2H), 7.06 (dd, J = 8.0, 2.1 Hz, 1H), 3.04 (s, 3H). MS (ESI) m/z: 491 [M + H]⁺ |
| IH-1 | 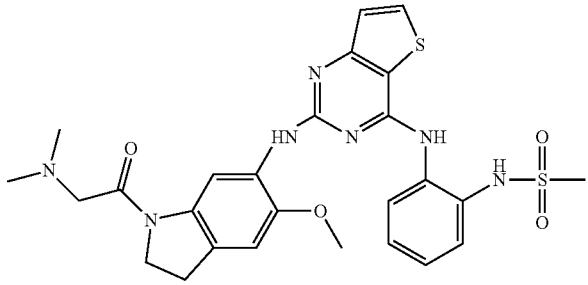 TFA salt | ¹H NMR (600 MHz, DMSO-$d_6$) δ 10.31 (s, 1H), 9.87 (s, 1H), 9.38 (s, 1H), 8.26 (s, 1H), 8.05 (s, 1H), 7.53 (s, 1H), 7.51-7.48 (m, 1H), 7.39 (s, 1H), 7.26 (d, J = 5.4 Hz, 1H), 7.22 (s, 1H), 7.17 (s, 1H), 4.37 (s, 2H), 4.08 (t, J = 8.4 Hz, 2H), 3.76 (s, 3H), 3.26 (t, J = 8.3 Hz, 2H), 2.98 (s, 3H), 2.88 (s, 6H). MS (ESI) m/z: 568 [M + H]⁺. |

TABLE 2-continued

Structure and characterization of compounds ID-IK

| No. | Structure | ¹H NMR and/or MS data |
|---|---|---|
| IH-2 | (structure) TFA salt | ¹H NMR (600 MHz, DMSO-$d_6$) δ 8.82 (s, 1H), 8.05 (d, J = 5.4 Hz, 1H), 7.85 (d, J = 8.7 Hz, 1H), 7.73-7.71 (m, 1H), 7.47-7.45 (m, 1H), 7.41 (s, 1H), 7.29-7.27 (m, 2H), 7.18 (d, J = 5.3 Hz, 1H), 6.60 (d, J = 2.6 Hz, 1H), 6.38 (d, J = 2.5 Hz, 1H), 3.79 (s, 3H), 3.66 (d, J = 12.2 Hz, 2H), 2.91 (s, 3H), 2.64 (s, 2H), 2.62 (s, 2H), 2.60 (s, 1H), 2.36 (s, 3H), 1.87 (d, J = 12.1 Hz, 2H), 1.54 (dd, J = 11.7, 3.7 Hz, 2H). MS (ESI) m/z: 623 [M + H]⁺. |
| IH-3 | (structure) TFA salt | ¹H NMR (600 MHz, DMSO-$d_6$) δ 10.50 (s, 1H), 10.27 (s, 1H), 9.40 (s, 1H), 8.29 (s, 1H), 7.58 (d, J = 8.2 Hz, 1H), 7.47 (d, J = 7.9 Hz, 1H), 7.42 (s, 1H), 7.28 (t, J = 8 4 Hz, 3H), 6.73 (s, 1H), 3.89 (d, J = 9.5 Hz, 2H), 3.79 (s, 3H), 3.56 (d, J = 10.9 Hz, 2H), 3.16 (s, 2H), 2.97 (s, 3H), 2.89 (s, 3H), 2.55 (s, 2H). MS (ESI) m/z: 540 [M + H]⁺. |
| IH-4 | (structure) TFA salt | ¹H NMR (600 MHz, DMSO-$d_6$) δ 10.36 (s, 1H), 10.23 (s, 1H), 9.34 (s, 1H), 8.28 (d, J = 5.5 Hz, 1H), 7.58 (dd, J = 8.2, 1.4 Hz, 2H), 7.54 (d, J = 7.8 Hz, 2H), 7.44 (t, J = 7.8 Hz, 2H), 7.33 (dd, J = 7.7, 1.5 Hz, 1H), 7.32-7.30 (m, 2H), 3.82 (s, 1H), 3.55 (s, 2H), 3.27 (s, 2H), 2.93 (s, 3H), 1.99 (s, 2H), 1.71 (s, 2H). MS (ESI) m/z: 511 [M + H]⁺. |

TABLE 2-continued

Structure and characterization of compounds ID-IK

| No. | Structure | ¹H NMR and/or MS data |
|---|---|---|
| IH-5 | 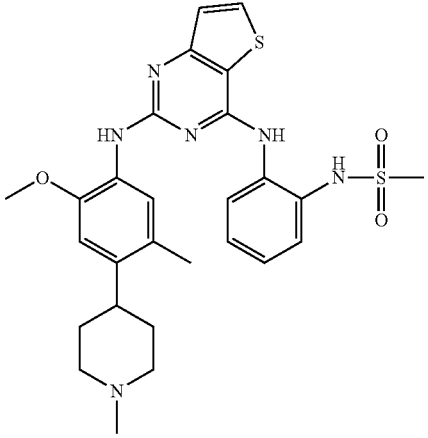<br>TFA salt | ¹H NMR (600 MHz, DMSO-d$_6$) δ 10.40 (s, 1H), 9.85 (s, 1H), 9.38 (s, 1H), 8.30 (s, 1H), 7.57 (d, J = 8.1 Hz, 1H), 7.50 (d, J = 8.0 Hz, 1H), 7.41 (t, J = 7.8 Hz, 1H), 7.34 (d, J = 5.2 Hz, 1H), 7.29-7.26 (m, 1H), 6.80 (s, 1H), 3.80 (s, 3H), 3.14-3.09 (m, 3H), 2.94 (d, J = 5.6 Hz, 3H), 2.83 (d, J = 4.1 Hz, 3H), 2.08 (s, 2H), 1.94-1.91 (m, 2H), 1.86 (d, J = 13.8 Hz, 2H). MS (ESI) m/z: 553 [M + H]⁺. |
| IH-6 | 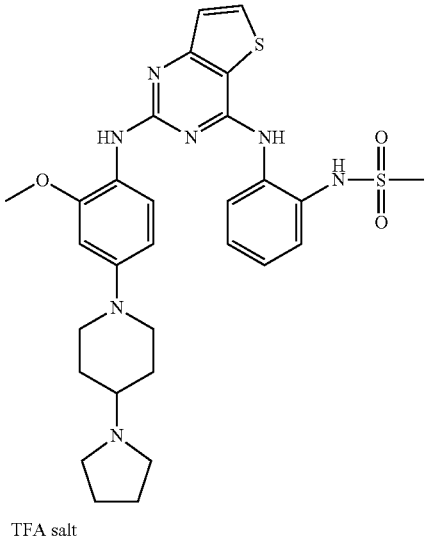<br>TFA salt | ¹H NMR (600 MHz, DMSO-d$_6$) δ 10.47 (s, 1H), 9.92 (s, 1H), 9.40 (s, 1H), 8.28 (s, 1H), 7.59 (d, J = 8.2 Hz, 1H), 7.47 (d, J = 7.8 Hz, 1H), 7.43 (s, 1H), 7.28 (td, J = 7.7, 1.4 Hz, 2H), 6.69 (s, 1H), 3.79 (s, 3H), 3.29 (d, J = 9.6 Hz, 2H), 3.13-3.09 (m, 2H), 2.99 (s, 3H), 2.72 (t, J = 12.7 Hz, 2H), 2.14 (d, J = 11.9 Hz, 2H), 2.03 (s, 2H), 1.87 (d, J = 5.9 Hz, 2H), 1.68 (dd, J = 12.1, 3.9 Hz, 2H). MS (ESI) m/z: 594 [M + H]⁺. |
| IH-7 | 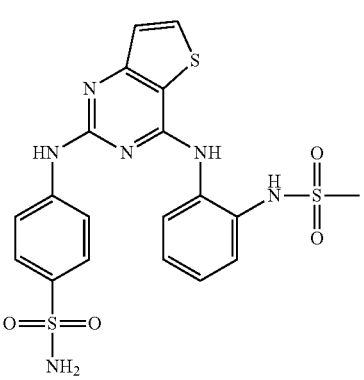<br>TFA salt | ¹H NMR (600 MHz, DMSO-d$_6$) δ 10.03 (s, 1H), 9.67 (s, 1H), 9.31 (s, 1H), 8.22 (d, J = 5.4 Hz, 1H), 7.72 (d, J = 8.4 Hz, 2H), 7.62 (d, J = 7.9 Hz, 1H), 7.57 (d, J = 3.0 Hz, 3H), 7.42 (t, J = 7.8 Hz, 1H), 7.34 (t, J = 7.8 Hz, 1H), 7.31 (d, J = 5.4 Hz, 1H), 7.20 (s, 2H), 2.92 (s, 3H). MS (ESI) m/z: 491 [M + H]⁺. |

TABLE 2-continued

Structure and characterization of compounds ID-IK

| No. | Structure | ¹H NMR and/or MS data |
|---|---|---|
| II-1 | 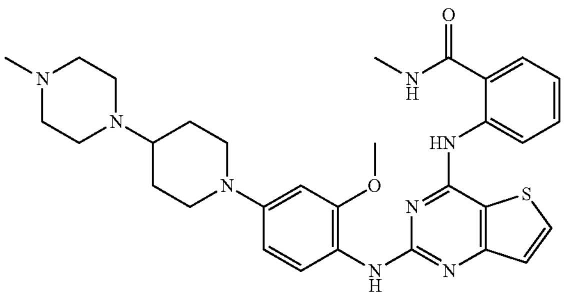 | ¹H NMR (600 MHz, DMSO-d₆) δ 11.88 (s, 1H), 8.81 (d, J = 4.6 Hz, 1H), 8.79-8.76 (m, 1H), 8.07 (d, J = 5.3 Hz, 1H), 7.82-7.74 (m, 2H), 7.71 (d, J = 8.4 Hz, 1H), 7.42 (t, J = 7.9 Hz, 1H), 7.20 (d, J = 5.3 Hz, 1H), 7.09 (td, J = 7.6, 1.2 Hz, 1H), 6.64 (d, J = 2.5 Hz, 1H), 6.51 (dd, J = 8.8, 2.6 Hz, 1H), 3.79 (s, 3H), 3.70 (d, J = 12.3 Hz, 2H), 2.82 (d, J = 4.5 Hz, 3H), 2.65 (td, J = 12.2, 2.4 Hz, 2H), 2.15 (s, 3H), 1.85 (d, J = 12.0 Hz, 2H), 1.52 (qd, J = 12.1, 3.8 Hz, 2H). MS (ESI) m/z: 587 [M + H]⁺ |
| II-2 | 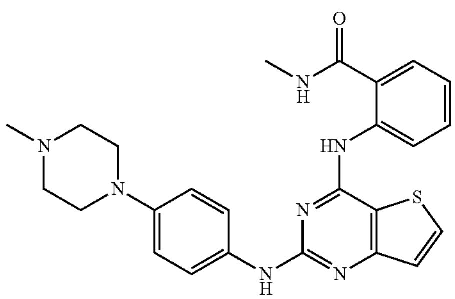 [SMILES: CNC(=O)c1ccccc1Nc1nc(Nc2ccc(N3CCN(C)CC3)cc2)nc2ccsc12] | ¹H NMR (600 MHz, DMSO-d₆) δ 11.88 (s, 1H), 8.98 (s, 1H), 8.93 (d, J = 8.4 Hz, 1H), 8.78 (d, J = 4.6 Hz, 1H), 8.04 (d, J = 5.3 Hz, 1H), 7.75 (d, J = 9.5 Hz, 1H), 7.57 (d, J = 8.4 Hz, 2H), 7.46 (t, J = 8.6 Hz, 1H), 7.19 (d, J = 5.3 Hz, 1H), 7.08 (t, J = 8.1 Hz, 1H), 6.85 (d, J = 9.0 Hz, 2H), 3.02 (t, J = 4.9 Hz, 4H), 2.78 (d, J = 4.5 Hz, 3H), 2.41 (t, J = 5.0 Hz, 4H), 2.17 (s, 3H). MS (ESI) m/z: 474 [M + H]⁺. |
| II-3 | TFA salt | ¹H NMR (600 MHz, DMSO-d₆) δ 12.65 (s, 1H), 10.25 (S, 1H), 8.85 (s, 1H), 8.44 (s, 1H), 8.29 (d, J = 5.3 Hz, 1H), 7.82 (d, J = 7.9 Hz, 1H), 7.51-7.35 (m, 2H), 7.33-7.24 (m, 2H), 6.80 (d, J = 2.6 Hz, 1H), 6.64 (d, J = 6.5 Hz, 1H), 3.96 (d, J = 13.1 Hz, 2H), 3.80 (s, 3H), 3.57 (d, J = 11.9 Hz, 2H), 3.19 (s, 2H), 3.03 (t, J = 12.5 Hz, 2H), 2.89 (s, 3H), 2.81 (d, J = 4.5 Hz, 3H). MS (ESI) m/z: 504 [M + H]⁺. |
| II-4 | 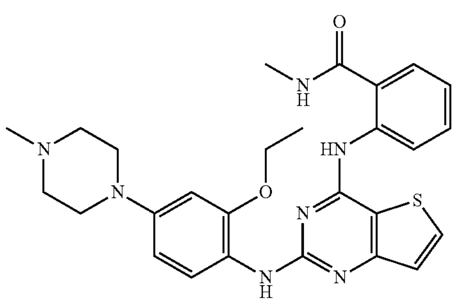 [SMILES: CCOc1cc(N2CCN(C)CC2)ccc1Nc1nc(Nc2ccccc2C(=O)NC)c2sccc2n1] | ¹H NMR (600 MHz, DMSO-d₆) δ 11.88 (s, 1H) 8.82 (d, J = 4.6 Hz, 1H), 8.77 (d, J = 8.4 Hz, 1H), 8.08 (d, J = 5.3 Hz, 1H), 7.80-7.76 (m, 2H), 7.73 (s, 1H), 7.42 (t, J = 7.9 Hz, 1H), 7.21 (d, J = 5.3 Hz, 1H), 7.10 (td, J = 7.6, 1.2 Hz, 1H), 6.64 (d, J = 2.6 Hz, 1H), 6.51 (dd, J = 8.8, 2.6 Hz, 1H), 4.07 (q, J = 7.0 Hz, 2H), 3.35 (s, 8H), 2.82 (d, J = 4.5 Hz, 3H), 2.26 (s, 3H), 1.29 (t, J = 6.9 Hz, 3H). MS (ESI) m/z: 518 [M + H]⁺. |
| II-5 | TFA salt | ¹H NMR (600 MHz, DMSO-d₆) δ 12.22 (s, 1H), 10.04 (S, 1H), 8.83 (d, J = 4.9 Hz, 1H), 8.69 (s, 1H), 8.23 (d, J = 5.3 Hz, 1H), 7.82 (dd, J = 7.9, 1.5 Hz, 1H), 7.78 (s, 1H), 7.55 (t, J = 7.9 Hz, 1H), 7.48 (s, 2H), 7.33 (d, J = 5.3 Hz, 1H), 7.27-7.20 (m, 1H), 3.96 (s, 1H), 3.62 (s, 2H), 3.38 (s, 2H), 2.82 (d, J = 4.4 Hz, 3H), 2.54 (s, 1H), 2.02 (s, 2H), 1.76 (s, 2H). MS (ESI) m/z: 475 [M + H]⁺. |

TABLE 2-continued

Structure and characterization of compounds ID-IK

| No. | Structure | $^1$H NMR and/or MS data |
|---|---|---|
| II-6 | 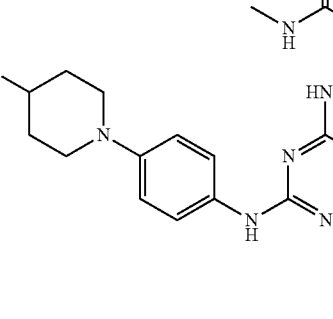<br>TFA salt | $^1$H NMR (600 MHz, DMSO-$d_6$) δ 12.42 (s, 1H), 10.16 (s, 1H), 8.84 (s, 1H), 8.59 (s, 1H), 8.26 (d, J = 5.3 Hz, 1H), 7.82 (dd, J = 8.0, 1.5 Hz, 1H), 7.51 (s, 3H), 7.31 (d, J = 5.3 Hz, 1H), 7.26 (t, J = 7.6 Hz, 1H), 7.15 (s, 2H), 3.84 (d, J = 12.2 Hz, 2H), 2.86 (s, 3H), 2.81 (d, J = 4.5 Hz, 3H), 2.12 (d, J = 12.0 Hz, 2H), 1.74 (d, J = 12.4 Hz, 2H). MS (ESI) m/z: 557 [M + H]$^+$. |
| II-7 | 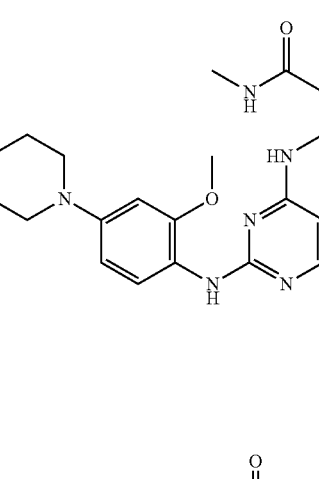<br>TFA salt | $^1$H NMR (600 MHz, DMSO-$d_6$) δ 12.70 (s, 1H), 9.97 (s, 1H), 8.83 (s, 1H), 8.43 (s, 1H), 8.30 (d, J = 5.3 Hz, 1H), 7.82 (d, J = 9.4 Hz, 1H), 7.48 (s, 1H), 7.31 (s, 3H), 6.77 (d, J = 2.5 Hz, 1H), 6.63 (d, J = 11.4 Hz, 1H), 3.97-3.91 (m, 2H), 3.79 (s, 3H), 3.62-3.50 (m, 2H), 3.34-3.27 (m, 1H), 3.16 - 3.06 (m, 2H), 2.81 (d, J = 4.5 Hz, 3H), 2.77 (t, J = 12.4 Hz, 2H), 2.16 (d, J = 12.0 Hz, 2H), 2.06-1.99 (m, 2H), 1.91-.82 (m, 2H), 1.77-1.65 (m, 2H). MS (ESI) m/z: 558 [M + H]$^+$. |
| II-8 | 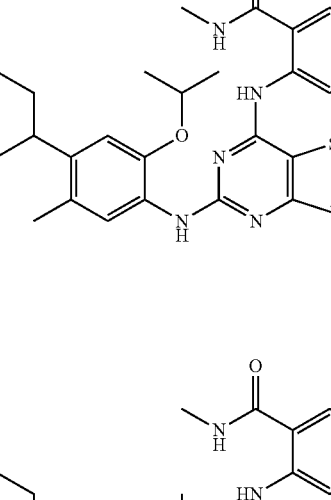<br>TFA salt | $^1$H NMR (600 MHz, DMSO-$d_6$) δ 12.36 (s, 1H), 10.05 (s, 1H), 8.84 (d, J = 5.3 Hz, 1H), 8.51 (s, 1H), 8.26 (d, J = 5.3 Hz, 1H), 7.82 (dd, J = 7.9, 1.5 Hz, 1H), 7.65 (s, 1H), 7.45 (s, 1H), 7.32 (d, J = 5.3 Hz, 1H), 7.23 (s, 1H), 6.86 (s, 1H), 4.57 (p, J = 6.0 Hz, 1H), 3.53 (d, J = 11.9 Hz, 2H), 3.19-3.09 (m, 2H), 3.05-2.94 (m, 1H), 2.83 (d, J = 4.0 Hz, 3H), 2.81 (d, J = 4.5 Hz, 3H), 2.24 (s, 3H), 2.03-1.84 (m, 4H), 1.23 (d, J = 6.1 Hz, 6H). MS (ESI) m/z: 545 [M + H]$^+$. |
| II-9 | 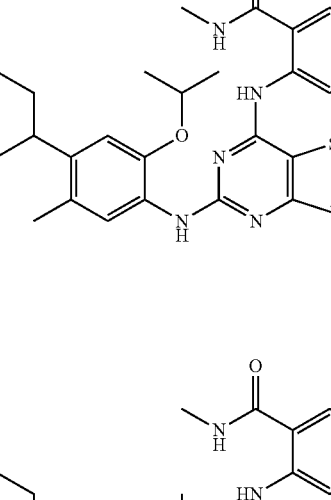<br>TFA salt | $^1$H NMR (600 MHz, DMSO-$d_6$) δ 12.43 (s, 1H), 10.02 (s, 1H), 8.84 (s, 1H), 8.46 (s, 1H), 8.27 (d, J = 5.3 Hz, 1H), 7.81 (dd, J = 7.9, 1.5 Hz, 1H), 7.54 (s, 1H), 7.43 (s, 1H), 7.33 (d, J = 5.3 Hz, 1H), 7.24 (s, 1H), 6.88 (s, 1H), 3.80 (s, 3H), 3.54 (d, J = 11.9 Hz, 2H), 3.19-3.09 (m, 2H), 3.05-2.97 (m, 1H), 2.83 (d, J = 4.4 Hz, 3H), 2.81 (d, J = 4.5 Hz, 3H), 2.26 (s, 3H), 2.06-1.96 (m, 2H), 1.95-1.87 (m, 2H). MS (ESI) m/z: 517 [M + H]$^+$. |

TABLE 2-continued

Structure and characterization of compounds ID-IK

| No. | Structure | ¹H NMR and/or MS data |
|---|---|---|
| IJ-1 | 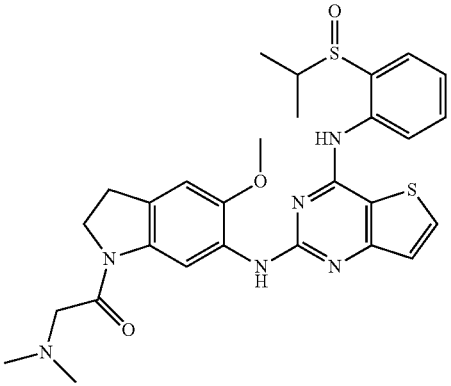<br>TFA salt | 1H NMR (600 MHz, Methanol-d4) δ 8.23 (d, J = 5.4 Hz, 1H), 8.16 (s, 1H), 7.91 (s, 1H), 7.70 (s, 1H), 7.56 (s, 2H), 7.31 (d, J = 5.4 Hz, 1H), 7.12 (s, 1H), 4.34 (s, 2H), 4.16~4.11 (m, 2H), 3.82 (s, 3H), 3.34 (t, J = 8.3 Hz, 2H), 3.13 (p, J = 6.9 Hz, 1H), 3.01 (s, 6H), 1.22 (d, J = 6.9 Hz, 3H), 1.16 (d, J = 6.7 Hz, 3H). MS (ESI) m/z: 565 [M + H]⁺. |
| IJ-2 | 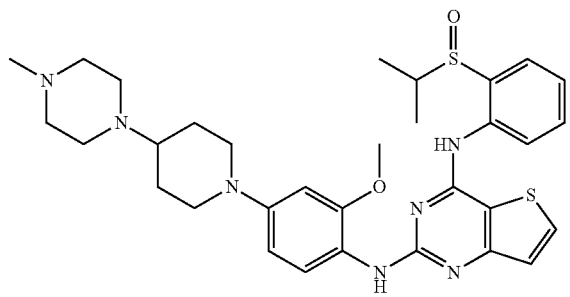<br>TFA salt | ¹H NMR (600 MHz, Methanol-d₄) δ 8.25 (d, J = 5.4 Hz, 1H), 7.84 (s, 1H), 7.79 (dd, J = 7.7, 1.7 Hz, 1H), 7.68 (td, J = 7.6, 1.7 Hz, 1H), 7.63 (t, J = 7.6 Hz, 1H), 7.39 (s, 1H), 7.32 (d, J = 5.4 Hz, 1H), 6.93 (d, J = 2.4 Hz, 1H), 6.69 (d, J = 8.7 Hz, 1H), 3.87 (s, 3H), 3.56 (s, 4H), 3.46 (s, 4H), 3.14 (t, J = 12.4 Hz, 2H), 3.08 (p, J = 6.8 Hz, 1H), 2.97 (s, 3H), 2.25 (dt, J = 13.1, 2.7 Hz, 2H), 1.99 (qd, J = 12.3, 3.9 Hz, 2H), 1.21 (d, J = 7.0 Hz, 3H), 1.12 (d, J = 6.7 Hz, 3H). MS (ESI) m/z: 620 [M + H]⁺. |
| IJ-3 | 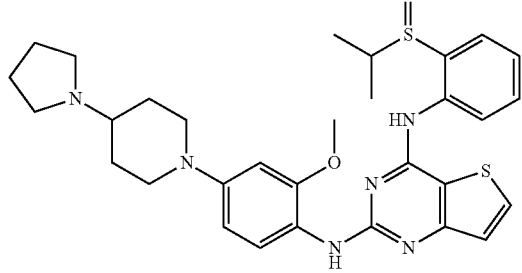<br>TFA salt | ¹H NMR (600 MHz, Methanol-d₄) δ 8.22 (d, J = 5.5 Hz, 1H), 7.88 (s, 1H), 7.77 (d, J = 7.7 Hz, 1H), 7.70-7.56 (m, 2H), 7.35-7.19 (m, 2H), 6.76 (d, J = 2.6 Hz, 1H), 6.56 (s, 1H), 3.89 (d, J = 12.5 Hz, 2H), 3.84 (s, 3H), 3.76-3.67 (m, 2H), 3.38-3.32 (m, 1H), 3.23-3.15 (m, 2H), 3.14-3.06 (m, 1H), 2.92 (td, J = 12.7, 2.4 Hz, 2H), 2.29 (dt, J = 14.0, 2.7 Hz, 2H), 2.19 (d, J = 9.8 Hz, 2H), 2.03 (q, J = 7.1 Hz, 2H), 1.90 (qd, J = 12.3, 4.1 Hz, 2H), 1.18 (dd, J = 43.3, 6.8 Hz, 6H). MS (ESI) m/z: 591 [M + H]⁺. |
| IJ-4 | 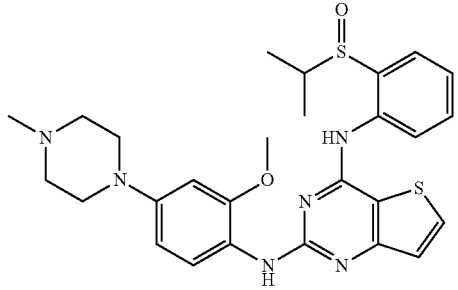<br>TFA salt | ¹H NMR (600 MHz, Methanol-d₄) δ 8.03 (dd, J = 8.1, 1.2 Hz, 1H), 7.95 (d, J = 5.4 Hz, 1H), 7.81 (d, J = 8.7 Hz, 1H), 7.69 (dd, J = 7.8, 1.5 Hz, 1H), 7.63 (ddd, J = 8.1, 7.4, 1.6 Hz, 1H), 7.49 (td, J = 7.6, 1.2 Hz, 1H), 7.18 (d, J = 5.3 Hz, 1H), 6.67 (d, J = 2.6 Hz, 1H), 6.40 (dd, J = 8.8, 2.6 Hz, 1H), 3.89 (s, 3H), 3.24 (t, J = 5.0 Hz, 4H), 3.18 (p, J = 6.8 Hz, 1H), 2.86 (t, J = 5.0 Hz, 4H), 2.54 (s, 3H), 1.21~1.13 (m, 6H). MS (ESI) m/z: 537 [M + H]⁺. |

TABLE 2-continued

Structure and characterization of compounds ID-IK

| No. | Structure | ¹H NMR and/or MS data |
|---|---|---|
| IJ-5 | (structure) TFA salt | ¹H NMR (600 MHz, Methanol-$d_4$) δ 8.26 (d, J = 5.4 Hz, 1H), 7.83 (s, 1H), 7.80 (dd, J = 7.7, 1.8 Hz, 1H), 7.67 (dt, J = 7.8, 3.7 Hz, 1H), 7.63 (t, J = 7.5 Hz, 1H), 7.34-7.28 (m, 2H), 6.88 (s, 1H), 3.86 (s, 3H), 3.67-3.61 (m, 2H), 3.20 (td, J = 11.7, 11.2, 4.9 Hz, 2H), 3.08 (dq, J = 28.2, 6.7, 6.2 Hz, 1H), 2.94 (s, 3H), 2.18 (s, 3H), 2.02 (d, J = 7.2 Hz, 4H), 1.15 (dd, J = 62.2, 6.8 Hz, 6H). MS (ESI) m/z: 550 [M + H]⁺. |
| IJ-6 | (structure) TFA salt | ¹H NMR (600 MHz, Methanol-$d_4$) δ 8.02 (d, J = 8.1 Hz, 1H), 7.93 (d, J = 5.4 Hz, 1H), 7.79-7.73 (m, 1H), 7.67 (dd, J = 7.8, 1.5 Hz, 1H), 7.61 (td, J = 7.7, 1.5 Hz, 1H), 7.47 (td, J = 7.6, 1.2 Hz, 1H), 7.16 (d, J = 5.3 Hz, 1H), 6.66-6.64 (m, 1H), 6.40 (dd, J = 8.8, 2.6 Hz, 1H), 3.86 (s, 3H), 3.66 (dd, J = 9.3, 6.4 Hz, 2H), 3.16 (p, J = 6.9 Hz, 1H), 2.72-2.63 (m, 2H), 2.38 (s, 6H), 2.01 (dd, J = 12.3, 3.3 Hz, 2H), 1.67 (qd, J = 12.2, 3.9 Hz, 2H), 1.15 (dd, J = 23.0, 6.9 Hz, 6H). MS (ESI) m/z: 565 [M + H]⁺. |
| IK-1 | (structure) TFA salt | ¹H NMR (600 MHz, Methanol-$d_4$) δ 8.42 (s, 1H), 8.25 (s, 1H), 8.23 (d, J = 5.4 Hz, 1H), 7.68 (dd, J = 14.0, 7.7 Hz, 1H), 7.47 (s, 1H), 7.37 (d, J = 7.7 Hz, 1H), 7.31 (d, J = 5.4 Hz, 1H), 7.17 (s, 1H), 4.34 (s, 2H), 4.15 (dd, J = 8.8, 7.9 Hz, 2H), 3.85 (s, 3H), 3.38 (t, J = 8.3 Hz, 2H), 2.99 (s, 6H), 1.92 (d, J = 13.6 Hz, 6H). MS (ESI) m/z: 551 [M + H]⁺. |
| IK-2 | (structure) TFA salt | ¹H NMR (600 MHz, Methanol-$d_4$) δ 8.47 (s, 1H), 8.21 (d, J = 5.4 Hz, 1H), 7.71 (dd, J = 13.9, 7.7 Hz, 1H), 7.58 (d, J = 8.4 Hz, 1H), 7.42 (d, J = 8.0 Hz, 2H), 7.29 (d, J = 5.4 Hz, 1H), 6.91 (d, J = 2.5 Hz, 1H), 6.77 (dd, J = 8.6, 2.5 Hz, 1H), 3.93 (d, J = 12.6 Hz, 2H), 3.87 (s, 3H), 3.49 (s, 4H), 3.37 (s, 4H), 3.19 (s, 1H), 3.07 (t, J = 12.5 Hz, 2H), 2.93 (d, J = 1.4 Hz, 3H), 2.22 (d, J = 12.5 Hz, 2H), 1.90 (d, J = 13.6 Hz, 6H). MS (ESI) m/z: 606 [M + H]⁺. |

TABLE 2-continued

Structure and characterization of compounds ID-IK

| No. | Structure | ¹H NMR and/or MS data |
|---|---|---|
| IK-3 | 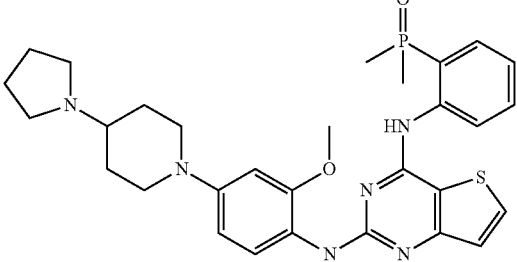<br>TFA salt | ¹H NMR (600 MHz, Methanol-$d_4$) δ 8.55 (s, 1H), 8.20 (d, J = 5.4 Hz, 1H), 7.70 (dd, J = 14.0, 7.7 Hz, 1H), 7.58 (s, 1H), 7.39 (s, 1H), 7.30 (s, 1H), 7.27 (d, J = 5.3 Hz, 1H), 6.77 (d, J = 2.6 Hz, 1H), 6.66 (d, J = 8.6 Hz, 1H), 3.95 (d, J = 12.7 Hz, 2H), 3.85 (s, 3H), 3.75-3.66 (m, 2H), 3.20 (q, J = 9.0 Hz, 2H), 2.88 (td, J = 12.7, 2.3 Hz, 2H), 2.29 (d, J = 12.4 Hz, 2H), 2.20 (t, J = 7.4 Hz, 2H), 2.04 (t, J = 6.6 Hz, 2H), 1.91 (d, J = 13.6 Hz, 6H), 1.85 (tt, J = 12.2, 6.1 Hz, 2H). MS (ESI) m/z: 577 [M + H]⁺. |
| IK-4 | 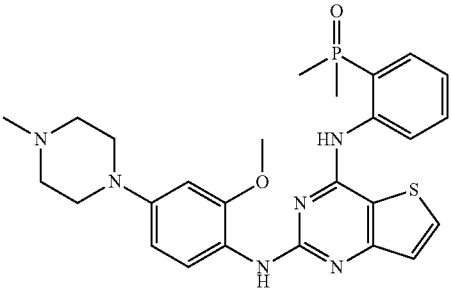<br>TFA salt | ¹H NMR (600 MHz, Methanol-$d_4$) δ 8.51 (s, 1H), 8.21 (d, J = 5.4 Hz, 1H), 7.70 (dd, J = 14.0, 7.7 Hz, 1H), 7.56 (s, 1H), 7.44-7.32 (m, 2H), 7.28 (d, J = 5.4 Hz, 1H), 6.82 (d, J = 2.5 Hz, 1H), 6.68 (d, J = 7.6 Hz, 1H), 3.96 (m, 2H), 3.65 (m, 2H), 3.14 (s, 2H), 3.01 (s, 3H), 1.91 (d, J = 13.5 Hz, 6H). MS (ESI) m/z: 523 [M + H]⁺. |
| IK-5 | 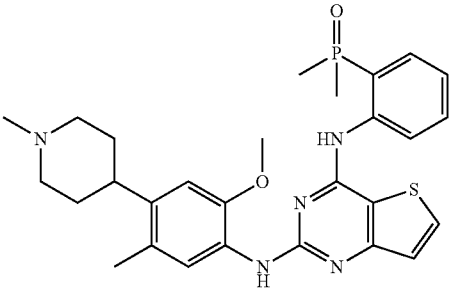<br>TFA salt | ¹H NMR (600 MHz, Methanol-$d_4$) δ 8.50 (dd, J = 8.4, 4.4 Hz, 1H), 7.93 (d, J = 5.3 Hz, 1H), 7.88 (s, 1H), 7.64 (ddd, J = 14.0, 7.8, 1.5 Hz, 1H), 7.54 (ddt, J = 8.5, 7.2, 1.4 Hz, 1H), 7.26 (tdd, J = 7.6, 2.3, 1.0 Hz, 1H), 7.16 (d, J = 5.4 Hz, 1H), 6.82 (s, 1H), 3.87 (s, 3H), 3.05 (dt, J = 12.1, 3.0 Hz, 2H), 2.75 (tt, J = 10.4, 5.5 Hz, 1H), 2.38 (s, 3H), 2.24 (td, J = 11.3, 4.5 Hz, 2H), 2.18 (s, 3H), 1.86 (d, J = 13.5 Hz, 6H), 1.79 (d, J = 3.4 Hz, 2H), 1.27 (s, 2H). MS (ESI) m/z: 536 [M + H]⁺. |
| IK-6 | 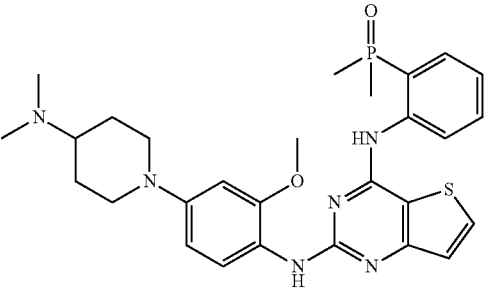<br>TFA salt | ¹H NMR (600 MHz, Methanol-$d_4$) δ 8.54 (s, 1H), 8.20 (d, J = 5.5 Hz, 1H), 7.70 (dd, J = 14.2, 7.7 Hz, 1H), 7.57 (s, 1H), 7.39 (s, 1H), 7.30 (d, J = 8.6 Hz, 1H), 7.28 (d, J = 5.3 Hz, 1H), 6.77 (d, J = 2.5 Hz, 1H), 6.66 (dd, J = 8.9, 2.5 Hz, 1H), 4.03-3.94 (m, 2H), 3.85 (s, 3H), 3.41 (tt, J = 12.1, 3.9 Hz, 1H), 2.93 (s, 6H), 2.89 (td, J = 12.6, 2.3 Hz, 2H), 2.22 (dt, J = 13.1, 2.7 Hz, 2H), 1.91 (d, J = 13.5 Hz, 6H). MS (ESI) m/z: 551 [M + H]⁺. |

TABLE 2-continued

Structure and characterization of compounds ID-IK

| No. | Structure | $^1$H NMR and/or MS data |
|---|---|---|
| IK-7 | 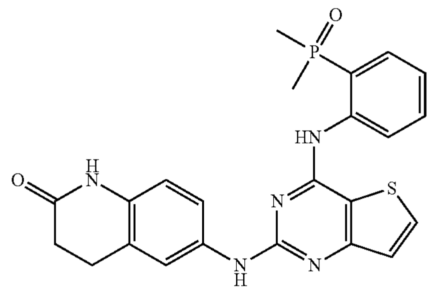 | MS (ESI) m/z: 464 [M + H]$^+$ |

Example 3

Synthetic Scheme of Compound IL

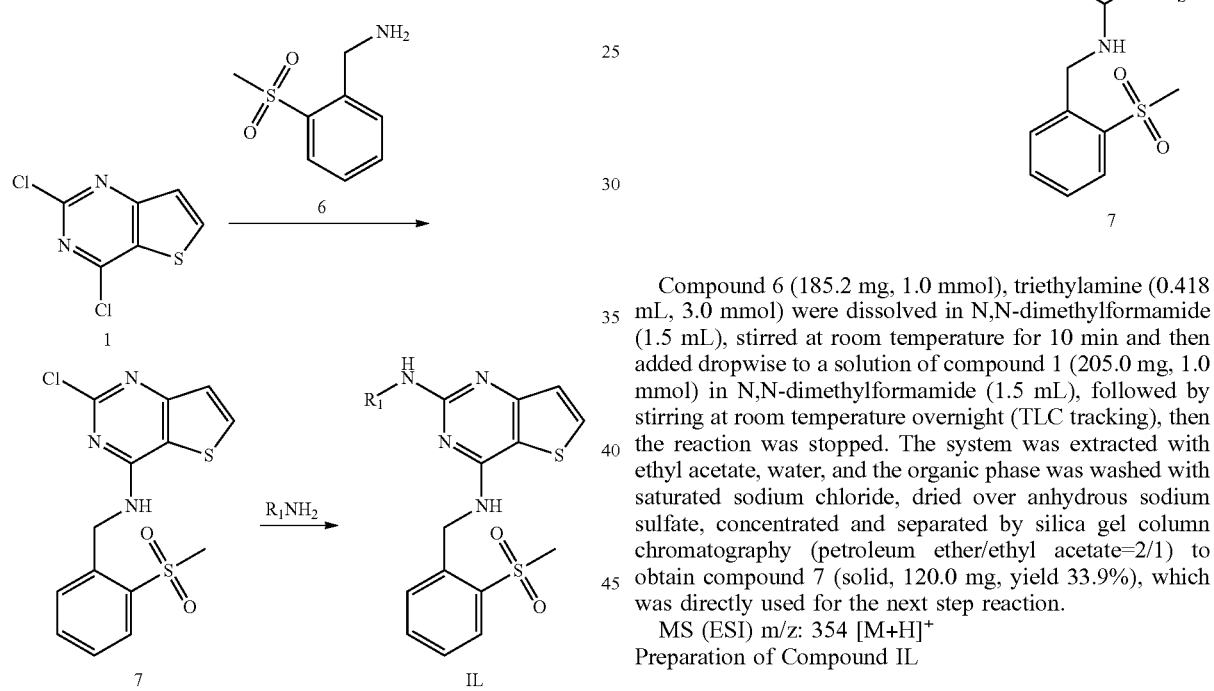

Preparation of Compound 7

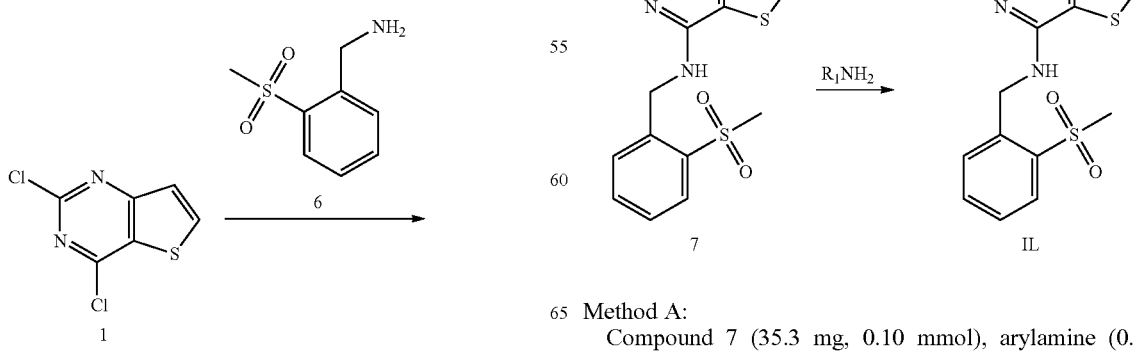

Compound 6 (185.2 mg, 1.0 mmol), triethylamine (0.418 mL, 3.0 mmol) were dissolved in N,N-dimethylformamide (1.5 mL), stirred at room temperature for 10 min and then added dropwise to a solution of compound 1 (205.0 mg, 1.0 mmol) in N,N-dimethylformamide (1.5 mL), followed by stirring at room temperature overnight (TLC tracking), then the reaction was stopped. The system was extracted with ethyl acetate, water, and the organic phase was washed with saturated sodium chloride, dried over anhydrous sodium sulfate, concentrated and separated by silica gel column chromatography (petroleum ether/ethyl acetate=2/1) to obtain compound 7 (solid, 120.0 mg, yield 33.9%), which was directly used for the next step reaction.

MS (ESI) m/z: 354 [M+H]$^+$

Preparation of Compound IL

Method A:

Compound 7 (35.3 mg, 0.10 mmol), arylamine (0.09 mmol) were dissolved in 1 mL of tert-butanol, then to the solution were added 2-dicyclohexylphosphino-2,4,6-triisopropylbiphenyl (0.018 mmol), tris(dibenzylideneacetone)dipalladium (0.012 mmol), potassium carbonate (0.30 mmol); under the protection of nitrogen, the resulting reaction solution was heated and stirred in an oil bath preheated to 110° C. until complete reaction of compound 7 (LC-MS and TLC tracking), then the reaction was stopped. Methanol and dichloromethane were added to the reaction solution, and the system was filtered, concentrated and separated by silica gel chromatograph (dichloromethane/methanol) to obtain compound IL.

Method B:

Compound 7 (35.3 mg, 0.10 mmol), arylamine (0.09 mmol) were dissolved in 1 mL of tert-butanol, then to the solution were added 2-dicyclohexylphosphino-2,4,6-triisopropylbiphenyl (0.018 mmol), tris(dibenzylideneacetone)dipalladium (0.012 mmol), potassium carbonate (0.30 mmol); under the protection of nitrogen, the resulting reaction solution was heated and stirred in an oil bath preheated to 110° C. until complete reaction of compound 7 (LC-MS and TLC tracking), then the reaction was stopped. Methanol and dichloromethane were added to the reaction solution, and the system was filtered, concentrated, purified by reverse-phase preparative HPLC (aqueous solution containing 0.35% trifluoroacetic acid and methanol as mobile phase), and then concentrated in vacuo to obtain compound IL.

Compound IM could be synthesized by a similar method.

The table below lists the specific compounds and structure identification data.

TABLE 3

Structure and characterization of compounds IL-IM

| No. | Structure | $^1$H NMR and/or MS data |
|---|---|---|
| IL-1 | 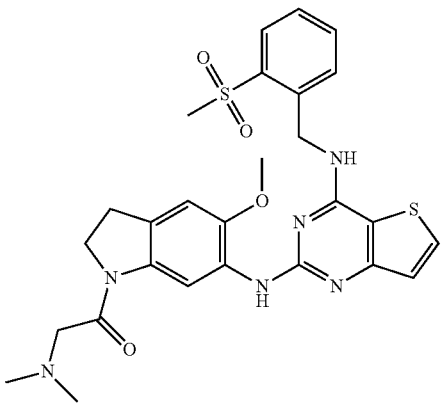<br>TFA salt | $^1$H NMR (600 MHz, Methanol-$d_4$) δ 8.66 (s, 1H), 8.19 (d, J = 5.4 Hz, 1H), 8.04 (dd, J = 8.2, 1.4 Hz, 1H), 7.64 (td, J = 7.6, 1.5 Hz, 1H), 7.58~7.51 (m, 2H), 7.29 (d, J = 5.4 Hz, 1H), 7.03 (s, 1H), 5.36 (s, 2H), 4.27 (s, 2H), 4.09 (t, J = 8.3 Hz, 2H), 3.84 (s, 3H), 3.30~3.26 (m, 2H), 3.19 (s, 3H), 2.95 (s, 6H). MS (ESI) m/z: 567 [M + H]$^+$. |
| IL-2 | 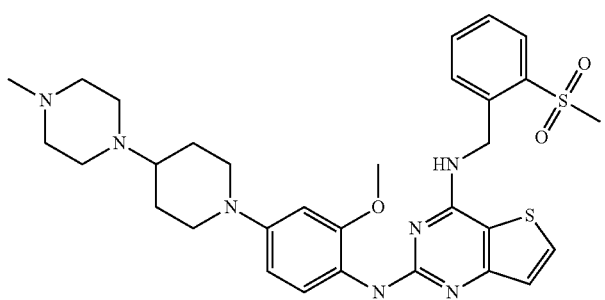<br>TFA salt | $^1$H NMR (600 MHz, Methanol-$d_4$) δ 8.19 (d, J = 5.4 Hz, 1H), 8.08 (dd, J = 7.9, 1.4 Hz, 1H), 7.71~7.66 (m, 1H), 7.61~7.52 (m, 2H), 7.32 (d, J = 8.7 Hz, 1H), 7.28 (d, J = 5.4 Hz, 1H), 6.87 (d, J = 2.6 Hz, 1H), 6.67 (d, J = 8.7 Hz, 1H), 5.25 (s, 2H), 3.90~3.84 (m, 3H), 3.83 (s, 3H), 3.45 (s, 4H), 3.15 (s, 3H), 3.11 (s, 2H), 2.93 (s, 3H), 2.19 (d, J = 12.1 Hz, 2H), 1.92 (p, J = 10.5, 9.2 Hz, 2H). MS (ESI) m/z: 622 [M + H]$^+$. |
| IL-3 | 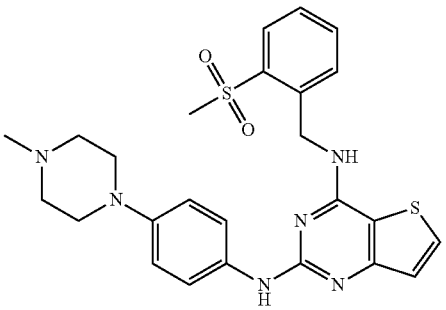<br>TFA salt | $^1$H NMR (600 MHz, Chloroform-d) δ 10.88 (s, 1H), 8.00 (dd, J = 7.9, 1.4 Hz, 1H), 7.79 (d, J = 5.3 Hz, 1H), 7.52~7.48 (m, 1H), 7.44 (dd, J = 14.7, 6.6 Hz, 4H), 7.26 (d, J = 5.5 Hz, 1H), 7.20 (d, J = 7.6 Hz, 1H), 6.95 (d, J = 8.5 Hz, 2H), 5.00 (d, J = 6.2 Hz, 2H), 3.68 (dd, J = 24.9, 12.5 Hz, 4H), 3.29 (d, J = 13.6 Hz, 2H), 3.15 (s, 2H), 3.10 (s, 3H), 2.92 (s, 3H). MS (ESI) m/z: 509 [M + H]$^+$. |

TABLE 3-continued

Structure and characterization of compounds IL-IM

| No. | Structure | ¹H NMR and/or MS data |
|---|---|---|
| IL-4 | 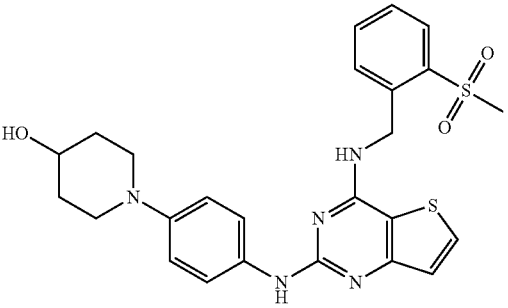<br>TFA salt | ¹H NMR (600 MHz, Methanol-$d_4$) δ 8.23 (d, J = 5.4 Hz, 1H), 8.12 (dd, J = 7.9, 1.3 Hz, 1H), 7.69 (td, J = 7.6, 1.4 Hz, 1H), 7.59 (td, J = 7.6, 1.2 Hz, 1H), 7.56 (dd, J = 7.8, 1.1 Hz, 1H), 7.49~7.40 (m, 2H), 7.39~7.33 (m, 3H), 5.30 (s, 2H), 4.04 (dq, J = 7.6, 3.7 Hz, 1H), 3.75 (ddd, J = 11.8, 7.9, 3.6 Hz, 2H), 3.45 (ddd, J = 12.0, 7.9, 3.6 Hz, 2H), 3.15 (s, 3H), 2.19 (ddt, J = 14.6, 7.4, 3.6 Hz, 2H), 1.95 (dtd, J = 14.2, 7.6, 3.6 Hz, 2H). MS (ESI) m/z: 510 [M + H]⁺. |
| IM-1 | 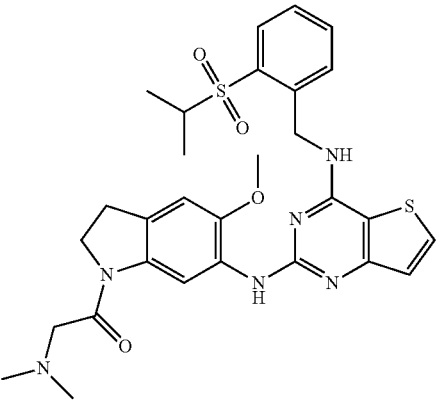<br>TFA salt | ¹H NMR (600 MHz, DMSO-$d_6$) δ 9.80 (s, 1H), 9.66 (s, 1H), 8.27 (d, J = 5.4 Hz, 1H), 8.24 (s, 1H), 7.90 (dd, J = 7.9, 1.5 Hz, 1H), 7.71 (td, J = 7.6, 1.4 Hz, 1H), 7.59 (td, J = 7.6, 1.2 Hz, 1H), 7.53 (d, J = 7.8 Hz, 1H), 7.30 (d, J = 5.4 Hz, 1H), 7.12 (s, 1H), 5.14 (d, J = 5.5 Hz, 2H), 4.37~4.28 (m, 2H), 4.05 (t, J = 8.4 Hz, 2H), 3.74 (s, 3H), 3.45 (p, J = 6.8 Hz, 1H), 3.23 (t, J = 8.4 Hz, 2H), 2.88~2.80 (m, 6H), 1.17 (d, J = 6.7 Hz, 6H). MS (ESI) m/z: 595 [M + H]⁺. |
| IM-2 | 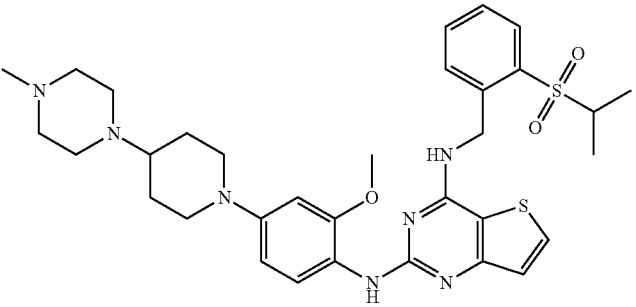<br>TFA salt | ¹H NMR (600 MHz, Methanol-$d_4$) δ 8.18 (d, J = 5.4 Hz, 1H), 8.01 (dd, J = 7.9, 1.3 Hz, 1H), 7.68 (td, J = 7.6, 1.4 Hz, 1H), 7.56 (q, J = 7.5 Hz, 2H), 7.44 (d, J = 8.7 Hz, 1H), 7.28 (d, J = 5.4 Hz, 1H), 6.92 (d, J = 2.5 Hz, 1H), 6.74 (dd, J = 8.8, 2.5 Hz, 1H), 5.27 (s, 2H), 3.87 (s, 1H), 3.85 (s, 4H), 3.49 (s, 4H), 3.42 (q, J = 6.8 Hz, 1H), 3.35 (s, 4H), 3.15 (t, J = 11.8 Hz, 3H), 2.94 (s, 3H), 2.21 (d, J = 12.7 Hz, 2H), 1.96 (qd, J = 11.7, 3.8 Hz, 2H), 1.29 (d, J = 6.8 Hz, 6H). MS (ESI) m/z: 650 [M + H]⁺. |
| IM-3 | 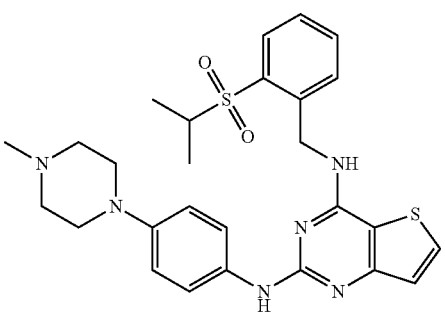<br>TFA salt | ¹H NMR (600 MHz, DMSO-$d_6$) δ 10.30 (s, 1H), 10.00 (s, 1H), 9.60 (s, 1H), 8.26 (d, J = 5.3 Hz, 1H), 7.94 (dd, J = 7.9, 1.4 Hz, 1H), 7.72 (td, J = 7.6, 1.4 Hz, 1H), 7.61 (td, J = 7.6, 1.2 Hz, 1H), 7.58~7.53 (m, 1H), 7.31~7.27 (m, 2H), 7.26 (s, 1H), 6.85 (d, J = 8.5 Hz, 2H), 5.16 (d, J = 5.6 Hz, 2H), 3.73 (d, J = 13.2 Hz, 2H), 3.52 (d, J = 11.9 Hz, 2H), 3.44 (p, J = 6.8 Hz, 1H), 3.16 (d, J = 12.5 Hz, 2H), 2.91 (s, 2H), 2.86 (s, 3H), 1.16 (d, J = 6.8 Hz, 6H). MS (ESI) m/z: 537 [M + H]⁺. |

TABLE 3-continued

Structure and characterization of compounds IL-IM

| No. | Structure | ¹H NMR and/or MS data |
|---|---|---|
| IM-4 | 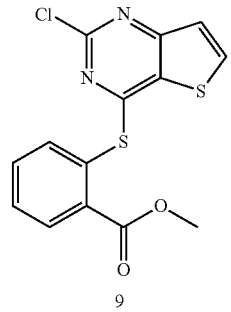<br>TFA salt | ¹H NMR (600 MHz, Chloroform-d) δ 11.66 (s, 1H), 7.97~7.89 (m, 2H), 7.83 (d, J = 5.3 Hz, 1H), 7.77 (d, J = 8.6 Hz, 2H), 7.59 (d, J = 8.6 Hz, 2H), 7.51 (tt, J = 7.4, 5.6 Hz, 2H), 7.40~7.35 (m, 1H), 7.28 (d, J = 5.3 Hz, 1H), 5.09 (d, J = 6.2 Hz, 2H), 4.18 (s, 1H), 3.79 (t, J = 10.6 Hz, 2H), 3.46 (dd, J = 8.8, 4.2 Hz, 2H), 3.27 (p, J = 6.8 Hz, 1H), 2.40~2.25 (m, 2H), 2.06 (d, J = 14.2 Hz, 2H), 1.32 (d, J = 6.8 Hz, 6H). MS (ESI) m/z: 538 [M + H]⁺. |

Example 4

Synthetic Scheme of Compound

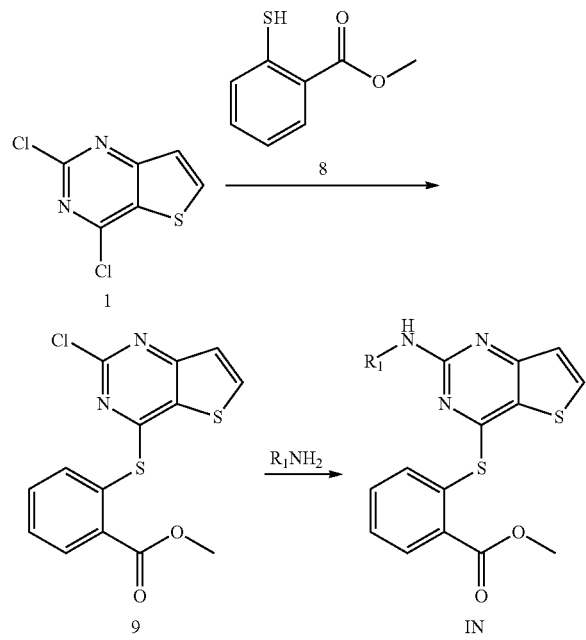

Preparation of Compound 9

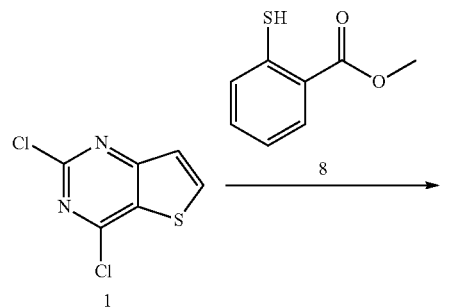

Compound 1 (500 mg, 2.44 mmol), compound 8 (0.09 mmol) were dissolved in mL of tert-butanol, then to the solution were added 2-dicyclohexylphosphino-2,4,6-triisopropylbiphenyl (135 mg, 0.17 mmol), tris(dibenzylideneacetone)dipalladium (90 mg, 0.06 mmol), potassium carbonate (1.01 g, 3.0 mmol); under the protection of nitrogen, the resulting reaction solution was heated and stirred in an oil bath preheated to 45° C. until complete reaction of compound 1 (LC-MS and TLC tracking), then the reaction was stopped. The system was filtered, and washed with methanol, the filtrate was concentrated and separated by silica gel column chromatography (dichloromethane/aminomethanol=5/1) to obtain compound 9 (yellow solid, 540 mg, yield 65.7%), which was directly used for the next step reaction.

MS (ESI) m/z: 337 [M+H]⁺

Preparation of Compound IN

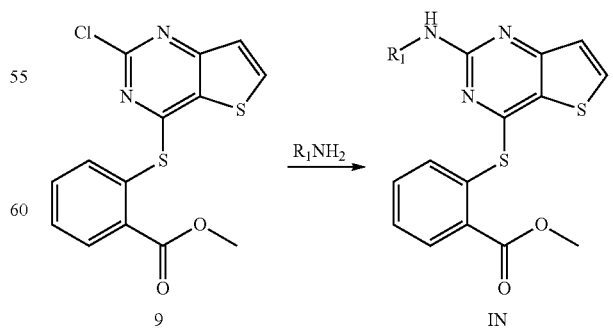

Compound 9 (50 mg, 0.15 mmol) and arylamine (0.13 mmol) were dissolved in 1 mL of tert-butanol, then to the solution was added trifluoroacetic acid (35 µL, 0.45 mmol). The resulting reaction solution was heated and stirred in an oil bath preheated to 110° C. until complete reaction of arylamine (LC-MS and TLC tracking), then the reaction was stopped. The reaction solution was concentrated, purified by reverse-phase preparative HPLC (aqueous solution containing 0.35% trifluoroacetic acid and methanol as mobile phase), and then concentrated in vacuo to obtain compound IN.

The table below lists the specific compounds and structure identification data.

TABLE 4

Structure and characterization of compounds IN

| No. | Structure | ¹H NMR and/or MS data |
|---|---|---|
| IN-1 | 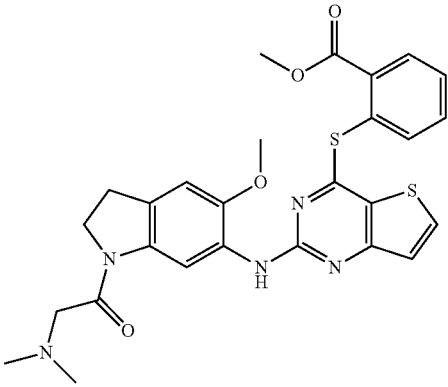 TFA salt | ¹H NMR (600 MHz, DMSO-d$_6$) δ 8.74 (s, 1H), 8.23 (d, J = 5.3 Hz, 1H), 8.11 (s, 1H), 7.92-7.90 (m, 1H), 7.71 (dd, J = 7.0, 2.1 Hz, 1H), 7.62-7.56 (m, 2H), 7.20 (d, J = 5.4 Hz, 1H), 7.02 (s, 1H), 4.34 (d, J = 4.1 Hz, 2H), 4.05 (t, J = 8.3 Hz, 2H), 3.78 (s, 3H), 3.73 (s, 3H), 3.21 (t, J = 8.3 Hz, 2H), 2.89 (d, J = 3.8 Hz, 6H). MS (ESI) m/z: 550 [M + H]⁺. |
| IN-2 | 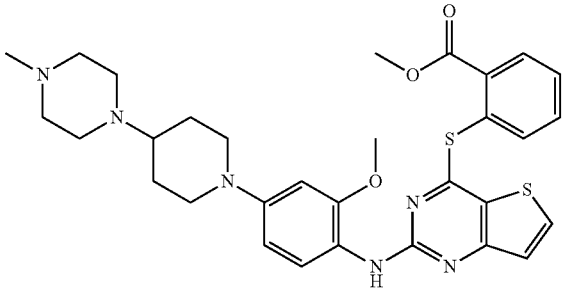 TFA salt | ¹H NMR (600 MHz, DMSO-d$_6$) δ 8.26 (d, J = 5.4 Hz, 1H), 7.97-7.95 (m, 2H), 7.79-7.76 (m, 1H), 7.67-7.65 (m, 2H), 7.57 (s, 1H), 7.30 (d, J = 5.4 Hz, 1H), 6.82 (s, 1H), 6.50 (s, 1H), 3.82 (s, 3H), 3.79 (d, J = 12.5 Hz, 2H), 3.73 (s, 3H), 3.17 (s, 1H), 2.88 (s, 3H), 2.14 (d, J = 12.0 Hz, 2H), 1.77 (d, J = 12.7 Hz, 2H). MS (ESI) m/z: 605 [M + H]⁺. |
| IN-3 | 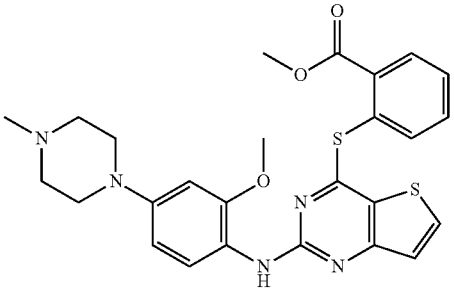 TFA salt | ¹H NMR (600 MHz, DMSO-d$_6$) δ 9.95 (s, 1H), 8.24 (d, J = 5.4 Hz, 1H), 7.97-7.94 (m, 1H), 7.91 (s, 1H), 7.77-7.74 (m, 1H), 7.66-7.64 (m, 2H), 7.28 (d, J = 5.4 Hz, 1H), 6.67 (d, J = 2.6 Hz, 1H), 6.34 (d, J = 8.7 Hz, 1H), 3.80 (s, 5H), 3.73 (s, 3H), 3.55 (d, J = 11.9 Hz, 2H), 3.18 (d, J = 9.5 Hz, 2H), 2.93 (t, J = 12.8 Hz, 2H), 2.89 (d, J = 3.1 Hz, 3H). MS (ESI) m/z: 522 [M + H]⁺. |

TABLE 4-continued

Structure and characterization of compounds IN

| No. | Structure | $^1$H NMR and/or MS data |
|---|---|---|
| IN-4 | 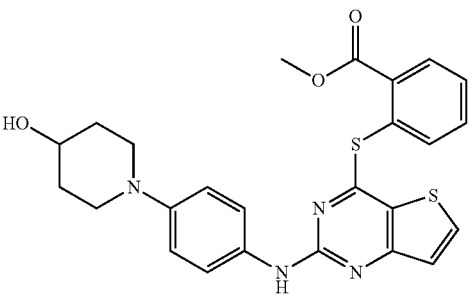<br>TFA salt | $^1$H NMR (600 MHz, DMSO-$d_6$) δ 9.95 (s, 1H), 8.24 (d, J = 5.4 Hz, 1H), 7.97-7.94 (m, 1H), 7.91 (s, 1H), 7.77-7.74 (m, 1H), 7.66-7.64 (m, 2H), 7.28 (d, J = 5.4 Hz, 1H), 6.67 (d, J = 2.6 Hz, 1H), 6.34 (d, J = 8.7 Hz, 1H), 3.80 (s, 5H), 3.73 (s, 3H), 3.55 (d, J = 11.9 Hz, 2H), 3.18 (d, J = 9.5 Hz, 2H), 2.93 (t, J = 12.8 Hz, 2H), 2.89 (d, J = 3.1 Hz, 3H). MS (ESI) m/z: 493 [M + H]$^+$. |
| IN-5 | 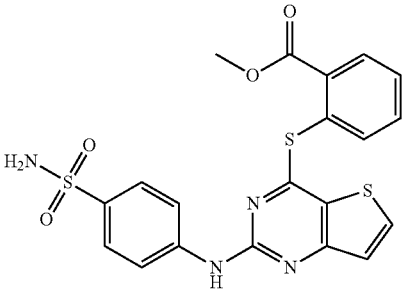<br>TFA salt | $^1$H NMR (600 MHz, DMSO-$d_6$) δ 10.03 (s, 1H), 8.33 (d, J = 5.4 Hz, 1H), 8.02-7.99 (m, 1H), 7.85-7.82 (m, 1H), 7.73-7.70 (m, 2H), 7.54 (d, J = 8.4 Hz, 2H), 7.50 (d, J = 8.6 Hz, 2H), 7.40 (d, J = 5.4 Hz, 1H), 7.18 (s, 2H), 3.72 (s, 3H). MS (ESI) m/z: 473 [M + H]$^+$. |
| IN-6 | 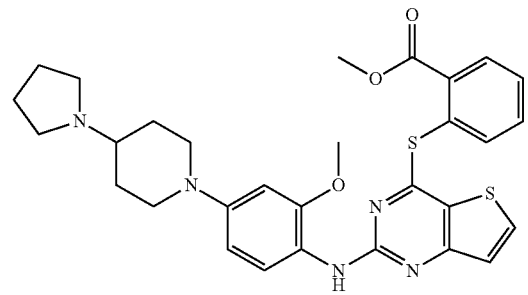<br>TFA salt | $^1$H NMR (600 MHz, DMSO-$d_6$) δ 9.83 (S, 1H), 8.23 (d, J = 5.4 Hz, 1H), 7.97-7.95 (m, 1H), 7.88 (s, 1H), 7.77-7.75 (m, 1H), 7.65 (dd, J = 5.8, 3.4 Hz, 2H), 7.28 (d, J = 5.4 Hz, 1H), 6.68 (d, J = 2.6 Hz, 1H), 6.37 (d, J = 8.7 Hz, 1H), 3.80 (s, 3H), 3.61-3.55 (m, 3H), 3.29 - 3.27 (m, 1H), 3.13-3.09 (m, 2H), 2.74 (t, J = 12.3 Hz, 2H), 2.15 (d, J = 12.3 Hz, 2H), 2.03 (d, J = 7.5 Hz, 2H), 1.87 (d, J = 6.6 Hz, 2H), 1.73 (d, J = 8.9 Hz, 2H). MS (ESI) m/z: 576 [M + H]$^+$. |
| IN-7 | 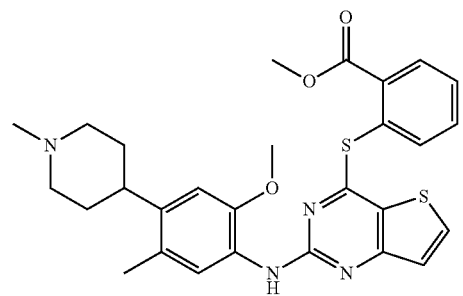<br>TFA salt | $^1$H NMR (600 MHz, DMSO-$d_6$) δ 8.26 (d, J = 5.4 Hz, 1H), 7.96 (s, 1H), 7.94-7.92 (m, 1H), 7.76-7.73 (m, 1H), 7.69 (s, 1H), 7.62-7.59 (m, 2H), 7.33 (d, J = 5.4 Hz, 1H), 6.73 (s, 1H), 3.79 (s, 3H), 3.71 (s, 3H), 3.52 (d, J = 11.9 Hz, 2H), 3.15-3.08 (m, 2H), 2.82 (d, J = 4.5 Hz, 3H), 2.13 (s, 3H), 1.95-1.85 (m, 4H). MS (ESI) m/z: 535 [M + H]$^+$. |

Example 5

Compound IO

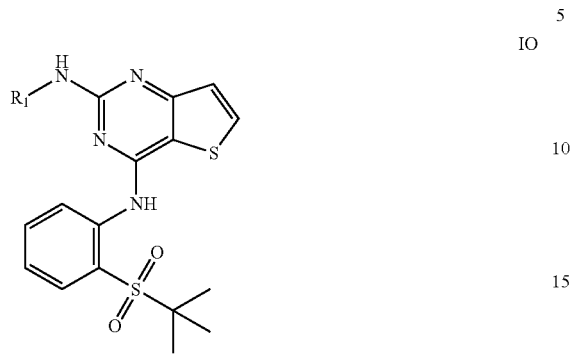

Compound IO was synthesized by a method similar to that for the synthesis of IA.

The table below lists the specific compounds and structure identification data.

TABLE 5

Structure and characterization of compounds IO

| No. | Structure | $^1$H NMR and/or MS data |
|---|---|---|
| IO-1 | 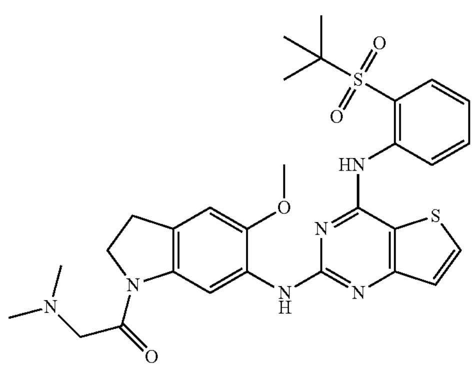 [SMILES: COc1cc2c(cc1Nc1nc(Nc3ccccc3S(=O)(=O)C(C)(C)C)c3sccc3n1)N(C(=O)CN(C)C)CC2] | MS (ESI) m/z: 595 [M + H]$^+$. |
| IO-2 (TFA salt) | | $^1$H NMR (600 MHz, Methanol-d4) δ 8.46 (s, 1H), 8.26 (d, J = 5.4 Hz, 1H), 7.95 (dd, J = 8.0, 1.6 Hz, 1H), 7.73 (t, J = 7.9 Hz, 1H), 7.49 (t, J = 7.8, 1.2 Hz, 1H), 7.46 (d, J = 8.5 Hz, 1H), 7.33 (d, J = 5.4 Hz, 1H), 6.93 (d, J = 2.5 Hz, 1H), 6.80 (dd, J = 8.7, 2.6 Hz, 1H), 3.96-3.90 (m, 2H), 3.87 (s, 3H), 3.58 (s, 4H), 3.49 (s, 4H), 3.12 (t, J = 12.5, 2.4 Hz, 2H), 2.97 (s, 3H), 2.26 (d, J = 13.0, 2.9 Hz, 2H), 1.98 (qd, J = 12.3, 4.0 Hz, 2H), 1.30 (s, 9H). MS (ESI) m/z: 650 [M + H]$^+$. |

TABLE 5-continued

Structure and characterization of compounds IO

| No. | Structure | $^1$H NMR and/or MS data |
|---|---|---|
| IO-3 | 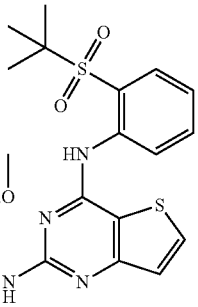<br>TFA salt | $^1$H NMR (600 MHz, Methanol-d4) δ 8.49 (s, 1H), 8.25 (d, J = 5.4 Hz, 1H), 7.93 (dd, J = 7.9, 1.7 Hz, 1H), 7.68 (s, 1H), 7.46 (t, J = 7.7 Hz, 1H), 7.36 (d, J = 8.5 Hz, 1H), 7.33 (d, J = 5.5 Hz, 1H), 6.79 (d, J = 2.6 Hz, 1H), 6.66 (d, 1H), 3.95 (d, J = 12.8 Hz, 2H), 3.84 (s, 3H), 3.66 (d, 2H), 3.34-3.27 (m, 2H), 3.16 (t, J = 12.9 Hz, 2H), 3.00 (s, 3H), 1.30 (s, 9H). MS (ESI) m/z: 567 [M + H]$^+$. |
| IO-4 | 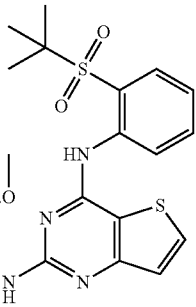<br>TFA salt | $^1$H NMR (600 MHz, Methanol-d4) δ 8.49 (s, 1H), 8.25 (d, J = 5.3 Hz, 1H), 7.93 (dd, J = 8.0, 1.5 Hz, 1H), 7.70 (s, 1H), 7.47 (t, J = 7.7 Hz, 1H), 7.37 (d, J = 8.5 Hz, 1H), 7.33 (d, J = 5.4 Hz, 1H), 6.84 (d, J = 2.5 Hz, 1H), 6.72 (dd, J = 8.7, 2.5 Hz, 1H), 4.00-3.93 (m, 2H), 3.85 (s, 3H), 3.45 (tt, J = 12.1, 3.9 Hz, 1H), 3.01 (t, J = 12.6, 2.3 Hz, 2H), 2.93 (s, 6H), 2.26 (dt, J = 12.6, 2.9 Hz, 2H), 1.96 (qd, J = 12.5, 4.2 Hz, 2H), 1.30 (s, 9H). MS (ESI) m/z: 595 [M + H]$^+$. |

Example 6

Compounds IP, IQ

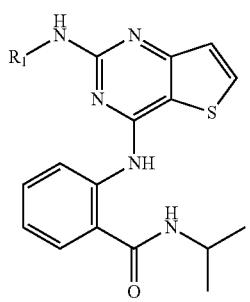

IP

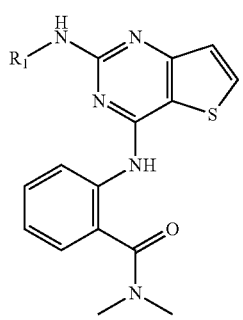

IQ

Compounds IP, IQ were synthesized by a method similar to that for the synthesis of IA.

The table below lists the specific compounds and structure identification data.

TABLE 6

Structure and characterization of compounds IP, IQ

| No. | Structure | $^1$H NMR and/or MS data |
|---|---|---|
| IP-1 | TFA salt | $^1$H NMR (600 MHz, Methanol-d4) δ 8.31 (s, 1H), 8.20 (d, J = 5.4 Hz, 1H), 7.77 (dd, J = 7.8, 1.5 Hz, 1H), 7.51 (t, J = 7.8 Hz, 1H), 7.39 (s, 1H), 7.34 (t, J = 7.6 Hz, 1H), 7.27 (d, J = 5.4 Hz, 1H), 6.86 (d, J = 1.8 Hz, 1H), 6.74 (dd, J = 8.7, 2.5 Hz, 1H), 4.19 (hept, J = 6.6 Hz, 1H), 3.94-3.88 (m, 2H), 3.86 (s, 3H), 3.40 (s, 4H), 3.28 (s, 4H), 3.13-2.96 (m, 3H), 2.89 (s, 3H), 2.17 (dt, J = 12.6, 2.9 Hz, 2H), 1.87 (qd, J = 12.1, 4.0 Hz, 2H), 1.21 (d, J = 6.6 Hz, 6H). MS (ESI) m/z: 615 [M + H]$^+$. |
| IP-2 | TFA salt | $^1$H NMR (600 MHz, Methanol-d4) δ 8.40-8.25 (m, 1H), 8.21 (d, J = 5.4 Hz, 1H), 7.78 (dd. J = 7.8, 1.5 Hz, 1H), 7.50 (s, 1H), 7.43-7.30 (m, 2H), 7.27 (d, J = 5.4 Hz, 1H), 6.82 (d, J = 2.5 Hz, 1H), 6.68 (dd, J = 8.7, 2.5 Hz, 1H), 4.20 (h, J = 6.5 Hz, 1H), 4.03-3.91 (m, 2H), 3.86 (s, 3H), 3.73-3.56 (m, 2H), 3.37-3.25 (m, 2H), 3.22-3.08 (m, 2H), 3.00 (s, 3H), 1.21 (d, J = 6.7 Hz, 6H). MS (ESI) m/z: 532 [M + H]$^+$. |
| IP-3 | TFA salt | $^1$H NMR (600 MHz, Methanol-d4) δ 8.43-8.26 (m, 1H), 8.20 (d, J = 5.4 Hz, 1H), 7.77 (dd, J = 7.8, 1.5 Hz, 1H), 7.51 (s, 1H), 7.30 (dd, J = 33.6, 7.5 Hz, 3H), 6.77 (d, J = 2.6 Hz, 1H), 6.66 (dd, J = 8.6, 2.5 Hz, 1H), 4.20 (hept, J = 6.5 Hz, 1H), 3.99 (dt, J = 15.0, 3.3 Hz, 2H), 3.85 (s, 3H), 3.40 (tt, J = 12.2, 4.0 Hz, 1H), 2.93 (s, 6H), 2.89 (td, J = 12.7, 2.3 Hz, 2H), 2.25-2.18 (m, 2H), 1.89 (tt, J = 12.3, 6.2 Hz, 2H), 1.21 (d, J = 6.6 Hz, 6H). MS (ESI) m/z: 560 [M + H]$^+$. |
| IQ-1 | 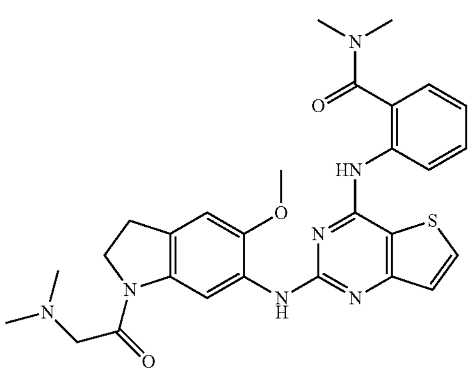 [SMILES: COc1cc2c(cc1Nc1nc(Nc3ccccc3C(=O)N(C)C)c3sccc3n1)N(C(=O)CN(C)C)CC2] | MS (ESI) m/z: 546 [M + H]$^+$. |

Example 7

Compounds IR, IS

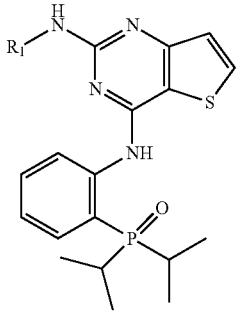

IR

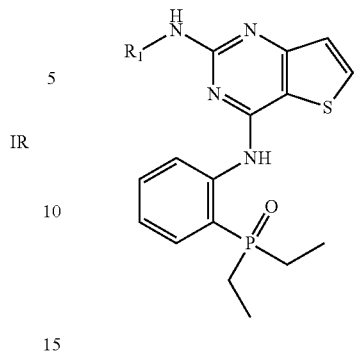

IS

Compounds IR, IS were synthesized by a method similar to that for the synthesis of IA.

The table below lists the specific compounds and structure identification data.

TABLE 7

Structure and characterization of compounds IR, IS

| No. | Structure | $^1$H NMR and/or MS data |
|---|---|---|
| IR-1 | (structure shown; TFA salt) | $^1$H NMR (600 MHz, Methanol-d4) δ 8.69 (s, 1H), 8.27 (s, 1H), 8.26 (d, J = 5.4 Hz, 1H), 7.52 (dd, J = 11.4, 7.7, 1.5 Hz, 1H), 7.44 (s, 1H), 7.33 (d, J = 5.4 Hz, 1H), 7.30 (t, J = 7.5, 4.1 Hz, 1H), 7.20 (s, 1H), 4.34 (s, 2H), 4.21-4.15 (m, 2H), 3.84 (s, 3H), 3.41 (t, J = 8.3 Hz, 2H), 2.98 (s, 6H), 2.66-2.56 (m, 2H), 1.24 (dd. J = 15.9, 7.1 Hz, 6H), 1.12 (dd, J = 16.5, 7.1 Hz, 6H). MS (ESI) m/z: 607 [M + H]$^+$. |
| IR-2 | (structure shown) | $^1$H NMR (600 MHz, Methanol-d4) δ 8.79 (dd, J = 8.5, 3.8 Hz, 1H), 7.95 (d, J = 5.4 Hz, 1H), 7.91 (d, J = 8.6 Hz, 1H), 7.52 (ddt, J = 8.6, 7.3, 1.3 Hz, 1H), 7.44 (ddd, J = 11.6, 7.8, 1.6 Hz, 1H), 7.20-7.15 (m, 2H), 6.71 (d, J = 2.6 Hz, 1H), 6.60 (dd, J = 8.7, 2.5 Hz, 1H), 3.88 (s, 3H), 3.80 (d, J = 12.8, 2.1 Hz, 2H), 3.42 (s, 4H), 3.25 (tt, J = 11.9, 4.1 Hz, 1H), 2.80 (td, J = 12.5, 2.2 Hz, 2H), 2.57 (dp, J = 8.6, 7.0 Hz, 2H), 2.29-2.21 (m, 2H), 2.10 (s, 4H), 1.86 (qd, J = 12.2, 4.1 Hz, 2H), 1.23 (dd, J = 15.6, 7.1 Hz, 6H), 1.12 (dd, J = 16.4, 7.1 Hz, 6H). MS (ESI) m/z: 633 [M + H]$^+$. |

TABLE 7-continued

Structure and characterization of compounds IR, IS

| No. | Structure | ¹H NMR and/or MS data |
|---|---|---|
| IR-3 | TFA salt | MS (ESI) m/z: 579 [M + H]⁺. |
| IR-4 | TFA salt | ¹H NMR (600 MHz, Methanol-d4) δ 8.71 (s, 1H), 8.24 (d, J = 5.4 Hz, 1H), 7.59-7.50 (m, 2H), 7.46 (d, J = 8.3 Hz, 1H), 7.33 (dd, J = 7.5, 3.6 Hz, 2H), 6.97 (s, 1H), 6.86 (dd, J = 8.7, 2.5 Hz, 1H), 3.97 (d, J = 13.9, 3.3 Hz, 2H), 3.87 (s, 3H), 3.61 (s, 4H), 3.56 (s, 4H), 3.38 (tt, J = 11.8, 3.9 Hz, 1H), 3.14 (t, J = 12.3 Hz, 2H), 2.98 (s, 3H), 2.65-2.57 (m, 2H), 2.29 (d, J = 13.0, 3.0 Hz, 2H), 2.01 (qd, J = 12.4, 4.0 Hz, 2H), 1.18 (ddd, J = 70.7, 16.2, 7.1 Hz, 12H). MS (ESI) m/z: 662 [M + H]⁺. |
| IR-5 | 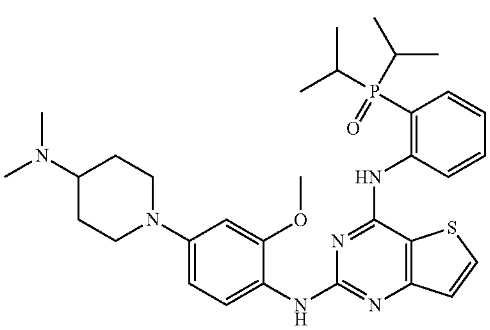 [SMILES: COc1cc(N2CCC(N(C)C)CC2)ccc1Nc1nc(Nc2ccccc2P(=O)(C(C)C)C(C)C)c2sccc2n1] | ¹H NMR (600 MHz, Methanol-d4) δ 8.76 (d, J = 8.6, 4.0, 1.0 Hz, 1H), 7.91 (d, J = 5.3 Hz, 1H), 7.87 (d, J = 8.7 Hz, 1H), 7.48 (ddt, J = 8.6, 7.3, 14 Hz, 1H), 7.37 (ddd, J = 11.4, 7.8, 1.5 Hz, 1H), 7.16-7.12 (m, 2H), 6.65 (d, J = 2.5 Hz, 1H), 6.54 (dd, J = 8.7, 2.6 Hz, 1H), 3.83 (s, 3H), 3.70-3.63 (m, 2H), 2.64 (td, J = 12.3, 2.4 Hz, 2H), 2.51 (dp, J = 8.4, 7.0 Hz, 2H), 2.29 (s, 6H), 2.25 (ddt, J = 11.5, 7.6, 3.8 Hz, 1H), 1.98-1.93 (m, 2H), 1.61 (qd, J = 12.3, 4.0 Hz, 2H), 1.20 (dd, J = 15.6, 7.1 Hz, 6H), 1.08 (dd, J = 16.4, 7.1 Hz, 6H). MS (ESI) m/z: 607 [M + H]⁺. |
| IR-6 | TFA salt | ¹H NMR (600 MHz, Methanol-d4) δ 8.72 (s, 1H), 8.25 (d, J = 5.4 Hz, 1H), 7.54 (m, 2H), 7.47-7.40 (m, 2H), 7.36-7.28 (m, 2H), 7.20-7.14 (m, 2H), 3.94 (d, J = 13.4 Hz, 2H), 3.66 (d, J = 11.5 Hz, 2H), 3.37-3.27 (m, 2H), 3.15 (d, J = 13.3 Hz, 2H), 3.00 (s, 3H), 2.61 (dp, J = 8.6, 7.1 Hz, 2H), 1.18 (ddd, J = 72.0, 16.2, 7.1 Hz, 12H). MS (ESI) m/z: 549 [M + H]⁺. |

TABLE 7-continued

Structure and characterization of compounds IR, IS

| No. | Structure | ¹H NMR and/or MS data |
|---|---|---|
| IS-1 | (structure shown; TFA salt) | ¹H NMR (600 MHz, Methanol-d4) δ 8.59 (s, 1H), 8.26 (s, 1H), 8.24 (d, J = 5.3 Hz, 1H), 7.56 (dd, J = 13.0, 7.7 Hz, 1H), 7.43 (s, 1H), 7.35-7.29 (m, 2H), 7.18 (s, 1H), 4.34 (s, 2H), 4.17 (t, J = 8.4 Hz, 2H), 3.84 (s, 3H), 3.39 (t, J = 8.3 Hz, 2H), 2.99 (s, 6H), 2.24-2.09 (m, 4H), 1.14 (dt, J = 17.7, 7.6 Hz, 6H). MS (ESI) m/z: 579 [M + H]⁺. |
| IS-2 | (structure shown; TFA salt) | ¹H NMR (600 MHz, Methanol-d4) δ 8.67 (s, 1H), 8.21 (d, J = 5.4 Hz, 1H), 7.59 (dd, J = 12.9, 7.7 Hz, 1H), 7.54 (s, 1H), 7.32 (dt, J = 23.9, 6.5 Hz, 3H), 6.80-6.77 (m, 1H), 3.96 (dt, J = 12.7, 2.3 Hz, 2H), 3.85 (s, 3H), 3.75-3.68 (m, 2H), 3.39-3.32 (m, 1H), 3.20 (q, J = 9.5, 9.0 Hz, 2H), 2.91 (td, J = 12.8, 2.3 Hz, 2H), 2.30 (dq, J = 12.0, 2.5 Hz, 2H), 2.24-2.10 (m, 6H), 2.05 (dd, J = 16.1, 9.9 Hz, 2H), 1.89 (qd, J = 12.3, 4.1 Hz, 2H), 1.14 (dt, J = 17.8, 7.6 Hz, 6H). MS (ESI) m/z: 605 [M + H]⁺. |
| IS-3 | (structure shown; TFA salt) | ¹H NMR (600 MHz, Methanol-d4) δ 8.63 (s, 1H), 8.23 (d, J = 5.4 Hz, 1H), 7.60 (ddd, J = 12.9, 7.8, 1.5 Hz, 1H), 7.56 (t, J = 7.3 Hz, 1H), 7.42 (d, J = 8.6 Hz, 1H), 7.36 (ddd, J = 8.6, 5.4, 1.9 Hz, 1H), 7.30 (d, J = 5.4 Hz, 1H), 6.92 (d, J = 2.5 Hz, 1H), 6.80 (dd, J = 8.7, 2.5 Hz, 1H), 3.95 (d, J = 12.8 Hz, 2H), 3.87 (s, 3H), 3.52 (s, 4H), 3.42 (s, 4H), 3.24 (t, J = 10.9 Hz, 1H), 3.08 (t, J = 12.2 Hz, 2H), 2.95 (s, 3H), 2.23 (d, J = 12.1 Hz, 2H), 2.20-2.11 (m, 4H), 1.95 (q, J = 11.6 Hz, 2H), 1.14 (dt, J = 17.7, 7.6 Hz, 6H). MS (ESI) m/z: 634 [M + H]⁺. |
| IS-4 | (structure shown; TFA salt) | ¹H NMR (600 MHz, Methanol-d4) δ 8.60 (s, 1H), 8.21 (d, J = 5.4 Hz, 1H), 7.58 (dd, J = 12.9, 7.8 Hz, 1H), 7.51 (s, 1H), 7.35 (q, J = 8.9, 7.5 Hz, 2H), 7.31 (d, J = 5.4 Hz, 1H), 6.81 (d, J = 2.5 Hz, 1H), 6.69 (dd, J = 8.7, 2.5 Hz, 1H), 3.96 (d, J = 13.2 Hz, 2H), 3.85 (s, 3H), 3.67 (d, J = 10.4 Hz, 2H), 3.36-3.27 (m, 2H), 3.18 (t, J = 12.8 Hz, 2H), 3.00 (s, 3H), 2.23-2.08 (m, 4H), 1.14 (dt, J = 17.7, 7.6 Hz, 6H). MS (ESI) m/z: 551 [M + H]⁺. |

TABLE 7-continued

Structure and characterization of compounds IR, IS

| No. | Structure | ¹H NMR and/or MS data |
|---|---|---|
| IS-5 | 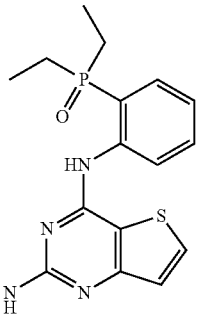<br>TFA salt | ¹H NMR (600 MHz, Methanol-d4) δ 8.63 (s, 1H), 8.24 (d, J = 5.4 Hz, 1H), 7.60 (dd, J = 12.9, 7.6 Hz, 1H), 7.53 (s, 1H), 7.45-7.39 (m, 2H), 7.36 (t, J = 7.5 Hz, 1H), 7.32 (d, J = 5.4 Hz, 1H), 7.18-7.13 (m, 2H), 3.93 (d, J = 13.8 Hz, 2H), 3.73-3.58 (m, 2H), 3.36-3.32 (m, 2H), 3.11 (s, 2H), 3.01 (s, 3H), 2.24-2.09 (m, 4H), 1.13 (dt, J = 17.8, 7.6 Hz, 6H). MS (ESI) m/z: 521 [M + H]⁺. |
| IS-6 | 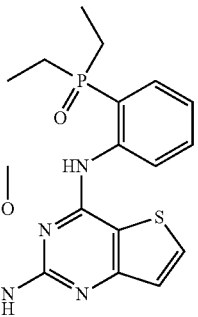<br>TFA salt | ¹H NMR (600 MHz, Methanol-d4) δ 8.61 (s, 1H), 8.21 (d, J = 5.4 Hz, 1H), 7.59 (ddd, J = 12.9, 7.7, 1.5 Hz, 1H), 7.53 (s, 1H), 7.41-7.33 (m, 2H), 7.31 (d, J = 5.4 Hz, 1H), 6.85 (d, J = 2.6 Hz, 1H), 6.74 (dd, J = 8.6, 2.5 Hz, 1H), 3.98 (dp, J = 13.0, 2.1 Hz, 2H), 3.85 (s, 3H), 3.45 (tt, J = 12.1, 3.9 Hz, 1H), 3.02 (td, J = 12.8, 12.4, 2.3 Hz, 2H), 2.94 (s, 6H), 2.26 (dt, J = 13.5, 2.7 Hz, 2H), 2.22-2.08 (m, 4H), 1.96 (qd, J = 12.3, 4.0 Hz, 2H), 1.13 (dt, J = 17.7, 7.6 Hz, 6H). MS (ESI) m/z: 579 [M + H]⁺. |

Example 8

Compound IT

IT

Compound IT was synthesized by a method similar to that for the synthesis of IA.

The table below lists the specific compounds and structure identification data.

TABLE 8

Structure and characterization of compounds IT

| No. | Structure | ¹H NMR and/or MS data |
|---|---|---|
| IT-1 | 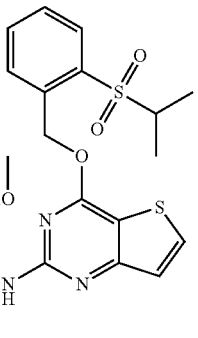 TFA salt | ¹H NMR (600 MHz, Methanol-d4) δ 8.87 (s, 1H), 8.25 (d, J = 5.4 Hz, 1H), 8.04 (dd, J = 7.9, 1.3 Hz, 1H), 7.85 (dd, J = 7.7, 1.4 Hz, 1H), 7.79 (td, J = 7.5, 1.4 Hz, 1H), 7.69 (td, J = 7.7, 1.4 Hz, 1H), 7.35 (d, J = 5.4 Hz, 1H), 7.10 (s, 1H), 6.16 (s, 2H), 4.28 (s, 2H), 4.10 (t, J = 8.3 Hz, 2H), 3.91 (s, 3H), 3.53 (hept, J = 6.8 Hz, 1H), 3.33-3.29 (m, 2H), 2.91 (s, 6H), 1.24 (d, J = 6.8 Hz, 6H). MS (ESI) m/z: 596 [M + H]⁺. |
| IT-2 | 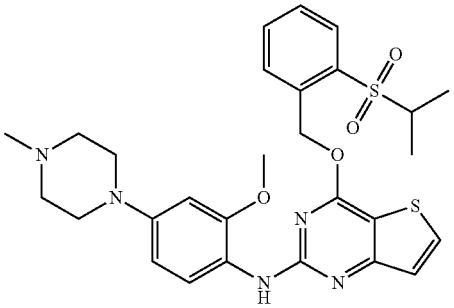 TFA salt | ¹H NMR (600 MHz, Methanol-d4) δ 8.28 (d, J = 5.3 Hz, 1H), 8.05 (dt, J = 7.9, 0.9 Hz, 1H), 7.81-7.78 (m, 2H), 7.72-7.67 (m, 1H), 7.49 (d, J = 8.7 Hz, 1H), 7.33 (d, J = 5.4 Hz, 1H), 6.80 (s, 1H), 6.69 (d, J = 8.1 Hz, 1H), 6.09 (s, 2H), 3.95 (d, J = 12.8 Hz, 2H), 3.88 (s, 3H), 3.65 (d, J = 12.1 Hz, 2H), 3.49 (hept, J = 6.8 Hz, 1H), 3.33-3.26 (m, 2H), 3.15 (s, 2H), 2.99 (s, 3H), 1.27 (d, J = 6.8 Hz, 6H). MS (ESI) m/z: 568 [M + H]⁺. |
| IT-3 | 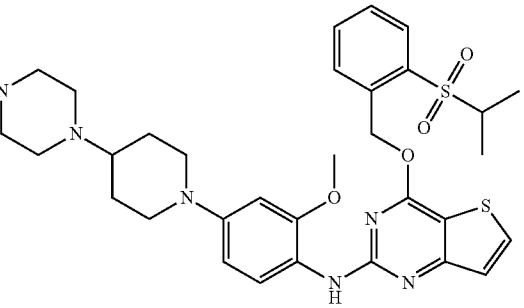 | MS (ESI) m/z: 651 [M + H]⁺. |
| IT-4 | 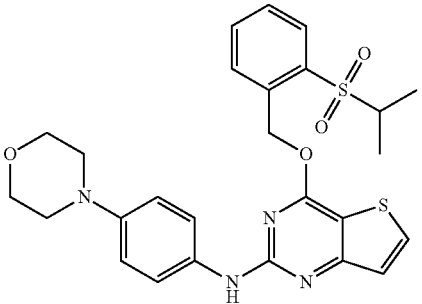 TFA salt | ¹H NMR (600 MHz, Methanol-d4) δ 8.01 (dd, J = 7.9, 1.3 Hz, 1H), 7.94 (d, J = 5.4 Hz, 1H), 7.79 (dd, J = 7.9, 1.3 Hz, 1H), 7.72 (td, J = 7.6, 1.4 Hz, 1H), 7.62 (td, J = 7.6, 1.4 Hz, 1H), 7.56-7.52 (m, 2H), 7.19 (d, J = 5.3 Hz, 1H), 6.97-6.92 (m, 2H), 6.02 (s, 2H), 3.85-3.80 (m, 4H), 3.56 (p, J = 6.8 Hz, 1H), 3.08 (t, J = 4.7 Hz, 4H), 1.24 (d, J = 6.8 Hz, 6H). MS (ESI) m/z: 525 [M + H]⁺. |

TABLE 8-continued

Structure and characterization of compounds IT

| No. | Structure | ¹H NMR and/or MS data |
|---|---|---|
| IT-5 | 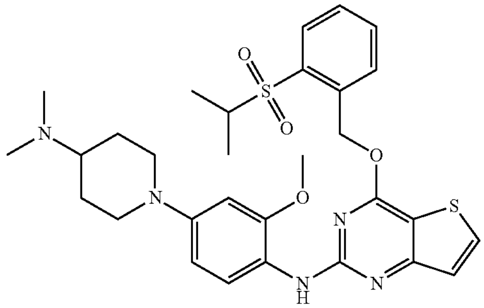 [SMILES: COc1cc(N2CCC(N(C)C)CC2)ccc1Nc1nc(OCc2ccccc2S(=O)(=O)C(C)C)c2sccc2n1] | ¹H NMR (600 MHz, Methanol-d4) δ 8.07 (d, J = 8.7 Hz, 1H), 8.01 (dd, J = 7.9, 1.3 Hz, 1H), 7.96 (d, J = 5.4 Hz, 1H), 7.75 (dd, J = 7.9, 1.4 Hz, 1H), 7.71 (td, J = 7.5, 1.4 Hz, 1H), 7.61 (td, J = 7.6, 1.5 Hz, 1H), 7.19 (d, J = 5.3 Hz, 1H), 6.66 (d, J = 2.6 Hz, 1H), 6.59 (dd, J = 8.8, 2.6 Hz, 1H), 6.00 (s, 2H), 3.87 (s, 3H), 3.68 (dt, J = 12.9, 3.2 Hz, 2H), 3.59 (p, J = 6.8 Hz, 1H), 2.66 (td, J = 12.3, 2.3 Hz, 2H), 2.37-2.31 (m, 7H), 1.98 (dt, J = 12.7, 2.8 Hz, 2H), 1.64 (qd, J = 12.3, 4.0 Hz, 2H), 1.27 (d, J = 6.9 Hz, 6H). MS (ESI) m/z: 596 [M + H]⁺. |
| IT-6 | 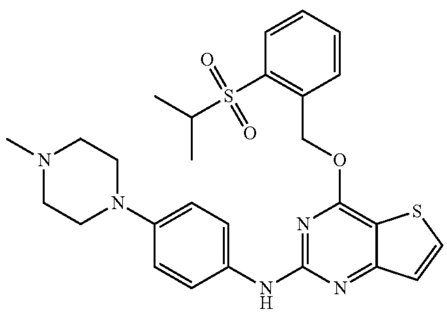 [SMILES: CC(C)S(=O)(=O)c1ccccc1COc1nc(Nc2ccc(N3CCN(C)CC3)cc2)nc2ccsc12] | ¹H NMR (600 MHz, Methanol-d4) δ 8.02 (dd, J = 7.9, 1.4 Hz, 1H), 7.95 (d, J = 5.3 Hz, 1H), 7.80 (dd, J = 7.8, 1.3 Hz, 1H), 7.74 (td, J = 7.6, 1.4 Hz, 1H), 7.63 (td, J = 7.7, 1.3 Hz, 1H), 7.56-7.52 (m, 2H), 7.20 (d, J = 5.3 Hz, 1H), 6.98-6.96 (m, 2H), 6.03 (s, 2H), 3.57 (p, J = 6.8 Hz, 1H), 3.17 (t, J = 5.0 Hz, 4H), 2.66 (t, J = 5.0 Hz, 4H), 2.37 (s, 3H), 1.25 (d, J = 6.8 Hz, 6H). MS (ESI) m/z: 538 [M + H]⁺. |

Example 9

Compound IU

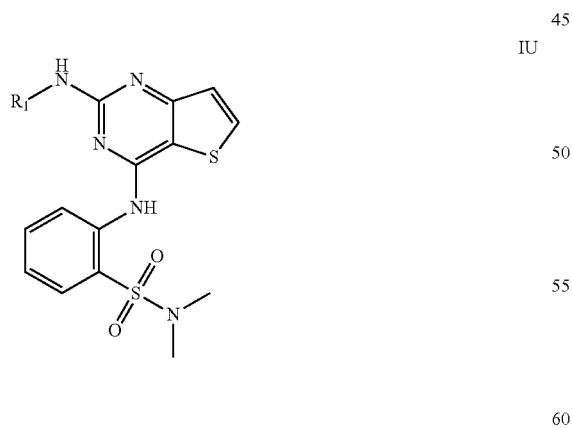

IU

Compound IU was synthesized by a method similar to that for the synthesis of IA.

The table below lists the specific compounds and structure identification data

TABLE 9

Structure and characterization of compound IU

| No. | Structure | ¹H NMR and/or MS data |
|---|---|---|
| IU-1 | TFA salt | ¹H NMR (600 MHz, Methanol-d4) δ 8.22 (d, J = 5.4 Hz, 1H), 8.20 (s, 1H), 8.13 (d, J = 8.1 Hz, 1H), 7.93 (dd, J = 7.9, 1.6 Hz, 1H), 7.63 (t, J = 8.0 Hz, 1H), 7.52 (t, J = 7.7 Hz, 1H), 7.31 (d, J = 5.4 Hz, 1H), 7.14 (s, 1H), 4.34 (s, 2H), 4.15 (t, J = 8.3 Hz, 2H), 3.83 (s, 3H), 3.35 (t, J = 8.3 Hz, 2H), 3.01 (s, 6H), 2.69 (s, 6H). MS (ESI) m/z: 582 [M + H]⁺. |
| IU-2 | TFA salt | ¹H NMR (600 MHz, Methanol-d4) δ 8.24 (d, J = 5.4 Hz, 1H), 8.04 (d, J = 7.6 Hz, 1H), 7.99 (dd, J = 8.1, 1.5 Hz, 1H), 7.75 (td, J = 7.8, 1.5 Hz, 1H), 7.64 .57 (m, 1H), 7.43 (d, J = 8.7 Hz, 1H), 7.31 (d, J = 5.4 Hz, 1H), 6.94 (s, 1H), 6.72 (dd, J = 8.7, 2.5 Hz, 1H), 3.90-3.85 (m, 5H), 3.53 (s, 4H), 3.40 (s, 4H), 3.27-3.20 (m, 1H), 3.14 (t, J = 12.3 Hz, 2H), 2.95 (s, 3H), 2.68 (s, 6H), 2.23 (d, J = 13.0, 2.9 Hz, 2H), 1.97 (tt, J = 12.2, 6.2 Hz, 2H). MS (ESI) m/z: 637 [M + H]⁺. |
| IU-3 | TFA salt | ¹H NMR (600 MHz, Methanol-d4) δ 8.22 (d, J = 5.4 Hz, 1H), 8.08 (s, 1H), 7.97 (dd, J = 8.0, 1.5 Hz, 1H), 7.72 (t, J = 7.8 Hz, 1H), 7.57 (t, J = 7.7 Hz, 1H), 7.32 (d, J = 8.6 Hz, 1H), 7.30 (d, J = 5.4 Hz, 1H), 6.76 (d, J = 2.6 Hz, 1H), 6.56 (s, 1H), 3.91 (d, 2H), 3.85 (s, 3H), 3.65 (d, J = 12.1 Hz, 2H), 3.31-3.26 (m, 2H), 3.12 (t, J = 12.9 Hz, 2H), 2.99 (s, 3H), 2.68 (s, 6H). MS (ESI) m/z: 554 [M + H]⁺. |

Test Example

Biological Activity Assay:

Growth Inhibitory Activity of Compounds on Cell Lines Stably Transfected with Kinase The activity of compounds against kinase ALK is evaluated by their effect of inhibiting growth of cell lines stably transfected with kinase EML4-ALK-BaF3, EML4-ALK (L1196M)-BaF3, NPM-ALK-BaF3, and wild-type BaF3 (Proc. Natl. Acad. Sci. USA., 2006, 103, 3153-8.). The growth of the cell lines stably transfected with kinase EML4-ALK-BaF3, EML4-ALK(L1196M)-BaF3 and NPM-ALK-BaF3 depends on their kinase activity. If a compound can inhibit the activity of the kinase ALK per se or the activity of the ALK signaling pathway, the compound can inhibit the growth of BaF3 cells stably transfected with kinase. While the growth of wild-type BaF3 cells does not depend on the activity of ALK and ALK signaling pathway, the effect of a compound on the growth of wild-type BaF3 cells can be used to evaluate its broad-spectrum toxicity. Therefore, a larger ratio between $IC_{50}$ of a compound to wild-type BaF3 and $IC_{50}$ of the compound to the cell lines stably transfected with kinase EML4-ALK-BaF3, EML4-ALK(L1196M)-BaF3, NPM-ALK-BaF3 indicates better targeting.

The specific test method is given as follows:

1) Medium: DMEM (Dulbecco's modified eagle medium) or RPMI 1640 (containing 10% fetal bovine serum, 100 µg/mL ampicillin, 100 µg/mL streptomycin).

2) Reagent: MTS reaction solution (containing 2 mg/mL of MTS [3-(4,5-dimethylthiazol-2-yl)-5-(3-carboxymethoxyphenyl)-2-(4-sulfophenyl)-2H-tetrazolium, inner Salt]; 100 g/mL PES (phenazine methosulfate)).

3) Compound test: cells stably transfected with kinase (EML4-ALK-BaF3, or EML4-ALK (L1196M)-BaF3 or NPM-ALK-BaF3) ($2\times10^4$ cells/well) were incubated into a 96-well culture plate, the volume of cytosol was 90 μL, and then 10 μL of the compound at each gradient concentration was added (the highest concentration was 10 μM, which was diluted stepwise by 1/3, and 8 concentration points were set in total; the system contained 0.1% DMSO (dimethyl sulfoxide)). The cell plate with uniformly mixed compound was cultured in a cell culture incubator (37° C.; 5% $CO_2$) for 48 h, then 20 μL of MTS reaction solution was added, uniformly mixed and incubated in the cell culture incubator (37° C.; 5% $CO_2$) for 1-4 hr; OD values at 490 nm were measured by a microplate reader (VARIOSKAN FLASH, Thermo). Three parallels were set in each group of experiments, with 0.1% (a final concentration) DMSO as a negative control, and a medium without cells or compounds as a blank control. The cell growth inhibition rate was calculated by the following formula:

$$\text{Cell growth inhibition rate \%} = 1 - (OD_{experimental\ group} - OD_{blank\ group})/(OD_{negative\ group} - OD_{blank\ group}) \times 100\%$$

4) $IC_{50}$ calculation: The semi-inhibitory concentration of the compound acting on cell growth was calculated using GradPad Prism 5 software according to the measured cell growth inhibition rate.

TABLE 10

Growth inhibitory activity of compounds Series I on cell lines stably transfected with kinase

| No. of compounds | NPM-ALK | EML4-ALK | EML4-ALK L1196M |
|---|---|---|---|
| IA-1 | 87.60% | 94.91% | 99.02% |
| IA-2 | 87.64% | 98.91% | 99.84% |
| IA-3 | 92.74% | 99.76% | >99% |
| IA-4 | 86.01% | 99.57% | 98.09% |
| IA-5 | 90.94% | ND | ND |
| IB-1 | 96.70% | 87.30% | 83.47% |
| IB-2 | 94.40% | 82.88% | 81.71% |
| IB-3 | 94.23% | ND | ND |
| IB-4 | 95.97% | ND | ND |
| IB-5 | 88.89% | ND | ND |
| IB-6 | 93.25% | ND | ND |
| IB-7 | 92.75% | ND | ND |
| IB-8 | 83.67% | ND | ND |
| IB-9 | 88.45% | ND | ND |
| IB-10 | 80.02% | ND | ND |
| IB-11 | 60.90% | ND | ND |
| IB-12 | 55.87% | ND | ND |
| IB-13 | 90.34% | ND | ND |
| IB-14 | 48.05% | ND | ND |
| IB-15 | 83.28% | ND | ND |
| IB-16 | 77.49% | ND | ND |
| IB-17 | 85.95% | ND | ND |
| IB-18 | 66.06% | ND | ND |
| IB-19 | 84.89% | ND | ND |
| IB-20 | 65.96% | ND | ND |
| IB-21 | 72.14% | ND | ND |
| IB-22 | 87.35% | ND | ND |
| IB-23 | 96.71% | ND | ND |
| IB-24 | 97.41% | ND | ND |
| IB-25 | 61.42% | ND | ND |
| IB-26 | 97.28% | ND | ND |
| IB-27 | ND | ND | ND |
| IB-28 | 96.55% | ND | ND |
| IB-29 | 97.53% | ND | ND |
| IB-30 | ND | ND | ND |
| IB-31 | ND | 98.13% | 97.34% |
| IB-32 | ND | 95.03% | 96.34% |
| IB-33 | ND | 98.33% | 98.19% |
| IB-34 | ND | ND | ND |
| IB-35 | ND | 96.77% | 96.56% |
| IC-1 | 82.36% | ND | ND |
| IC-2 | 54.98% | ND | ND |
| IC-3 | 46.54% | ND | ND |
| IC-4 | 53.21% | ND | ND |
| ID-1 | 73.44% | ND | ND |
| ID-2 | 44.70% | ND | ND |
| ID-3 | 83.62% | 92.94% | 93.96% |
| ID-4 | 90.69% | 98.45% | 99.40% |
| ID-5 | 93.89% | >99% | >99% |
| ID-6 | −24.08% | 99.88% | 100.75% |
| IE-1 | 69.50% | 96.95% | 100.10% |
| IE-2 | 50.46% | 98.18% | 97.77% |
| IE-3 | 85.47% | 96.71% | 99.06% |
| IE-4 | 93.60% | 96.73% | 97.75% |
| IE-5 | 87.58% | 98.98% | 99.45% |
| IE-6 | 0.00% | 98.46% | 98.86% |
| IE-7 | 86.09% | 98.83% | 99.80% |
| IE-8 | 84.16% | 97.96% | 99.46% |
| IF-1 | 6.16% | >99% | 99.15% |
| IF-2 | 2.77% | 3.41% | 13.02% |
| IF-3 | 12.03% | 87.14% | 81.18% |
| IG-1 | 22.16% | ND | ND |
| IG-2 | 17.41% | ND | ND |
| IG-3 | 21.60% | ND | ND |
| IG-4 | 87.62% | 97.81% | 97.53% |
| IG-5 | 10.90% | >99% | >99% |
| IG-6 | 3.07% | ND | ND |
| IH-1 | 12.73% | ND | ND |
| IH-2 | 85.14% | ND | ND |
| IH-3 | 79.24% | ND | ND |
| IH-4 | 26.67% | ND | ND |
| IH-5 | 84.15% | 98.00% | 96.03% |
| IH-6 | 84.52% | 97.79% | 97.60% |
| IH-7 | 15.13% | ND | ND |
| II-1 | 46.34% | ND | ND |
| II-2 | 28.08% | ND | ND |
| II-3 | 84.13% | ND | ND |
| II-4 | 46.65% | ND | ND |
| II-5 | 31.55% | ND | ND |
| II-6 | 36.87% | 92.94% | 93.96% |
| II-7 | 79.49% | 98.45% | 99.40% |
| II-8 | 86.63% | >99% | >99% |
| II-9 | 89.95% | 99.88% | >99% |
| IJ-1 | 87.09% | >99% | >99% |
| IJ-2 | 87.74% | 99.30% | 99.78% |
| IJ-3 | 84.77% | 99.93% | >99% |
| IJ-4 | 88.85% | >99% | >99% |
| IJ-6 | 81.90% | >99% | >99% |
| IK-1 | 86.74% | >99% | >99% |
| IK-2 | 82.80% | 99.99% | >99% |
| IK-3 | 82.53% | >99% | >99% |
| IK-4 | 77.36% | 99.28% | 99.95% |
| IK-5 | 85.47% | 99.64% | 100.40% |
| IK-6 | 90.17% | 99.31% | 100.37% |
| IL-1 | 73.70% | ND | ND |
| IL-2 | 54.80% | ND | ND |
| IL-3 | 56.77% | ND | ND |
| IL-4 | 45.79% | ND | ND |
| IM-1 | 94.18% | ND | ND |
| IM-2 | 20.59% | ND | ND |
| IM-3 | 52.52% | ND | ND |
| IM-4 | 53.12% | ND | ND |
| IN-1 | 17.66% | 99.99% | 98.86% |
| IN-2 | 16.21% | 99.24% | 98.76% |
| IN-3 | 12.26% | 98.77% | 98.28% |
| IN-4 | 7.09% | 98.26% | 98.44% |
| IN-5 | 6.73% | 30.88% | 46.70% |
| IN-6 | 46.71% | 98.43% | 97.84% |
| IN-7 | 70.02% | >99% | >99% |
| Crizotinib | 96.54% | 98.47% | 85.88% |
| IO-1 | ND | 97.09% | 96.58% |
| IO-2 | ND | 96.03% | 98.13% |
| IO-3 | ND | 98.68% | 97.65% |
| IO-4 | ND | 96.97% | 97.86% |
| IP-1 | ND | 97.43% | 97.42% |
| IP-2 | ND | 97.29% | 97.48% |
| IP-3 | ND | 99.09% | 98.26% |
| IQ-1 | ND | 96.91% | 94.32% |

TABLE 10-continued

Growth inhibitory activity of compounds Series I on cell lines stably transfected with kinase

| No. of compounds | NPM-ALK | EML4-ALK | EML4-ALK L1196M |
|---|---|---|---|
| IR-1 | ND | 97.50% | 97.63% |
| IR-2 | ND | 96.34% | 93.30% |
| IR-3 | ND | 99.24% | 98.46% |
| IR-4 | ND | 98.42% | 97.88% |
| IR-5 | ND | 98.28% | 97.84% |
| IR-6 | ND | 98.29% | 97.84% |
| IS-1 | ND | 98.74% | 98.38% |
| IS-2 | ND | 98.19% | 97.72% |
| IS-3 | ND | 101.14% | 100.43% |
| IS-4 | ND | 102.67% | 100.85% |
| IS-5 | ND | 102.85% | 100.86% |
| IS-6 | ND | 99.55% | 98.48% |
| IT-1 | ND | 99.75% | 99.20% |
| IT-2 | ND | ND | ND |
| IT-3 | ND | 87.79% | 78.32% |
| IT-4 | ND | 100.27% | 99.71% |
| IT-5 | ND | 100.97% | 99.92% |
| IT-6 | ND | ND | ND |
| IU-1 | ND | ND | ND |
| IU-2 | ND | ND | ND |
| IU-3 | ND | ND | ND |
| Crizotinib | 96.54% | 98.47% | 85.88% |

* Values represent cell growth inhibition rate of compounds at a concentration of 3.3 μM, Crizotinib acts as a positive control, and ND means not determined.

TABLE 11

Growth inhibitory activity of compound IB-1 on BaF3 cells stably transfected with other ALK point mutations ($IC_{50}$/nM)

| Cmpd ID | EML4-ALK-I1171T | EML4-ALK-G1202R | EML4-ALK-S1206Y | EML4-ALK-G1269A | EML4-ALK-L1196M |
|---|---|---|---|---|---|
| IB-1 | <4 | 10 | <4 | <4 | <4 |
| Crizotinib* | 216 | 704 | 46 | 319 | 565 |

Growth Inhibitory Activity of Compounds on Tumor Cells

If the tumor cells tested were suspension cells, the assay was carried out in accordance with the method (1) above.

If the tumor cells tested were adherent cells, cells were incubated 1000-10000 cells/well in a 96-well culture plate until adherent, and then compounds were added. Others were carried out in accordance with the method (1) above.

Compound IB-1 had a good inhibitory activity against both kinase ALK-positive lung cancer cell line H3122 and anaplastic large cell lymphoma Karpas-299. It could be seen from the above activity data that the compounds with better activity all had better targeting selectivity.

TABLE 12

Growth inhibitory activity of compound IB-1 on tumor cells and BaF3 cells

| Cmpd ID | H3122 ($IC_{50}$/nM) | Karpas-299 ($IC_{50}$/nM) | BaF3 ($IC_{50}$/nM) |
|---|---|---|---|
| IB-1 | 15 | <4 | 1601 |
| Crizotinib* | 185 | 61 | 1327 |

*Crizotinib acts as a positive control, and ND means not determined.

In Vivo Efficacy Evaluation

1. Compound IB-1 Significantly Inhibited Tumor Growth in Nude Mouse Xenograft Model of EML4-ALK(G1202R)-Ba/F3 (FIG. 1)

In this test, BALB/c (nu/nu) nude mice were used, male and female in half, 4-6 weeks old, weighing about 18±2 g, and fed in SPF level environment, strictly sterile operation. The animals to be tested were adapted to the experimental environment 1 week in advance, free access to food and water, and maintained a 12-hour circadian rhythm.

The EML4-ALK(G1202R)-Ba/F3 cells used in the test were cultured with 10% fetal bovine serum in PRMI-1640 medium, and placed in a 37° C., 5% $CO_2$ incubator environment.

A subcutaneous transplantation model of tumor nude mice was established by using cell inoculation method: cells in logarithmic growth phase were collected by filtration, washed with PBS after centrifugation, and resuspended as a single cell suspension with PRMI-1640 medium, $1\times10^6$ cells/200 μL per nude mouse. The cell suspension was injected subcutaneously in the vicinity of right anterior axillary of a nude mouse using a 1 mL syringe (No. 4.5 needle). When the tumor of tumor-bearing mice grew to a measurable size, the tumor volume was measured daily. When the tumor volume reached about 150 mm³, the mice were randomly divided into 3 groups, 8 mice each group, and administration was started on the day of grouping. The administration component was IB-1 60 mg/kg (once/day), 40 mg/kg (twice/day, bid), orally administered for 10 consecutive days, and negative control group was administered an equal amount of solvent. Animal weight and tumor size were measured daily during the test. The state of the mice was recorded daily. After the last administration, the mice were anesthetized with 5% chloral hydrate and killed 6 hours. The tumors were taken, weighed and photographed for recording. Tumor Volume (TV) was calculated as: $TV = \frac{1}{2} \times a \times b^2$, where a, b represent long diameter and short diameter of tumor, respectively.

As shown in FIG. 1, Compound IB-1 significantly inhibited tumor growth in the nude mouse xenograft model of EML4-ALK(G1202R)-Ba/F3. A) Compound IB-1 was orally administered at doses of 60 mg/kg (once/day) and 40 mg/kg (twice/day, bid), respectively, for 10 consecutive days, both of which significantly inhibited tumor growth; B) during administration, the mice in the drug group showed no significant changes in body weight, indicating that the mice were well tolerable to the drug, and IB-1 had no obvious side effects.

Figure 2:
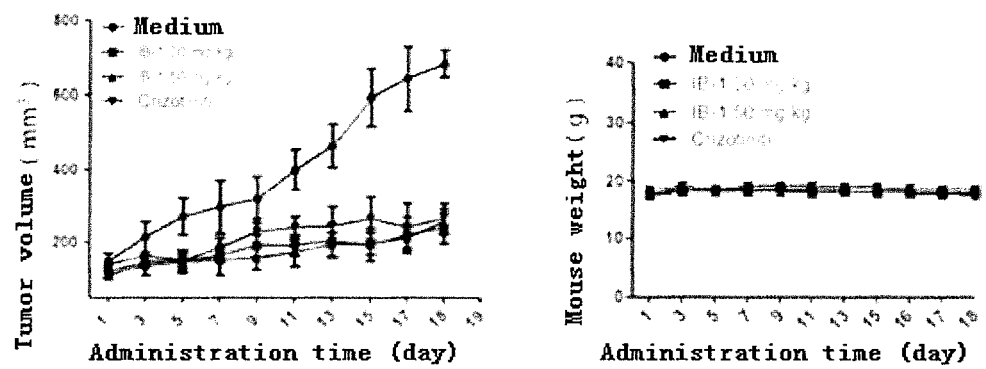
FIG. 2 shows that compound IB-1 significantly inhibits tumor growth in the nude mouse xenograft model of non-small cell lung cancer H3122 cells. A) Compound IB-1 was orally administered at doses of 30 mg/kg (once/day), 50 mg/kg (once/day), respectively, for 18 consecutive days, both of which significantly inhibited tumor growth; B) during administration, the mice in the drug group showed no significant changes in body weight, indicating that the mice were well tolerable to the drug, and IB-1 had no obvious side effects.

2. Compound IB-1 Significantly Inhibited Tumor Growth in Nude Mouse Xenograft Model of H3122 Tumor Cells (FIG. 2)

In this test, BALB/c (nu/nu) nude mice were used, male and female in half, 4-6 weeks old, weighing about 18±2 g, and fed in SPF level environment, strictly sterile operation. The animals to be tested were adapted to the experimental environment 1 week in advance, free access to food and water, and maintained a 12-hour circadian rhythm.

The NCI-H3122 cells used in the test were cultured with 10% fetal bovine serum in PRMI-1640 medium, and placed in a 37° C., 5% $CO_2$ incubator environment.

A subcutaneous transplantation model of tumor nude mice was established by using cell inoculation method: cells in logarithmic growth phase were collected by filtration, washed with PBS after centrifugation, and resuspended as a single cell suspension with PRMI-1640 medium, $5\times10^6$ cells/200 μL per nude mouse. The cell suspension was injected subcutaneously in the vicinity of right anterior axillary of a nude mouse using a 1 mL syringe (No. 4.5 needle). When the tumor of tumor-bearing mice grew to a measurable size, the tumor volume was measured daily. When the tumor volume reached about 150 mm³, the mice were randomly divided into 4 groups, 5 mice each group, and administration was started on the day of grouping. The administration component was IB-1 30 mg/kg (once/day), 50 mg/kg (once/day), positive control group was administered Crizotinib 50 mg/kg (once/day), and negative control group was administered an equal amount of solvent. The administration was conducted for 18 consecutive days. Animal weight and tumor size were measured every other day during the test. The state of the mice was recorded daily. After the last administration, the mice were anesthetized with 5% chloral hydrate and killed 6 hours. The tumors were taken, weighed and photographed for recording. Tumor Volume (TV) was calculated as: TV=½×a×b$^2$, where a, b represent long diameter and short diameter of tumor, respectively.

As shown in FIG. 2, Compound IB-1 significantly inhibited tumor growth in the nude mouse xenograft model of non-small cell lung cancer H3122 cells. A) Compound IB-1 was orally administered at doses of 30 mg/kg (once/day), 50 mg/kg (once/day), respectively, for 18 consecutive days, both of which significantly inhibited tumor growth; B) during administration, the mice in the drug group showed no significant changes in body weight, indicating that the mice were well tolerable to the drug, and IB-1 had no obvious side effects.

What has been described above are only some embodiments of the invention. It will be apparent to those skilled in the art that various modifications and improvements can be made without departing from the spirit of the invention, all of which fall into the protection scope of the invention.

The invention claimed is:

1. A compound of Formula I

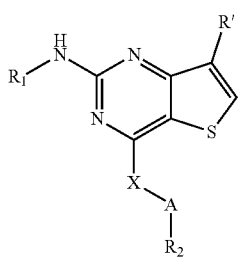

I wherein:

R' is H;

R$_1$ is selected from the group consisting of:

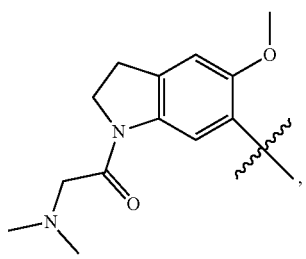

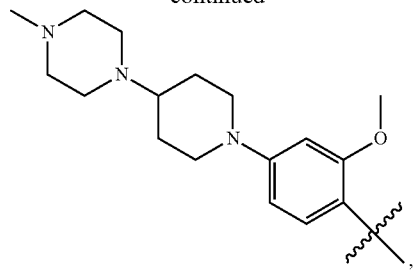

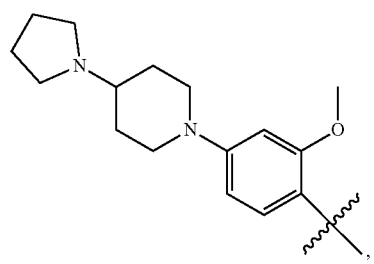

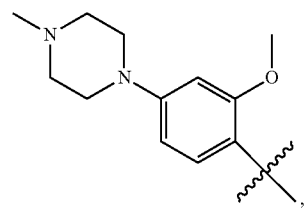

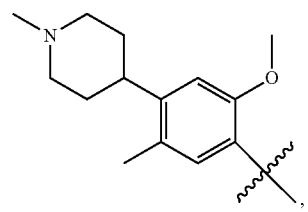

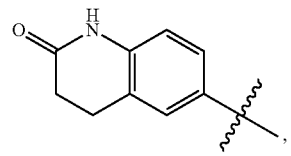

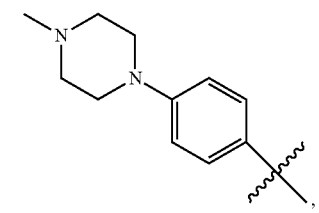

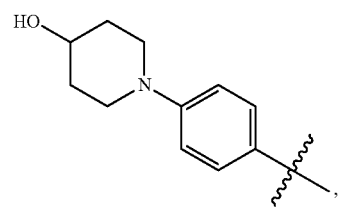

-continued
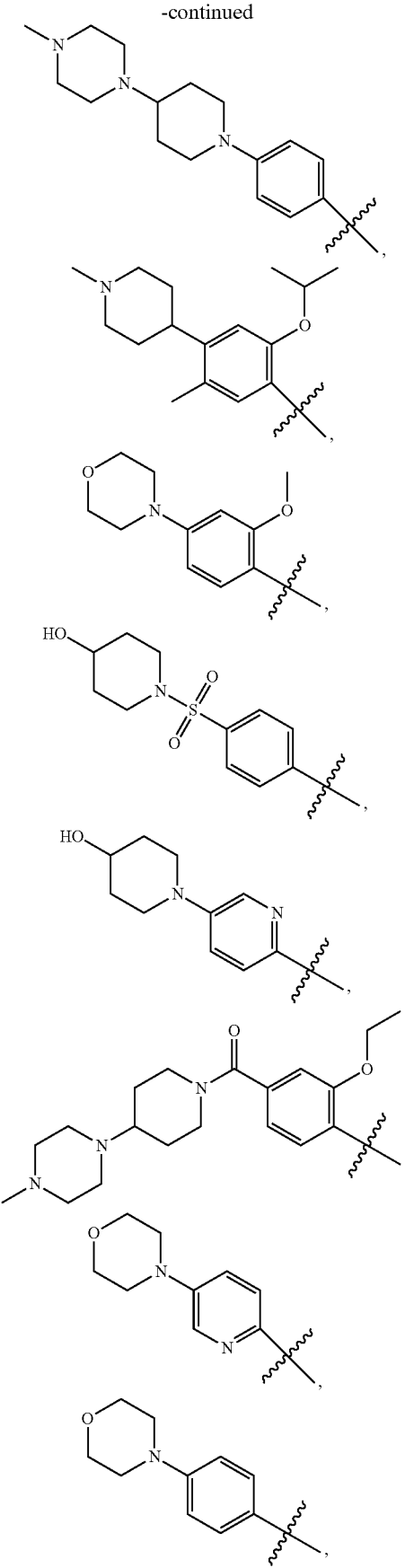
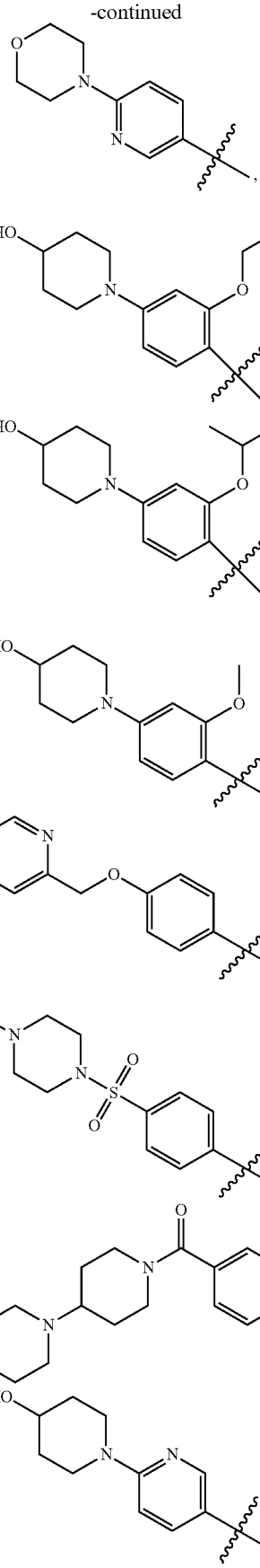

215
-continued
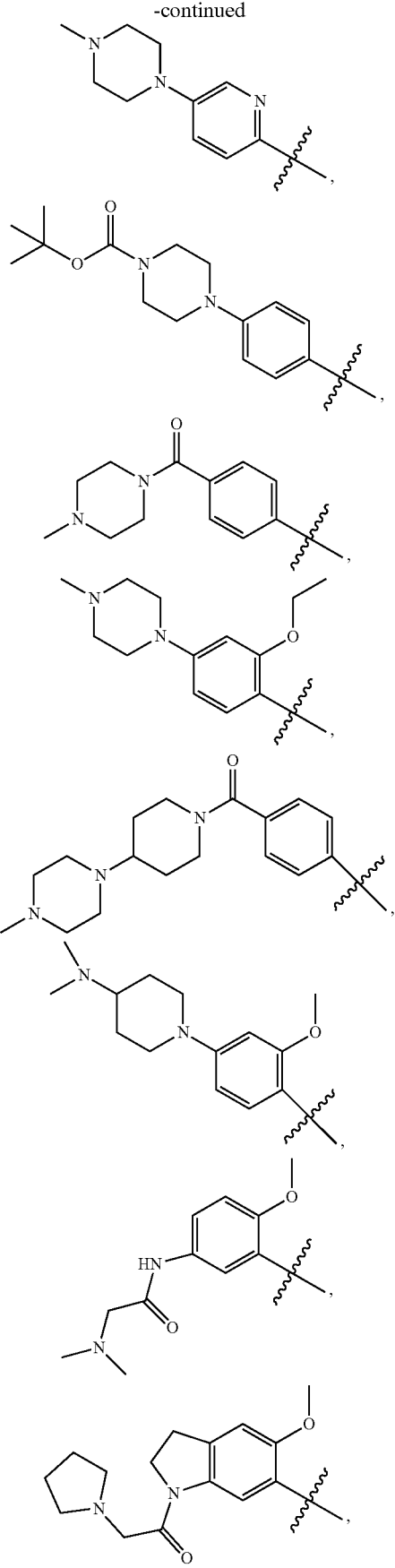
216
-continued
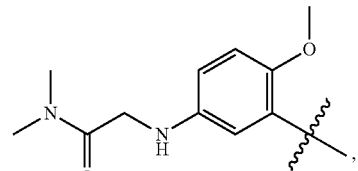
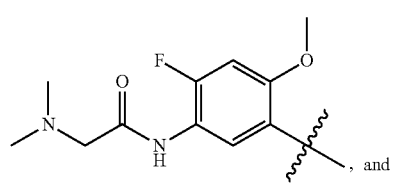, and
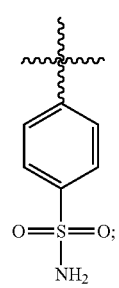
A is a direct on or methylene;
X is NH, S or O;
R$_2$ is selected from the group consisting of:
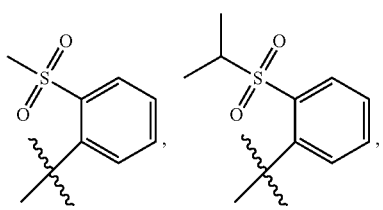
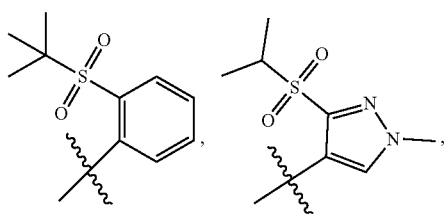
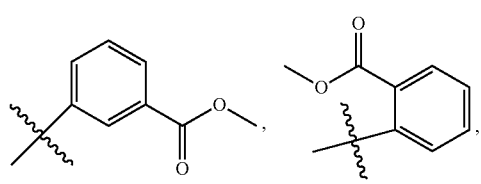

-continued
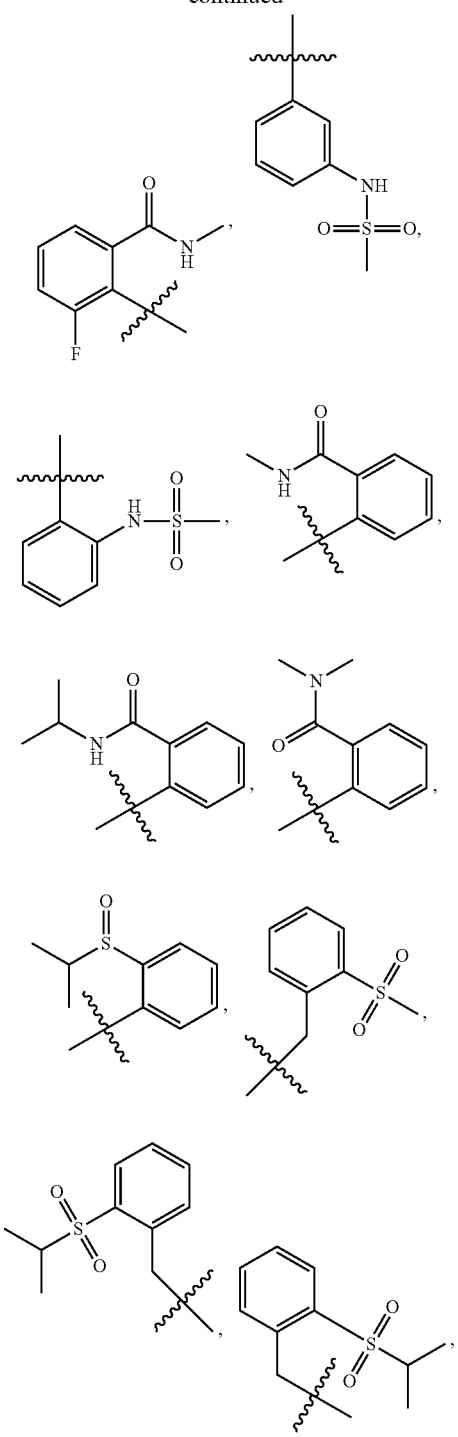
or a pharmaceutically acceptable salt thereof.
2. A compound according to claim 1, which is a compound of Formula IPQ
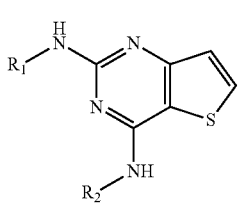
wherein,
$R_1$ is selected from the group consisting of:
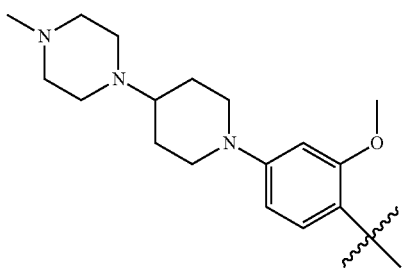
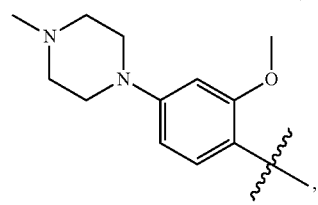
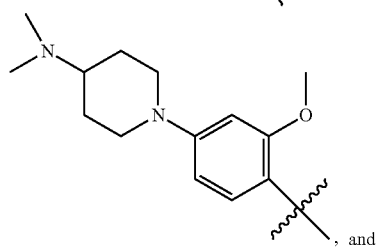
, and
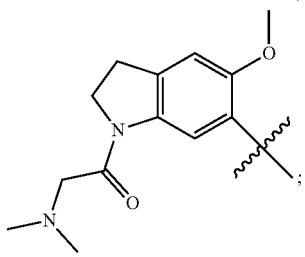
;
$R_2$ is
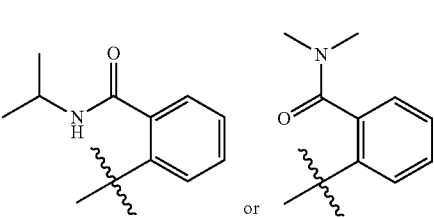
or a pharmaceutically acceptable salt thereof.

3. A compound according to claim 1, which is a compound of Formula IRS
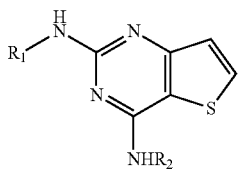
wherein, R₁ is selected from the group consisting of:
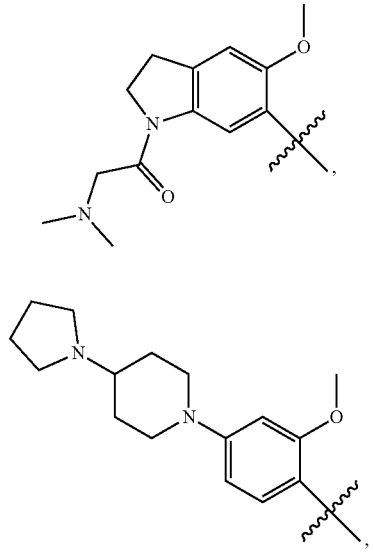
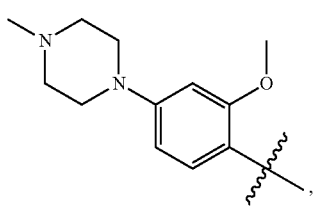
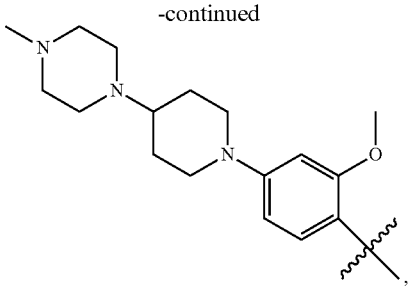
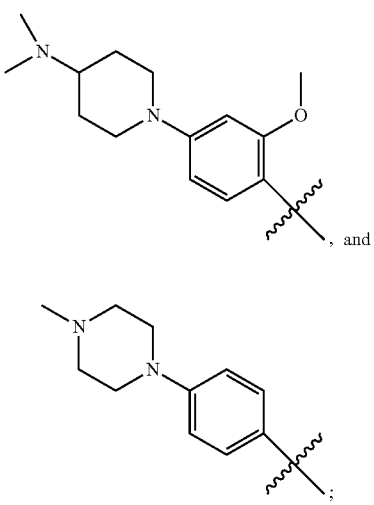
, and
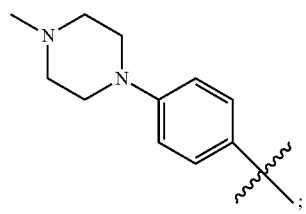
;
R₂ is
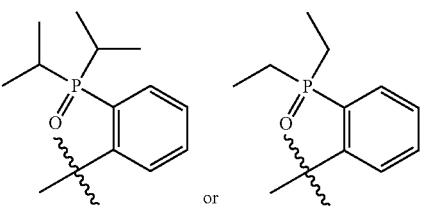
or a pharmaceutically acceptable salt thereof.
4. A compound according to claim 1, selected from:
| No. | Structure |
|---|---|
| IA-1 | 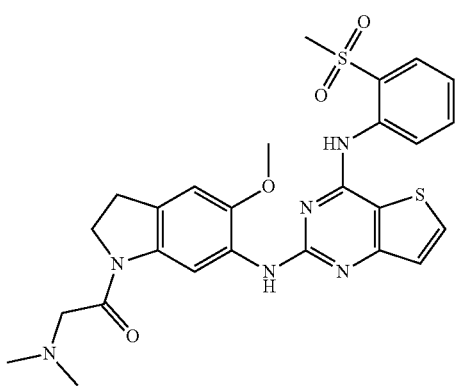 [SMILES: COc1cc2c(cc1Nc1nc(Nc3ccccc3S(C)(=O)=O)c3sccc3n1)N(C(=O)CN(C)C)CC2] |

-continued
| No. | Structure |
|---|---|
| IA-2 | 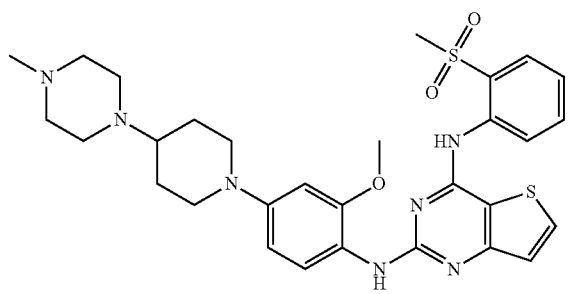 [SMILES: COc1cc(N2CCC(N3CCN(C)CC3)CC2)ccc1Nc1nc(Nc2ccccc2S(C)(=O)=O)c2sccc2n1] |
| IA-3 | 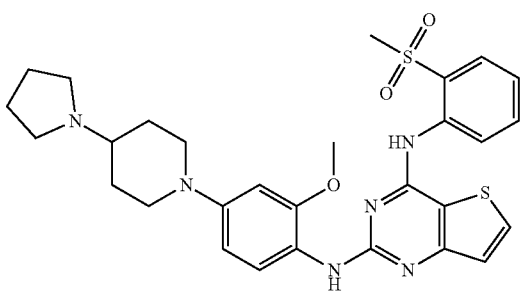 [SMILES: COc1cc(N2CCC(N3CCCC3)CC2)ccc1Nc1nc(Nc2ccccc2S(C)(=O)=O)c2sccc2n1] |
| IA-4 | 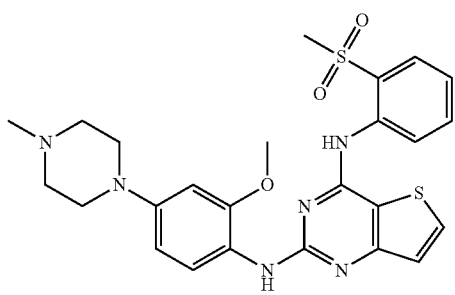 [SMILES: COc1cc(N2CCN(C)CC2)ccc1Nc1nc(Nc2ccccc2S(C)(=O)=O)c2sccc2n1] |
| IA-5 | 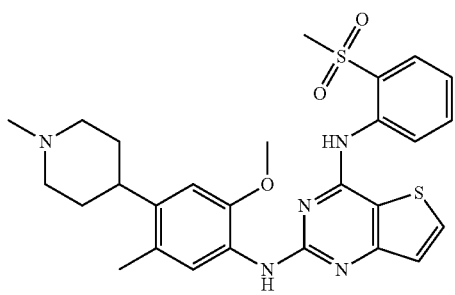 [SMILES: COc1cc(C2CCN(C)CC2)c(C)cc1Nc1nc(Nc2ccccc2S(C)(=O)=O)c2sccc2n1] |
| IA-6 | 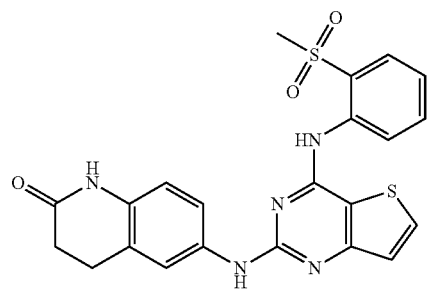 [SMILES: CS(=O)(=O)c1ccccc1Nc1nc(Nc2ccc3c(c2)CCC(=O)N3)nc2ccsc12] |

-continued
| No. | Structure |
|---|---|
| IB-1 | 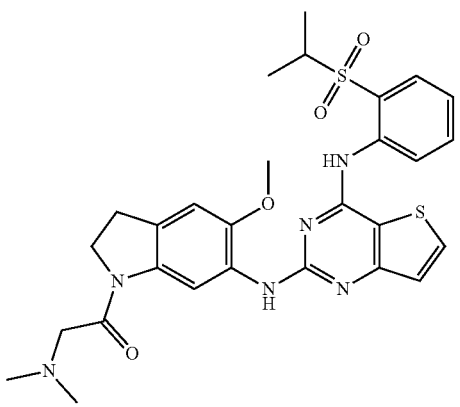 [SMILES: COc1cc2c(cc1Nc1nc(Nc3ccccc3S(=O)(=O)C(C)C)c3sccc3n1)N(C(=O)CN(C)C)CC2] |
| IB-2 | 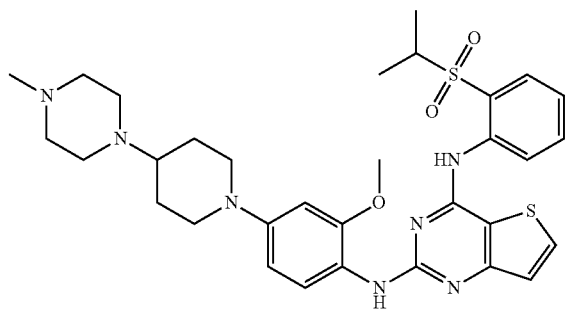 [SMILES: COc1cc(N2CCC(N3CCN(C)CC3)CC2)ccc1Nc1nc(Nc2ccccc2S(=O)(=O)C(C)C)c2sccc2n1] |
| IB-3 | 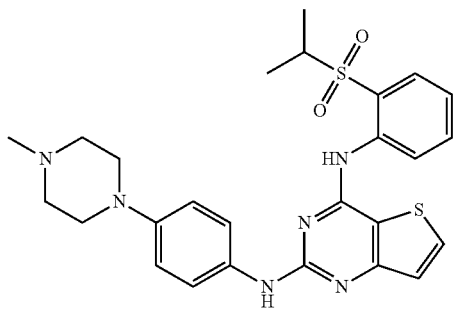 [SMILES: CC(C)S(=O)(=O)c1ccccc1Nc1nc(Nc2ccc(N3CCN(C)CC3)cc2)nc2ccsc12] |
| IB-4 | 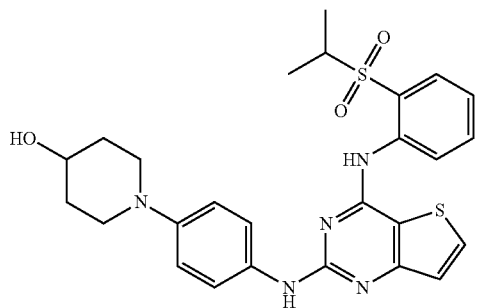 |

-continued
| No. | Structure |
|---|---|
| IB-5 | 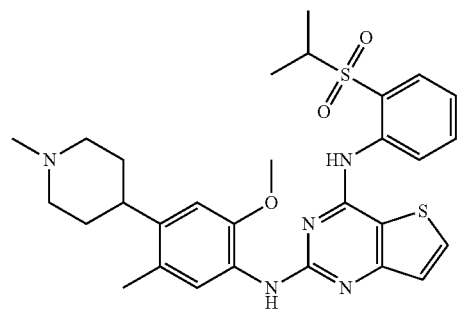 [SMILES: COc1cc(C2CCN(C)CC2)c(C)cc1Nc1nc(Nc2ccccc2S(=O)(=O)C(C)C)c2sccc2n1] |
| IB-6 | 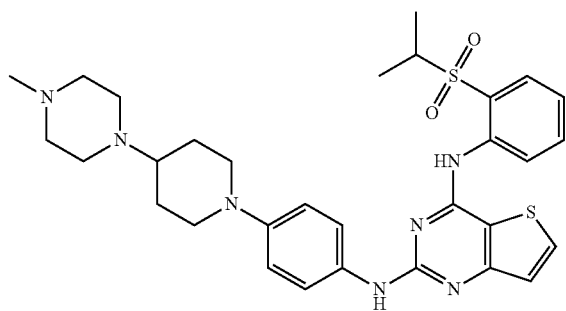 [SMILES: CC(C)S(=O)(=O)c1ccccc1Nc1nc(Nc2ccc(N3CCC(N4CCN(C)CC4)CC3)cc2)nc2ccsc12] |
| IB-7 | 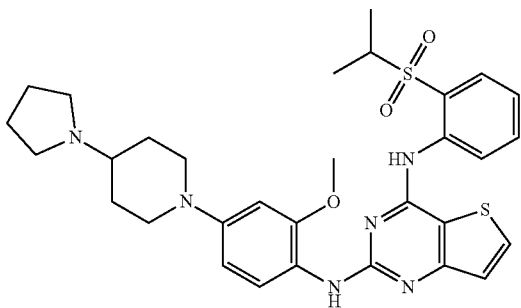 [SMILES: COc1cc(N2CCC(N3CCCC3)CC2)ccc1Nc1nc(Nc2ccccc2S(=O)(=O)C(C)C)c2sccc2n1] |
| IB-8 | 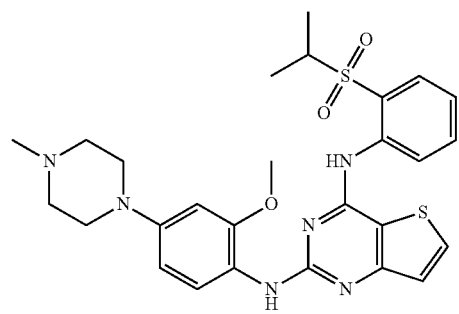 [SMILES: COc1cc(N2CCN(C)CC2)ccc1Nc1nc(Nc2ccccc2S(=O)(=O)C(C)C)c2sccc2n1] |
| IB-9 | 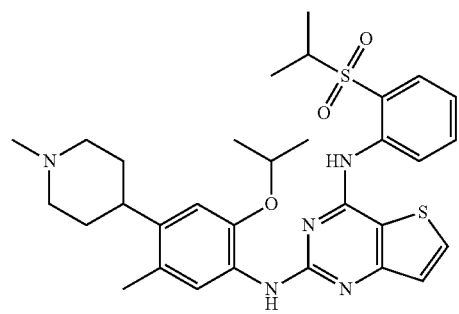 [SMILES: Cc1cc(Nc2nc(Nc3ccccc3S(=O)(=O)C(C)C)c3sccc3n2)c(OC(C)C)cc1C1CCN(C)CC1] |

-continued

| No. | Structure |
|---|---|
| IB-10 | 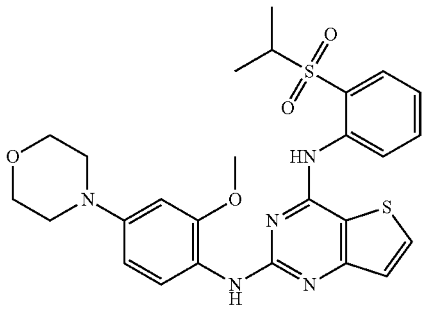 [SMILES: COc1cc(N2CCOCC2)ccc1Nc1nc(Nc2ccccc2S(=O)(=O)C(C)C)c2sccc2n1] |
| IB-11 | 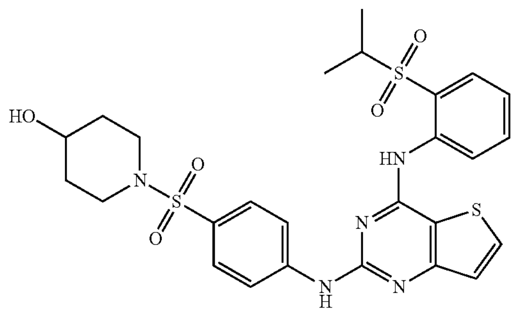 [SMILES: CC(C)S(=O)(=O)c1ccccc1Nc1nc(Nc2ccc(S(=O)(=O)N3CCC(O)CC3)cc2)nc2ccsc12] |
| IB-12 | 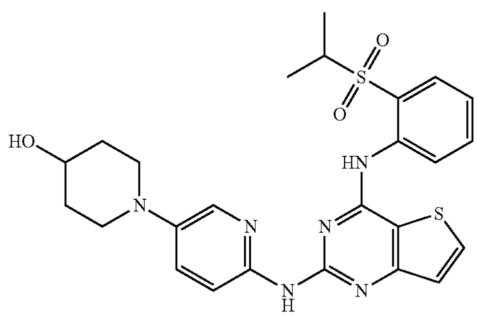 [SMILES: CC(C)S(=O)(=O)c1ccccc1Nc1nc(Nc2ccc(N3CCC(O)CC3)cn2)nc2ccsc12] |
| IB-13 | 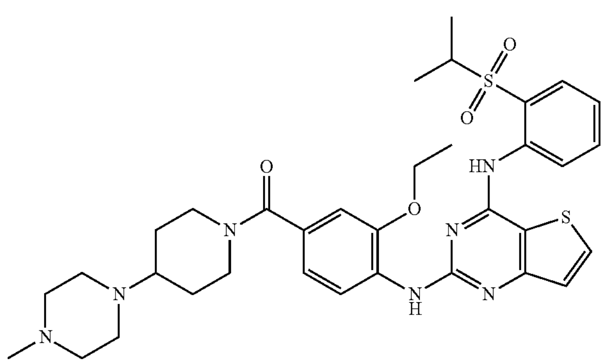 [SMILES: CCOc1cc(C(=O)N2CCC(N3CCN(C)CC3)CC2)ccc1Nc1nc(Nc2ccccc2S(=O)(=O)C(C)C)c2sccc2n1] |
| IB-14 | 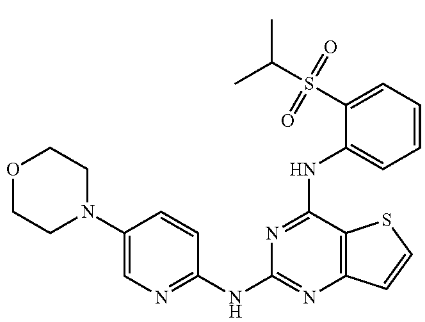 [SMILES: CC(C)S(=O)(=O)c1ccccc1Nc1nc(Nc2ccc(N3CCOCC3)cn2)nc2ccsc12] |

| No. | Structure |
|---|---|
| IB-15 | 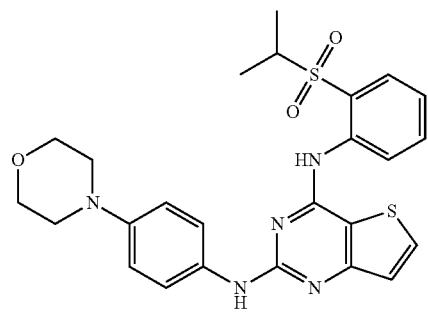 [SMILES: CC(C)S(=O)(=O)c1ccccc1Nc1nc(Nc2ccc(N3CCOCC3)cc2)nc2ccsc12] |
| IB-16 | 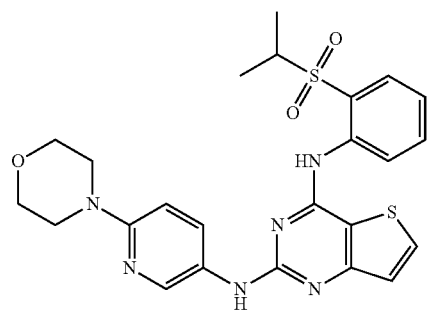 |
| IB-17 | 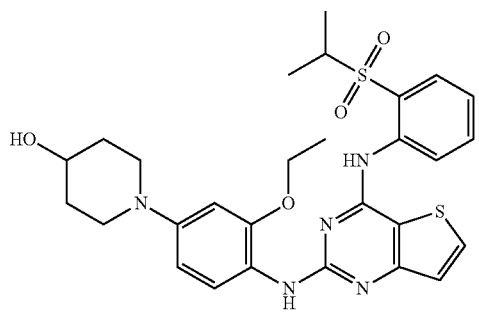 [SMILES: CCOc1cc(N2CCC(O)CC2)ccc1Nc1nc(Nc2ccccc2S(=O)(=O)C(C)C)c2sccc2n1] |
| IB-18 | 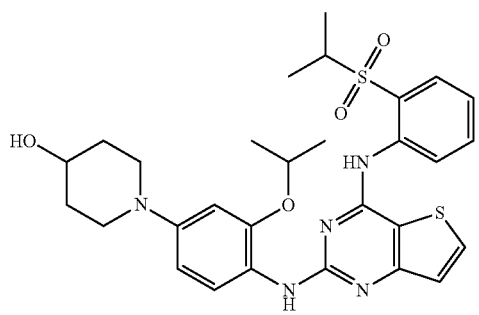 [SMILES: CC(C)Oc1cc(N2CCC(O)CC2)ccc1Nc1nc(Nc2ccccc2S(=O)(=O)C(C)C)c2sccc2n1] |
| IB-19 | 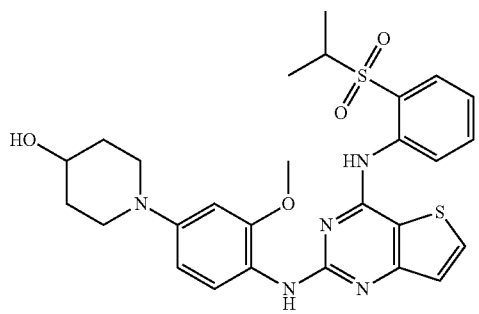 [SMILES: COc1cc(N2CCC(O)CC2)ccc1Nc1nc(Nc2ccccc2S(=O)(=O)C(C)C)c2sccc2n1] |

-continued
| No. | Structure |
|---|---|
| IB-20 | 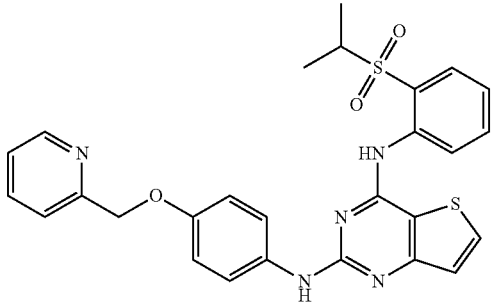 [SMILES: CC(C)S(=O)(=O)c1ccccc1Nc1nc(Nc2ccc(OCc3ccccn3)cc2)nc2ccsc12] |
| IB-21 | 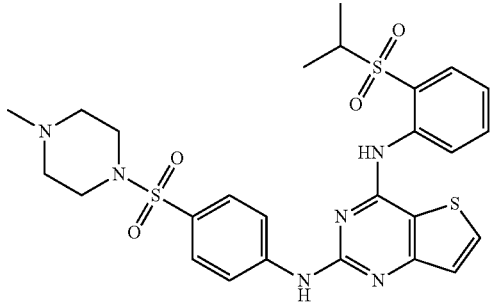 [SMILES: CC(C)S(=O)(=O)c1ccccc1Nc1nc(Nc2ccc(S(=O)(=O)N3CCN(C)CC3)cc2)nc2ccsc12] |
| IB-22 | 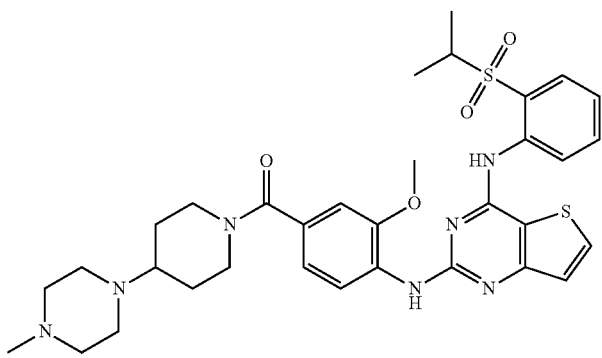 [SMILES: COc1cc(C(=O)N2CCC(N3CCN(C)CC3)CC2)ccc1Nc1nc(Nc2ccccc2S(=O)(=O)C(C)C)c2sccc2n1] |
| IB-23 | 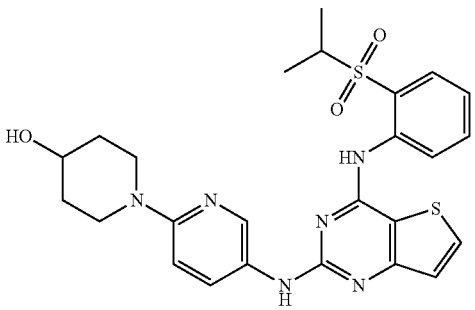 [SMILES: CC(C)S(=O)(=O)c1ccccc1Nc1nc(Nc2ccc(N3CCC(O)CC3)nc2)nc2ccsc12] |
| IB-24 | 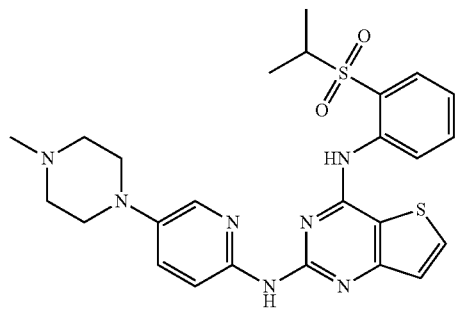 [SMILES: CC(C)S(=O)(=O)c1ccccc1Nc1nc(Nc2ccc(N3CCN(C)CC3)cn2)nc2ccsc12] |

| No. | Structure |
|---|---|
| IB-25 | 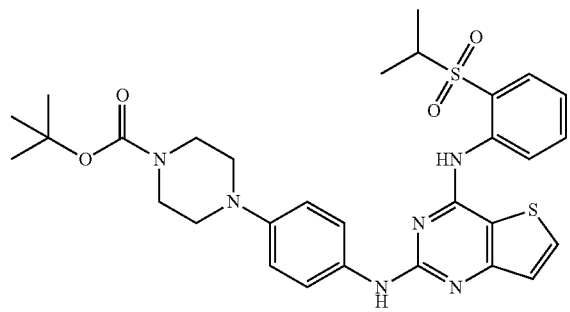 [SMILES: CC(C)S(=O)(=O)c1ccccc1Nc1nc(Nc2ccc(N3CCN(C(=O)OC(C)(C)C)CC3)cc2)nc2ccsc12] |
| IB-26 | 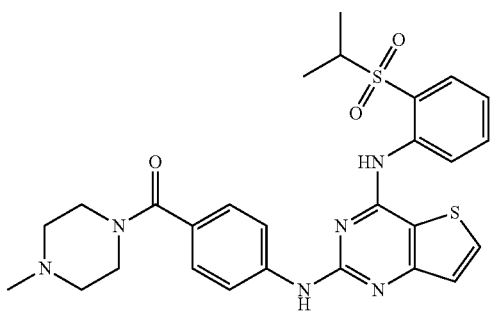 [SMILES: CC(C)S(=O)(=O)c1ccccc1Nc1nc(Nc2ccc(C(=O)N3CCN(C)CC3)cc2)nc2ccsc12] |
| IB-28 | 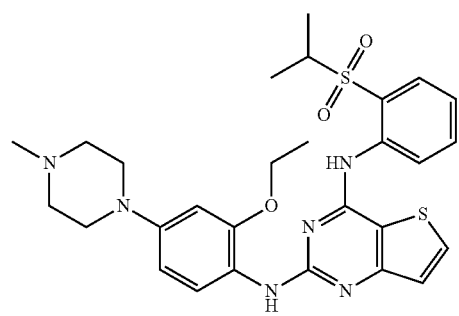 [SMILES: CCOc1cc(N2CCN(C)CC2)ccc1Nc1nc(Nc2ccccc2S(=O)(=O)C(C)C)c2sccc2n1] |
| IB-29 | 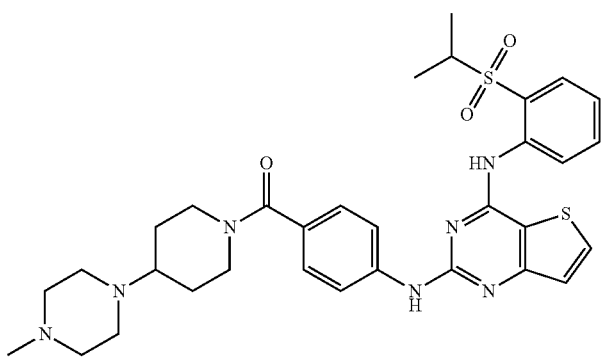 [SMILES: CC(C)S(=O)(=O)c1ccccc1Nc1nc(Nc2ccc(C(=O)N3CCC(N4CCN(C)CC4)CC3)cc2)nc2ccsc12] |
| IB-30 | 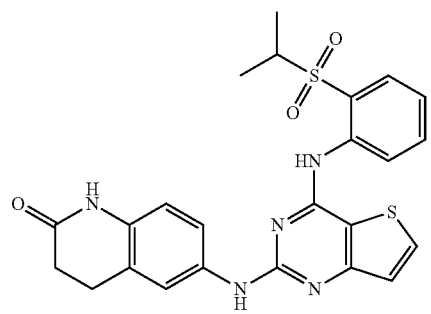 |

-continued
| No. | Structure |
|---|---|
| IC-1 | 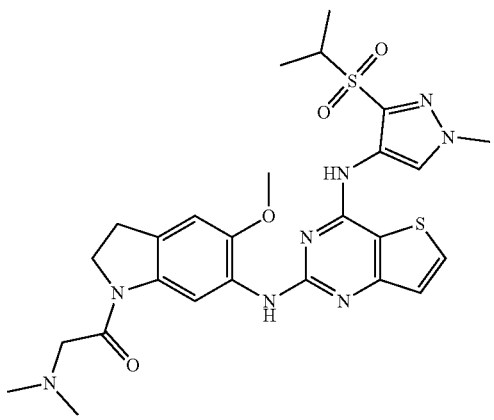 |
| IC-2 | 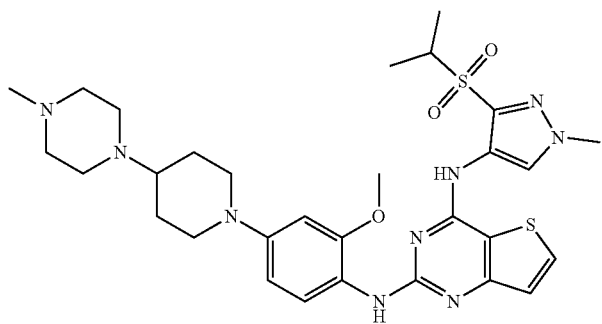 |
| IC-3 | 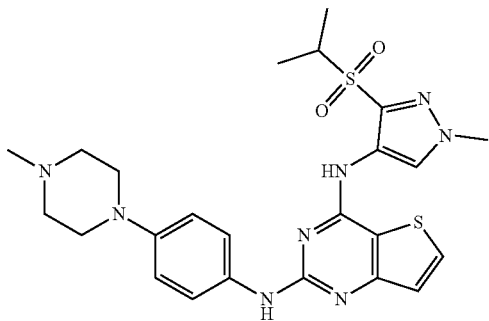 |
| IC-4 | 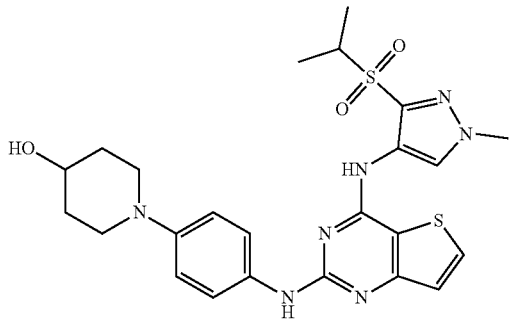 [SMILES: CC(C)S(=O)(=O)c1nn(C)cc1Nc1nc(Nc2ccc(N3CCC(O)CC3)cc2)nc2ccsc12] |

-continued
| No. | Structure |
|---|---|
| ID-1 | 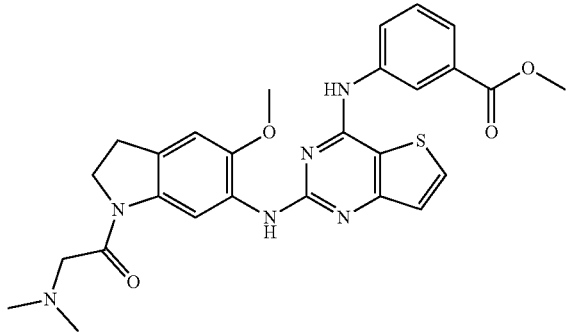 |
| ID-2 | 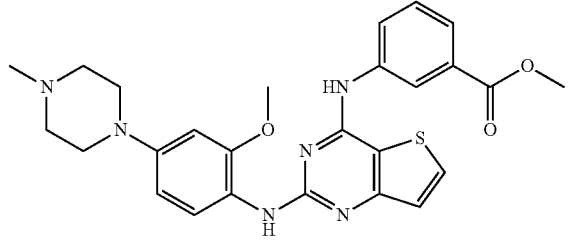 |
| ID-3 | 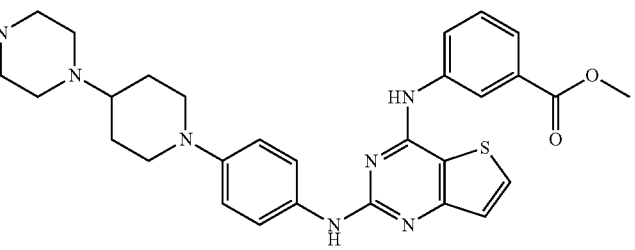 |
| ID-4 | 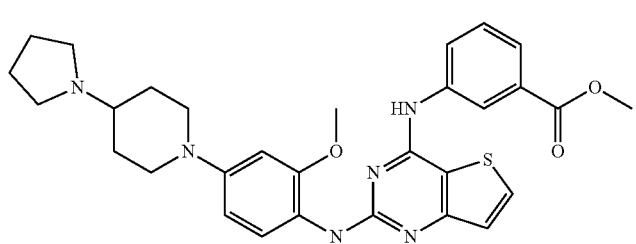 |
| ID-5 | 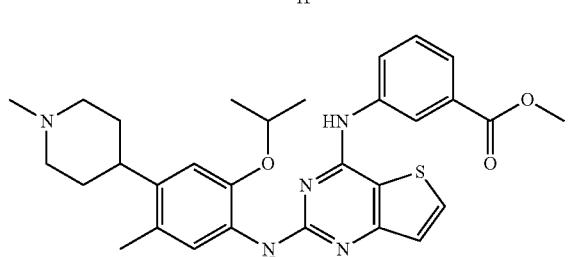 |
| ID-6 | 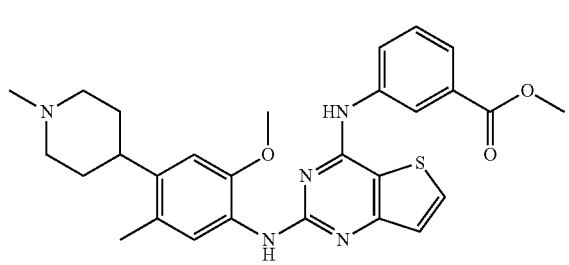 |

| No. | Structure |
|---|---|
| IE-1 | 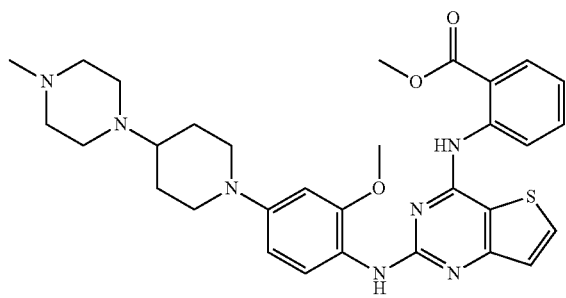 [SMILES: COC(=O)c1ccccc1Nc1nc(Nc2ccc(N3CCC(N4CCN(C)CC4)CC3)cc2OC)nc2ccsc12] |
| IE-2 | 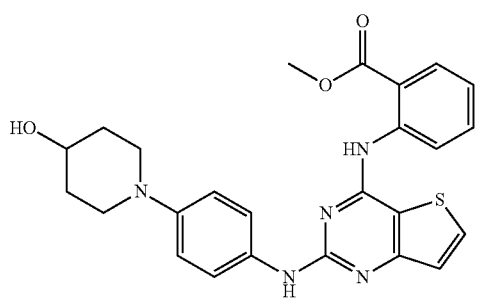 [SMILES: COC(=O)c1ccccc1Nc1nc(Nc2ccc(N3CCC(O)CC3)cc2)nc2ccsc12] |
| IE-3 | 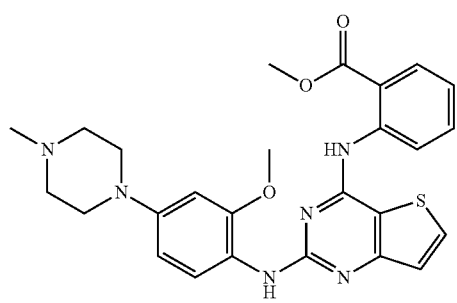 [SMILES: COC(=O)c1ccccc1Nc1nc(Nc2ccc(N3CCN(C)CC3)cc2OC)nc2ccsc12] |
| IE-4 | 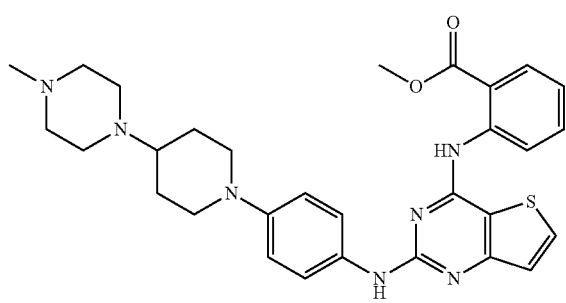 [SMILES: COC(=O)c1ccccc1Nc1nc(Nc2ccc(N3CCC(N4CCN(C)CC4)CC3)cc2)nc2ccsc12] |
| IE-5 | 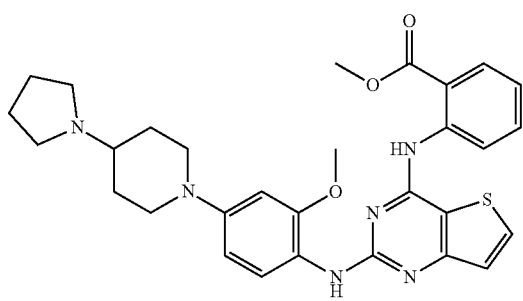 [SMILES: COC(=O)c1ccccc1Nc1nc(Nc2ccc(N3CCC(N4CCCC4)CC3)cc2OC)nc2ccsc12] |

-continued

| No. | Structure |
|---|---|
| IE-6 | (structure) |
| IE-7 | (structure) |
| IE-8 | (structure) |
| IB-32 | (structure) |
| IB-34 | (structure) |

| No. | Structure |
|---|---|
| IO-1 | 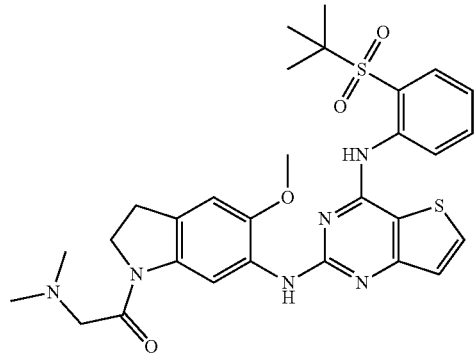 [SMILES: COc1cc2c(cc1Nc1nc(Nc3ccccc3S(=O)(=O)C(C)(C)C)c3sccc3n1)N(C(=O)CN(C)C)CC2] |
| IO-3 | 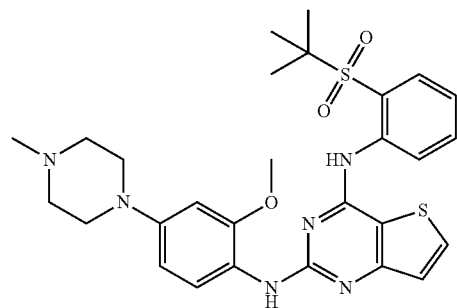 [SMILES: COc1cc(N2CCN(C)CC2)ccc1Nc1nc(Nc2ccccc2S(=O)(=O)C(C)(C)C)c2sccc2n1] |
| IP-1 | 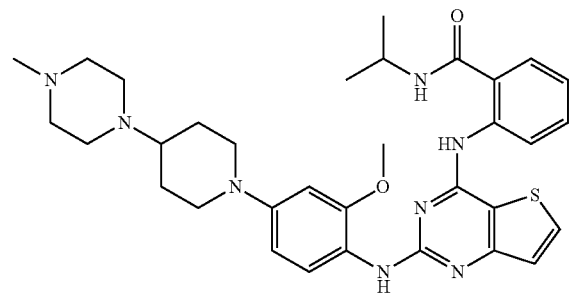 [SMILES: COc1cc(N2CCC(N3CCN(C)CC3)CC2)ccc1Nc1nc(Nc2ccccc2C(=O)NC(C)C)c2sccc2n1] |
| IP-3 | 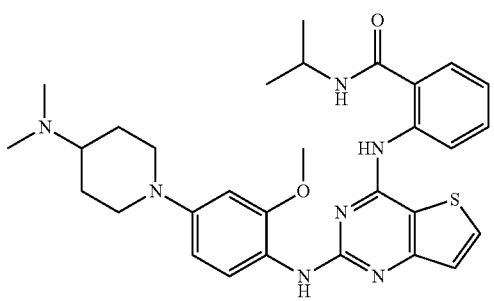 [SMILES: COc1cc(N2CCC(N(C)C)CC2)ccc1Nc1nc(Nc2ccccc2C(=O)NC(C)C)c2sccc2n1] |

| No. | Structure |
|---|---|
| IT-1 | 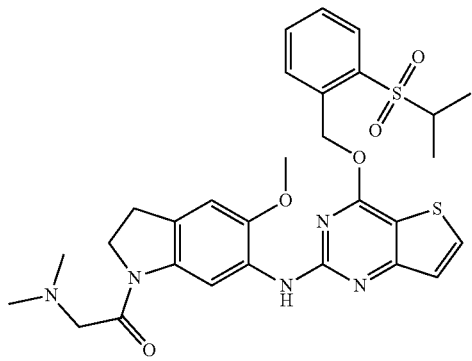 [SMILES: COc1cc2c(cc1Nc1nc(OCc3ccccc3S(=O)(=O)C(C)C)c3sccc3n1)N(C(=O)CN(C)C)CC2] |
| IT-3 | 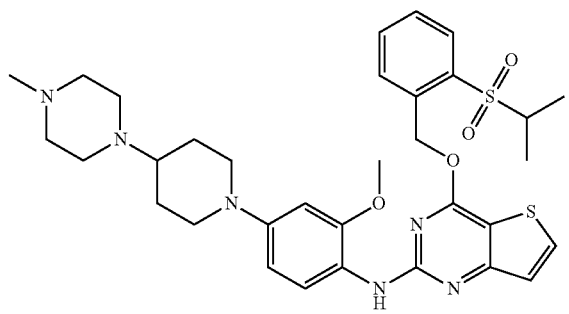 [SMILES: COc1cc(N2CCC(N3CCN(C)CC3)CC2)ccc1Nc1nc(OCc2ccccc2S(=O)(=O)C(C)C)c2sccc2n1] |
| IT-5 | 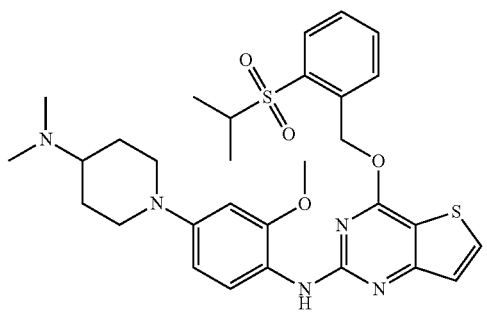 [SMILES: COc1cc(N2CCC(N(C)C)CC2)ccc1Nc1nc(OCc2ccccc2S(=O)(=O)C(C)C)c2sccc2n1] |
| IU-1 | 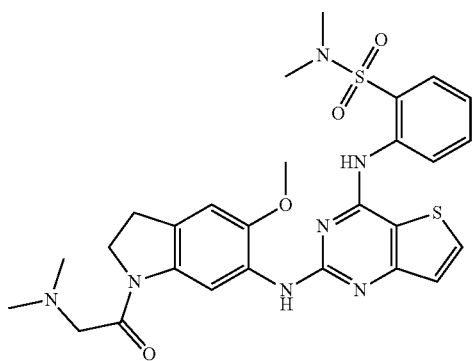 [SMILES: COc1cc2c(cc1Nc1nc(Nc3ccccc3S(=O)(=O)N(C)C)c3sccc3n1)N(C(=O)CN(C)C)CC2] |

| No. | Structure |
|---|---|
| IU-3 | 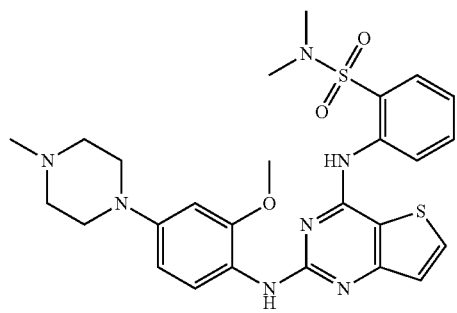 [SMILES: COc1cc(N2CCN(C)CC2)ccc1Nc1nc(Nc2ccccc2S(=O)(=O)N(C)C)c2sccc2n1] |
| IF-1 | 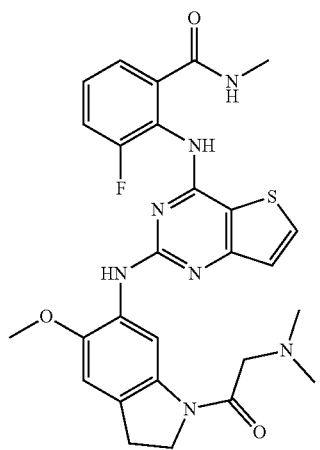 |
| IF-2 | 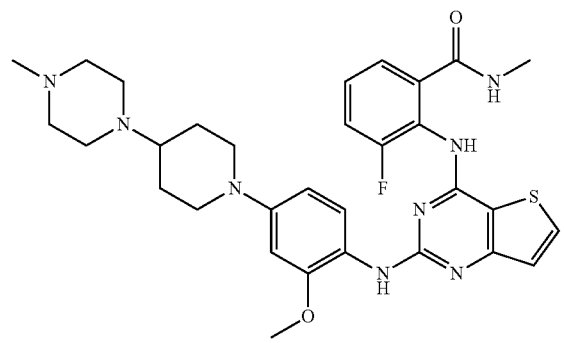 [SMILES: CNC(=O)c1cccc(F)c1Nc1nc(Nc2ccc(N3CCC(N4CCN(C)CC4)CC3)cc2OC)nc2ccsc12] |
| IF-3 | 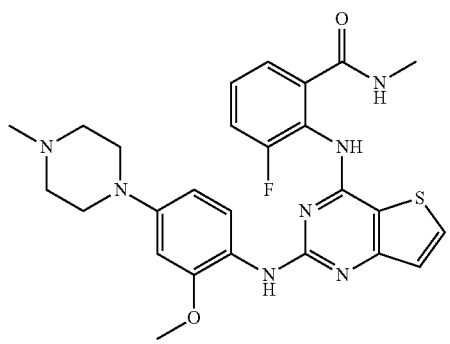 [SMILES: CNC(=O)c1cccc(F)c1Nc1nc(Nc2ccc(N3CCN(C)CC3)cc2OC)nc2ccsc12] |

| No. | Structure |
|---|---|
| IG-1 | 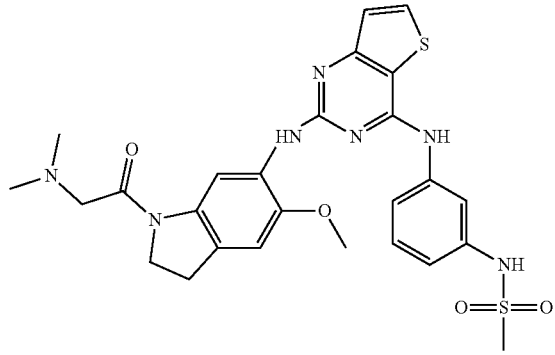 [SMILES: COc1cc2c(cc1Nc1nc(Nc3cccc(NS(C)(=O)=O)c3)c3sccc3n1)N(C(=O)CN(C)C)CC2] |
| IG-2 | 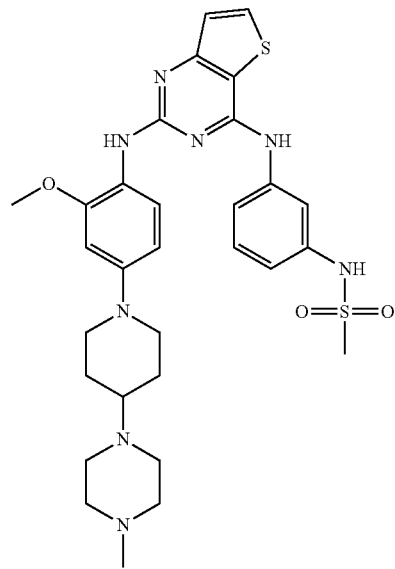 [SMILES: COc1cc(N2CCC(N3CCN(C)CC3)CC2)ccc1Nc1nc(Nc2cccc(NS(C)(=O)=O)c2)c2sccc2n1] |
| IG-3 | 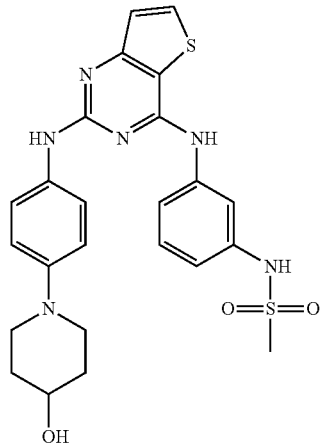 [SMILES: CS(=O)(=O)Nc1cccc(Nc2nc(Nc3ccc(N4CCC(O)CC4)cc3)nc3ccsc23)c1] |

-continued
| No. | Structure |
|---|---|
| IG-4 | 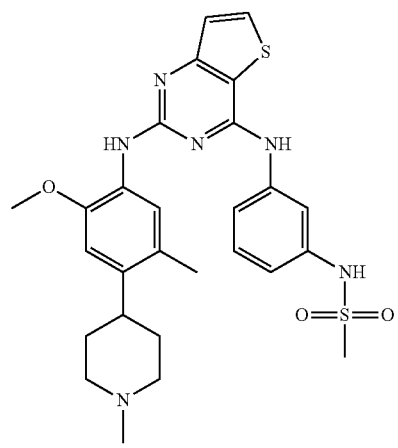 [SMILES: COc1cc(C2CCN(C)CC2)c(C)cc1Nc1nc(Nc2cccc(NS(C)(=O)=O)c2)c2sccc2n1] |
| IG-5 | 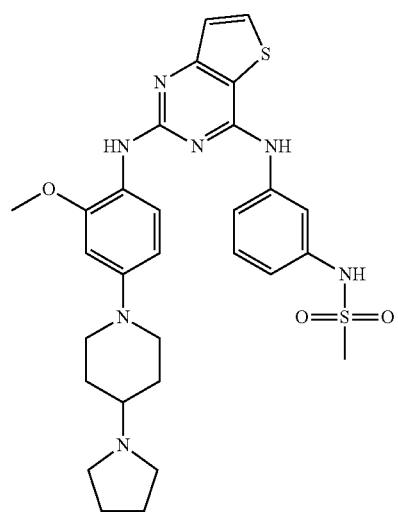 [SMILES: COc1cc(N2CCC(N3CCCC3)CC2)ccc1Nc1nc(Nc2cccc(NS(C)(=O)=O)c2)c2sccc2n1] |
| IG-6 | 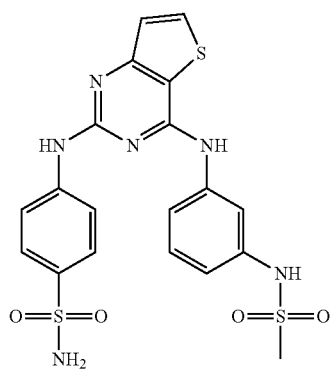 [SMILES: CS(=O)(=O)Nc1cccc(Nc2nc(Nc3ccc(S(N)(=O)=O)cc3)nc3ccsc23)c1] |
| IH-1 | 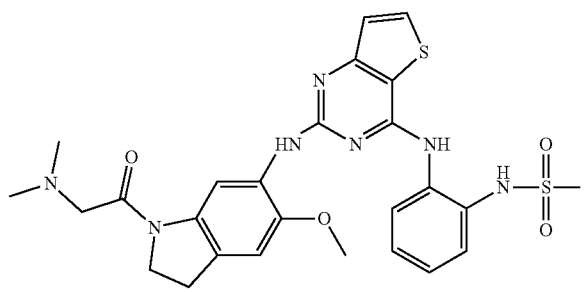 |

-continued
| No. | Structure |
|---|---|
| IH-2 | 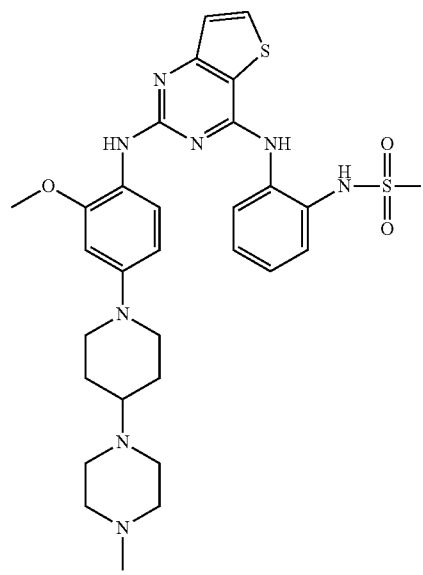 |
| IH-3 | 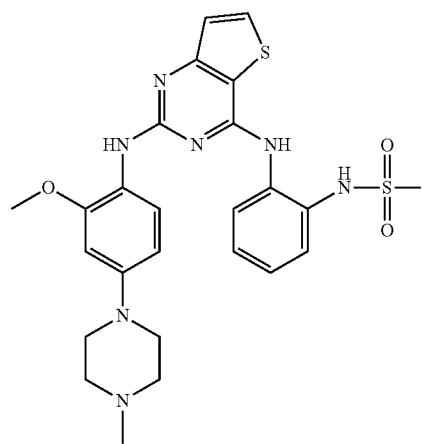 |
| IH-4 | 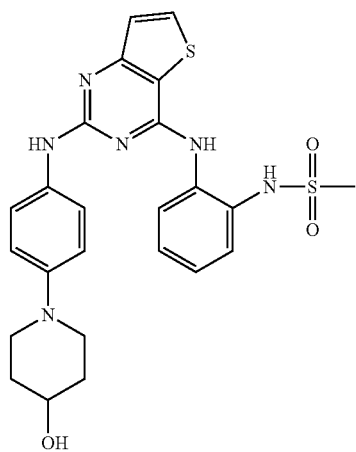 [SMILES: CS(=O)(=O)Nc1ccccc1Nc1nc(Nc2ccc(N3CCC(O)CC3)cc2)nc2ccsc12] |

| No. | Structure |
|---|---|
| IH-5 | 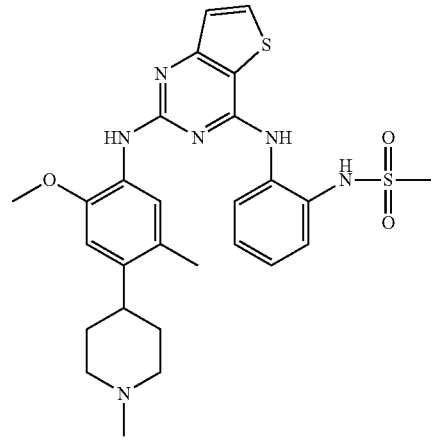 |
| IH-6 | 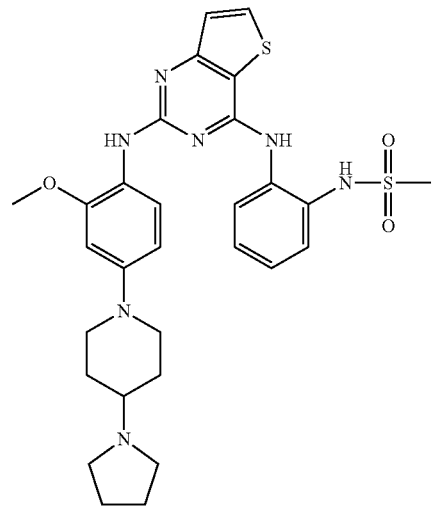 |
| IH-7 | 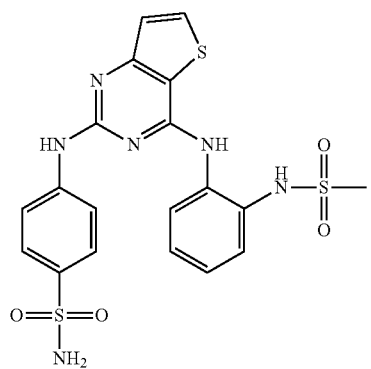 [SMILES: CS(=O)(=O)Nc1ccccc1Nc1nc(Nc2ccc(S(N)(=O)=O)cc2)nc2ccsc12] |

| No. | Structure |
|---|---|
| II-1 | 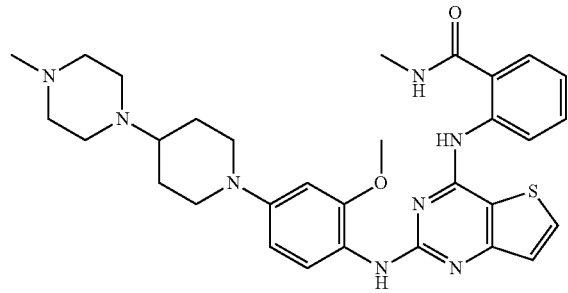 [SMILES: CNC(=O)c1ccccc1Nc1nc(Nc2ccc(N3CCC(N4CCN(C)CC4)CC3)cc2OC)nc2ccsc12] |
| II-2 | 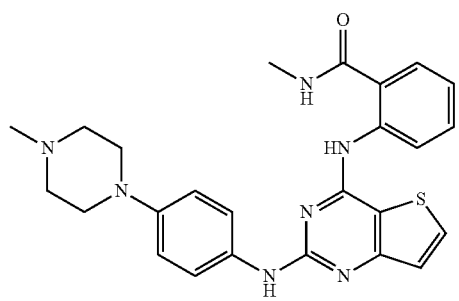 [SMILES: CNC(=O)c1ccccc1Nc1nc(Nc2ccc(N3CCN(C)CC3)cc2)nc2ccsc12] |
| II-3 | 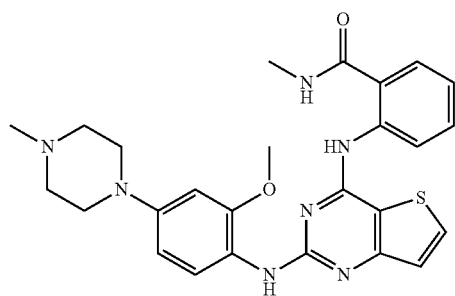 [SMILES: CNC(=O)c1ccccc1Nc1nc(Nc2ccc(N3CCN(C)CC3)cc2OC)nc2ccsc12] |
| II-4 | 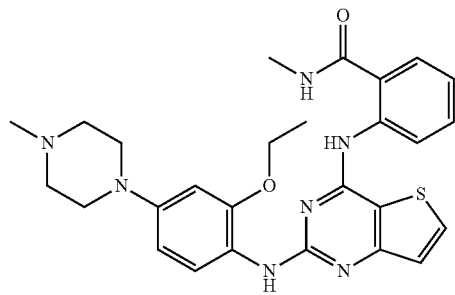 [SMILES: CCOc1cc(N2CCN(C)CC2)ccc1Nc1nc(Nc2ccccc2C(=O)NC)c2sccc2n1] |
| II-5 | 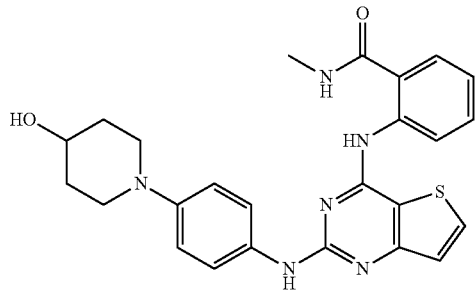 |

-continued
| No. | Structure |
|---|---|
| II-6 | 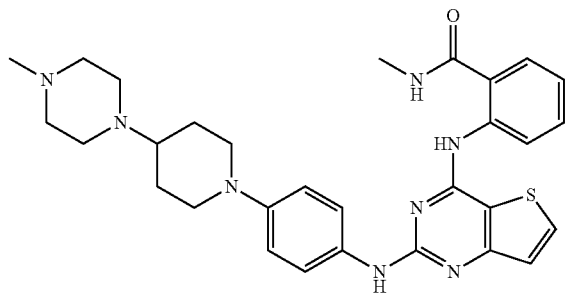 |
| II-7 | 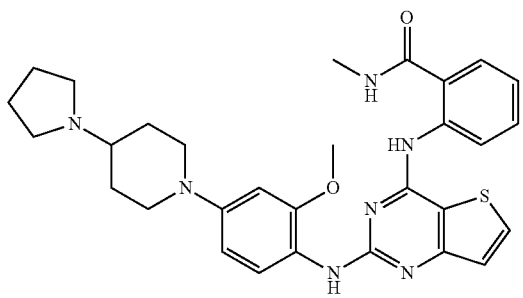 [SMILES: CNC(=O)c1ccccc1Nc1nc(Nc2ccc(N3CCC(N4CCCC4)CC3)cc2OC)nc2ccsc12] |
| II-8 | 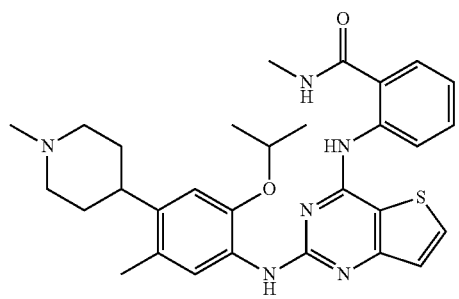 [SMILES: CNC(=O)c1ccccc1Nc1nc(Nc2cc(C)c(C3CCN(C)CC3)cc2OC(C)C)nc2ccsc12] |
| II-9 | 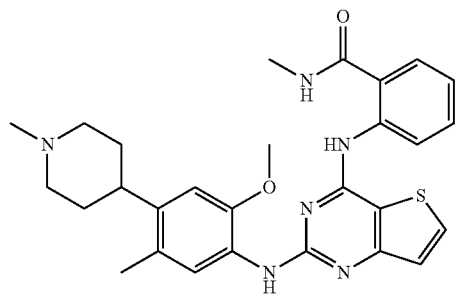 [SMILES: CNC(=O)c1ccccc1Nc1nc(Nc2cc(C)c(C3CCN(C)CC3)cc2OC)nc2ccsc12] |
| IJ-1 | 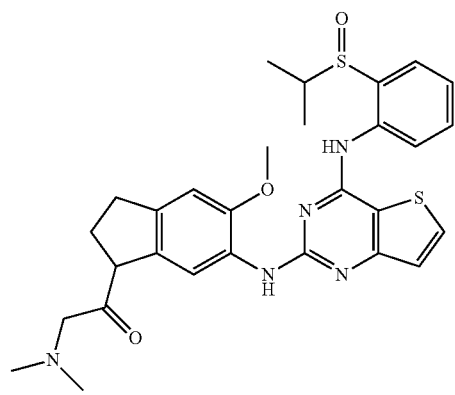 [SMILES: COc1cc2c(cc1Nc1nc(Nc3ccccc3S(=O)C(C)C)c3sccc3n1)C(C(=O)CN(C)C)CC2] |

| No. | Structure |
|---|---|
| IJ-2 | 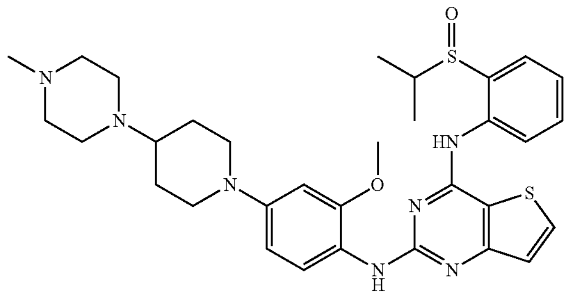 [SMILES: COc1cc(N2CCC(N3CCN(C)CC3)CC2)ccc1Nc1nc(Nc2ccccc2S(=O)C(C)C)c2sccc2n1] |
| IJ-3 | 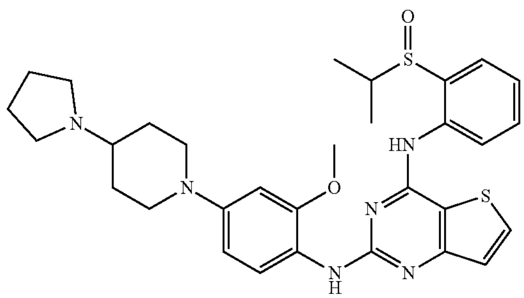 [SMILES: COc1cc(N2CCC(N3CCCC3)CC2)ccc1Nc1nc(Nc2ccccc2S(=O)C(C)C)c2sccc2n1] |
| IJ-4 | 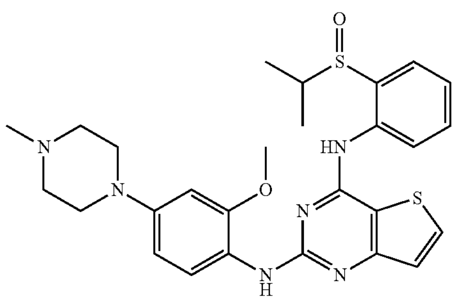 [SMILES: COc1cc(N2CCN(C)CC2)ccc1Nc1nc(Nc2ccccc2S(=O)C(C)C)c2sccc2n1] |
| IJ-5 | 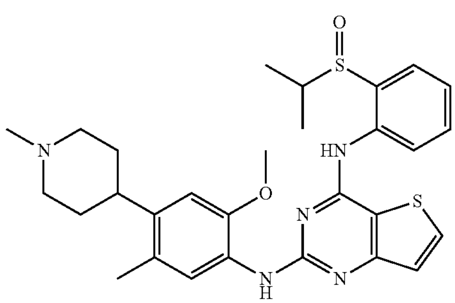 [SMILES: COc1cc(C2CCN(C)CC2)c(C)cc1Nc1nc(Nc2ccccc2S(=O)C(C)C)c2sccc2n1] |
| IJ-6 | 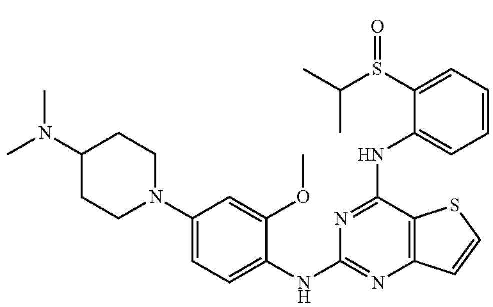 [SMILES: COc1cc(N2CCC(N(C)C)CC2)ccc1Nc1nc(Nc2ccccc2S(=O)C(C)C)c2sccc2n1] |

-continued
| No. | Structure |
|---|---|
| IL-1 | 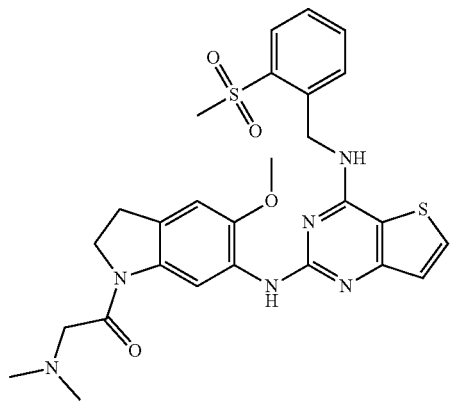 [SMILES: COc1cc2c(cc1Nc1nc(NCc3ccccc3S(C)(=O)=O)c3sccc3n1)N(C(=O)CN(C)C)CC2] |
| IL-2 | 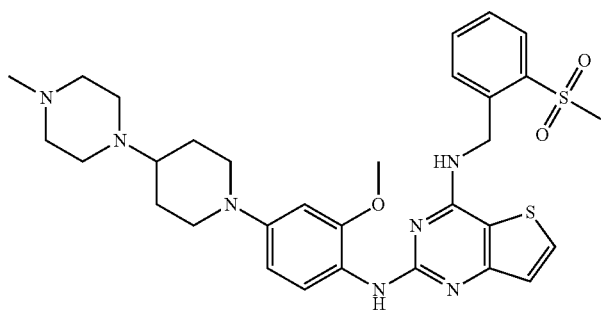 |
| IL-3 | 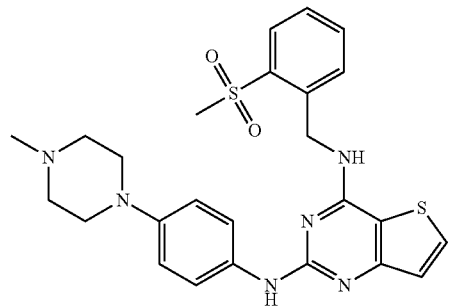 [SMILES: CN1CCN(c2ccc(Nc3nc(NCc4ccccc4S(C)(=O)=O)c4sccc4n3)cc2)CC1] |
| IL-4 | 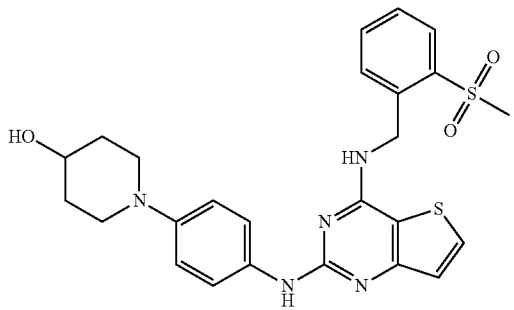 |

-continued

| No. | Structure |
|---|---|
| IM-1 | 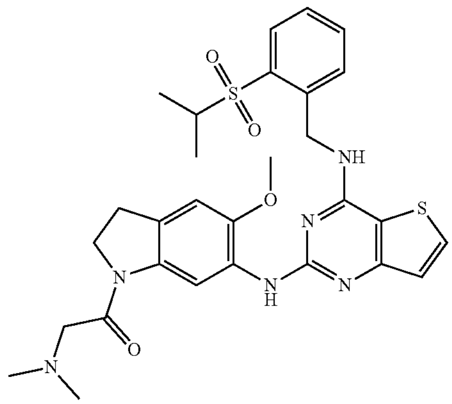 [SMILES: COc1cc2c(cc1Nc1nc(NCc3ccccc3S(=O)(=O)C(C)C)c3sccc3n1)N(C(=O)CN(C)C)CC2] |
| IM-2 | 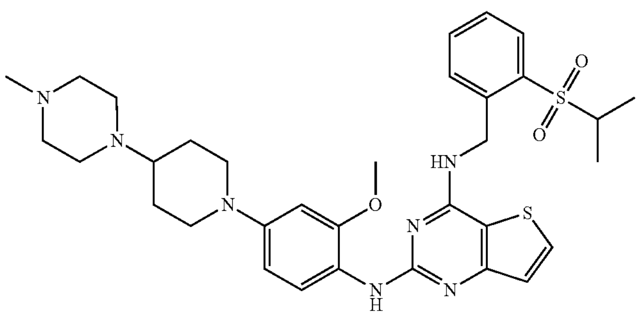 [SMILES: COc1cc(N2CCC(N3CCN(C)CC3)CC2)ccc1Nc1nc(NCc2ccccc2S(=O)(=O)C(C)C)c2sccc2n1] |
| IM-3 | 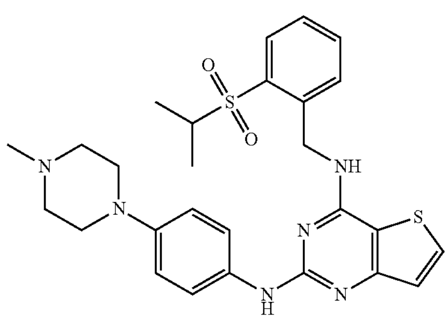 [SMILES: CC(C)S(=O)(=O)c1ccccc1CNc1nc(Nc2ccc(N3CCN(C)CC3)cc2)nc2ccsc12] |
| IM-4 | 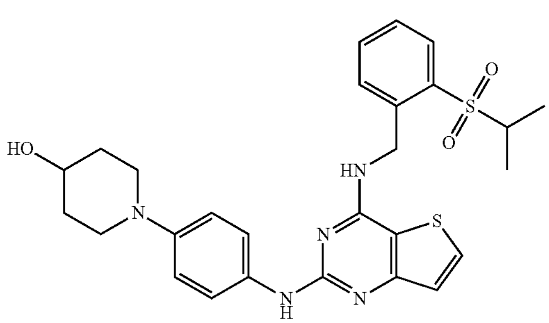 [SMILES: CC(C)S(=O)(=O)c1ccccc1CNc1nc(Nc2ccc(N3CCC(O)CC3)cc2)nc2ccsc12] |

| No. | Structure |
|---|---|
| IN-1 | 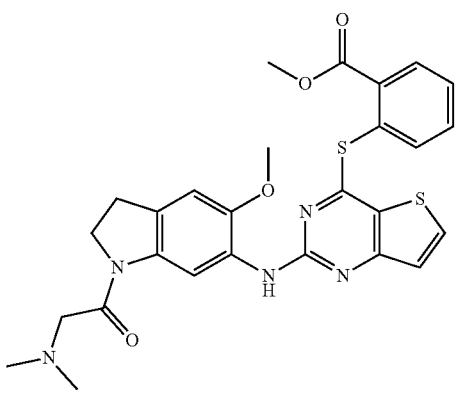 [SMILES: COC(=O)c1ccccc1Sc1nc(Nc2cc3c(cc2OC)CCN3C(=O)CN(C)C)nc2ccsc12] |
| IN-2 | 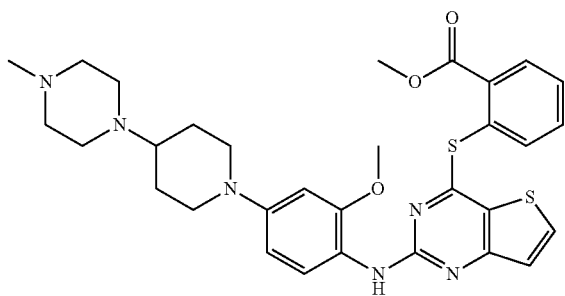 [SMILES: COC(=O)c1ccccc1Sc1nc(Nc2ccc(N3CCC(N4CCN(C)CC4)CC3)cc2OC)nc2ccsc12] |
| IN-3 | 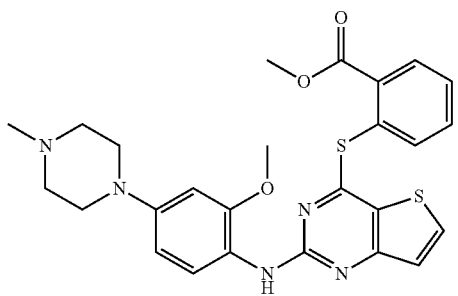 [SMILES: COC(=O)c1ccccc1Sc1nc(Nc2ccc(N3CCN(C)CC3)cc2OC)nc2ccsc12] |
| IN-4 | 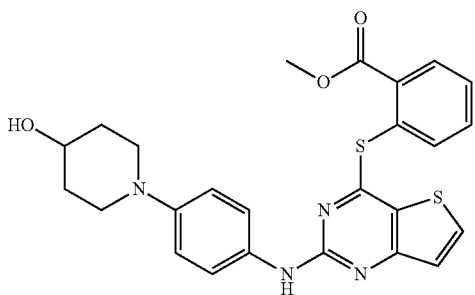 |
| IN-5 | 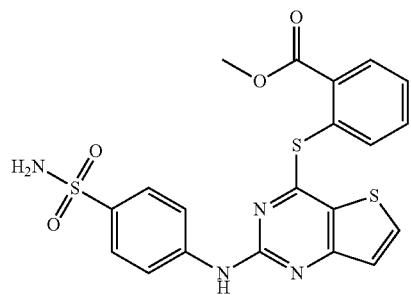 [SMILES: COC(=O)c1ccccc1Sc1nc(Nc2ccc(S(N)(=O)=O)cc2)nc2ccsc12] |

-continued
| No. | Structure |
|---|---|
| IN-6 | 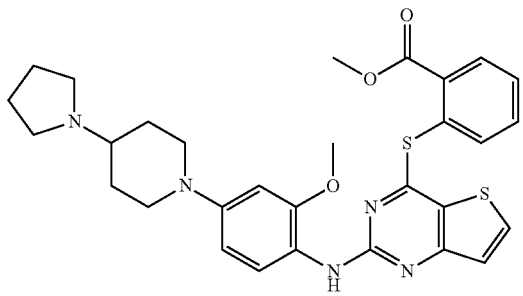 [SMILES: COC(=O)c1ccccc1Sc1nc(Nc2ccc(N3CCC(N4CCCC4)CC3)cc2OC)nc2ccsc12] |
| IN-7 | 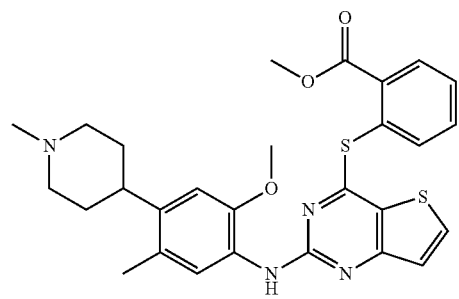 [SMILES: COC(=O)c1ccccc1Sc1nc(Nc2cc(C)c(C3CCN(C)CC3)cc2OC)nc2ccsc12] |
| IB-31 | 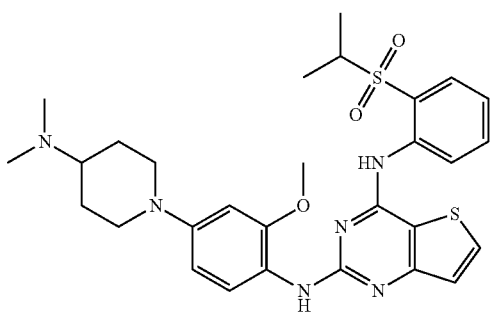 [SMILES: COc1cc(N2CCC(N(C)C)CC2)ccc1Nc1nc(Nc2ccccc2S(=O)(=O)C(C)C)c2sccc2n1] |
| IB-33 | 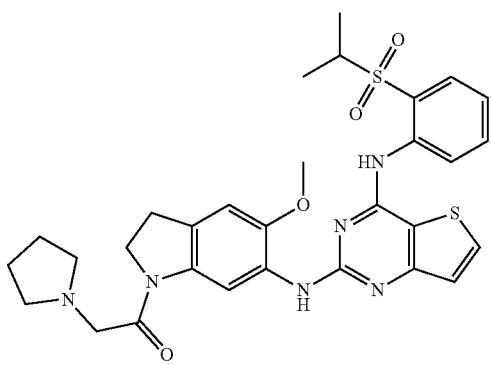 [SMILES: COc1cc2c(cc1Nc1nc(Nc3ccccc3S(=O)(=O)C(C)C)c3sccc3n1)N(C(=O)CN1CCCC1)CC2] |
| IB-35 | 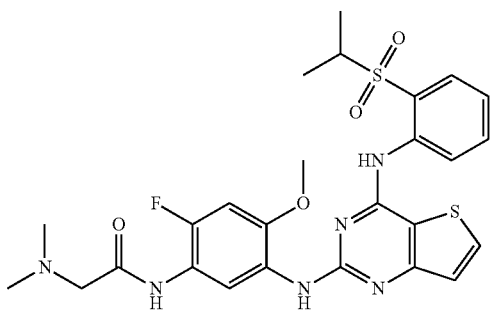 [SMILES: COc1cc(F)c(NC(=O)CN(C)C)cc1Nc1nc(Nc2ccccc2S(=O)(=O)C(C)C)c2sccc2n1] |

-continued
| No. | Structure |
|---|---|
| IO-2 | 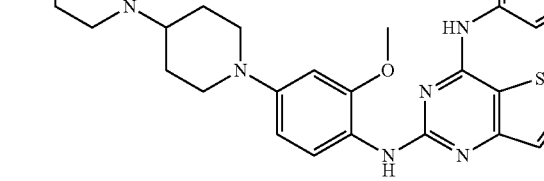 |
| IO-4 | 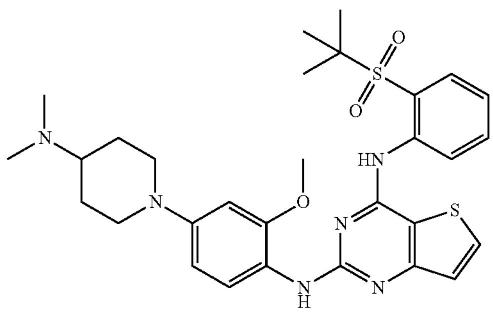 [SMILES: COc1cc(N2CCC(N(C)C)CC2)ccc1Nc1nc(Nc2ccccc2S(=O)(=O)C(C)(C)C)c2sccc2n1] |
| IP-2 | 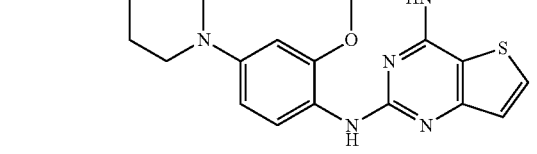 |
| IQ-1 | 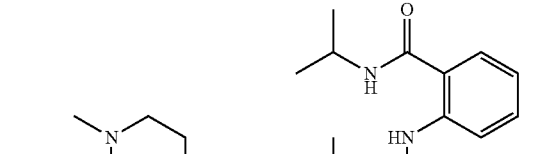 |
| IT-2 | 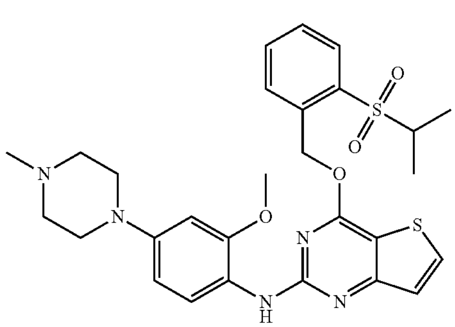 [SMILES: COc1cc(N2CCN(C)CC2)ccc1Nc1nc(OCc2ccccc2S(=O)(=O)C(C)C)c2sccc2n1] |

| No. | Structure |
|---|---|
| IT-4 | 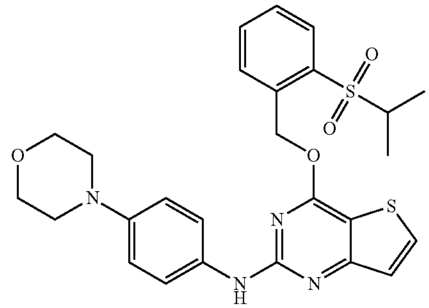 [SMILES: CC(C)S(=O)(=O)c1ccccc1COc1nc(Nc2ccc(N3CCOCC3)cc2)nc2ccsc12] |
| IT-6 | 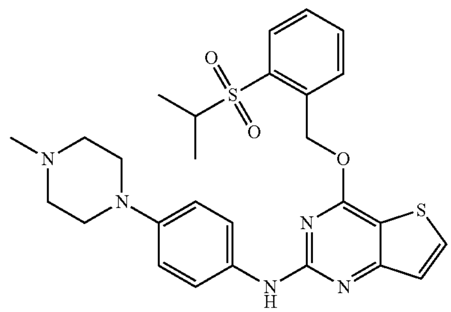 [SMILES: CC(C)S(=O)(=O)c1ccccc1COc1nc(Nc2ccc(N3CCN(C)CC3)cc2)nc2ccsc12] |
| IU-2 | | or a stereoisomer thereof, or a pharmaceutically acceptable salt thereof.

5. A pharmaceutical composition comprising a compound according to claim 1 or a stereoisomer thereof, or a pharmaceutically acceptable salt thereof and optionally a pharmaceutically acceptable excipient.

6. A method for treating a disease associated with anaplastic lymphoma kinase accompanied by abnormal cell proliferation, morphological changes, hyperkinesia in vivo, wherein the disease is any one selected from the group consisting of anaplastic large cell lymphoma, and non-small cell lung cancer, in a subject in need of such treatment comprising administering to the subject an effective amount of a compound according to claim 1 or a pharmaceutically acceptable salt thereof.

7. A pharmaceutical composition comprising a compound according to claim 4 or a pharmaceutically acceptable salt thereof and optionally a pharmaceutically acceptable excipient.

8. A method for treating a disease associated with anaplastic lymphoma kinase accompanied by abnormal cell proliferation, morphological changes, hyperkinesia in vivo wherein the disease is any one selected from the group consisting of anaplastic large cell lymphoma, and non-small cell lung cancer, in a subject in need of such treatment comprising administering to the subject an effective amount of a compound according to claim 4 or a pharmaceutically acceptable salt thereof.

9. A method for treating a disease associated with anaplastic lymphoma kinase accompanied by abnormal cell proliferation, morphological changes, hyperkinesia in vivo wherein the disease is any one selected from the group consisting of anaplastic large cell lymphoma, and non-small cell lung cancer, in a subject in need of such treatment comprising administering to the subject an effective amount of a pharmaceutical composition according to claim 5.

10. A compound according to claim 1, or a pharmaceutically acceptable salt thereof, wherein the pharmaceutically acceptable salt is an inorganic acid salt or an organic acid salt, wherein the inorganic acid salt is selected from hydrochloride, hydrobromide, hydroiodide, nitrate, bicarbonate, carbonate, sulfate, phosphate, and wherein the organic acid salt is selected from formate, acetate, propionate, benzoate, maleate, fumarate, succinate, tartrate, citrate, ascorbate, α-ketoglutarate, trifluoro acetate, α-glycero phosphate, alkyl sulfonate or aryl sulfonate.

11. A compound according to claim 2, or a pharmaceutically acceptable salt thereof, wherein the pharmaceutically acceptable salt is an inorganic acid salt or an organic acid salt, wherein the inorganic acid salt is selected from hydrochloride, hydrobromide, hydroiodide, nitrate, bicarbonate, carbonate, sulfate or phosphate, and wherein the organic acid salt is selected from formate, acetate, propionate, benzoate, maleate, fumarate, succinate, tartrate, citrate, ascorbate, α-ketoglutarate, trifluoro acetate, α-glycero phosphate, alkyl sulfonate or aryl sulfonate.

12. A compound according to claim 3, or a pharmaceutically acceptable salt thereof, wherein the pharmaceutically acceptable salt is an inorganic acid salt or an organic acid salt, wherein the inorganic acid salt is selected from hydrochloride, hydrobromide, hydroiodide, nitrate, bicarbonate, carbonate, sulfate or phosphate, and wherein the organic acid salt is selected from formate, acetate, propionate, benzoate, maleate, fumarate, succinate, tartrate, citrate, ascorbate, α-ketoglutarate, trifluoro acetate, α-glycero phosphate, alkyl sulfonate or aryl sulfonate.

13. A compound according to claim 4, or a pharmaceutically acceptable salt thereof, wherein the pharmaceutically acceptable salt is an inorganic acid salt or an organic acid salt, wherein the inorganic acid salt is selected from hydrochloride, hydrobromide, hydroiodide, nitrate, bicarbonate, carbonate, sulfate or phosphate, and wherein the organic acid salt is selected from formate, acetate, propionate, benzoate, maleate, fumarate, succinate, tartrate, citrate, ascorbate, α-ketoglutarate, trifluoro acetate, α-glycero phosphate, alkyl sulfonate or aryl sulfonate.

* * * * *